United States Patent
Zhang et al.

(10) Patent No.: US 12,016,312 B2
(45) Date of Patent: Jun. 25, 2024

(54) ANIMAL MODELS, SCREENING METHODS, AND TREATMENT METHODS FOR INTRAOCULAR DISEASES OR DISORDERS

(71) Applicant: ZHUHAI QIWEI BIO-TECHNOLOGY LTD., Guangdong (CN)

(72) Inventors: Yan Zhang, Beijing (CN); Lai Wei, Guangdong (CN); Hui Ouyang, Guangdong (CN)

(73) Assignee: SMILEBIOTEK ZHUHAI LIMITED, Zhuhai (CN)

( * ) Notice: Subject to any disclaimer, the term of this patent is extended or adjusted under 35 U.S.C. 154(b) by 301 days.

(21) Appl. No.: 17/293,991

(22) PCT Filed: Nov. 12, 2019

(86) PCT No.: PCT/CN2019/117444
§ 371 (c)(1),
(2) Date: May 14, 2021

(87) PCT Pub. No.: WO2020/098630
PCT Pub. Date: May 22, 2020

(65) Prior Publication Data
US 2022/0015338 A1 Jan. 20, 2022

(30) Foreign Application Priority Data

Nov. 14, 2018 (CN) .......................... 201811351660.9
Dec. 3, 2018 (WO) ................ PCT/CN2018/118929

(51) Int. Cl.
| | |
|---|---|
| *A61K 31/085* | (2006.01) |
| *A01K 67/00* | (2006.01) |
| *A61K 31/12* | (2006.01) |
| *A61K 31/235* | (2006.01) |
| *A61K 31/437* | (2006.01) |
| *A61K 31/704* | (2006.01) |
| *C12N 1/20* | (2006.01) |
| *C12R 1/11* | (2006.01) |
| *C12R 1/40* | (2006.01) |
| *G01N 33/50* | (2006.01) |

(52) U.S. Cl.
CPC ............ *A01K 67/00* (2013.01); *A61K 31/085* (2013.01); *A61K 31/12* (2013.01); *A61K 31/235* (2013.01); *A61K 31/437* (2013.01); *A61K 31/704* (2013.01); *C12N 1/20* (2013.01); *G01N 33/5044* (2013.01); *A01K 2207/10* (2013.01); *A01K 2227/106* (2013.01); *A01K 2267/03* (2013.01); *C12R 2001/11* (2021.05); *C12R 2001/40* (2021.05)

(58) Field of Classification Search
CPC .. A61K 31/736; A61K 9/0056; A61K 31/085; A61K 31/12; A61K 31/235; A61K 31/437; A61K 31/704; A23K 20/147; A23K 50/80; A23K 10/30; A01K 67/00; A01K 2207/10; A01K 2227/106; A01K 2267/03; C12N 1/20; G01N 33/5044; C12R 2001/40; C12R 2001/11
USPC ...................................................... 514/54, 23
See application file for complete search history.

(56) References Cited

U.S. PATENT DOCUMENTS

| | | | |
|---|---|---|---|
| 6,218,368 B1 | 4/2001 | Wirostko | |
| 7,169,555 B2 | 1/2007 | Stueber et al. | |
| 7,709,031 B2 | 5/2010 | Greenway | |
| 2003/0153524 A1 | 8/2003 | Hinton et al. | |
| 2007/0031332 A1* | 2/2007 | Greenway ................ | A61P 3/04 514/6.9 |
| 2009/0082470 A1 | 3/2009 | Farjo | |
| 2010/0255474 A1 | 10/2010 | Russwurm et al. | |
| 2012/0282330 A1 | 11/2012 | Wu | |
| 2013/0316985 A1 | 11/2013 | Deng et al. | |
| 2014/0162308 A1 | 6/2014 | Nickel et al. | |
| 2014/0328951 A1 | 11/2014 | Shim et al. | |
| 2018/0272009 A1 | 9/2018 | Takamatsu | |
| 2020/0340030 A1 | 10/2020 | Wei | |
| 2022/0010352 A1 | 1/2022 | Wei | |
| 2022/0016146 A1 | 1/2022 | Wei et al. | |

FOREIGN PATENT DOCUMENTS

| | | |
|---|---|---|
| CN | 1129585 A | 8/1996 |
| CN | 1436074 A | 8/2003 |
| CN | 1602207 A | 3/2005 |

(Continued)

OTHER PUBLICATIONS

Glossary of medical education terms, Institute of International Medical Education. http://www.iime.org/glossary.htm Accessed in Mar. 2013. (Year: 2013).*
Wen et al. Epigenetics, microbiota, and intraocular inflammation: New paradigms of immune regulation in the eye. Progress in Retinal and Eye Research 64 (2018) 84-95, Available online Jan. 19, 2018. (Year: 2018).*
Sadaka et al. Bacterial endophthalmitis in the age of outpatient intravitreal therapies and cataract surgeries: Hostemicrobe interactions in intraocular infection. Progress in Retinal and Eye Research 31 (2012) 316-331. (Year: 2012).*

(Continued)

*Primary Examiner* — Yih-Horng Shiao
(74) *Attorney, Agent, or Firm* — NIXON & VANDERHYE, PC

(57) ABSTRACT

Provided herein are screening methods and animal models related to intraocular diseases such as age-related macular degeneration (AMD), for example, for identifying candidate therapeutics for treating or preventing eye diseases, such as AMD. Also provided herein are compounds/compositions that are useful for killing or inhibiting the growth of a microorganism, such as *Bacillus megaterium*. Further provided herein are methods of using the compounds/compositions for treating infections with a microorganism, such as *Bacillus megaterium* and for treating or preventing diseases or disorders associated with such infections, such as AMD.

20 Claims, 7 Drawing Sheets

(56) References Cited

FOREIGN PATENT DOCUMENTS

| | | |
|---|---|---|
| CN | 101041864 A | 9/2007 |
| CN | 101137370 A | 3/2008 |
| CN | 101296916 A | 10/2008 |
| CN | 101474368 A | 7/2009 |
| CN | 101880705 A | 11/2010 |
| CN | 102058845 B | 5/2011 |
| CN | 102202673 A | 9/2011 |
| CN | 102558178 A | 7/2012 |
| CN | 103045761 A | 4/2013 |
| CN | 103805678 A | 5/2014 |
| CN | 104623670 A | 5/2015 |
| CN | 106834548 A | 6/2017 |
| CN | 107789430 A | 3/2018 |
| CN | 108272964 A | 7/2018 |
| CN | 108349867 A | 7/2018 |
| CN | 108498698 A | 9/2018 |
| CN | 109706238 A | 5/2019 |
| JP | 2014094917 A | 5/2014 |
| JP | 6036193 B2 | 11/2016 |
| KR | 10-2012-0041390 A | 5/2012 |
| KR | 101706389 B1 | 2/2017 |
| WO | 00/40262 A1 | 7/2000 |
| WO | 02/085248 A2 | 10/2002 |
| WO | 2006/086750 | 8/2006 |
| WO | 2007/029008 A2 | 3/2007 |
| WO | 2013/152313 A1 | 10/2013 |
| WO | 2015/023596 A1 | 2/2015 |
| WO | 2016/090005 A1 | 6/2016 |
| WO | 2016/196367 A1 | 12/2016 |
| WO | 2017/031161 | 2/2017 |
| WO | 2018/058078 A1 | 3/2018 |
| WO | 2018/119439 A1 | 6/2018 |
| WO | 2019/080916 A1 | 5/2019 |
| WO | 2020/098231 A1 | 5/2020 |
| WO | 2020/098630 A1 | 5/2020 |
| WO | 2020/113373 A1 | 6/2020 |

OTHER PUBLICATIONS

Wei, U.S. Appl. No. 17/293,603, filed May 13, 2021, now U.S. Publication No. US-2022-0010352 A1 published on Jan. 13, 2022.
Wei et al., U.S. Appl. No. 17/293,752, filed May 13, 2021, now U.S. Publication No. US-2022-0016146 A1 published on Jan. 20, 2022.
Wei, U.S. Appl. No. 16/758,365, filed Apr. 22, 2020, now U.S. Publication No. US 2020-0340030 A1 published on Oct. 29, 2020.
Bui, Minh-Phuong Ngoc et al., "Single-Digit Pathogen and Attomolar Detection with the Naked Eye Using Liposome-Amplified Plasmonic Immunoassay", Nano Letters, US, (Aug. 26, 2015), vol. 15,No. 9, Aug. 26, 2015, pp. 6239-6246.
Extended EP Search Report and Opinion for EP18869530.8 dated Jun. 30, 2021, 23 pages.
Gilger, Brian C. et al., "Role of bacteria in the pathogenesis of recurrent uveitis in horses from the southeastern United States AbbreviAtions", Colitz) and Veterinary Biosciences, Oct. 1, 2008.
Gündüz, A. et al., "Conjunctival flora in Behçet patients", Canadian Journal of Ophthalmology, Aug. 1, 2008 (Aug. 1, 2008), vol. 43, No. 4, pp. 476-479.
International Search Report for PCT/CN2018/112022 dated Jan. 30, 2019, 7 pages.
Meri, T. et al., "Microbes Bind Complement Inhibitor Factor H via a Common Site", vol. 9, No. 4, Apr. 18, 2013.
Milder, Eugene et al., "Changes in Antibiotic Resistance Patterns of Conjunctival Flora Due to Repeated Use of Topical Antibiotics after Intravitreal Injection", Ophthalmology, Amsterdam, NL, (Jul. 1, 2012), vol. 119, No. 7, Jul. 1, 2012, pp. 1420-1424.
Okhravi, Narciss et al., "PCR-Based Evidence of Bacterial Involvement in Eyes with Suspected Intraocular Infection", Investigative ophthalmology & visual science, Rockville, MD, (Oct. 1, 2000), pp. 3474-3479 (Oct. 2000).
Robman, L. et al., "Exposure to Chlamydia pneumoniae infection and progression of age-related macular degeneration", American Journal of Epidemiology, Oxford University Press, US, (Jan. 1, 2005), vol. 161, No. 11, doi:10.1093/AJE/KWI130, ISSN 0002-9262, pp. 1013-1019 (Jun. 2005).
Thanathanee, Onsiri et al., "Conjunctivitis: Systematic Approach to Diagnosis and Therapy", Curr Infect Dis Rep, Feb. 5, 2011, pp. 141-148.
Yu, X. et al., "PCR Assay for Detection of Bacillus Licheniformis", SDAIT-06-11-14, Abstract, Jan. 26, 2015.
Yang, B.X., et al., "Identification of pathogenic bacteria in aqueous and vitreous of endophthalmitis by 16S rDNA Sequencing technique", Chin. J. Expl. Ophthalmol, vol. 34, No. 10, Oct. 31, 2016, Abstract, pp. 883-887.
International Search Report for PCT/CN2018/118929, mailed Sep. 5, 2019, 6 pages.
International Search Report for PCT/CN2019/117444, mailed Mar. 6, 2020, 4 pages.
Zheng, Wei et al., "Microbiome Characterization in Retina and Choroid of Patients with Age-related Macular Degeneration", Author AAliations & Notes Investigative Ophthalmology & Visual Science, May 1, 2016.
Knox, C. Michele et al., "Identification of Bacterial Pathogens in Patients With Endophthalmitis by 16S Ribosomal DNA Typing", American Journal of Ophthalmology, vol. 128, No. 4, Oct. 31, 1999, pp. 511-512.
Han, Song et al, "The study on rapid diagnosis of infective endophthalmitis with polymerase chain reaction combined with direct gene sequencing", Beijing Medical, vol. 30, No. 7, Dec. 31, 2008, pp. 418-420.
Liu, Y.B. "Chapter 16 Ocular trauma", Ophthalmology Foundation and Diagnosis and Treatment Practice, Jul. 31, 2015, pp. 295-296, see International Search Report for PCT/CN2018/112022 dated Jan. 30, 2019 for relevancy.
Extended Search Opinion for EP19883906.0 dated Jan. 5, 2022, 4 pages.
International Search Report for PCT/CN2019/084396 mailed Aug. 19, 2019, 7 pages.
Hosaka, S. et al., "In vivo evaluation of ocular inserts of hydrogen impregnated with antibiotics fop trachoma therapy", Biomaterials, vol. 4, No. 4, 1983, pp. 243-248.
Wen, Xiaofeng et al., "Epigenetics, microbiota, and intraocular inflammation: New paradigms of immune regulation in the eye", Progress in Retinal and Eye Research, vol. 64, Jan. 19, 2018, pp. 84-95.
Guedez Liliana et al., "Antibiotic Treatment Exacerbates Focal Retinal Degeneration in a Mouse Model of AMD", Investigative Ophthalmology & Visual Science, vol. 56, (2015), p. 276, URL: https://iovs.arvojournals.org/article.aspx?articleid=2332559, (Dec. 3, 2021), XP055868840 [A] 1-13 * abstract *.
Kalayoglu, M. V. et al., "Serological association between Chlamydia pneumoniae infection and age-related macular degeneration", Archives of Ophthalmology, vol. 121, No. 4, 2003, pp. 478-482.
EP Search Report and Opinion for EP189421993 dated Mar. 21, 2022, 7 pages.
Kang Jung-Hwan et al., "Protective effects of resveratrol and its analogs on age-related macular degeneration in vitro", Archives of Pharmacal Research, Natl. Fisheries University, Pusan, KR, vol. 39, No. 12, Sep. 22, 2016, pp. 1703-1715.
Extended Search Report for EP19885011.7 dated Apr. 20, 2022, 8 pages.
Kubo Isao et al., "Anti-MRSA activity of alkyl gallates", Bioorganic & Medicinal Chemistry Letters, (2002), vol. 12, No. 2, pp. 113-116.
International Search Report for PCT/CN2019/070572 dated Sep. 2, 2019, 4 pages.
Yu, F. et al., "Overview of traditional Chinese medicine research on age-related macular degeneration" China Healthcare Frontiers, vol. 3, No. 16, Aug. 31, 2008, pp. 13-15, see International Search Report for PCT/CN2019/070572 dated Sep. 2, 2019 for relevancy.
Ys, Ho et al., "From Small to Big Molecules: How Do We Prevent and Delay the Progression of Age-Related Neurodegeneration?", Current Pharmaceutical Design, 2012, 18, pp. 15-26.
Lee, Yunhee et al., "Modulating the Transport Characteristics of Bruch's Membrane With Steroidal Glycosides and its Relevance to

(56) References Cited

OTHER PUBLICATIONS

Age-Related Macular Degeneration (AMD)", Invest Ophthalmol Vis Sci., Dec. 2015, vol. 56, No. 13, pp. 8403-8418.

* cited by examiner

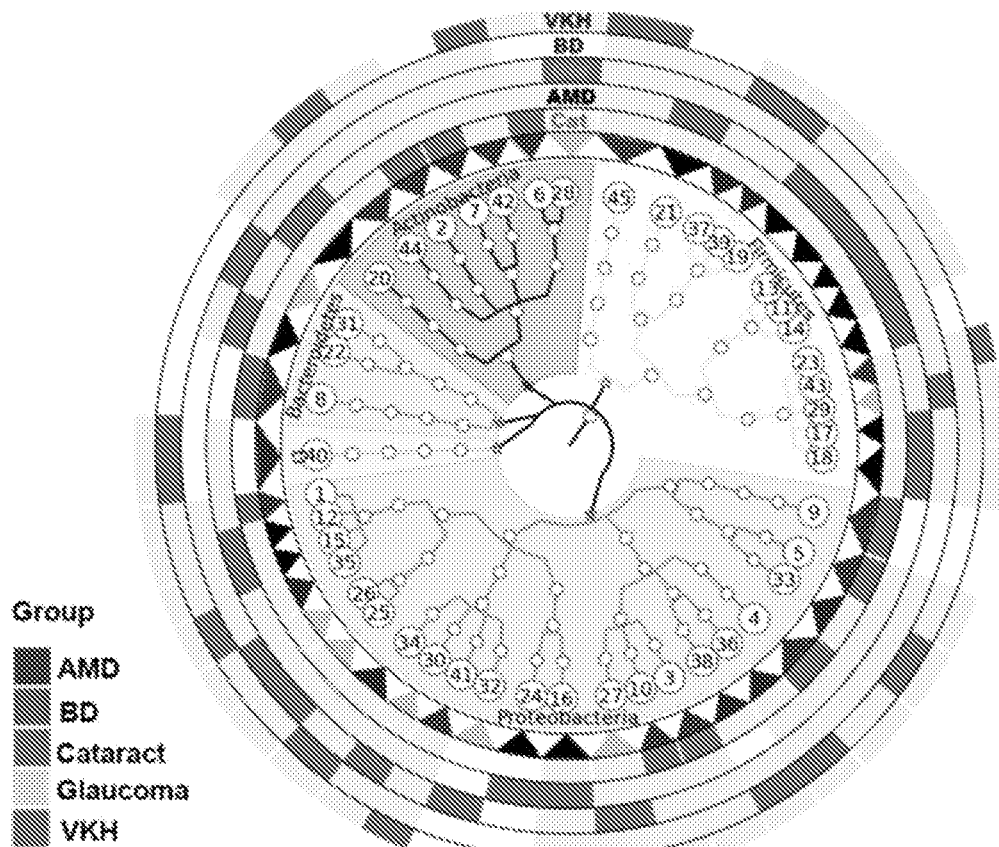

| | | |
|---|---|---|
| 1 Pseudomonas mendocina | 16 Stenotrophomonas maltophilia | 31 Cyanobacter [illegible] |
| 2 Kytococcus sedentarius | 17 Bacillus cereus | 32 Serratia marcescens |
| 3 Alicyclobacillus denitrificans | 18 Bacillus megaterium | 33 Sphingomonas wittichii |
| 4 Achromobacter xylosoxidans | 19 Lactobacillus reuteri | 34 Klebsiella pneumoniae |
| 5 Sphingobium japonicum | 20 Gardnerella vaginalis | 35 Pseudomonas fluorescens |
| 6 Mycobacterium abscessus | 21 Enterococcus faecium | 36 Ralstonia pickettii |
| 7 Arthrobacter aurescens | 22 Cytophaga hutchinsonii | 37 Lactobacillus crispatus |
| 8 Prevotella dentalis | 23 Bacillus licheniformis | 38 Burkholderia multivorans |
| 9 Sinorhizobium meliloti | 24 Xanthomonas oryzae | 39 Lactobacillus delbrueckii |
| 10 Acidovorax ebreus | 25 Acinetobacter baumannii | 40 Meiothermus silvanus (D) |
| 11 Staphylococcus epidermidis | 26 Acinetobacter calcoaceticus | 41 Escherichia coli |
| 12 Pseudomonas aeruginosa | 27 Comamonas testosteroni | 42 Micrococcus luteus |
| 13 Staphylococcus aureus | 28 Mycobacterium kansasii | 43 Bacillus subtilis |
| 14 Staphylococcus haemolyticus | 29 Bacillus thuringiensis | 44 Corynebacterium aurimucosum |
| 15 Pseudomonas putida | 30 Citrobacter koseri | 45 Finegoldia magna |

Figure 9

ANIMAL MODELS, SCREENING METHODS, AND TREATMENT METHODS FOR INTRAOCULAR DISEASES OR DISORDERS

CROSS REFERENCE TO RELATED APPLICATIONS

The present application is the U.S. National Phase of International Application No. PCT/CN2019/117444, filed Nov. 12, 2019, which claims priority to Chinese patent application No. 201811351660.9, filed on Nov. 14, 2018 and International Application No. PCT/CN2018/118929, filed Dec. 3, 2018, the disclosure of each of which is incorporated by reference in its entirety for all purposes.

BACKGROUND OF THE INVENTION

Field of the Invention

The invention generally belongs to the technical field of diagnosis and treatment of eye diseases, and more particularly relates to screening methods, animal models, and methods of treatment or prevention of eye diseases or disorders. In various embodiments, the present disclosure also relates to compounds, compositions and methods for treating and/or preventing age-related macular degeneration (AMD) in a subject, e.g., a human patient or a vertebrate such as a dog, a cat, a horse or a monkey.

Background Art

The eyes are the windows of the soul which are very important for everyone. People use their eyes every day, but at the same time the eyes are very fragile. It is easy to cause eye discomfort or lesions due to various factors. Common eye diseases include conjunctivitis and dry eye syndrome, and more serious intraocular diseases or disorders include cataract (Cat), age-related macular degeneration (AMD), glaucoma (GLA), Behcet's disease (BD), Vogt-Koyanagi-Harada Syndrome (VKH), uveitis and so on.

In the elderly population, Age-related macular degeneration (AMD) is the leading cause of irreversible vision loss worldwide. It is characterized by confluent soft drusen deposited between retinal pigment epithelium (RPE) and the Bruch's membrane and/or retinal pigmentary changes in the macula at the early stage (intermediate AMD). At later stages, advanced AMD is characterized by two major sub-types, geographic atrophy (dry AMD) or choroidal neovascularization (wet AMD) in the macula. While anti-VEGF therapies have been used to control wet AMD, currently there is no approved therapy for dry AMD.

The pathogenesis of AMD involves both genetic and environmental factors. Currently, the environmental factors triggering the local inflammation and leading to the early soft drusen in AMD pathology are not clear. Numerous studies have identified variations at the loci of genes that are associated with AMD susceptibility, including complement factor H (CFH), age-related maculopathy susceptibility 2 (ARMS2), HtrA serine peptidase 1 (HTRA1), indicating that AMD is possible an inflammatory disease.

Currently, the environmental factors triggering the local inflammation and leading to the early soft drusen in AMD pathology are not clear. There is a need for improved compositions and methods for assessing, treating or preventing intraocular diseases or disorders in a subject, e.g., a mammal or a human. The present disclosure addresses this and other related needs.

BRIEF SUMMARY OF THE INVENTION

In various embodiments, the present invention is directed to screening methods and animal models for various eye diseases, such as human eye diseases. The screening methods and animal models are based in part on the unexpected discovery that the intraocular environment is not sterile and certain intraocular microbiota such as *Bacillus megaterium* can be pathogenic causes of various eye diseases, such as AMD.

In some embodiments, the present invention provides a screening method for identifying candidate therapeutics for treating or preventing eye diseases, such as AMD. The screening method can be an in vitro screening method, e.g., in a petri dish, or an in vivo screening method, e.g., using an animal model described herein.

In some embodiments, the present invention provides a screening method, which comprises a) culturing a microorganism in a suitable culture medium in the presence of a test compound; b) measuring the growth of the microorganism in the culture medium in the presence of the test compound; and optionally c) identifying a candidate therapeutics that inhibits the growth of the microorganism compared to a control. In some embodiments, the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having an eye disease compared to a healthy subject, wherein the eye disease is selected from age-related macular degeneration (AMD), Behcet's disease (BD), cataract (Cat), endophthalmitis (EOS), glaucoma (GLA), Vogt-Koyanagi-Harada Syndrome (VKH), and combinations thereof. In some embodiments, the subject is a human subject. In some embodiments, the method is for identifying a candidate therapeutics for treating or preventing a human eye disease, such as AMD, BD, Cat, EOS, GLA, VKH, or combinations thereof.

In some specific embodiments, the screening method is for identifying a candidate therapeutics for treating or preventing AMD. In some embodiments, the microorganism comprises a species that is enriched in the intraocular space (e.g., aqueous humor, vitreous humor, soft drusen) in a subject having AMD compared to a healthy subject. In some embodiments, the microorganism comprises one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis,* and *Xanthomonas oryzae*. In some embodiments, the microorganism comprises *Bacillus megaterium* and/or *Pseudomonas putida*. In some embodiments, the microorganism at least comprises *Bacillus megaterium*. In some embodiments, the microorganism comprises a mixture of microbial species substantially similar to those observed from an aqueous humor, vitreous humor, and/or soft drusen of a subject having AMD. In some embodiments, the microorganism is derived, in part or in whole, from an aqueous humor and/or vitreous humor of a subject having age-related macular degeneration.

Screening methods for identifying a candidate therapeutics for treating or preventing other eye diseases such as BD, Cat, EOS, GLA, VKH, are similar to those described for AMD, but with a different microorganism, as detailed herein. For example, for BD, the microorganism cultured in the presence of a test compound typically can include one or more species selected from *Sphingomonas wittichii, Klebsiella pneumoniae, Pseudomonas fluorescens, Ralstonia pickettii, Lactobacillus crispatus, Burkholderia multivorans, Lactobacillus delbrueckii*, and *Meiothermus silvanus*(D). For Cat, the microorganism cultured in the presence of a test compound typically can include one or more species selected from *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti*, and *Acidovorax ebreus*. For GLA, the microorganism cultured in the presence of a test compound typically can include one or more species selected from *Acinetobacter baumannii, Acinetobacter calcoaceticus, Comamonas testosteroni, Mycobacterium kansasii, Bacillus thuringiensis, Citrobacter koseri, Dyadobacter fermentans*, and *Serratia marcescens*. For VKH, the microorganism cultured in the presence of a test compound typically can include one or more species selected from *Escherichia coli, Micrococcus luteus, Bacillus subtilis, Corynebacterium aurimucosum*, and *Finegoldia magna*. In some embodiments, the microorganism used for the screening method can also include a mixture of microbial species substantially similar to those observed from an aqueous humor, and/or vitreous humor of a subject having BD, Cat, EOS, GLA, or VKH, respectively. In some embodiments, the microorganism used for the screening method can also be derived, in part or in whole, from an aqueous humor and/or vitreous humor of a subject having BD, Cat, EOS, GLA, or VKH, respectively.

The screening methods herein are not limited to any particular test compounds or any particular types of test compounds. Some exemplary test compounds are described herein. The screening methods herein can be a low throughput, medium throughput, or high throughput method, and can test a plurality of test compounds in parallel when needed. The identifying in the screening methods is also not limited to any particular technique. For example, in some embodiments, the identifying can include identifying a candidate therapeutics that prevents visible growth of the microorganism at or below the maximum tested concentration. In some embodiments, the identifying can include identifying a candidate therapeutics that prevents visible colony formation of the microorganism at or below the maximum tested concentration.

The screening methods herein can further include determining or having determined one or more microbial species as enriched in the intraocular space in a subject having an eye disease compared to a healthy subject, wherein the eye disease is selected from age-related macular degeneration (AMD), Behcet's disease (BD), cataract (Cat), endophthalmitis (EOS), glaucoma (GLA), Vogt-Koyanagi-Harada Syndrome (VKH), and combinations thereof. For example, in some embodiments, the present invention provides a screening method, which includes a) determining or having determined one or more microbial species as enriched in the intraocular space in a subject having age-related macular degeneration (AMD) compared to a healthy subject; b) culturing a microorganism comprising at least one of the enriched microbial species in a suitable culture medium in the presence of a test compound; c) measuring the growth of the microorganism in the culture medium in the presence of the test compound; and optionally d) identifying a candidate therapeutics that inhibits the growth of the microorganism compared to a control.

Some embodiments of the present invention are directed to a method of preparing an animal model for an eye disease described herein. Typically, the animal model is for a human eye disease. The animal models prepared by the methods are also embodiments of the present invention.

Typically, the method of preparing an animal model includes introducing a microorganism and/or inactivated protein therefrom to an intraocular space of an eye of an animal, wherein the microorganism comprises a species that is enriched in the intraocular space in a subject having an eye disease compared to a healthy subject, wherein the eye disease is selected from cataract (Cat), age-related macular degeneration (AMD), glaucoma (GLA), Behcet's disease (BD), Vogt-Koyanagi-Harada Syndrome (VKH), endophthalmitis (EOS), and combinations thereof, and wherein the introducing induces one or more symptoms of the eye disease.

In some specific embodiments, the present invention provides a method of preparing an animal model for AMD. In some embodiments, the method comprises introducing a microorganism and/or inactivated protein therefrom to an intraocular space of an eye of an animal, wherein the microorganism comprises a species that is enriched in the intraocular space in a subject having AMD compared to a healthy subject, and wherein the introducing induces one or more symptoms of AMD. The method typically introduces live microorganism to the intraocular space of the animal. In some embodiments, the microorganism introduced includes at least live *Bacillus megaterium*. Preferably, the animal is a non-human primate (e.g., monkey). In some embodiments, the animal is macaque.

The animal models for AMD produced herein can also be used for identifying candidate therapeutics for treating or preventing AMD. For example, in some embodiments, the present invention also provides a screening method comprising a) administering a test compound to the animal model for AMD as described herein; b) determining the severity of the one or more symptoms of the eye disease post administration; and optionally c) identifying a candidate therapeutics that relieves at least one of the symptoms compared to a control.

In some embodiments, the present invention also provides a method of treating or preventing an eye disease described herein, such as AMD. In some embodiments, the method comprises administering to a subject in need thereof an effective amount of any of the candidate therapeutics identified in any of the screening methods herein directed to the respective eye disease, such as AMD.

In some embodiments, the present disclosure is directed to various compounds and/or compositions comprising the compounds that can kill or inhibit the growth of microorganisms related to AMD, such as *Bacillus megaterium*. In some embodiments, the present disclosure provides a compound according to any of Formula I, II, III, IV-1, IV-2, V, and any of the sub-formulae thereof, as defined herein, or a pharmaceutically acceptable salt or ester thereof. In some embodiments, the present disclosure provides a compound according to any of compounds 1-8, or a pharmaceutically acceptable salt or ester thereof. In some embodiments, the compounds of the present disclosure can be derived from synthetic sources. In some embodiments, the compounds of the present disclosure can be an isolated compound or a substantially pure compound.

Certain embodiments are directed to a pharmaceutical composition comprising one or more of the compounds of the present disclosure, and optionally a pharmaceutically acceptable excipient. For example, in some embodiments, the pharmaceutical composition comprises a compound of Formula I, II, III, IV-1, IV-2, V, any sub-formulae thereof, or any one or more of compounds 1-8, or a pharmaceutically acceptable salt or ester thereof, for example, in an amount effective to kill or inhibit the growth of a microorganism herein, such as *B. megaterium*, for example, in the eye (e.g., intraocular space), blood, and/or GI tract, such as intestine of the subject. The pharmaceutical composition described herein can be formulated for delivery via any of the known routes of delivery, such as for oral, topical, intravitreous, intramuscular, subcutaneous, or intravenous administration. In some embodiments, the pharmaceutical composition described herein can further include an antibiotic and/or an anti-VEGF medication, e.g., as described herein.

In various embodiments, the present disclosure also provides a method of using the compounds of the present disclosure or the pharmaceutical compositions herein for treating infections (e.g., ocular infections, such as in the intraocular space) with a microorganism herein, such as *Bacillus megaterium*, and for treating or preventing diseases or disorders associated with such infections, such as AMD.

In some embodiments, the present disclosure provides a method for killing or inhibiting the growth of a microorganism herein, such as *Bacillus megaterium*, in a subject in need thereof. In some embodiments, the method comprises administering to the subject a therapeutically effective amount of a compound of the present disclosure (e.g., compound of Formula I, II, III, IV-1, IV-2, V, any subformulae thereof, or any one or more of compounds 1-8, or a pharmaceutically acceptable salt or ester thereof, or a pharmaceutical composition herein. In some embodiments, the subject suffers from AMD. In some embodiments, the subject does not suffer from AMD. In some embodiments, the subject is at risk of developing AMD. In some embodiments, the subject has ocular infection with the microorganism, such as *Bacillus megaterium*. In some embodiments, the method further comprises identifying, or having identified, the subject as being infected with, e.g., in the intraocular space, the microorganism, such as *Bacillus megaterium*. In some embodiments, the subject is further administered an antibiotic and/or an anti-VEGF medication, e.g., as described herein.

In some embodiments, the present disclosure provides a method of treating or preventing AMD in a subject in need thereof. In some embodiments, the method comprises administering to the subject a therapeutically effective amount of a compound of the present disclosure (e.g., a compound of Formula I, II, III, IV-1, IV-2, V, any subformulae thereof, or any one or more of compounds 1-8, or a pharmaceutically acceptable salt or ester thereof). In some embodiments, the method further comprises administering to the subject an antibiotic and/or an anti-VEGF medication, e.g., as described herein. In some embodiments, the AMD can be dry or wet age-related macular degeneration with drusen symptoms, including a hard drusen, a soft drusen, a mixed drusen and/or a degraded drusen, for example, dry or wet age-related macular degeneration with soft drusen symptoms. In some embodiments, the method further comprises identifying, or having identified, the subject as being infected with, e.g., in the intraocular space, a microorganism herein, such as *Bacillus megaterium*. In some embodiments, the subject is infected with, e.g., in the intraocular space, a microorganism herein, such as *Bacillus megaterium*.

In some embodiments, the present disclosure provides a method of using extracts of Traditional Chinese Medicine(s) (TCMs) that have antibacterial activities. In some embodiments, the method is for killing or inhibiting the growth of a microorganism herein, a method of treating an infection (e.g., ocular infection, such as in the intraocular space) with a microorganism herein, such as *Bacillus megaterium*, or for treating or preventing AMD in a subject in need thereof. In some embodiments, the method comprises administering to the subject an extract from one or more TCMs selected from Licorice (e.g., *Glycyrrhiza uralensis*), White Peony Root (e.g., *Cynanchum otophyllum*), Forsythia (e.g., *Forsythia suspense*), Fructus Aurantii (e.g., *Citrus aurantium* L.), Rehmannia glutinosa (e.g., *Rehmannia glutinosa* Libosch), Tangerine Peel (e.g., *Citrus reticulata* Blanco), and Notoginseng (e.g., *Panax notoginseng*). In some embodiments, the method further comprises identifying, or having identified, the subject as being infected with, e.g., in the intraocular space, a microorganism herein, such as *Bacillus megaterium*. In some embodiments, the subject is infected with, e.g., in the intraocular space, a microorganism herein, such as *Bacillus megaterium*. The extract can be an extract of a single TCM or an extract of more than one TCMs. Typically, the extract is an aqueous extract. In some embodiments, the extracts can exist in liquid, semisolid, or solid form or any other form. In some embodiments, the subject is further administered an antibiotic and/or anti-VEGF medication, e.g., as described herein.

In some embodiments, the present disclosure provides a method of using an antibiotic, for example, for killing or inhibiting the growth of a microorganism herein, treating an infection (e.g., ocular infection, such as in the intraocular space) with a microorganism herein, such as *Bacillus megaterium*, or for treating or preventing AMD, in a subject in need thereof. In some embodiments, the method comprises administering to the subject an effective amount of an antibiotic, e.g., as described herein. In some embodiments, any of the commercially available antibiotics, e.g., those approved by the U.S. FDA, can be used. In some embodiments, the method further comprises identifying, or having identified, the subject as being infected with, e.g., in the intraocular space, a microorganism herein, such as *Bacillus megaterium*. In some embodiments, the subject is infected with, e.g., in the intraocular space, a microorganism herein, such as *Bacillus megaterium*. In some embodiments, the subject is further administered an anti-VEGF medication, e.g., as described herein.

The administering herein is not limited to any particular route of administration. For example, in some embodiments, the administering can be orally, topically, intravitreously, intramuscularly, subcutaneously, or intravenously.

It is to be understood that both the foregoing summary and the following detailed description are exemplary and explanatory only, and are not restrictive of the invention herein.

BRIEF DESCRIPTION OF THE DRAWINGS/FIGURES

Figure 3:
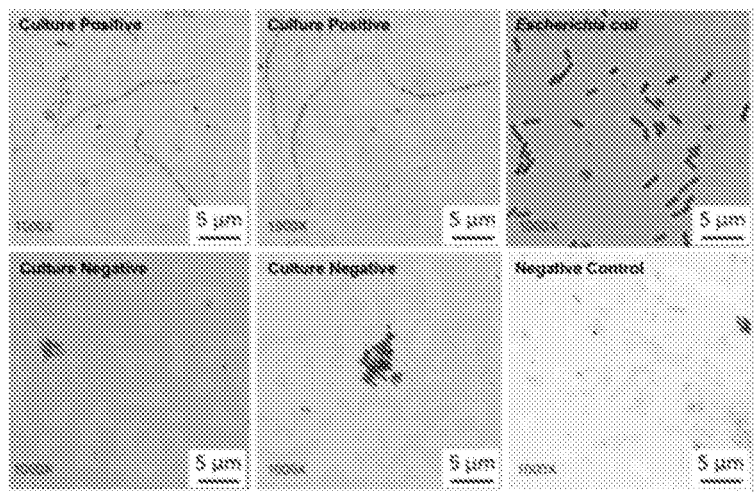

FIG. 3 shows detection of bacteria in cultures under standard light microscopes. Cultured *E. coli* was visualized by light microscopy. The negative control consists of sample preparation buffer without any AH or VH inoculation. Bacteria in cultured AH or VH samples (examples of culture positive and negative samples) were visualized by light microscopy.

Figure 4:
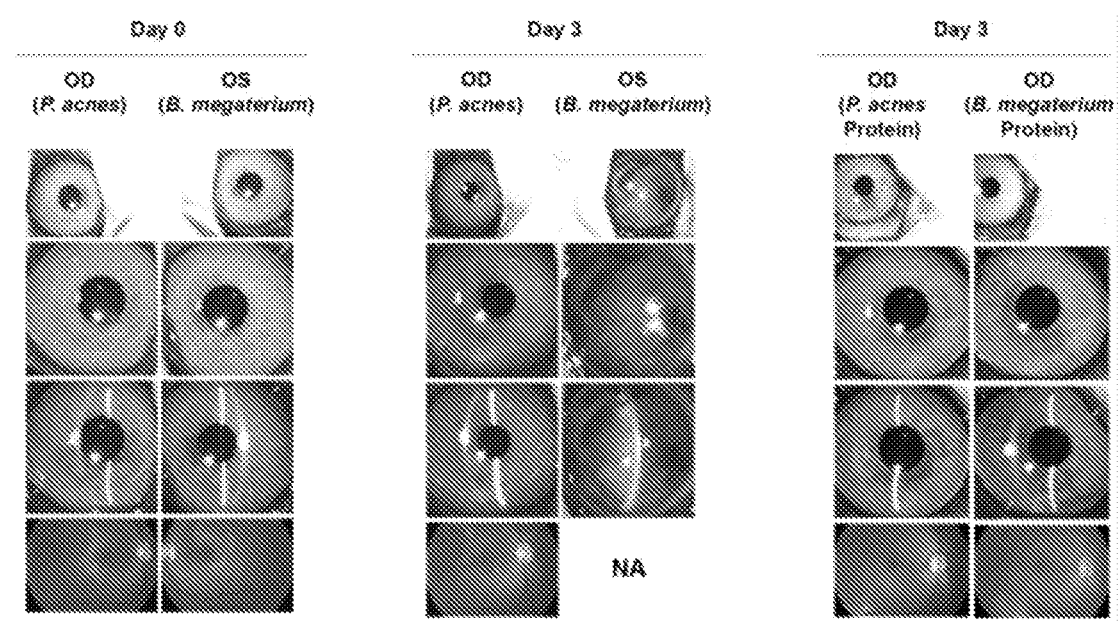

FIG. 4 shows macaques ocular surface and fundus view before and after bacterial inoculation (*P. acnes* and *Bacillus megaterium*). The right (OD) and left (OS) eyes of macaques were inoculated with *P. acnes* and *B. megaterium*, respectively. The ocular surface and fundus view before bacterial inoculation and 3 days post inoculation are shown.

Figure 5:
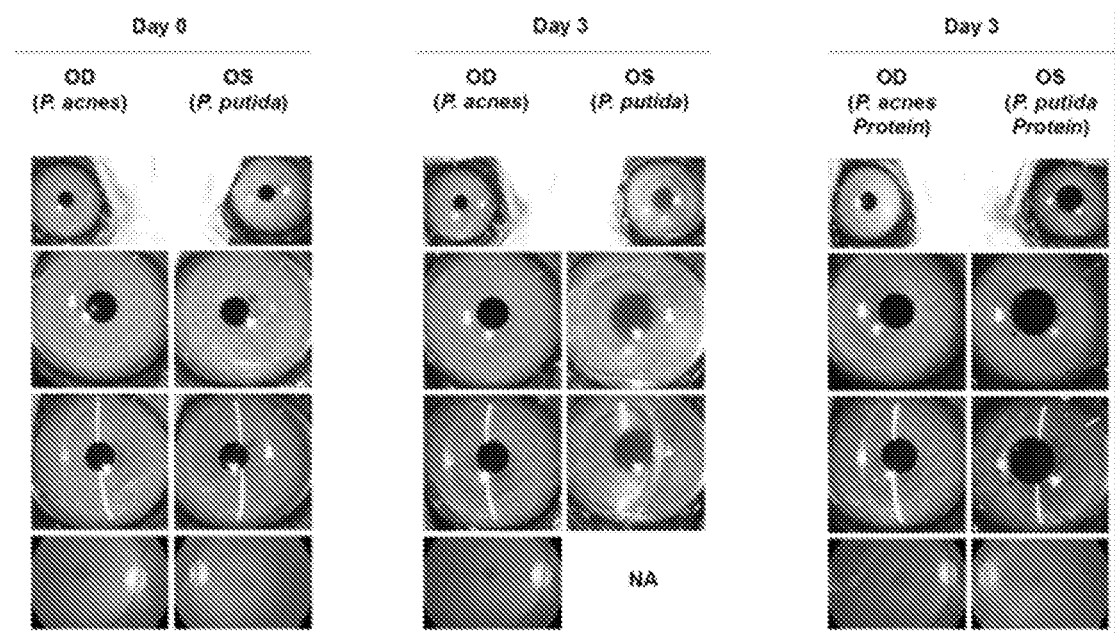

FIG. 5 shows macaques ocular surface and fundus view before and after bacterial inoculation (*P. acnes* and *Pseudomonas putida*). The right (OD) and left (OS) eyes of macaques were inoculated with *P. acnes* and *Pseudomonas putida*, respectively. The ocular surface and fundus view before bacterial inoculation and 3 days post inoculation are shown.

Figure 6:
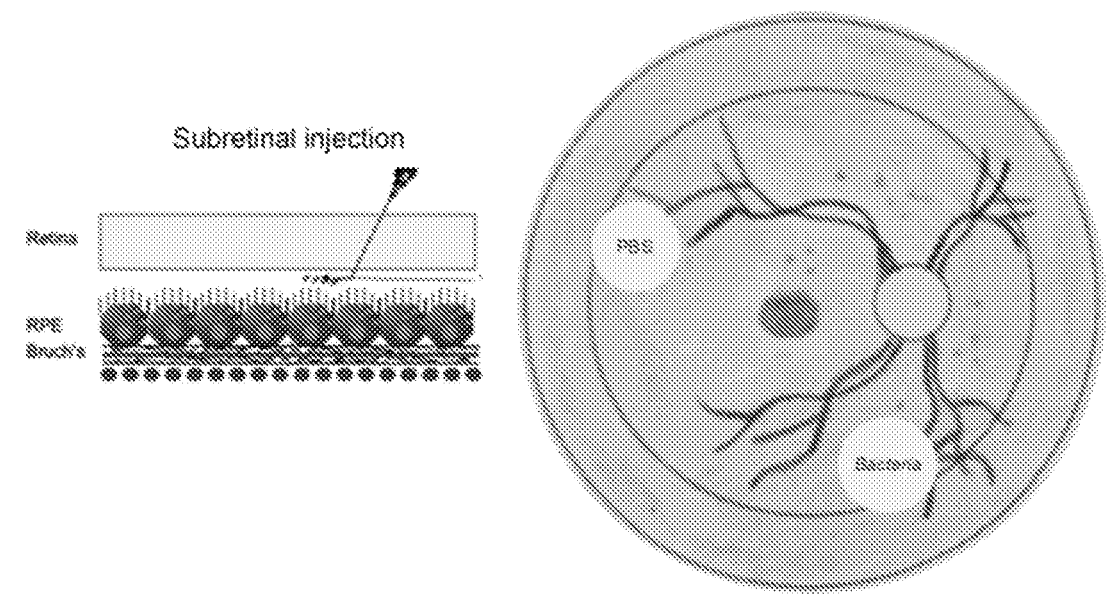

FIG. 6 illustrates subretinal injection anatomical and retinal locations.

Figure 7:
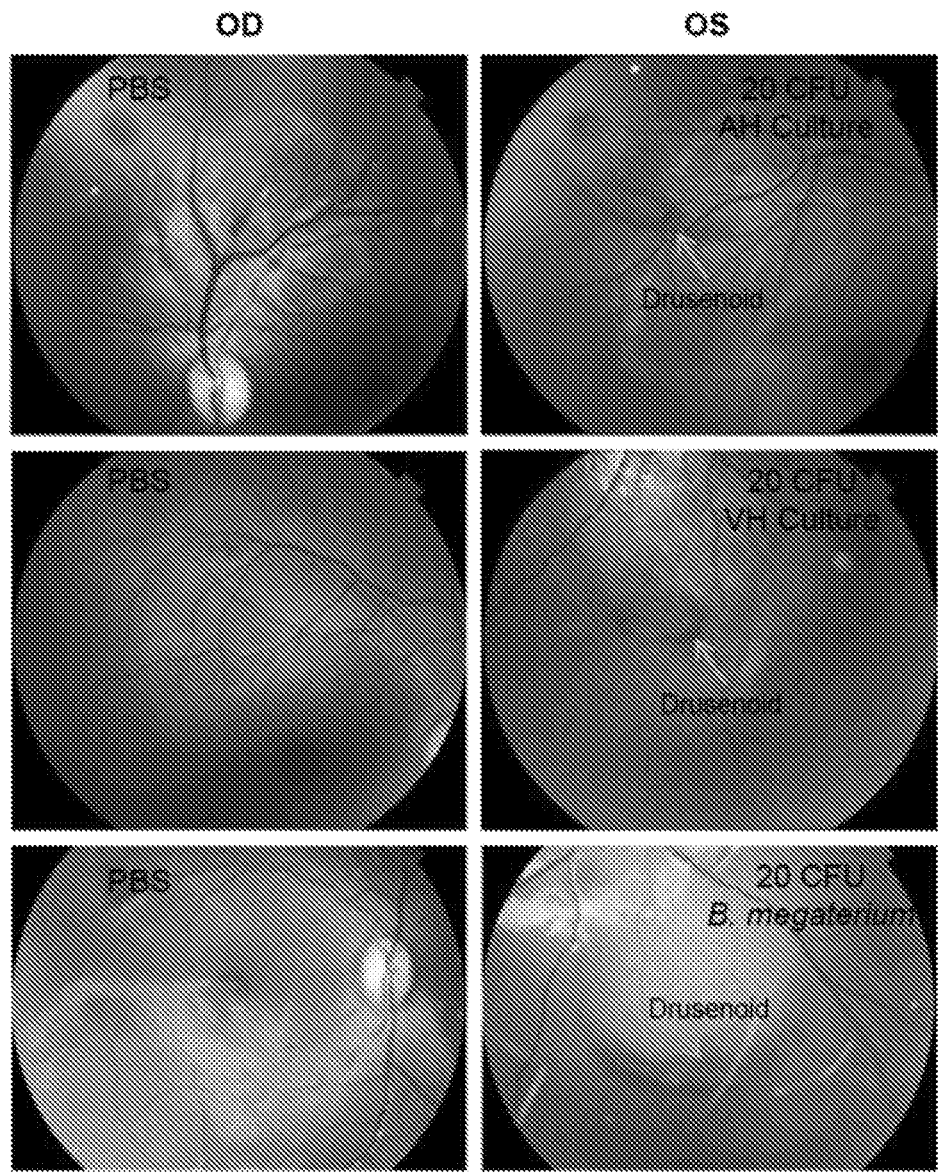

FIG. 7 presents macaque fundus view on Day 47 post injection of the macaque receiving subretinal inoculation of 20 CFU of AH culture, VH culture and *B. megaterium*.

Figure 8:
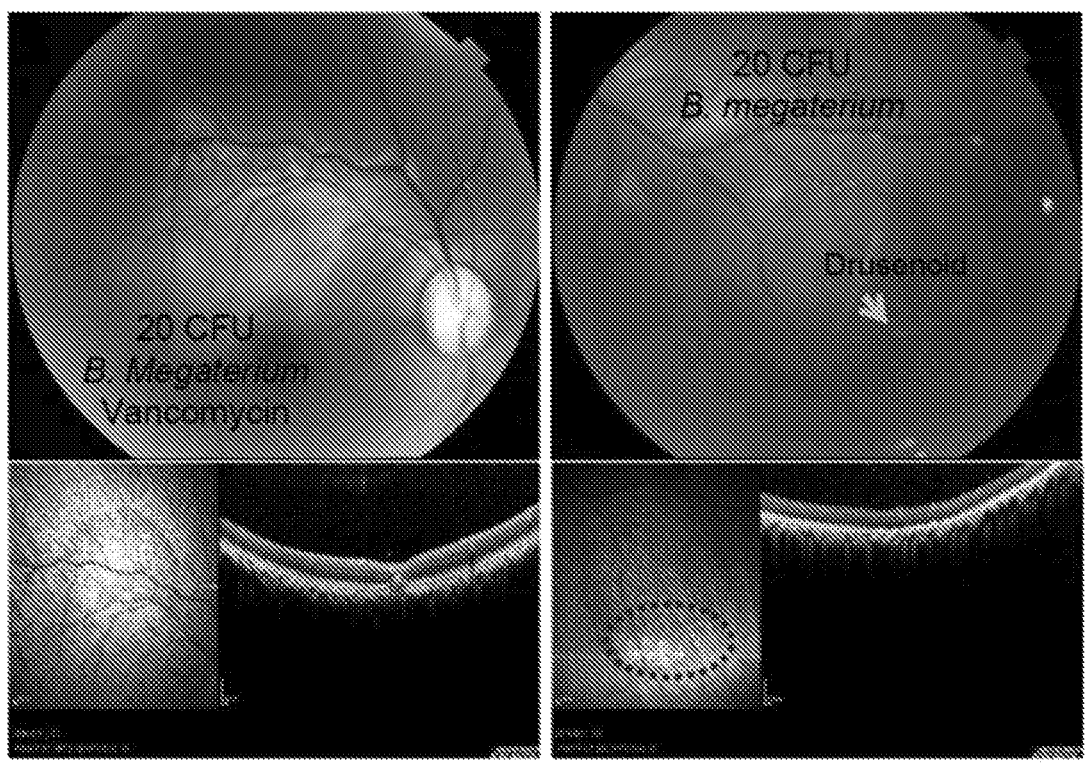

FIG. 8 illustrates that an antibiotic treatment is able to change the bacteria-induced drusenoid pathology in monkey retinal tissues.

FIG. 9 illustrates species highly enriched in intraocular metagenomes in patients with cataract, AMD, glaucoma, BD, VKH, identified using LefSe.

Figure 10:
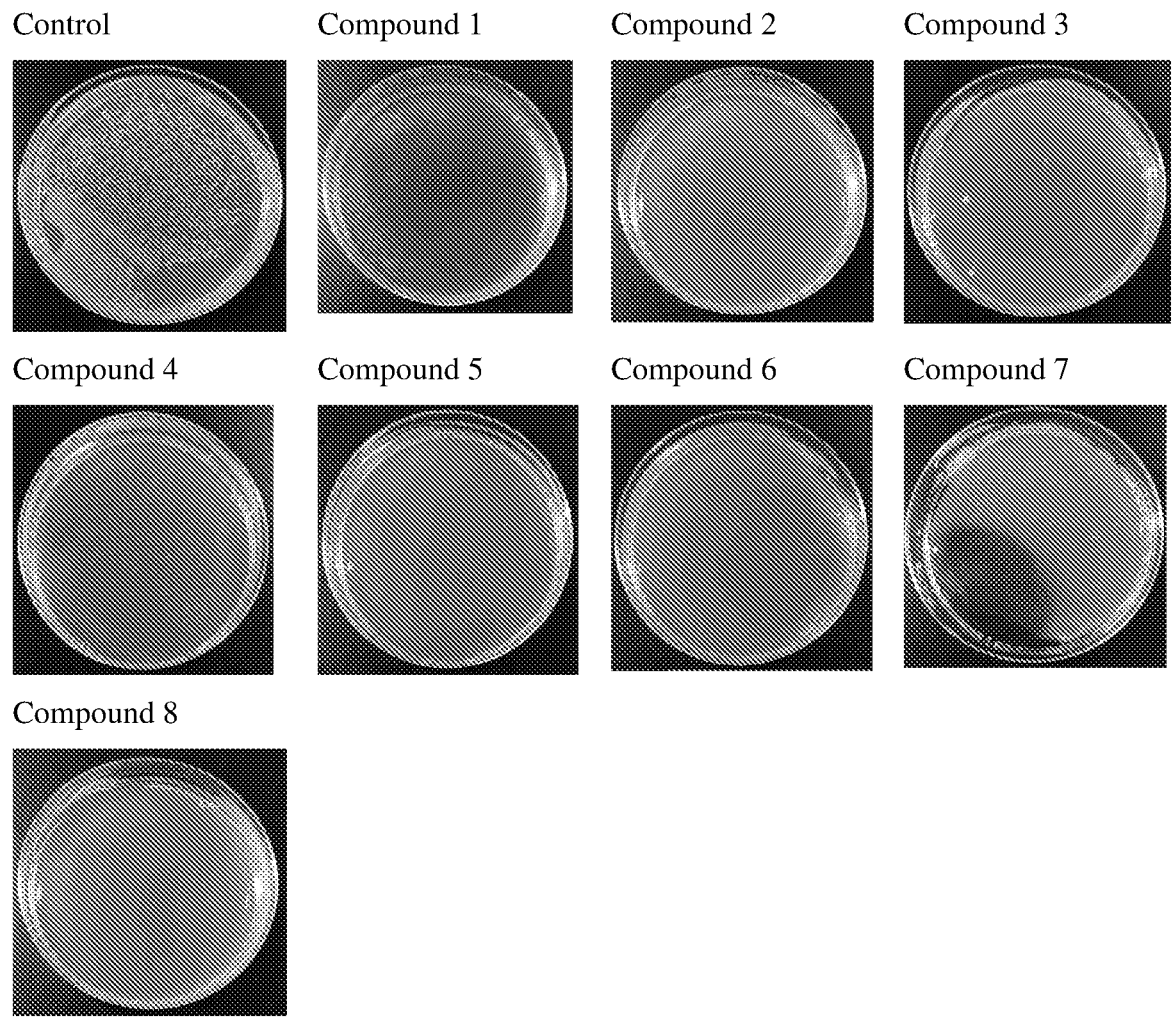

FIG. 10 shows that each of compounds 1-8 is effective in controlling growth of *Bacillus megaterium*. Testing condition: 1 mg compound, *B. megaterium*, at $1\times10^5/100$ ul in 15 ml medium.

DETAILED DESCRIPTION OF THE INVENTION

In various embodiments, the present disclosure is based in part on the unexpected discovery that the intraocular environment is not sterile and certain intraocular microbiota can be pathogenic causes of various eye diseases, such as AMD. From this initial discovery, which is detailed in PCT Application No. PCT/CN2018/112022, filed Oct. 26, 2018, entitled METHODS AND COMPOSITIONS FOR ASSESSING AND TREATING INTRAOCULAR DISEASES AND DISORDERS, the content of which is incorporated by reference in its entirety, it was also found that such microorganisms, e.g., *Bacillus megaterium* (*B. megaterium*), when administered alive, can activate complement system and induce drusenoid lesions in macaque in vivo. Further, killing or inhibiting the growth of such microorganisms, such as by intravitreous administration of an antibiotic, vancomycin, can result in a reduction in the size of drusenoid lesion in retinal tissue of macaque as compared to control. See also Example 9 herein. These data and results establish that agents capable of killing or inhibiting the growth of such microorganisms, such as *Bacillus megaterium*, are useful in treating age-related macular degeneration.

As detailed in PCT Application No. PCT/CN2018/112022, metagenomic sequencing analysis were carried out on aqueous humor (AH) specimens from 41 cataract (Cat), 20 AMD, 18 glaucoma (GLA), 9 Betch's disease (BD), 9 Vogt-Koyanagi-Harada Syndrome (VKH), and 8 endophthalmitis (EOS) patients. Interestingly, the alpha diversity and evenness of the intraocular microbial communities were significantly different among these 6 types of patients, despite all patients having bacteria as the major component of their intraocular microbiome. The principal component analysis (PCA) on the composition of the intraocular microbiota (using all microbial species) showed clear differences among cataract, EOS, and some glaucoma patients. However, AMD, VKH, BD, and some glaucoma patients shared indistinguishable features in their intraocular microbiome. Similarly, hierarchical clustering analysis of the abundance of functional microbial genes from all metagenomes indicated that each ocular manifestation had a general signature of microbial function, while there were outliers in every disease group that could be classified to other disease clusters. In spite of the significant individuality presented by the intraocular microbiome, we were able to identify the signature bacterial species for each ocular disease group we tested. Taken together, our results suggest that the composition and function of intraocular microbiota can differentiate ocular diseases such as AMD, cataract, glaucoma, BD, VKH, and EOS.

14 bacterial species were identified as highly enriched in the AH of AMD patients using metagenomic analysis. While *P. acnes* was the most abundant microorganism in the AH of AMD patients, *Bacillus licheniformis* (*B. licheniformis*) and *Bacillus megaterium* (*B. megaterium*) were the most enriched species, among the 14 AMD-specific ones, in AMD AH specimens. The present inventors then carried out PCR analysis to investigate whether the 14 AMD-specific bacteria could be detected in the hard or soft drusen tissues, as compared to the non-drusen retinal tissues from 6 archived ocular slides of AMD patients. The results showed only 8 bacteria could be detected, among which *P. acnes* was the most abundant species and *B. megaterium* was the species enriched in soft drusen. The relative abundance of *P. acnes* was comparable in hard drusen, soft drusen, and dry AMD lesion tissues as compared to the non-drusen non-lesion retinal tissues. The relative abundance of *B. megaterium* was elevated by ~18 fold in soft drusen but not the AMD lesions when compared to the non-drusen/non-lesion tissues. These data suggest a possible role of *B. megaterium* in drusen formation and AMD pathogenesis.

Previous studies demonstrate that drusen contains a variety of complement components and polysaccharides in addition to many other proteins. In addition, the drusen components activate inflammasomes and promote expression of IL-1β and IL-18. The present inventors therefore first examined whether *B. megaterium*, as a component of drusen, was able to induce the activation of complement system and promote the secretion of IL-1β and IL-18, by acute retinal pigment epitheliitis-19 (ARPE19) cells in vitro. The present inventors found *B. megaterium* but not *P. acnes* significantly increased the pyroptosis of RPE cells in a time dependent manner. The activation of complement system was confirmed by the production of active form of C5A protein. Both bacteria induced secretion of CFH proteins secreted by ARPE19 cell, while the induction of CFH was more profound by *B. megaterium* than by *P. acnes*. As the result of pyroptosis, in vitro infection of *B. megaterium*, but not *P. acnes*, led to secretion of active IL-1β and IL-18 by RPE cells. These results indicate that infection of *B. megaterium* can lead to inflammation similarly found in soft drusen.

The present inventors next tested whether *B. megaterium* was able to induce inflammation in vivo. The non-human primate macaque (*Macaca fascicularis*) as a model system considering the ocular anatomy and intraocular environment shared by human and macaque. Infection of live *P. acnes* bacterium or inoculation of its sonication-inactivated proteins into the eye did not induce significant intraocular inflammation. However, infection of live *B. megaterium* but not its proteins into the eye led to a profound intraocular inflammation. The intraocular inflammation induced by live *B. megaterium* was characterized by the elevation of TNFA and IL6 but not IFNG and IL17A expression. Importantly, only live *B. megaterium* was able to activate complement system including C5A and CFH and induce pyroptotic cytokines IL-1β and IL-18 in vivo. The bacteria remained alive in the eyes after inflammation was initiated, suggesting the intraocular inflammation can be long lasting in nature. Taken together, our data demonstrate that infection of *B. megaterium* can activate complement system and induce pyroptosis of ocular cells in vitro and in vivo.

Without wishing to be bound by theories, the fact that bacteria such as *B. megaterium* located in drusen and activated local complement-mediated immune response can explain the formation of diversified drusen between RPE and Bruch's membrane. The major proteins found in drusen including complement components such as C1Q and immunoglobulin are all first line of anti-infectious agents. Other drusen proteins such as vitronectin and Apolipoprotein E are all recently proved as anti-infectious agents. Therefore, the formation of drusen is very possible the key response of the aging retina in controlling infiltrated bacterial pathogens. Due to the diversity of bacteria, the shape and size of drusen could vary. In the case of hard drusen, where the infection may be cleared, drusen will disappear. However, certain pathogens such as *B. megaterium* will induce long term activation of immune responses in soft drusen and result in the damage of RPE cells and photoreceptors. Activation of the inflammation of macrophage and pyroptosis of RPE cells are protective responses against local infection, which is consistent with the previous finding that NLRP3 mediated inflammasome activation and IL-18 production protect the retina from neovascularization.

Without wishing to be bound by theories, the infectious etiology of AMD is also consistent with the conclusions reached by all genetic studies. For example, a defective CFH, the negative regulator of complement activation induced by *B. megaterium* infection, will result in uncontrolled complement activation. A defective HTRA1, the protease producing the active form of immunosuppressive cytokine TGF-β, will result in decrease of local TGF-β family proteins. Both of these genetic variations can lead to dysregulation of local anti-infectious responses that damages RPE cells and photoreceptors.

In addition, the potential difference in pathogenic microbiota found in drusen may explain the association of varied genetic risk factors with different ethnic groups (e.g. Caucasian vs Asian). Therefore, evidence shows that the infectious etiology of AMD is one mechanism by which early AMD pathology is initiated in the elderly.

In summary, in various embodiments, the present inventors show that killing and/or inhibiting growth of microorganisms can treat and/or prevent AMD, such as dry or wet age-related macular degeneration with drusen symptoms, including a hard drusen, a soft drusen, a mixed drusen and/or a degraded drusen, for example, dry or wet age-related macular degeneration with soft drusen symptoms.

Screening Methods

The discovery that various intraocular diseases are associated with specific microorganisms also supports screening methods for identifying candidate therapeutics for the intraocular diseases, such as AMD. Accordingly, some embodiments of the present invention are directed to various screening methods. The screening methods herein can be an in vitro method (e.g., in a petri dish) or an in vivo method (e.g., using an animal model described herein).

In some embodiments, the present invention provides a screening method, which comprises a) culturing a microorganism in a suitable culture medium in the presence of a test compound; b) measuring the growth of the microorganism in the culture medium in the presence of the test compound, and optionally c) identifying a candidate therapeutics that inhibits the growth of the microorganism compared to a control. Typically, the microorganism comprises at least one species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having an eye disease compared to a healthy subject, and the eye disease is selected from age-related macular degeneration (AMD), Behcet's disease (BD), cataract (Cat), endophthalmitis (EOS), glaucoma (GLA), Vogt-Koyanagi-Harada Syndrome (VKH), and combinations thereof. In some embodiments, the method further comprises d) determining or having determined one or more microbial species as enriched in the intraocular space in a subject having an eye disease compared to a healthy subject, wherein the eye disease is selected from age-related macular degeneration (AMD), Behcet's disease (BD), cataract (Cat), endophthalmitis (EOS), glaucoma (GLA), Vogt-Koyanagi-Harada Syndrome (VKH), and combinations thereof. The healthy subject for comparison purposes in the method refers to a subject that does not have the eye disease. The term "control" referenced in the method refers to placebo control where the test compound is not used. Those skilled in the art would know how to conduct proper control experiment for comparison purposes. In any of the embodiments described herein, to the extent not directly contradictory, the subject can be a human subject. In any of the embodiments described herein, to the extent not directly contradictory, the screening method can be for identifying a candidate therapeutics for treating or preventing a human disease, e.g., a human eye disease described herein.

In some embodiments, the present invention provides a method for screening a compound or combination of compounds for efficacy in treating or preventing an ocular disease, comprising: obtaining a sample taken from aqueous humor or vitreous humor of a subject selected from a subject having the ocular disease, a family member or close genetic relation of a subject having the ocular disease, or a deceased subject known to have had the ocular disease; culturing one or more organisms in the sample under conditions selected from conditions that mimic human intraocular space or in cooked meat medium to produce one or more cultures; adding the compound or combination of compounds to the one or more cultures; and determining whether the compound or combination of compounds reduces growth or reduces population of the one or more cultures. In some embodiments, the method can further comprise identifying, based on the determining, a compound or combination of compounds that reduces growth or reduces population of the one or more cultures in vitro.

In some embodiments, a family member can include a member of a subject's immediate family, such as a parent, child, or sibling. In some embodiments, a family member can include a person occupying the same living space as a subject having the ocular disease for an extended period of time. In some embodiments, a close genetic relation can include a relation to a subject having the disease such that the relation is within 3 lineal generations of genetic relations of the subject, such as a great-grandparent, a grandparent, a parent, a child, a grandchild, or a great-grandchild of the subject. In some embodiments, a close genetic relation can include a sibling of a subject. In some embodiments, a close genetic relation can include a relation to a subject having the disease such that the relation is a collateral relation, including an aunt or uncle, a first cousin, or a niece or nephew of the subject.

In some embodiments, the present invention provides a method for screening a compound or combination of compounds for efficacy in treating or preventing an ocular disease, comprising: culturing one or more organisms under conditions selected from conditions that mimic human intraocular space or in cooked meat medium to produce one or more cultures, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentants, Serratia marcescens, Escherichia coli, Micrococcus luteus, Bacillus subtilis, Corynebacterium aurimucosum, Finegoldia magna*, and combinations thereof; adding the compound or combination of compounds to the one or more cultures; and determining whether the compound or combination of compounds reduces growth or reduces population of the one or more cultures. In some embodiments, the method can further comprise identifying, based on the determining, a compound or combination of compounds that reduces growth or reduces population of the one or more cultures in vitro.

In some embodiments, the present invention provides a method for screening a compound or combination of compounds for efficacy in treating or preventing an ocular disease, comprising: obtaining a sample taken from aqueous humor or vitreous humor of a subject selected from a subject having the ocular disease, a family member or close genetic relation of a subject having the ocular disease, or a deceased subject known to have had the ocular disease; culturing one or more organisms in the sample under conditions selected from conditions that mimic human intraocular space or in cooked meat medium to produce one or more cultures; obtaining a solution of one or more inactivated proteins derived from the one or more cultures; mixing the compound or combination of compounds with the solution of one or more inactivated proteins; and determining whether the compound or combination of compounds bind to the one or more inactivated proteins.

In some embodiments, the present invention provides a method for screening a compound or combination of compounds for efficacy in treating an ocular disease, comprising: obtaining a sample taken from aqueous humor or vitreous humor of a subject selected from a subject having the ocular disease, a family member or close genetic relation of a subject having the ocular disease, or a deceased subject known to have had the ocular disease; culturing one or more organisms in the sample under conditions selected from conditions that mimic human intraocular space or in cooked meat medium to produce one or more cultures; obtaining a solution of one or more inactivated proteins derived from the one or more cultures; introducing the one or more inactivated proteins into a model for mammalian inflammation; introducing the compound or combination of compounds in the model for mammalian inflammation; and determining whether the compound or combination of compounds reduces inflammatory activity in the model.

In some embodiments, the present invention provides a method for screening a compound or combination of compounds for efficacy in treating or preventing an ocular disease, comprising: culturing one or more organisms under conditions selected from conditions that mimic human intraocular space or in cooked meat medium to produce one or more cultures, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentants, Serratia marcescens, Escherichia coli, Micrococcus luteus, Bacillus subtilis, Corynebacterium aurimucosum, Finegoldia magna*, and combinations thereof; obtaining a solution of one or more inactivated proteins derived from the one or more cultures; mixing the compound or combination of compounds with the solution of one or more inactivated proteins; and determining whether the compound or combination of compounds bind to the one or more inactivated proteins. In some embodiments, the method can further comprise identifying, based on the determining, a compound or combination of compounds that binds the one or more inactivated proteins in vitro.

In some embodiments, the present invention provides a method for screening a compound or combination of compounds for efficacy in treating or preventing an ocular disease, comprising: culturing one or more organisms under conditions selected from conditions that mimic human intraocular space or in cooked meat medium to produce one or more cultures wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentants, Serratia marcescens, Escherichia coli, Micrococcus luteus, Bacillus subtilis, Corynebacterium aurimucosum, Finegoldia magna*, and combinations thereof; obtaining a solution of one or more inactivated proteins derived from the one or more cultures; introducing the one or more inactivated proteins into a model for mammalian inflammation; introducing the compound or combination of compounds in the model for mammalian inflammation; and determining whether the compound or combination of compounds reduces inflammatory activity in the model. In some embodiments, the method can further comprise identifying, based on the determining, a compound or combination of compounds that reduces growth or reduces population of the one or more cultures in vitro. In some embodiments, the compound or combination of compounds can be one or more anti-inflammatory compounds.

In some embodiments, the present invention provides a method for screening a compound or combination of compounds for efficacy in treating or preventing an ocular disease, comprising: administering the compound or combination of compounds to a mammalian model described herein; and determining whether the compound or combination of compounds is effective to reduce or prevent one or more symptoms of the ocular disease. In some embodiments, administering the compound or combination of compounds occurs after the formation of drusenoid lesions in the mammalian model. In some embodiments, the compound or combination of compounds is one or more compounds or combination of compounds identified according to an in vitro screening method described herein. In some embodiments, injecting can comprise intraocular injection. In some embodiments, the one or more symptoms are selected from the group consisting of formation of drusenoid lesions, microbial growth or load, inflammatory molecule or marker production, and combinations thereof.

The microorganism used in the methods can be a substantially biologically pure species or a plurality of different biological species. In some embodiments, the microorganism comprises at least one species that is a pathogenic cause of the eye disease. In some embodiments, the microorganism comprises at least one species, wherein killing or inhibiting growth of the at least one species is beneficial for treating or preventing the eye disease. Culturing microorganism and selection of culture medium can use any technique known in the art, some exemplary details are shown in the Examples section. In some embodiments, the microorganism can be cultured in liquid cooked meat medium. Methods of measuring or determining growth of a microorganism are also not particularly limited and are generally known in the art, some exemplary methods are described herein in the Examples section. For the avoidance of doubt, measuring or determining growth of a microorganism herein does not require a quantitative measurement. In some embodiments, visual observation can be sufficient, for example, when the test compound prevents visible growth of the microorganism at or below the maximum tested concentration and/or the test compound prevents visible colony formation of the microorganism at or below the maximum tested concentration.

The candidate therapeutics can be identified via any suitable techniques known in the art. In some embodiments, when the test compound inhibits the growth of the microorganism compared to a control at or below its maximum tested concentration, it can be identified as a candidate therapeutics, e.g., for treating or preventing the respective eye disease(s). In some embodiments, when the test compound prevents visible growth of the microorganism at or below the maximum tested concentration, it can be identified as a candidate therapeutics. In some embodiments, when the test compound prevents visible colony formation of the microorganism at or below the maximum tested concentration, it can be identified as a candidate therapeutics.

The test compounds can be tested at a single concentration or tested at various concentrations. In some embodiments, a minimum inhibitory concentration (MIC) can also be established for a respective test compound, which allows comparisons among different test compounds and assists further identification/selection of candidate therapeutics.

Screening Method for AMD

In some specific embodiments, the screening method can be used for identifying a candidate therapeutics for treating or preventing AMD. In any of the embodiments described herein, unless obviously contradictory from context, the AMD can be dry or wet age-related macular degeneration with drusen symptoms, including a hard drusen, a soft drusen, a mixed drusen and/or a degraded drusen, for example, dry or wet age-related macular degeneration with soft drusen symptoms. In some embodiments, the method comprises a) culturing a microorganism in a suitable culture medium in the presence of a test compound; and b) measuring the growth of the microorganism in the culture medium in the presence of the test compound. Typically, the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having AMD compared to a healthy subject. For example, in some embodiments, the microorganism comprises a species that is enriched in the aqueous humor, vitreous humor, and/or soft drusen in a subject having AMD compared to a healthy control. In some embodiments, the microorganism can include one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*. In some embodiments, the microorganism can include *Bacillus megaterium* and/or *Pseudomonas putida*. In some embodiments, the microorganism at least includes *Bacillus megaterium*. In some embodiments, the microorganism can also be a substantially biologically pure population of *Bacillus megaterium*.

Different initial concentrations of the microorganism can be used for the screening methods herein. For example, in some embodiments, for the screening methods herein, about 10 uL (microliter) to about 500 uL (such as about 100 uL) of a suspension of *Bacillus megaterium* at a concentration of about $1*10^5$ to $1*10^9$ (such as about $1*10^6$, about $1*10^8$ or about $1*10^8$) per mL can be placed into a culture dish with about 10-15 mL of culture medium, which can be incubated under suitable temperature and conditions, for example, at 37° C. for 24 hours. For example, in some embodiments, for the screening methods herein, about $1*10^5$ to $1*10^9$ (e.g., about $1*10^5$ or $1*10^7$) *Bacillus megaterium* per culture can be used.

In some embodiments, the microorganism can comprise a mixture of microbial species substantially similar to those observed from an aqueous humor, vitreous humor, and/or soft drusen of a subject having age-related macular degeneration. For example, in some embodiments, the pathogenic species that are identified in the aqueous humor, vitreous humor, and/or soft drusen of a subject having AMD can be included in the microorganism for the screening methods. The term "substantially similar" does not require that the microorganism has the same composition of microbial species as those found in the aqueous humor, vitreous humor, and/or soft drusen of a subject having AMD. It is sufficient that the microorganism includes a majority of the identified enriched (preferably pathogenic) microbial species in the aqueous humor, vitreous humor, and/or soft drusen of a subject having AMD, e.g., as described herein. The term "substantially similar" used in connection with other eye diseases should be understood similarly. In some embodiments, the microorganism can be derived, in part or in whole, from an aqueous humor and/or vitreous humor of a subject having age-related macular degeneration. For example, in some embodiments, the microorganism can be obtained from culturing a sample obtained from an aqueous humor and/or vitreous humor of a subject having age-related macular degeneration. In some embodiments, when the test compound inhibits the growth of the microorganism (e.g., *Bacillus megaterium*) compared to a control, it can be identified as a candidate therapeutics for treating or preventing AMD.

In some embodiments, the screening methods for identifying a candidate therapeutics for treating or preventing AMD can also include a) determining or having determined one or more microbial species as enriched in the intraocular space in a subject having age-related macular degeneration (AMD) compared to a healthy subject; b) culturing a microorganism comprising at least one of the enriched microbial species in a suitable culture medium in the presence of a test compound; c) measuring the growth of the microorganism in the culture medium in the presence of the test compound; and optionally d) identifying a candidate therapeutics that inhibits the growth of the microorganism compared to a control.

In some embodiments, the determining can be obtaining information that one or more microbial species is enriched in the intraocular space of a subject having AMD compared to a healthy subject. In some embodiments, the determining can be assessing the presence, absence and/or quantity of a microorganism in a sample from the intraocular space of a subject having AMD and optionally comparing the presence, absence and/or quantity of the microorganism with that of a healthy control. Methods for assessing the presence, absence and/or quantity of a microorganism include those described in PCT Application No. PCT/CN2018/112022. In some embodiments, the microorganism can comprise a mixture of microbial species substantially similar to those observed from an aqueous humor, vitreous humor, and/or soft drusen of a subject having age-related macular degeneration. In some embodiments, the microorganism can be derived, in part or in whole, from an aqueous humor and/or vitreous humor of a subject having age-related macular degeneration. For example, in some embodiments, the microorganism can be obtained from culturing a sample obtained from an aqueous humor and/or vitreous humor of a subject having age-related macular degeneration. In some embodiments, when the test compound inhibits the growth of the microorganism compared to a control, it can be identified as a candidate therapeutics for treating or preventing AMD.

In some embodiments, the screening methods for identifying a candidate therapeutics for treating or preventing AMD can also comprise a) obtaining a sample from the intraocular space of a subject having AMD, such as the aqueous humor, vitreous humor, and/or soft drusen; b) incubating the sample in a culture medium in the presence of a test compound; c) measuring the growth of microorganism in the culture medium in the presence of the test compound; and optionally d) identifying a candidate therapeutics that inhibits the growth of the microorganism compared to a control. In some embodiments, the sample is obtained from the aqueous humor of the subject having AMD. In some embodiments, the sample is obtained from the vitreous humor of the subject having AMD. In some embodiments, the sample is obtained from the soft drusen of the subject having AMD. As shown in the Examples section herein, incubating the sample typically can be carried out in a sterile culture medium in a sterile environment, such as a sealed environment, so as not to introduce a microbial species not originally present in the sample from the subject. In some embodiments, a negative control can be used. In some embodiments, when the test compound inhibits the growth of microorganism in the culture medium compared to a control, it can be identified as a candidate therapeutics for treating or preventing AMD.

In some embodiments, the present invention provides a method for screening a compound or combination of compounds for efficacy in treating or preventing AMD, comprising: obtaining a sample taken from aqueous humor or vitreous humor of a subject selected from a subject having AMD, a family member or close genetic relation of a subject having AMD, or a deceased subject known to have had AMD; culturing one or more organisms in the sample under conditions selected from conditions that mimic human intraocular space or in cooked meat medium to produce one or more cultures; adding the compound or combination of compounds to the one or more cultures; and determining whether the compound or combination of compounds reduces growth or reduces population of the one or more cultures. In some embodiments, the method can further comprise identifying, based on the determining, a compound or combination of compounds that reduces growth or reduces population of the one or more cultures in vitro.

In some embodiments, the present invention provides a method for screening a compound or combination of compounds for efficacy in treating an ocular disease, comprising: culturing one or more organisms under conditions selected from conditions that mimic human intraocular space or in cooked meat medium to produce one or more cultures, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Escherichia coli, Micrococcus luteus, Bacillus subtilis, Corynebacterium aurimucosum, Finegoldia magna*, and combinations thereof; adding the compound or combination of compounds to the one or more cultures; and determining whether the compound or combination of compounds reduces growth or reduces population of the one or more cultures. In some embodiments, the method can further comprise identifying, based on the determining, a compound or combination of compounds that reduces growth or reduces population of the one or more cultures in vitro.

In some embodiments, the present invention provides a method for screening a compound or combination of compounds for efficacy in treating or preventing AMD, comprising: obtaining a sample taken from aqueous humor or vitreous humor of a subject selected from a subject having AMD, a family member or close genetic relation of a subject having AMD, or a deceased subject known to have had AMD; culturing one or more organisms in the sample under conditions that mimic human intraocular space or in cooked meat medium to produce one or more cultures; obtaining a solution of one or more inactivated proteins derived from the one or more cultures; mixing the compound or combination of compounds with the solution of one or more inactivated proteins; and determining whether the compound or combination of compounds bind to the one or more inactivated proteins.

In some embodiments, the present invention provides a method for screening a compound or combination of compounds for efficacy in treating or preventing AMD, comprising: obtaining a sample taken from aqueous humor or vitreous humor of a subject selected from a subject having AMD, a family member or close genetic relation of a subject having AMD, or a deceased subject known to have had AMD; culturing one or more organisms in the sample under conditions selected from conditions that mimic human intraocular space or in cooked meat medium to produce one or more cultures; obtaining a solution of one or more inactivated proteins derived from the one or more cultures; introducing the one or more inactivated proteins into a model for mammalian inflammation; introducing the compound or combination of compounds in the model for mammalian inflammation; and determining whether the compound or combination of compounds reduces inflammatory activity in the model.

In some embodiments, the present invention provides a method for screening a compound or combination of compounds for efficacy in treating or preventing an ocular disease, comprising: culturing one or more organisms under conditions selected from conditions that mimic human intraocular space or in cooked meat medium to produce one or more cultures, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D)*, Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Escherichia coli, Micrococcus luteus, Bacillus subtilis, Corynebacterium aurimucosum, Finegoldia magna*, and combinations thereof; obtaining a solution of one or more inactivated proteins derived from the one or more cultures; mixing the compound or combination of compounds with the solution of one or more inactivated proteins; and determining whether the compound or combination of compounds bind to the one or more inactivated proteins. In some embodiments, the method can further comprise identifying, based on the determining, a compound or combination of compounds that binds the one or more inactivated proteins in vitro.

In some embodiments, the present invention provides a method for screening a compound or combination of compounds for efficacy in treating an ocular disease, comprising: culturing one or more organisms under conditions selected from conditions that mimic human intraocular space or in cooked meat medium to produce one or more cultures wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D)*, Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Escherichia coli, Micrococcus luteus, Bacillus subtilis, Corynebacterium aurimucosum, Finegoldia magna*, and combinations thereof; obtaining a solution of one or more inactivated proteins derived from the one or more cultures; introducing the one or more inactivated proteins into a model for mammalian inflammation; introducing the compound or combination of compounds in the model for mammalian inflammation; and determining whether the compound or combination of compounds reduces inflammatory activity in the model. In some embodiments, the method can further comprise identifying, based on the determining, a compound or combination of compounds that reduces growth or reduces population of the one or more cultures in vitro. In some embodiments, the compound or combination of compounds can be one or more anti-inflammatory compounds.

In some embodiments, the present invention provides a method for screening a compound or combination of compounds for efficacy in treating an ocular disease, comprising: administering the compound or combination of compounds to a mammalian model described herein; and determining whether the compound or combination of compounds is effective to reduce or prevent one or more symptoms of AMD. In some embodiments, administering the compound or combination of compounds occurs after the formation of drusenoid lesions in the mammalian model. In some embodiments, the compound or combination of compounds is one or more compounds or combination of compounds identified according to an in vitro screening method described herein. In some embodiments, the administering can comprise intraocular injection. In some embodiments, the one or more symptoms are selected from the group consisting of formation of drusenoid lesions, microbial growth or load, inflammatory molecule or marker production, and combinations thereof.

Screening Method for Other Diseases

In some embodiments, the screening method can be used for identifying a candidate therapeutics for treating or preventing BD. In some embodiments, the method comprises a) culturing a microorganism in a suitable culture medium in the presence of a test compound; and b) measuring the growth of the microorganism in the culture medium in the presence of the test compound, wherein the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having BD compared to a healthy subject. For example, in some embodiments, the microorganism comprises a species that is enriched in the aqueous humor and/or vitreous humor in a subject having BD compared to a healthy control. In some embodiments, the microorganism can include one or more species selected from *Sphingomonas wittichii, Klebsiella pneumoniae, Pseudomonas fluorescens, Ralstonia pickettii, Lactobacillus crispatus, Burkholderia multivorans, Lactobacillus delbrueckii*, and *Meiothermus silvanus*(D). In some embodiments, the microorganism can comprise a mixture of microbial species substantially similar to those observed from an aqueous humor and/or vitreous humor of a subject having BD. In some embodiments, the microorganism can be derived, in part or in whole, from an aqueous humor and/or vitreous humor of a subject having BD. For example, in some embodiments, the microorganism can be obtained from culturing a sample obtained from an aqueous humor and/or vitreous humor of a subject having BD. In some embodiments, when the test compound inhibits the growth of the microorganism compared to a control, it can be identified as a candidate therapeutics for treating or preventing BD.

In some embodiments, the screening methods for identifying a candidate therapeutics for treating or preventing BD can also include a) determining or having determined one or more microbial species as enriched in the intraocular space in a subject having BD compared to a healthy subject; b) culturing a microorganism comprising at least one of the enriched microbial species in a suitable culture medium in the presence of a test compound; c) measuring the growth of the microorganism in the culture medium in the presence of the test compound; and optionally d) identifying a candidate therapeutics that inhibits the growth of the microorganism compared to a control. In some embodiments, the determining can be obtaining information that one or more microbial species is enriched in the intraocular space of a subject having BD compared to a healthy subject. In some embodiments, the determining can be assessing the presence, absence and/or quantity of a microorganism in a sample from the intraocular space of a subject having BD and optionally comparing the presence, absence and/or quantity of the microorganism with that of a healthy control. Methods for assessing the presence, absence and/or quantity of a microorganism include those described in PCT Application No. PCT/CN2018/112022. In some embodiments, the microorganism can comprise a mixture of microbial species substantially similar to those observed from an aqueous humor and/or vitreous humor of a subject having BD. In some embodiments, the microorganism can be derived, in part or in whole, from an aqueous humor and/or vitreous humor of a subject having BD. For example, in some embodiments, the microorganism can be obtained from culturing a sample obtained from an aqueous humor and/or vitreous humor of a subject having BD. In some embodiments, when the test compound inhibits the growth of the microorganism compared to a control, it can be identified as a candidate therapeutics for treating or preventing BD.

In some embodiments, the screening methods for identifying a candidate therapeutics for treating or preventing BD can also comprise a) obtaining a sample from the intraocular space of a subject having BD, such as the aqueous humor and/or vitreous humor; b) incubating the sample in a culture medium in the presence of a test compound; c) measuring the growth of microorganism in the culture medium in the presence of the test compound; and optionally d) identifying a candidate therapeutics that inhibits the growth of the microorganism compared to a control. In some embodiments, the sample is obtained from the aqueous humor of the subject having BD. In some embodiments, the sample is obtained from the vitreous humor of the subject having BD. As shown in the Examples section herein, incubating the sample typically can be carried out in a sterile culture medium in a sterile environment, such as a sealed environment, so as not to introduce a microbial species not originally present in the sample from the subject. In some embodiments, a negative control can be used. In some embodiments, when the test compound inhibits the growth of microorganism in the culture medium compared to a control, it can be identified as a candidate therapeutics for treating or preventing BD.

In some embodiments, the screening method can be used for identifying a candidate therapeutics for treating or preventing cataract. In some embodiments, the method comprises a) culturing a microorganism in a suitable culture medium in the presence of a test compound; and b) measuring the growth of the microorganism in the culture medium in the presence of the test compound, wherein the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having cataract compared to a healthy subject. For example, in some embodiments, the microorganism comprises a species that is enriched in the aqueous humor and/or vitreous humor in a subject having cataract compared to a healthy control. In some embodiments, the microorganism can include one or more species selected from *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti*, and *Acidovorax ebreus*. In some embodiments, the microorganism can comprise a mixture of microbial species substantially similar to those observed from an aqueous humor and/or vitreous humor of a subject having cataract. In some embodiments, the microorganism can be derived, in part or in whole, from an aqueous humor and/or vitreous humor of a subject having cataract. For example, in some embodiments, the microorganism can be obtained from culturing a sample obtained from an aqueous humor and/or vitreous humor of a subject having cataract. In some embodiments, when the test compound inhibits the growth of the microorganism compared to a control, it can be identified as a candidate therapeutics for treating or preventing cataract.

In some embodiments, the screening methods for identifying a candidate therapeutics for treating or preventing cataract can also include a) determining or having determined one or more microbial species as enriched in the intraocular space in a subject having cataract compared to a healthy subject; b) culturing a microorganism comprising at least one of the enriched microbial species in a suitable culture medium in the presence of a test compound; c) measuring the growth of the microorganism in the culture medium in the presence of the test compound; and optionally d) identifying a candidate therapeutics that inhibits the growth of the microorganism compared to a control. In some embodiments, the determining can be obtaining information that one or more microbial species is enriched in the intraocular space of a subject having cataract compared to a healthy subject. In some embodiments, the determining can be assessing the presence, absence and/or quantity of a microorganism in a sample from the intraocular space of a subject having cataract and optionally comparing the presence, absence and/or quantity of the microorganism with that of a healthy control. Methods for assessing the presence, absence and/or quantity of a microorganism include those described in PCT Application No. PCT/CN2018/112022. In some embodiments, the microorganism can comprise a mixture of microbial species substantially similar to those observed from an aqueous humor and/or vitreous humor of a subject having cataract. In some embodiments, the microorganism can be derived, in part or in whole, from an aqueous humor and/or vitreous humor of a subject having cataract. For example, in some embodiments, the microorganism can be obtained from culturing a sample obtained from an aqueous humor and/or vitreous humor of a subject having cataract. In some embodiments, when the test compound inhibits the growth of the microorganism compared to a control, it can be identified as a candidate therapeutics for treating or preventing cataract.

In some embodiments, the screening methods for identifying a candidate therapeutics for treating or preventing cataract can also comprise a) obtaining a sample from the intraocular space of a subject having cataract, such as the aqueous humor and/or vitreous humor; b) incubating the sample in a culture medium in the presence of a test compound; c) measuring the growth of microorganism in the culture medium in the presence of the test compound; and optionally d) identifying a candidate therapeutics that inhibits the growth of the microorganism compared to a control. In some embodiments, the sample is obtained from the aqueous humor of the subject having cataract. In some embodiments, the sample is obtained from the vitreous humor of the subject having cataract. As shown in the Examples section herein, incubating the sample typically can be carried out in a sterile culture medium in a sterile environment, such as a sealed environment, so as not to introduce a microbial species not originally present in the sample from the subject. In some embodiments, a negative control can be used. In some embodiments, when the test compound inhibits the growth of microorganism in the culture medium compared to a control, it can be identified as a candidate therapeutics for treating or preventing cataract.

In some embodiments, the screening method can be used for identifying a candidate therapeutics for treating or preventing GLA. In some embodiments, the method comprises a) culturing a microorganism in a suitable culture medium in the presence of a test compound; and b) measuring the growth of the microorganism in the culture medium in the presence of the test compound, wherein the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having GLA compared to a healthy subject. For example, in some embodiments, the microorganism comprises a species that is enriched in the aqueous humor and/or vitreous humor in a subject having GLA compared to a healthy control. In some embodiments, the microorganism can include one or more species selected from *Acinetobacter baumannii, Acinetobacter calcoaceticus, Comamonas testosteroni, Mycobacterium kansasii, Bacillus thuringiensis, Citrobacter koseri, Dyadobacter fermentants*, and *Serratia marcescens*. In some embodiments, the microorganism can comprise a mixture of microbial species substantially similar to those observed from an aqueous humor and/or vitreous humor of a subject having GLA. In some embodiments, the microorganism can be derived, in part or in whole, from an aqueous humor and/or vitreous humor of a subject having GLA. For example, in some embodiments, the microorganism can be obtained from culturing a sample obtained from an aqueous humor and/or vitreous humor of a subject having GLA. In some embodiments, when the test compound inhibits the growth of the microorganism compared to a control, it can be identified as a candidate therapeutics for treating or preventing GLA.

In some embodiments, the screening methods for identifying a candidate therapeutics for treating or preventing GLA can also include a) determining or having determined one or more microbial species as enriched in the intraocular space in a subject having GLA compared to a healthy subject; b) culturing a microorganism comprising at least one of the enriched microbial species in a suitable culture medium in the presence of a test compound; c) measuring the growth of the microorganism in the culture medium in the presence of the test compound; and optionally d) identifying a candidate therapeutics that inhibits the growth of the microorganism compared to a control. In some embodiments, the determining can be obtaining information that one or more microbial species is enriched in the intraocular space of a subject having GLA compared to a healthy subject. In some embodiments, the determining can be assessing the presence, absence and/or quantity of a microorganism in a sample from the intraocular space of a subject having GLA and optionally comparing the presence, absence and/or quantity of the microorganism with that of a healthy control. Methods for assessing the presence, absence and/or quantity of a microorganism include those described in PCT Application No. PCT/CN2018/112022. In some embodiments, the microorganism can comprise a mixture of microbial species substantially similar to those observed from an aqueous humor and/or vitreous humor of a subject having GLA. In some embodiments, the microorganism can be derived, in part or in whole, from an aqueous humor and/or vitreous humor of a subject having GLA. For example, in some embodiments, the microorganism can be obtained from culturing a sample obtained from an aqueous humor and/or vitreous humor of a subject having GLA. In some embodiments, when the test compound inhibits the growth of the microorganism compared to a control, it can be identified as a candidate therapeutics for treating or preventing GLA.

In some embodiments, the screening methods for identifying a candidate therapeutics for treating or preventing GLA can also comprise a) obtaining a sample from the intraocular space of a subject having GLA, such as the aqueous humor and/or vitreous humor; b) incubating the sample in a culture medium in the presence of a test compound; c) measuring the growth of microorganism in the culture medium in the presence of the test compound; and optionally d) identifying a candidate therapeutics that inhibits the growth of the microorganism compared to a control. In some embodiments, the sample is obtained from the aqueous humor of the subject having GLA. In some embodiments, the sample is obtained from the vitreous humor of the subject having GLA. As shown in the Examples section herein, incubating the sample typically can be carried out in a sterile culture medium in a sterile environment, such as a sealed environment, so as not to introduce a microbial species not originally present in the sample from the subject. In some embodiments, a negative control can be used. In some embodiments, when the test compound inhibits the growth of microorganism in the culture medium compared to a control, it can be identified as a candidate therapeutics for treating or preventing GLA.

In some embodiments, the screening method can be used for identifying a candidate therapeutics for treating or preventing VKH. In some embodiments, the method comprises a) culturing a microorganism in a suitable culture medium in the presence of a test compound; and b) measuring the growth of the microorganism in the culture medium in the presence of the test compound, wherein the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having VKH compared to a healthy subject. For example, in some embodiments, the microorganism comprises a species that is enriched in the aqueous humor and/or vitreous humor in a subject having VKH compared to a healthy control. In some embodiments, the microorganism can include one or more species selected from *Escherichia coli, Micrococcus luteus, Bacillus subtilis, Corynebacterium aurimucosum*, and *Finegoldia magna*. In some embodiments, the microorganism can comprise a mixture of microbial species substantially similar to those observed from an aqueous humor and/or vitreous humor of a subject having VKH. In some embodiments, the microorganism can be derived, in part or in whole, from an aqueous humor and/or vitreous humor of a subject having VKH. For example, in some embodiments, the microorganism can be obtained from culturing a sample obtained from an aqueous humor and/or vitreous humor of a subject having VKH. In some embodiments, when the test compound inhibits the growth of the microorganism compared to a control, it can be identified as a candidate therapeutics for treating or preventing VKH.

In some embodiments, the screening methods for identifying a candidate therapeutics for treating or preventing VKH can also include a) determining or having determined one or more microbial species as enriched in the intraocular space in a subject having VKH compared to a healthy subject; b) culturing a microorganism comprising at least one of the enriched microbial species in a suitable culture medium in the presence of a test compound; c) measuring the growth of the microorganism in the culture medium in the presence of the test compound; and optionally d) identifying a candidate therapeutics that inhibits the growth of the microorganism compared to a control. In some embodiments, the determining can be obtaining information that one or more microbial species is enriched in the intraocular space of a subject having VKH compared to a healthy subject. In some embodiments, the determining can be assessing the presence, absence and/or quantity of a microorganism in a sample from the intraocular space of a subject having VKH and optionally comparing the presence, absence and/or quantity of the microorganism with that of a healthy control. Methods for assessing the presence, absence and/or quantity of a microorganism include those described in PCT Application No. PCT/CN2018/112022. In some embodiments, the microorganism can comprise a mixture of microbial species substantially similar to those observed from an aqueous humor and/or vitreous humor of a subject having VKH. In some embodiments, the microorganism can be derived, in part or in whole, from an aqueous humor and/or vitreous humor of a subject having VKH. For example, in some embodiments, the microorganism can be obtained from culturing a sample obtained from an aqueous humor and/or vitreous humor of a subject having VKH. In some embodiments, when the test compound inhibits the growth of the microorganism compared to a control, it can be identified as a candidate therapeutics for treating or preventing VKH.

In some embodiments, the screening methods for identifying a candidate therapeutics for treating or preventing VKH can also comprise a) obtaining a sample from the intraocular space of a subject having VKH, such as the aqueous humor and/or vitreous humor; b) incubating the sample in a culture medium in the presence of a test compound; c) measuring the growth of microorganism in the culture medium in the presence of the test compound; and optionally d) identifying a candidate therapeutics that inhibits the growth of the microorganism compared to a control. In some embodiments, the sample is obtained from the aqueous humor of the subject having VKH. In some embodiments, the sample is obtained from the vitreous humor of the subject having VKH. As shown in the Examples section herein, incubating the sample typically can be carried out in a sterile culture medium in a sterile environment, such as a sealed environment, so as not to introduce a microbial species not originally present in the sample from the subject. In some embodiments, a negative control can be used. In some embodiments, when the test compound inhibits the growth of microorganism in the culture medium compared to a control, it can be identified as a candidate therapeutics for treating or preventing VKH.

Test Compounds

The test compound for the screening methods herein (e.g., for identifying candidate therapeutics for treating or preventing AMD) are not particularly limited. For example, the test compound can be a small molecule, a biologics, including polypeptides and polynucleotides, or conjugates of a small molecule to a biologic, such as antibody drug conjugates. Other suitable categories of test compounds can also be screened with the methods herein. The test compound does not have to be a single compound. In some cases, a mixture of compounds can be used for the screening. For example, in some embodiments, an extract or a fraction thereof, such as an extract of a Traditional Chinese Medicine (TCM), can be used as a test compound for the screening.

For example, the test compound can be a small molecule drug, a chemical drug, a macromolecule drug, a biologic drug or a natural drug (traditional Chinese medicine or traditional Chinese medicine extracts). In some embodiments, the test compound can include a β-lactam antibiotic, an aminoglycoside antibiotic, a tetracycline antibiotic, a chloramphenicol antibiotic, a macrolide antibiotic, a glycopeptide antibiotic, a quinolone antibiotic, a nitroimidazole antibiotic, a rifamycin antibiotic, an echinocandins antibiotic, a polyene antibiotic, a pyrimidine antibiotic, an allylamines antibiotic, or an azoles antibiotic, or a combination thereof.

In some embodiments, the test compound can include one or more of the followings: (3-lactam antibiotics, including penicillins, cephalosporins, thienamycins, monobactams, (3-lactamase inhibitors, methoxypenicillins, etc.; Aminoglycoside antibiotics: including streptomycin, gentamicin, kanamycin, tobramycin, amikacin, neomycin, ribomycin, micronomicin, azithromycin, etc.; Tetracycline antibiotics: including tetracycline, oxytetracycline, chlortetracycline and doxycycline; chloramphenicol antibiotics: including chloramphenicol, thiamphenicol, etc.; macrolide antibiotics: including erythromycin, leucomycin, odorless erythromycin, acetylspiramycin, medimycin, josamycin, azithromycin, etc.; glycopeptide antibiotics: including vancomycin, norvancomycin, teicoplanin, etc.; quinolone antibiotics: including norfloxacin, ofloxacin, ciprofloxacin, pefloxacin, gatifloxacin; nitroimidazole antibiotics: including metronidazole, tinidazole, ornidazole, etc.; rifamycinoid antibiotics: including rifampicin; echinocandin antibiotics; polyene antibiotics; pyrimidines antibiotics; allylamine antibiotics; azole antibiotics; other antibiotics: fosfomycin, capreomycin, cycloserine, lincomycin, clindamycin, mitomycin, actinomycin D, bleomycin, doxorubicin, isoniazid, pyrazinamide, cyclosporine, etc.

In some embodiments, the test compound can include one or more of the followings: insect antibacterial peptides, for example, lepidopteran antibacterial peptide, diptera antibacterial peptide, coleoptera antibacterial peptide, odonata antibacterial peptide, hymenoptera antibacterial Peptide, silkworm antibacterial peptide, etc.; mammalian antibacterial peptides, for example, porcine antibacterial peptide, sheep antibacterial peptide, bovine antibacterial peptide, human antibacterial peptide, etc.; amphibian antibacterial peptides: xenopus, etc.; antibacterial peptides from fish, mollusks, crustaceans: pardachirus pavoninus antibacterial peptide, parasilurus asotus antibacterial peptide, mussel antibacterial peptide, shrimp antibacterial peptide, etc.; plant antibacterial peptide: Thionins, etc., bacterial antibacterial peptide: bacitracin, gramicidin, polymyxin and nisin.

In some embodiments, the test compound can include extracts or fractions thereof of one or more of the followings: Calcined ancient ink, *Salvia ciltiorrhiza, Arnebiaeuchroma, Radix isatidis, Houttuynia*, Honeysuckle, *Rhizoma coptis, Scutellaria*, Dandelion, Purslane, Hawthorn, *Isatidis Folium, Fructus Forsythiae, Herba Artemisiae Capillaris, Andrographis Paniculata Nees, Radix Bupleuri, Rhubarb, Euphorbia Humifusa, Stemonae*, Garlic, *Cortex Phellodendri, Eucommia, Cortex Fraxini, Fructus Cnidii, Galla Chinensis, viola yedoensis makino, Fructus Mume, Radix Glycyrrhizae, Pericarpium Granati, Schisandra chinensis, Spina Gleditsiae, Terminalia Chebula, Sophora flavescens, Cortex Pseudolaricis, Epimedium, Artemisia apiacea Hance*.

The screening methods hereinabove can be a low, medium or high throughput screening method, and typically can screen a plurality of test compounds. For example, in some embodiments, the screening methods can screen more than one test compound in parallel (including tests done substantially around the same time), for example, more than 10, more than 100, more than 1000 compounds can be screened in parallel. The test compounds can be tested at a single concentration or tested at various concentrations. In some embodiments, when a plurality of test compounds are screened, the plurality of test compounds comprise at least one test compound that is not a known broad spectrum antibiotic or a known antibiotic having efficacy against one or more species of the microorganism. In some embodiments, the plurality of test compounds comprise at least one test compound that is not ampicillin, vancomycin, neomycin, metronidazole, or tetracycline. In some embodiments, the test compound is not a known broad spectrum antibiotic or a known antibiotic having efficacy against one or more species of the microorganism. For example, in some embodiment, the test compound is not ampicillin, vancomycin, neomycin, metronidazole, or tetracycline.

In some embodiments, the test compound can include an anti-inflammatory compound. Suitable anti-inflammatory compounds can include those known in the art for ophthalmic use. In some embodiments, an anti-inflammatory compound can include as steroidal or non-steroidal anti-inflammatory compound, a plant extract or fraction of an extract, or combinations thereof.

Animal Models

In various embodiments, the present invention also provides an animal model for an eye disease and a method of preparing the animal model.

In some embodiments, the present invention provides a method of preparing an animal model, the method comprising introducing a microorganism and/or inactivated protein therefrom to an intraocular space of an eye of an animal. Typically, the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having an eye disease compared to a healthy subject, wherein the eye disease is selected from cataract (Cat), age-related macular degeneration (AMD), glaucoma (GLA), Behcet's disease (BD), Vogt-Koyanagi-Harada Syndrome (VKH), endophthalmitis (EOS), and combinations thereof, and the introducing induces one or more symptoms of the eye disease. In some embodiments, the method further comprises determining or having determined one or more microbial species as enriched in the intraocular space in a subject having an eye disease compared to a healthy subject, wherein the eye disease is selected from age-related macular degeneration (AMD), Behcet's disease (BD), cataract (Cat), endophthalmitis (EOS), glaucoma (GLA), Vogt-Koyanagi-Harada Syndrome (VKH), and combinations thereof.

In some embodiments, the method can introduce live microorganism to the intraocular space of an eye of an animal. In some embodiments, the method can introduce inactivated protein of the microorganism, for example, sonication-inactivated proteins from the microorganism, to the intraocular space of an eye of an animal. The subject and the animal referred to in the method herein can be the same or different. For example, in some embodiments, when the eye disease is a disease of a pet animal, the subject and the animal can be the same. In some embodiments, the eye disease can be a human disease, i.e., the subject is a human subject, and the animal is preferably a non-human mammal, more preferably, a non-human primate (e.g., monkey). In some embodiments, the animal has an ocular anatomy and/or intraocular environment similar to those of a human. Preferably, prior to the introducing of the microorganism and/or inactivated protein therefrom, the animal does not have an eye disease.

Animal Model for AMD

In some specific embodiments, the present invention provides a method of preparing an animal model for AMD. In some embodiments, the method comprises introducing a microorganism and/or inactivated protein therefrom to an intraocular space of an eye of an animal. Typically, the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having AMD compared to a healthy subject, and the introducing induces one or more symptoms of AMD. Unless otherwise obvious from context, microorganism introduced to the intraocular space of the animal should refer to live microorganism. In some embodiments, the microorganism comprises one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis,* and *Xanthomonas oryzae*. In some embodiments, the microorganism comprises *Bacillus megaterium*, and/or *Pseudomonas putida*. In some embodiments, the microorganism comprises at least *Bacillus megaterium*. In some embodiments, the microorganism is a substantially biologically pure population of *Bacillus megaterium*. In some embodiments, the microorganism comprises a mixture of microbial species substantially similar to those observed from an aqueous humor, vitreous humor, and/or soft drusen of a subject having age-related macular degeneration. In some embodiments, the microorganism is derived, in part or in whole, from an aqueous humor and/or vitreous humor of a subject having age-related macular degeneration. For example, in some embodiments, the microorganism can be obtained from culturing a sample obtained from an aqueous humor and/or vitreous humor of a subject having age-related macular degeneration. Preferably, the animal is a non-human mammal, more preferably, a non-human primate (e.g., monkey). In some embodiments, the animal has an ocular anatomy and/or intraocular environment similar to those of a human. In some embodiments, the animal is macaque such as *Macaca fascicularis*. In some embodiments, the animal is not macaque. In some embodiments, the animal is not *Macaca fascicularis*.

The microorganism and/or inactivated protein therefrom can be introduced to any suitable intraocular space of the animal. In some embodiments, the microorganism and/or inactivated protein therefrom is injected into the subretinal space of the animal. Although the microorganism and/or inactivated protein therefrom is typically injected into the eye of the animal, other delivery methods can also be suitable.

Typically, the microorganism and/or inactivated protein therefrom is introduced in an amount and concentration sufficient to induce one or more symptoms of AMD. For example, as shown in the Examples section, 20 CFU of bacterial in about 20 uL of PBS solution can induce one or more symptoms of AMD, such as drusenoid lesions. In some embodiments, microorganism and/or inactivated protein therefrom is introduced in an amount and concentration sufficient to induce 1) a drusenoid lesion, e.g., on retinal tissues, of the animal; 2) drusen-like nodules, e.g., under the retinal pigment epithelium layer in the eye of the animal; 3) pyroptosis, e.g., of the retinal pigment epithelium cells in the eye of the animal; 4) activation of the complement system and/or inflammation in the eye of the animal, e.g., with elevated expression of C5A, CFH, CASPASE1, and NLRP3 proteins; 5) secretion of active IL-1β and/or IL-18, e.g., by retinal pigment epithelium cells in the eye of the animal; or 6) any combination of 1)-5).

The animal used for the methods of preparing animal model herein preferably is a healthy animal, for example, the animal does not have an eye disease prior to the introducing of the microorganism and/or inactivated protein therefrom. Preferably, the animal is also not given any antibiotics prior to and during the introducing of the microorganism and/or inactivated protein therefrom, e.g., before the appearance of the one or more symptoms of AMD.

In some embodiments, the method of preparing an animal model for AMD can comprise introducing a sample from a subject having AMD to an intraocular space of an eye of an animal, wherein the sample is obtained from an intraocular space of the subject, and wherein the introducing induces one or more symptoms of AMD. In some embodiments, prior to the introducing to the animal, the sample is incubated in a culture medium and optionally purified and/or formulated for injection. In some embodiments, the method further comprises 1) obtaining a sample from the intraocular space of the subject, such as the aqueous humor, vitreous humor, and/or soft drusen; and 2) incubating the sample in a culture medium. In some embodiments, the sample is obtained from the aqueous humor of the subject having AMD. In some embodiments, the sample is obtained from the vitreous humor of the subject having AMD. In some embodiments, the sample is obtained from the soft drusen of the subject having AMD. As shown in the Examples section herein, incubating the sample typically can be carried out in a sterile culture medium in a sterile environment, such as a sealed environment, so as not to introduce a microbial species not originally present in the sample from the subject.

Typically, the methods of preparing animal model for AMD can provide an animal with one or more symptoms of AMD for a sustainable period of time. For example, without intervention, the animal model produced by the methods herein typically shows one or more symptoms of AMD for a period of longer than 1 week, 1 month, or during the life time of the animal. The animal models produced by the methods herein are also novel features of embodiments of the present invention.

The animal models for AMD produced herein can also be used for identifying candidate therapeutics for treating or preventing AMD. For example, in some embodiments, the present invention also provides a screening method comprising a) administering a test compound to the animal model for AMD as described herein; b) determining the severity of the one or more symptoms of the eye disease post administration; and optionally c) identifying a candidate therapeutics that relieves at least one of the symptoms compared to a control. In some embodiments, administering the test compound, when compared to a control, 1) reduces a drusenoid lesion, e.g., on retinal tissues, of the animal; 2) reduces drusen-like nodules, e.g., under the retinal pigment epithelium layer in the eye of the animal; 3) reduces pyroptosis of the retinal pigment epithelium cells in the eye of the animal; 4) reduces activation of the complement system and/or inflammation in the eye of the animal, e.g., reduces expression of C5A, CFH, CASPASE1, and NLRP3 proteins; 5) reduces secretion of active IL-1β and/or IL-18 by retinal pigment epithelium cells in the eye of the animal; or 6) any combination of 1)-5), and such test compound can be identified as a candidate therapeutics for treating or preventing AMD. In some embodiments, administering the test compound, when compared to a control, kills or inhibits growth of the microorganism in the eye (e.g., intraocular space or cavity), blood, and/or GI tract, such as intestine of the animal model, and such test compound can also be identified as a candidate therapeutics for treating or preventing AMD. In some embodiments, the relevant information of a "control" can be that observed from the animal prior to administering the test compound. In some embodiments, the relevant information of a "control" can be that observed from animals receiving a placebo treatment, e.g., administration of a placebo formulation without the test compound.

The test compound for the screening method using the animal model for AMD (as described herein) is not limited, although preferably, the test compound is prescreened (e.g., using any of the screening methods described herein) to be effective in killing or inhibiting the growth of the microorganism (e.g., *Bacillus megaterium*) enriched in the intraocular space of a subject having AMD compared to a healthy control. The test compound can also be administered via any suitable route with any tested dosing regimen with any appropriate tested dosage amount, which can be selected by those skilled in the art based on factors such as potencies of the tested compounds (if known). For example, the test compound can be administered orally, topically, intravitreously, intramuscularly, subcutaneously, or intravenously.

The screening method using the animal model for AMD (as described herein) typically is a low to medium throughput screening method. In some embodiments, a plurality of test compounds are screened, and the plurality of test compounds comprise at least one test compound that is not a known broad spectrum antibiotic or a known antibiotic having efficacy against one or more species of the microorganism. In some embodiments, the plurality of test compounds comprise at least one test compound that is not ampicillin, vancomycin, neomycin, metronidazole, or tetracycline. In some embodiments, the test compound is not a known broad spectrum antibiotic or a known antibiotic having efficacy against one or more species of the microorganism. For example, in some embodiment, the test compound is not ampicillin, vancomycin, neomycin, metronidazole, or tetracycline.

In some embodiments, the present invention provides a method for producing a mammalian model of an ocular disease, comprising: introducing one or more microorganisms and/or one or more inactivated proteins of the one or more microorganisms into an eye of a mammal, thereby generating the mammalian model. In some embodiments, the method can further comprise monitoring development and progression of one or more markers of the ocular disease. Markers of the ocular disease can include those biological and/or chemical markers known in the art for a given disease and can include, but are not limited to, symptoms of the ocular disease. In some embodiments, monitoring development and progression of one or more markers of the ocular disease can comprise monitoring ocular inflammatory response in the mammal. In some embodiments, monitoring development and progression of one or more markers of the ocular disease can comprise monitoring the formation or progression of drusenoid lesions. In some embodiments, the method can further comprise allowing sufficient time to pass after introducing the one or more microorganisms or one or more inactivated proteins of the one or more microorganisms, for the mammal to develop drusenoid lesions. In some embodiments, introducing the one or more microorganisms or one or more inactivated proteins of the one or more microorganisms can comprise intraocularly injecting the one or more microorganisms or one or more inactivated proteins of the one or more microorganisms. In some embodiments, intraocularly injecting can comprise injecting into the vitreous humor or the aqueous humor of the mammal.

Methods of Treatment

In some embodiments, the present invention also provides a method of treating or preventing AMD. In some embodiments, the method comprises administering to a subject in need thereof an effective amount of any of the candidate therapeutics identified in any of the screening methods herein directed to AMD. In some embodiments, the method comprises identifying or having identified a subject as being infected with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*, e.g., in the intraocular space, and administering to the subject an effective amount of any of the candidate therapeutics identified in any of the screening methods herein directed to AMD. In some embodiments, the method comprises identifying or having identified a subject as being infected with *Bacillus megaterium* and/or *Pseudomonas putida*, preferably at least with *Bacillus megaterium*, e.g., in the intraocular space, and administering to the subject an effective amount of any of the candidate therapeutics identified in any of the screening methods herein directed to AMD. In some embodiments, the method comprises selecting a subject infected with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*, e.g., in the intraocular space, and administering to the subject an effective amount of any of the candidate therapeutics identified in any of the screening methods herein directed to AMD. In some embodiments, the method comprises selecting a subject infected with *Bacillus megaterium* and/or *Pseudomonas putida*, preferably at least with *Bacillus megaterium*, e.g., in the intraocular space, and administering to the subject an effective amount of any of the candidate therapeutics identified in any of the screening methods herein directed to AMD. In some embodiments, the subject does not suffer from Behcet's disease (BD), cataract (Cat), endophthalmitis (EOS), glaucoma (GLA), Vogt-Koyanagi-Harada Syndrome (VKH), or any combinations thereof. In some embodiments, the subject suffers from AMD. In some embodiments, the subject is not diagnosed as having AMD. In some embodiments, the subject is at risk of developing AMD. The administering is not limited to any particular routes, for example, it can be oral, topical, intravitreous, intramuscular, subcutaneous, and/or intravenous.

In some embodiments, the method of treating or preventing AMD comprises identifying or having identified a subject as being infected with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*, e.g., in the intraocular space, and administering to the subject an effective amount of an antibiotic. Antibiotic as used herein refers broadly to a compound that has antibacterial activities, which can be naturally occurring or synthetic. Some antibiotics are exemplified herein. In some embodiments, the method comprises identifying or having identified a subject as being infected with *Bacillus megaterium* and/or *Pseudomonas putida*, preferably at least with *Bacillus megaterium*, e.g., in the intraocular space, and administering to the subject an effective amount of antibiotic. In some embodiments, the method comprises selecting a subject infected with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri,*

*Gardnerella vaginalis*, *Enterococcus faecium*, *Cytophaga hutchinsonii*, *Bacillus licheniformis*, and *Xanthomonas oryzae*, e.g., in the intraocular space, and administering to the subject an effective amount of an antibiotic. In some embodiments, the method comprises selecting a subject infected with *Bacillus megaterium* and/or *Pseudomonas putida*, preferably at least with *Bacillus megaterium*, e.g., in the intraocular space, and administering to the subject an effective amount of an antibiotic. In some embodiments, the method comprises selecting a subject infected with *Bacillus megaterium*, e.g., in the intraocular space, and administering to the subject an effective amount of an antibiotic. In some embodiments, the subject does not suffer from Behcet's disease (BD), cataract (Cat), endophthalmitis (EOS), glaucoma (GLA), Vogt-Koyanagi-Harada Syndrome (VKH), or any combinations thereof. In some embodiments, the subject suffers from AMD. In some embodiments, the subject is not diagnosed as having AMD. In some embodiments, the subject is at risk of developing AMD. The administering is not limited to any particular routes, for example, it can be oral, topical, intravitreous, intramuscular, subcutaneous, and/or intravenous. In any of the embodiments herein, the "effective amount" of antibiotic can be an amount that is effective in killing or inhibiting the growth of one or more microbial species in the eye of a treated subject, wherein the one or more microbial species is enriched in an AMD patient compared to a healthy control, for example, the one or more microbial species can be *Bacillus megaterium* and/or *Pseudomonas putida*, preferably at least with *Bacillus megaterium*.

In some embodiments, the present invention also provides a method of 1) reducing a drusenoid lesion, e.g., on retinal tissues; 2) reducing drusen-like nodules, e.g., under the retinal pigment epithelium layer in the eye; 3) reducing pyroptosis of the retinal pigment epithelium cells in the eye; 4) reducing activation of the complement system and/or inflammation in the eye, e.g., reducing expression of C5A, CFH, CASPASE1, and NLRP3 proteins; 5) reducing secretion of active IL-1β and/or IL-18 by retinal pigment epithelium cells in the eye; or 6) any combination of 1)-5), in a subject in need thereof, the method comprising administering to the subject an effective amount of any of the candidate therapeutics identified in any of the screening methods herein directed to AMD. In some embodiments, the present invention also provides a method of treating a drusen symptom (e.g., soft drusen) in a subject in need thereof, the method comprises administering to the subject an effective amount of any of the candidate therapeutics identified in any of the screening methods herein directed to AMD. The drusen symptom (e.g., soft drusen) can be induced by a microbial infection, such as by pathogenic bacteria described herein. The drusen symptom, e.g., soft drusen, can be associated with subjects having AMD.

In some embodiments, the present invention also provides a method of 1) reducing a drusenoid lesion, e.g., on retinal tissues; 2) reducing drusen-like nodules, e.g., under the retinal pigment epithelium layer in the eye; 3) reducing pyroptosis of the retinal pigment epithelium cells in the eye; 4) reducing activation of the complement system and/or inflammation in the eye, e.g., reducing expression of C5A, CFH, CASPASE1, and NLRP3 proteins; 5) reducing secretion of active IL-1β and/or IL-18 by retinal pigment epithelium cells in the eye; or 6) any combination of 1)-5), in a subject in need thereof, the method comprising administering to the subject an effective amount of an antibiotic. For example, in some embodiments, the method is for reducing a drusenoid lesion in the subject. In some embodiments, the method is for reducing drusen-like nodules in the subject. In some embodiments, the method is for reducing pyroptosis of the retinal pigment epithelium cells in the eye of the subject. In some embodiments, the method is for reducing activation of the complement system and/or inflammation in the eye of the subject. In some embodiments, the method is for reducing secretion of active IL-1 and/or IL-18 by retinal pigment epithelium cells in the eye in the subject. Without wishing to be bound by theories, it is believed that an antibiotic can kill or inhibit the growth of bacteria (e.g., a pathogenic bacterium), for example, in the intraocular space of the subject, and therefor can reduce drusen formation, drusenoid lesion, and/or drusen-like modules, such as in a subject having AMD, which is shown herein to be associated with infection with one or more pathogenic microorganism e.g., *Bacillus megaterium* and/or *Pseudomonas putida*. It is also believed that the pathogenic microorganism, e.g., those described herein such as *Bacillus megaterium* and/or *Pseudomonas putida*, can cause inflammation in the eye. Therefore, the antibiotic administered, which can kill or inhibit the growth of pathogenic microorganism, can also reduce eye inflammation in a subject, e.g., those having AMD. In some embodiments, the present invention also provides a method of treating a drusen symptom (e.g., soft drusen) in a subject in need thereof, the method comprises administering to the subject an effective amount of an antibiotic. The drusen symptom (e.g., soft drusen) can be induced by a microbial infection, such as by pathogenic bacteria described herein. The drusen symptom, e.g., soft drusen, can be associated with subjects having AMD. In some embodiments, the method reduces drusenoid lesions and/or nodules.

In some embodiments, the present invention also provides a method of 1) reducing a drusenoid lesion, e.g., on retinal tissues; 2) reducing drusen-like nodules, e.g., under the retinal pigment epithelium layer in the eye; 3) reducing pyroptosis of the retinal pigment epithelium cells in the eye; 4) reducing activation of the complement system and/or inflammation in the eye, e.g., reducing expression of C5A, CFH, CASPASE1, and NLRP3 proteins; 5) reducing secretion of active IL-1 and/or IL-18 by retinal pigment epithelium cells in the eye; or 6) any combination of 1)-5), in a subject in need thereof, the method comprising administering to the subject an effective amount of a compound of the present disclosure (e.g., a compound of Formula I (e.g., Formula I-1, Formula I-2, Formula I-3, Formula I-4, Formula I-5), Formula II (e.g., Formula II-1, Formula II-2, Formula II-3, Formula II-4, Formula II-5, Formula II-6, Formula II-7, Formula II-8, Formula II-9, Formula II-10), Formula III (e.g., Formula III-1, Formula III-2, Formula III-3), Formula IV-1 or IV-2 (e.g., Formula IV-3, Formula IV-4, Formula IV-5, Formula IV-6), a glycoside (e.g., Formula V), wherein the aglycone of the glycoside is a phenolic compound, a flavonoid, a coumarin, a benzoic acid, or a sterol, a compound selected from compounds 1-8, or a pharmaceutically acceptable salt or ester thereof, or a pharmaceutical composition comprising the compound or pharmaceutically acceptable salt or ester thereof). For example, in some embodiments, the method is for reducing a drusenoid lesion in the subject. In some embodiments, the method is for reducing drusen-like nodules in the subject. In some embodiments, the method is for reducing pyroptosis of the retinal pigment epithelium cells in the eye of the subject. In some embodiments, the method is for reducing activation of the complement system and/or inflammation in the eye of the subject. In some embodiments, the method is for reducing secretion of active IL-1 and/or IL-18 by retinal pigment epithelium cells in the eye in the subject. Without wishing to be bound by theories, it is believed that compounds of the present disclosure can kill or inhibit the growth of bacteria (e.g., a pathogenic bacterium), for example, in the intraocular space of the subject, and therefor can reduce drusen formation, drusenoid lesion, and/or drusen-like modules, such as in a subject having AMD, which is shown herein to be associated with infection with one or more pathogenic microorganism, e.g., *Bacillus megaterium* and/or *Pseudomonas putida*. It is also believed that the pathogenic microorganism, e.g., those described herein such as *Bacillus megaterium* and/or *Pseudomonas putida*, can cause inflammation in the eye. Therefore, the compound of the present disclosure administered, which can kill or inhibit the growth of pathogenic microorganism, can also reduce eye inflammation in a subject, e.g., those having AMD. In some embodiments, the present invention also provides a method of treating a drusen symptom (e.g., soft drusen) in a subject in need thereof, the method comprises administering to the subject an effective amount of a compound of the present disclosure. The drusen symptom (e.g., soft drusen) can be induced by a microbial infection, such as by pathogenic bacteria described herein. The drusen symptom, e.g., soft drusen, can be associated with subjects having AMD. In some embodiments, the method reduces drusenoid lesions and/or nodules.

The subject suitable to be treated by the methods herein are not particularly limited. In some preferred embodiments, the subject suffers from AMD. In some embodiments, the AMD can be dry or wet age-related macular degeneration with drusen symptoms, including a hard drusen, a soft drusen, a mixed drusen and/or a degraded drusen, for example, dry or wet age-related macular degeneration with soft drusen symptoms. In some embodiments, the subject does not suffer from AMD. In some embodiments, the subject is at risk of developing AMD. In some embodiments, the subject has soft drusen deposited between retinal pigment epithelium (RPE) and the Bruch's membrane. In some embodiments, the subject has retinal pigmentary changes in the macular. In some embodiments, the subject suffers from dry AMD. In some embodiments, the subject suffers from wet AMD. In some embodiments, the subject is a human subject. In some embodiments, the subject is infected in the intraocular space with one or more species enriched in the intraocular space of an AMD patient compared to a healthy subject, e.g., as described herein. In some embodiments, the subject is infected in the intraocular space with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*. In some embodiments, the subject is infected with *Bacillus megaterium* and/or *Pseudomonas putida*, preferably at least with *Bacillus megaterium* in the intraocular space. In some embodiments, the subject does not suffer from Behcet's disease (BD), cataract (Cat), endophthalmitis (EOS), glaucoma (GLA), Vogt-Koyanagi-Harada Syndrome (VKH), or any combinations thereof. In some embodiments, the method can further comprise identifying or having identified the subject as being infected in the intraocular space with one or more species enriched in the intraocular space of an AMD patient compared to a healthy subject, e.g., as described herein. In some embodiments, the method can further comprise identifying or having identified the subject as being infected in the intraocular space with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*. In some embodiments, the method can further comprise identifying or having identified the subject as being infected with *Bacillus megaterium* and/or *Pseudomonas putida*, preferably at least with *Bacillus megaterium* in the intraocular space.

The administering of the antibiotic is not limited to any particular route of administration. For example, the administering can be an oral, topical, intravitreous, intramuscular, subcutaneous, and/or intravenous administration. For example, in some embodiments, the antibiotic is administered via intravitreal injection, such as intravitreal depot injection, or intravitreal implant. In some embodiments, a combination of two or more routes of administration (e.g., oral and intravitreal routes) can be used. For example, in some embodiments, the antibiotic can be administered orally and intravitreously, either concurrently or sequentially in any order. For example, in some embodiments, the antibiotic can be administered orally and intravenously, either concurrently or sequentially in any order. Other routes of administration can also be used in combinations, for the same active ingredient or two different active ingredients. The antibiotic can be formulated as a solid, liquid, semi-solid, solution, suspension, implant, or any other suitable forms. For example, an oral antibiotic can typically be a solid or liquid form. In some embodiments, the antibiotic can be formulated as an implant. When intravitreal injection is performed, the site of injection is also not particularly limited. For example, in some embodiments, the injection can be a suprachoroid space injection. Other suitable sites are known in the art. The effective amount can vary depending on various factors such as the time of administration, the route of administration, the duration of treatment, the potency of the antibiotic (e.g., for killing or inhibiting growth of one or more microorganism that is enriched in the intraocular space compared to a healthy control), its rate of clearance and whether or not another drug is co-administered. Various antibiotics can be used for the methods herein, for example, any of those described herein, and any of those described in PCT/CN2019/070572, filed on Jan. 7, 2019, the content of which is herein incorporated by reference in its entirety.

In some embodiments, the antibiotic can be a β-lactam antibiotic, an aminoglycoside antibiotic, a tetracycline antibiotic, a chloramphenicol antibiotic, a macrolide antibiotic, a glycopeptide antibiotic, a quinolone antibiotic, a nitroimidazole antibiotic, a rifamycin antibiotic, an echinocandins antibiotic, a polyene antibiotic, a pyrimidine antibiotic, an allylamines antibiotic, or an azoles antibiotic, or a combination thereof.

In some embodiments, the antibiotics can include one or more of the following: β-lactam antibiotics, including penicillins (e.g., penicillin V), amoxicillin, ampicillin, bacampicillin, carbenicillin, cloxacillin, dicloxacillin, flucloxacillin, mezlocillin, nafcillin, oxacillin, penicillin G, piperacillin, pivampicillin, pivmecillinam, ticarcillin, cephalosporins such as cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicid, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinome, ceftobiprole, ceftaroline, cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, cefuracetime, ceftioxide, thienamycins, monobactams, β-lactamase inhibitors, methoxypenicillins, etc.; Aminoglycoside antibiotics: including streptomycin, gentamicin, kanamycin (e.g., kanamycin A), tobramycin, amikacin, neomycin (e.g., neomycin B, neomycin C, neomycin E), ribomycin, micronomicin, azithromycin, dibekacin, sisomicin, netilmicin, paramomycin, bramycin, etc.; Tetracycline antibiotics: including tetracycline, oxytetracycline, chlortetracycline and doxycycline; chloramphenicol antibiotics: including chloramphenicol, thiamphenicol, etc.; macrolide antibiotics: including erythromycin, leucomycin, odorless erythromycin, acetylspiramycin, medimycin, josamycin, azithromycin, clarithromycin, dirithromycin, oxithromycin, telithromycin, etc.; glycopeptide antibiotics: including vancomycin, norvancomycin, teicoplanin, etc.; quinolone antibiotics: including norfloxacin, ofloxacin, ciprofloxacin, pefloxacin, gatifloxacin, enoxacin, lomefloxacin, nalidixic acid, levofloxacin, moxifloxacin, besifloxacin; nitroimidazole antibiotics: including metronidazole, tinidazole, ornidazole, etc.; rifamycinoid antibiotics: including rifampicin; echinocandin antibiotics; polyene antibiotics; pyrimidines antibiotics; allylamine antibiotics; azole antibiotics; other antibiotics: fosfomycin, capreomycin, cycloserine, lincomycin, clindamycin, mitomycin, actinomycin D, bleomycin, doxorubicin, isoniazid, pyrazinamide, cyclosporine, polymyxin B combinations such as polymyxin B/trimethoprim, polymyxin B/bacitracin, polymyxin B/neomycin/gramicidin, etc.

In some embodiments, the antibiotic can be selected from Amikacin, Amoxicillin, Ampicillin, Arsphenamine, Azithromycin, Azlocillin, Aztreonam, Bacitracin, Capreomycin, Carbenicillin, Cefaclor, Cefadroxil, Cefalexin, Cefalotin, Cefamandole, Cefazolin, Cefdinir, Cefditoren, Cefixime, Cefoperazone, Cefotaxime, Cefoxitin, Cefpodoxime, Cefprozil, Ceftazidime, Ceftibuten, Ceftizoxime, Ceftriaxone, Cefuroxime, Chloramphenicol, Cilastatin, Clarithromycin, Clavulanate, Clindamycin, Clofazimine, Cloxacillin, Colistin, Cycloserine, Dalfopristin, Dapsone, Daptomycin, Dicloxacillin, Dirithromycin, Doripenem, Doxycycline, Erythromycin, Ethambutol, Ethionamide, Flucloxacillin, Fosfomycin, Furazolidone, Fusidic acid, Gentamicin, Imipenem, Isoniazid, Kanamycin, Lincomycin, Linezolid, Loracarbef, Mafenide, Meropenem, Methicillin, Metronidazole, Mezlocillin, Minocycline, Mupirocin, Nafcillin, Neomycin, Netilmicin, Nitrofurantoin, Oxacillin, Oxytetracycline, Paromomycin, Penicillin G, Penicillin V, Piperacillin, Platensimycin, Polymyxin B, Pyrazinamide, Quinupristin, Rapamycin, Rifabutin, Rifampicin, Rifampin, Rifapentine, Rifaximin, Roxithromycin, Silver sulfadiazine, Spectinomycin, Streptomycin, Sulbactam, Sulfacetamide, Sulfadiazine, Sulfamethizole, Sulfamethoxazole, Sulfanilimide, Sulfasalazine, Sulfisoxazole, Tazobactam, Teicoplanin, Telavancin, Telithromycin, Temocillin, Tetracycline, Thiamphenicol, Ticarcillin, Tigecycline, Tinidazole, Tobramycin, Trimethoprim, Troleandomycin Vancomycin, enoxacin, lomefloxacin, nalidixic acid, ciprofloxacin, levofloxacin, gatifloxacin, moxifloxacin, ofloxacin, norfloxacin, Cefotetan, Cefonicid, Cephradine, Cephapirin, Cephalothin, Cefmetazole, Cefotaxime, Moxalactam, Cefepime, Ceftaroline fosamil, Ceftobiprole, Dalbavancin, Demeclocycline, Metacycline, Ertapenem, Fidaxomicin, geldanamycin, herbimycin, Posizolid, Radezolid, Torezolid, Oritavancin, Spiramycin, Sulfadimethoxine, Sulfonamidochrysoidine, Gemifloxacin Nadifloxacin Trovafloxacin Grepafloxacin Sparfloxacin Temafloxacin, Teixobactin, Malacidins, and combinations thereof.

In some embodiments, the present invention also provides a candidate therapeutics identified in any of the screening methods herein or a pharmaceutical composition comprising the candidate therapeutics for treating or preventing AMD.

Compounds

In some embodiments, the present disclosure is directed to various compounds and/or compositions comprising the compounds that can kill or inhibit the growth of microorganisms related to AMD, such as *Bacillus megaterium*.

The compounds herein typically have antibacterial activity by themselves or in combination with another agent. The compounds herein can be bactericidal or bacteriostatic. Various compounds known to have antibacterial activities can be used for embodiments of the present invention. For example, in some embodiments, the compounds herein can include any of the alcohols, phenolic compounds, amines, sulfonamides, quinolones, anthraquinone, and/or benzoic acid related compounds that are known to have antibacterial activities. Nonlimiting examples of useful compounds include benzoid acid, benzyl alcohol, coumarins, catechols, polyphenols, chalconoids (including licochalcones), etc., stilbenes such as resveratrol, isoresveratrol, etc., phenolic acids, such as p-hydroxbenzoic acid, 2,4-dihydroxybenzoid acid, protocatechuic acid, gallic acid, vanillic acid, syringic acid, cinnamic acid, coumaric acids, caffeic acids, ferulic acids, chlorogenic acid, sinapic acids etc., flavonoids such as catechin, narigenin, quercetin, rutin, chrysin, etc., tannins, such as ellagic acid, and esters thereof and glycosides thereof.

The compounds herein are typically characterized by certain functional groups present in their molecular structures. For example, in some embodiments, the compounds herein are characterized by having alcoholic hydroxyl group, phenolic hydroxyl group, and/or carboxylic acid group, or derivatives thereof such as esters, amides, carbonates, carbamates, sulfonates, glycosides, etc. In some embodiments, compounds with an amino group, a sulfonamide group, a thiol group, and/or a sulfoxide or sulfone group can also be useful for the compositions and methods herein.

The compounds herein can have a polycyclic core structure, a bicyclic core structure, or a monocyclic core structure, each of which can be substituted with various groups as described herein.

In some embodiments, the compounds herein can be characterized by having a Formula I, or a pharmaceutically acceptable salt or ester thereof:

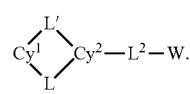

Formula I

For the avoidance of doubt, in Formula I, a cyclic structure $Cy^1$ is connected with another cyclic structure $Cy^2$, which can be the same or different, through two linkers, L and L', which form an additional ring structure between $Cy^1$ and $Cy^2$. It should be understood that both $Cy^1$ and $Cy^2$ are separately a ring structure, which is independent of L and L'.

In Formula I, $Cy^1$ and $Cy^2$ are each independently an optionally substituted cycloalkyl ring (e.g., $C_{3-7}$ cycloalkyl ring), an optionally substituted heterocyclic ring, such as an optionally substituted 4-7 membered heterocyclic ring (e.g., having one or two ring heteroatoms independently selected from N, O, and S), an optionally substituted aryl ring (e.g., $C_{6-10}$ aryl ring (e.g., Phenyl)), or an optionally substituted heteroaryl ring, such as an optionally substituted 5-10 membered heteroaryl ring (e.g., 5, or 6-membered heteroaryl ring with one or two ring heteroatoms independently selected from N, O, and S);

L and L are each independently null or a linker (e.g., described herein); as used herein, the term "linker" is not restricted to any particular types of linking groups. For example, in some embodiments, the linker can also form a ring structure with one of the moieties that it is attached to, for example, L and $Cy^1$ can form a ring structure independent of $Cy^2$;

$L^2$ is null, an optionally substituted $C_{1-6}$ alkylene, an optionally substituted $C_{1-6}$ heteroalkylene, an optionally substituted $C_{2-6}$ alkenylene, an optionally substituted $C_{2-6}$ alkynylene, an optionally substituted $C_{3-6}$ cycloalkylene, an optionally substituted arylene, an optionally substituted heteroarylene, or an optionally substituted 4-7 membered heterocyclylene;

W is $-OR^1$; $-COR^2$; $-COOR^{1a}$; $-OCOOR^{1a}$; $-NR^3R^4$; $-CONR^{3a}R^{4a}$; $-OCONR^{3b}R^{4b}$; $SO_2NR^{3c}R^{4c}$; $-OSO_2NR^{3d}R^{4d}$; $-SR^5$; $-SO_2R^{5a}$; $-OCOR^{2a}$; $-OSO_2R^{5a}$ or

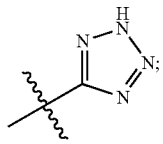

wherein:
$R^1$ and $R^{1a}$ are each independently hydrogen, optionally substituted alkyl, optionally substituted alkenyl, optionally substituted alkynyl, optionally substituted cycloalkyl, optionally substituted aryl, optionally substituted heteroaryl, or optionally substituted heterocyclyl;

$R^3$ and $R^4$ are each independently hydrogen, $-COR^{2b}$, $-SO_2R^{5b}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl, or $R^3$ and $R^4$ together with the atoms they are bound to form an optionally substituted 4-7 membered heterocyclyl;

$R^2$, $R^{2a}$, $R^{2b}$, $R^5$, $R^{5a}$, and $R^{5b}$ are each independently hydrogen, $-OH$, $-NR^{3e}R^{4e}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; and $R^{3a}$, $R^{3b}$, $R^{3c}$, $R^{3d}$, $R^{3e}$, $R^{4a}$, $R^{4b}$, $R^{4c}$, $R^{4d}$, and $R^{4e}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or $R^{3a}$ and $R^{4a}$, $R^{3b}$ and $R^{4b}$, $R^{3c}$ and $R^{4c}$, $R^{3d}$ and $R^{4d}$, or $R^{3e}$ and $R^{4e}$, together with the atoms they are bound to form an optionally substituted 4-7 membered heterocyclyl.

The $Cy^1$ and $Cy^2$ in Formula I can be either an aromatic or non-aromatic ring system, and can in some cases include heteroatoms. In preferred embodiments, at least one of $Cy^1$ and $Cy^2$ in Formula I is an aryl or heteroaryl ring, such as an optionally substituted $C_{6-10}$ aryl ring, or an optionally substituted 5-10 membered heteroaryl ring. For example, in some embodiments, the $Cy^1$ and $Cy^2$ are such that the core structure of Formula I, the structure of

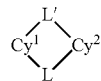

without showing optional substituents, can be any of the following:

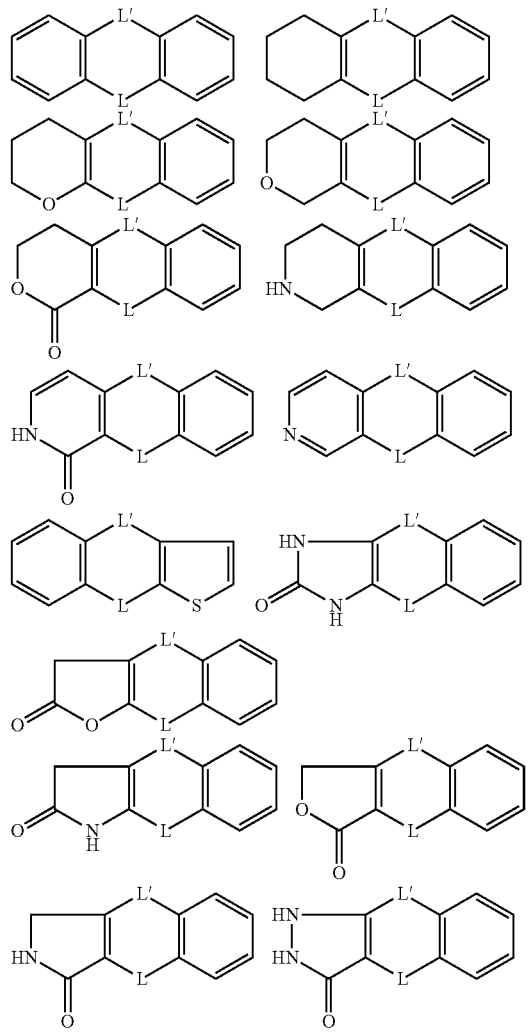

-continued

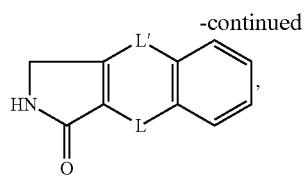

wherein L²-W can be attached to either the left or the right ring, wherein L and L can be any of those described herein and suitable substituents for the rings are described herein.

In some embodiments, both Cy¹ and Cy² in Formula I can be an aryl or heteroaryl ring. For example, in some embodiments, the compound of Formula I can have a Formula I-1:

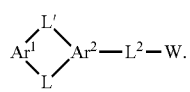

Formula I-1

In some embodiments, Ar¹ and Ar² in Formula I-1 are each independently an optionally substituted $C_{6-10}$ aryl ring, or an optionally substituted 5-10 membered heteroaryl ring. In some embodiments, Ar¹ and Ar² in Formula I-1 are each independently an optionally substituted phenyl ring or a 5 or 6 membered heteroaryl ring. For example, in some embodiments, Ar¹ and Ar² in Formula I-1 are each independently an optionally substituted phenyl ring, an optionally substituted thienyl ring, an optionally substituted furanyl ring, an optionally substituted pyridyl ring, or an optionally substituted pyrimidinyl ring.

Formula I-1 typically has a polycyclic core structure. For example, in some embodiments, the Ar¹ and Ar² are such that the core structure of Formula I-1,

without showing optional substituents, can be any of the following:

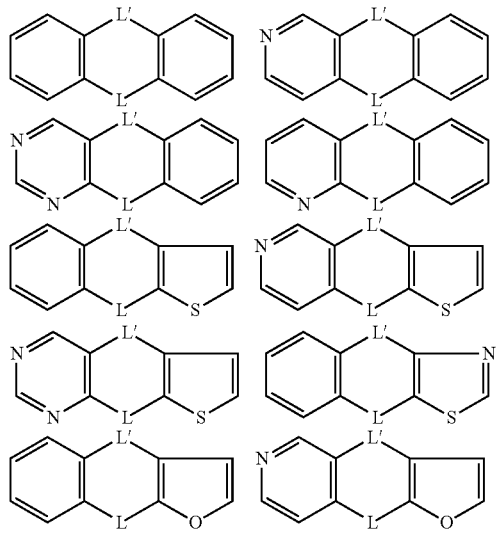

-continued

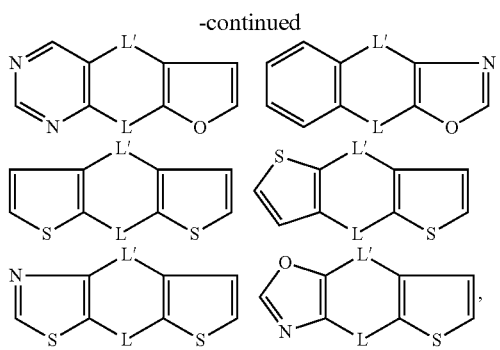

wherein L²-W can be attached to either the left or the right ring, wherein L and L are defined herein and suitable substituents for the rings are described herein.

In some embodiments, the compound of Formula I can have a Formula I-2:

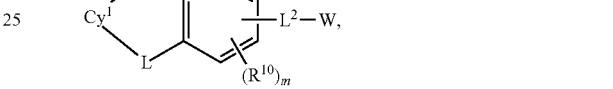

Formula I-2 wherein:
m is 0, 1, 2, or 3,
R¹⁰ at each occurrence is independently halogen, L²-W, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent R¹⁰, or one R¹⁰ and L or L, together with the atoms they are bound to, form an optionally substituted cycloalkyl, heterocyclyl, aryl, or heteroaryl ring;
wherein -L²'-W' at each occurrence is independently selected; and
L²' at each occurrence is independently null, an optionally substituted $C_{1-6}$ alkylene, an optionally substituted $C_{1-6}$ heteroalkylene, an optionally substituted $C_{2-6}$ alkenylene, an optionally substituted $C_{2-6}$ alkynylene, an optionally substituted $C_{3-6}$ cycloalkylene, an optionally substituted arylene, an optionally substituted heteroarylene, or an optionally substituted 4-7 membered heterocyclylene; and W at each occurrence is independently —OR¹; —COR²; —COOR¹ᵃ; —OCOOR¹ᵃ; —NR³R⁴; —CONR³ᵃR⁴ᵃ; —OCONR³ᵇR⁴ᵇ; —SO₂NR³ᶜR⁴ᶜ; —OSO₂NR³ᵈR⁴ᵈ; —SR⁵; —SO₂R⁵ᵃ; —OCOR²ᵃ; —OSO₂R⁵ᵃ or

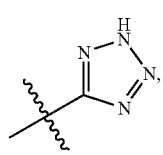

wherein $R^1$, $R^{1a}$, $R^2$, $R^{2a}$, $R^{2b}$, $R^3$, $R^4$, $R^{3a}$, $R^{3b}$, $R^{3c}$, $R^{3d}$, $R^{3e}$, $R^{4a}$, $R^{4b}$, $R^{4c}$, $R^{4d}$, $R^{4e}$, $R^5$, $R^{5a}$, and $R^{5b}$ are defined herein, see e.g., Formula I.

It should be noted that each instance of the structural unit -L$^{2'}$-W' and -L$^2$-W are independently selected and can be the same or different.

In some embodiments, Cy$^1$ in Formula I-2 is an optionally substituted phenyl ring, an optionally substituted thienyl ring, an optionally substituted furanyl ring, an optionally substituted pyridyl ring, or an optionally substituted pyrimidinyl ring. In some embodiments, Cy$^1$ in Formula I-2 is an optionally substituted $C_{3-6}$ cycloalkyl ring or an optionally substituted 4-7 heterocyclic ring with 1 or 2 ring heteroatoms independently selected from N, O, and S.

In some embodiments, the Cy$^1$ is such that the core structure of Formula I-2 can be any of the following:

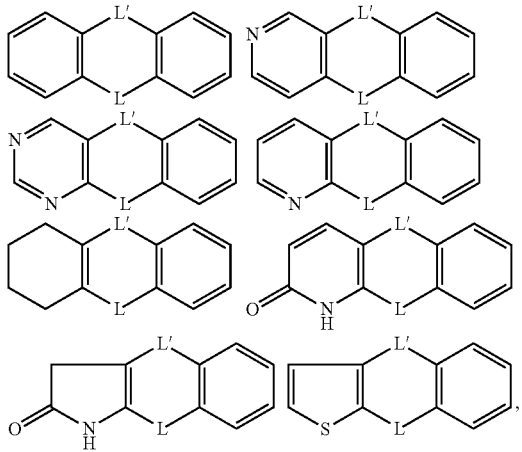

wherein -L$^2$-W is attached to the right phenyl ring, L and L' are defined herein and suitable substituents for the rings are described herein.

In more preferred embodiments, both Cy$^1$ and Cy$^2$ in Formula I are phenyl rings. For example, in some embodiments, the compound of Formula I-2 can have a Formula I-3:

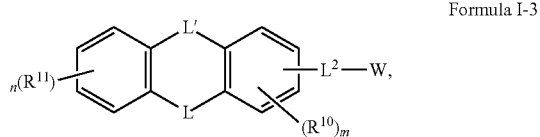

Formula I-3 wherein: L, L', L$^2$, W, R$^{10}$, and m are defined herein, see e.g., Formula I-2, n is 0, 1, 2, or 3, $R^{11}$ at each occurrence is independently halogen, -L$^{2'}$-W', an optionally substituted $C_{1-6}$ alkyl, an optionally substituted $C_{2-6}$ alkenyl, an optionally substituted $C_{2-6}$ alkynyl, an optionally substituted $C_{1-6}$alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent $R^{11}$, or one $R^{11}$ and L or L', together with the atoms they are bound to form an optionally substituted cycloalkyl, heterocyclyl, aryl, or heteroaryl ring; wherein L and W are defined herein, see e.g., for Formula I-2, and -L$^{2'}$-W' at each occurrence is independently selected.

L and L' in Formula I (e.g., any of the Formula I-1 to I-3) can be independently null or a linker. In some embodiments, L and L in Formula I are each independently null, —C(O)—, optionally substituted $C_{1-4}$alkylene, optionally substituted $C_{2-4}$ alkenylene, —O—, —S—, —NR$^{100}$—, —S(O)—, —SO$_2$—, —X$^1$G$^1$-, —X$^2$-G$^2$-X$^{2a}$—, or —CR$^{101}$R$^{102}$—, wherein:

$X^1$, $X^2$, and $X^{2a}$ are independently optionally substituted $C_{1-4}$ alkylene, optionally substituted $C_{2-4}$ alkenylene, —O—, —C(O)—, —S—, —NR$^{100a}$—, —S(O)—, —SO$_2$—, or —CR$^{101a}$R$^{102a}$—;

G$^1$ and G$^2$ are independently optionally substituted $C_{1-4}$ alkylene, optionally substituted $C_{2-4}$ alkenylene, —C(O)—, —NR$^{100a}$—, —S(O)—, —SO$_2$—, or —CR$^{101a}$R$^{102a}$—;

preferably, in some embodiments, —X$^1$G$^1$- or —X$^2$-G$^2$-X$^{2a}$— does not contain an O—N, S—S, S—N(other than SO$_2$—N), or —C(O)—S bond;

R$^{100}$ and R$^{100a}$ are each independently lone pair (as applicable), hydrogen, COR$^{2c}$, —SO$_2$R$^{5c}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl; or R$^{100}$ or R$^{100a}$ forms an optionally substituted heterocyclic or heteroaryl ring with a R$^{10}$ or R$^{11}$ group;

$R^{101}$, $R^{101a}$, $R^{102}$, and $R^{102a}$, when present, are each independently hydrogen, —OH, halogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$ alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl, or R$^{101}$ and R$^{102}$, or R$^{101a}$ and R$^{102a}$, together with the atoms they are bound to form an optionally substituted 3-7 membered cycloalkyl or heterocyclyl ring; or one of R$^{101}$ and R$^{102}$, or one of R$^{101a}$ and R$^{102a}$ forms an optionally substituted cycloalkyl or heterocyclyl ring together with a R$^{10}$ or R$^{11}$ group; and R$^{2c}$ and R$^{5c}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl.

When the linker L or L forms a double bond with one of the ring carbons, it cannot be CR$^{101}$R$^{102}$ with both R$^{101}$ and R$^{102}$ present, as the valence of the carbon will exceed 4. In such cases, it should be understood that one of R$^{101}$ and R$^{102}$ is absent and L or L is CR$^{101}$ or CR$^{102}$ as defined herein. When L or L forms a double bond with one of the ring carbons, it can be NR$^{100}$ with R$^{100}$ typically being a lone pair. Other similar situations in the present disclosure should be understood similarly.

In some embodiments, L and L in Formula I are each independently null, —O—, —C(O)—, —S—, —NR$^{100}$—, —S(O)—, —SO$_2$—, or —CR$^{101}$R$^{102}$—. In some embodiments, the compound of Formula I has a formula according to any one of 1-4 to 1-5:

Formula I-4

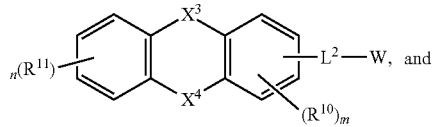

Formula I-5

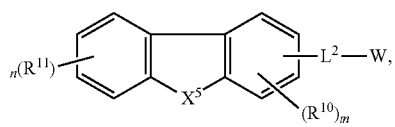

wherein:

X$^3$, X$^4$, and X$^5$ are each independently null, —O—, —C(O)—, —S—, —NR$^{100a}$—, —S(O)—, —SO$_2$—, or —CR$^{101a}$R$^{102a}$—, and R$^{10}$, R$^{11}$, R$^{100a}$, R$^{101a}$, R$^{102a}$, W, L$^2$, m, and n are defined herein.

In some embodiments, the compound has a Formula I-4, wherein X$^3$ and X$^4$ are each independently —O—, —C(O)—, —S—, —NR$^{100a}$—, or —SO$_2$—. In some embodiments, the compound has a Formula I-5, wherein X$^5$ is —O—, —C(O)—, —S—, —NR$^{100a}$—, or —SO$_2$—. In some embodiments, R$^{100a}$ is hydrogen or an optionally substituted C$_{1-4}$ alkyl.

L$^2$ in Formula I (e.g., any of the sub-formulae described herein, such as Formula I-1 to I-5) is typically null, i.e., the W group is directly attached to Cy$^2$. In some embodiments, L in Formula I can also be a C$_{1-4}$ alkylene, C$_{2-4}$ alkenylene, C$_{2-4}$ alkynylene or C$_{1-4}$ heteroalkylene. For example, the W group can be attached to Cy$^2$, through a methylene or vinyl group.

Various W groups are suitable for compounds of Formula I (e.g., any of the sub-formulae described herein, such as Formula I-1 to I-5). In preferred embodiments, W group at each occurrence is independently —OH, —NH$_2$, —SO$_2$NH$_2$, —SO$_2$NH(C$_{1-4}$ alkyl), —SO$_2$NH(C$_{1-4}$ alkanoyl), —COOH,

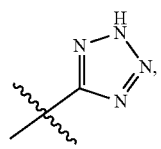

—C(O)(O—C$_{1-10}$ alkyl), —C(O)(O—C$_{2-10}$ alkenyl), —OC(O)NH$_2$, —OC(O)NH(C$_{1-4}$ alkyl)-, —O—(CO)—(C$_{1-4}$ alkyl), —O—(C$_{1-4}$ alkyl), wherein each of the C$_{1-4}$ alkyl is independently optionally substituted with 1-3 substituents independently selected from C$_{1-4}$ alkyl, C$_{1-4}$ alkoxy, —OH, —NH$_2$, and fluorine. In some embodiments, W in Formula I is —OH, —NH$_2$, —SO$_2$NH$_2$, —SO$_2$NH(Acetyl), —COOH,

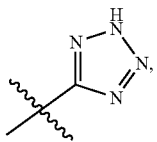

or —O—C(O)—CH$_3$.

As described herein, L$^{2'}$-W' can in some embodiments be selected as a substituent for Cy$^1$ or Cy$^2$, such as for Ar$^1$ or Ar$^2$. When applicable, L$^{2'}$ in Formula I, including any of the sub-formulae described herein, such as Formula I-1 to I-5, at each occurrence can be independently null, i.e., the W group is directly attached to Cy$^1$ or Cy$^2$, such as for Ar$^1$ or Ar$^2$, as applicable, or a C$_{1-4}$ alkylene, C$_{2-4}$ alkenylene, C$_{2-4}$ alkynylene or C$_{1-4}$ heteroalkylene. For example, the W group can be attached to Cy$^1$ or Cy$^2$, such as for Ar$^1$ or Ar$^2$, as applicable, through a methylene or vinyl group. When applicable, W in Formula I, including any of the sub-formulae described herein, such as Formula I-1 to I-5, at each occurrence can be independently —OH, —NH$_2$, —SO$_2$NH$_2$, —SO$_2$NH(C$_{1-4}$ alkyl), —SO$_2$NH(C$_{1-4}$ alkanoyl), —COOH,

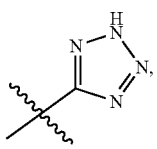 [SMILES: *c1nn[nH]n1]

—C(O)(O—C$_{1-10}$ alkyl), —C(O)(O—C$_{2-10}$ alkenyl), —OC(O)NH$_2$, —OC(O)NH(C$_{1-4}$ alkyl)-, —O—(CO)—(C$_{1-4}$ alkyl), —O—(C$_{1-4}$ alkyl), wherein each of the C$_{1-4}$ alkyl is independently optionally substituted with 1-3 substituents independently selected from C$_{1-4}$ alkyl, C$_{1-4}$ alkoxy, —OH, —NH$_2$, and fluorine. In some embodiments, each instance of W in Formula I, when applicable, can be —OH, —NH$_2$, —SO$_2$NH$_2$, —SO$_2$NH(Acetyl), —COOH,

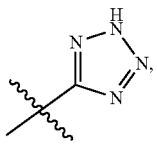 [SMILES: *c1nn[nH]n1]

or —O—C(O)—CH$_3$.

Various groups can be suitable for R$^{10}$ and R$^{11}$ in any of the applicable Formula I (e.g., any of the sub-formulae described herein, such as Formula I-2 to I-5, as applicable). In some embodiments, each of R$^{10}$ and R$^{11}$ at each occurrence can be independently F; Cl; —OH; —NH$_2$; —SO$_2$NH$_2$; —SO$_2$NH(C$_{1-4}$ alkyl); —SO$_2$NH(C$_{1-4}$alkanoyl); —COOH;

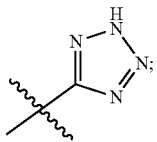 [SMILES: *c1nn[nH]n1]

—C(O)(O—C$_{1-10}$ alkyl), —C(O)(O—C$_{2-10}$ alkenyl), —OC(O)NH$_2$; —OC(O)NH(C$_{1-4}$ alkyl)-; —O—(CO)—(C$_{1-4}$ alkyl); C$_{1-4}$ alkyl optionally substituted with 1-3 substituents independently selected from C$_{1-4}$ alkyl, C$_{1-4}$ alkoxy, —OH, —NH$_2$, and fluorine; C$_{2-6}$ alkenyl optionally substituted with 1-3 substituents independently selected from C$_{1-4}$ alkyl, C$_{1-4}$ alkoxy, —OH, —NH$_2$, and fluorine; C$_{2-6}$ alkynyl optionally substituted with 1-3 substituents independently selected from C$_{1-4}$ alkyl, C$_{1-4}$ alkoxy, —OH, —NH$_2$, and fluorine; C$_{3-6}$ cycloalkyl optionally substituted with 1-3 substituents independently selected from C$_{1-4}$ alkyl and fluorine; C$_{3-6}$ cycloalkoxy optionally substituted with 1-3 substituents independently selected from C$_{1-4}$ alkyl and fluorine; or C$_{1-4}$ alkoxy optionally substituted with 1-3 substituents independently selected from C$_{1-4}$ alkyl, C$_{1-4}$ alkoxy, —OH, —NH$_2$, and fluorine. In some embodiments, each of R$^{10}$ and R$^{11}$ at each occurrence can be independently —OH; —NH$_2$; —SO$_2$NH$_2$; —SO$_2$NH(C$_{1-4}$ alkyl); —SO$_2$NH(C$_{1-4}$ alkanoyl); —COOH;

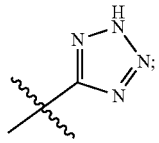

—C(O)(O—C$_{1-10}$ alkyl), —C(O)(O—C$_{2-10}$ alkenyl), —OC(O)NH$_2$; —OC(O)NH(C$_{1-4}$ alkyl)-; —O—(CO)—(C$_{1-4}$alkyl); C$_{1-4}$ alkyl; or C$_{1-4}$ alkoxy. In some embodiments, one or more instances of R$^{10}$ and/or one or more instances of R$^{11}$ can be independently selected L$^{2'}$-W' as described herein.

Typically, m, as applicable, is 0, 1, or 2; preferably, 1.

Typically, n, as applicable, is 0, 1, 2, or 3; preferably, 1 or 2.

In some embodiments, the compounds herein can be characterized by having a Formula II, or a pharmaceutically acceptable salt or ester thereof:

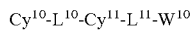

wherein:

Cy$^{10}$ and Cy$^{11}$ are each independently an optionally substituted cycloalkyl ring (e.g., C$_{3-7}$ cycloalkyl ring), an optionally substituted heterocyclic ring (e.g., 4-7 membered heterocyclic ring), an optionally substituted aryl ring (e.g., C$_{6-10}$ aryl ring), an optionally substituted heteroaryl ring (e.g., 5-10 membered heteroaryl ring), or an optionally substituted ring structure comprising a cycloalkyl ring or heterocyclic ring, and an aryl or heteroaryl ring, wherein the ring structure can be a fused ring or otherwise connected;

L$^{10}$ is null or a linker;

L$^{11}$ is null, an optionally substituted C$_{1-6}$alkylene, an optionally substituted C$_{1-6}$ heteroalkylene, an optionally substituted C$_{2-6}$ alkenylene, an optionally substituted C$_{2-6}$ alkynylene, an optionally substituted C$_{3-6}$ cycloalkylene, an optionally substituted arylene, an optionally substituted heteroarylene, or an optionally substituted 4-7 membered heterocyclylene, W$^{10}$ is —OR$^1$; —COOR$^{1a}$; —OCOOR$^{1a}$; —COR$^2$; —NR$^3$R$^4$; —CONR$^{3a}$R$^{4a}$; —OCONR$^{3b}$R$^{4b}$; —SO$_2$NR$^{3c}$R$^{4c}$; —OSO$_2$NR$^{3d}$R$^{4d}$; —SR$^5$; —SO$_2$R$^{5a}$; —OCOR$^{2a}$; —OSO$_2$R$^{5a}$; or

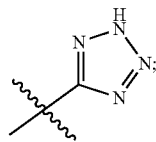

wherein:

R$^1$ and R$^{1a}$ are each independently hydrogen, optionally substituted alkyl, optionally substituted alkenyl, optionally substituted alkynyl, optionally substituted cycloalkyl, optionally substituted aryl, optionally substituted heteroaryl, or optionally substituted heterocyclyl;

R$^3$ and R$^4$ are each independently hydrogen, —COR$^{2b}$, —SO$_2$R$^{5b}$, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted phenyl, optionally substituted 5 or 6 membered heteroaryl, or optionally substituted 4-7 membered heterocyclyl, or R and R together with the atoms they are bound to form an optionally substituted 4-7 membered heterocyclyl;

R$^2$, R$^{2a}$, R$^{2b}$, R$^5$, R$^{5a}$, and R$^{5b}$ are each independently hydrogen, —OH, —NR$^{3e}$R$^{4e}$, an optionally substituted C$_{1-6}$ alkyl, an optionally substituted C$_{2-6}$ alkenyl, an optionally substituted C$_{2-6}$alkynyl, an optionally substituted C$_{1-6}$alkoxy, an optionally substituted C$_{3-6}$ cycloalkyl, an optionally substituted C$_{3-6}$ cycloalkoxy, an optionally substituted phenyl; an optionally substituted 5 or 6 membered heteroaryl; or an optionally substituted 4-7 membered heterocyclyl; and R$^{3a}$, R$^{3b}$, R$^{3c}$, R$^{3d}$, R$^{3e}$, R$^{4a}$, R$^{4b}$, R$^{4c}$, R$^{4d}$, and R$^{4e}$ are each independently hydrogen, an optionally substituted C$_{1-6}$ alkyl, an optionally substituted C$_{2-6}$ alkenyl, an optionally substituted C$_{2-6}$alkynyl, an optionally substituted C$_{1-6}$alkoxy, an optionally substituted C$_{3-6}$ cycloalkyl, an optionally substituted C$_{3-6}$ cycloalkoxy, an optionally substituted phenyl; an optionally substituted 5 or 6 membered heteroaryl; or an optionally substituted 4-7 membered heterocyclyl; or R$^{3a}$ and R$^{4a}$, R$^{3b}$ and R$^{4b}$, R$^{3c}$ and R$^{4c}$, R$^{3d}$ and R$^{4d}$, or R$^{3e}$ and R$^{4e}$, together with the atoms they are bound to form an optionally substituted 4-7 membered heterocyclyl.

In some embodiments, in Formula II, at least one of Cy$^{10}$ and Cy$^{11}$ is an optionally substituted C$_{6-10}$ aryl ring, or an optionally substituted 5-10 membered heteroaryl ring. In some embodiments, Cy$^{11}$ is an optionally substituted C$_{6-10}$ aryl ring, or an optionally substituted 5-10 membered heteroaryl ring. When Cy$^{11}$ is a bicyclic or polycyclic aryl or heteroaryl ring, the L$^{10}$-Cy$^{10}$ and L$^{11}$-W$^{10}$ can be independently connected to Cy$^{11}$ through any of the rings. In some embodiments, Cy$^{11}$ can have a fused ring structure comprising an aryl or heteroaryl ring and a cycloalkyl or heterocyclic ring structure. In such embodiments, Cy$^{11}$ can be connected to L$^{10}$-Cy$^{10}$ and L$^{11}$-W$^{10}$ through either of the aryl or heteroaryl ring and cycloalkyl or heterocyclic ring structure; or alternatively, one of L$^{10}$-Cy$^{10}$ and L$^{11}$-W$^{10}$ is connected to Cy$^{11}$ through the aryl or heteroaryl ring and the other of L$^{10}$-Cy$^{10}$ and L$^{11}$-W$^{10}$ is connected to Cy$^{11}$ through the cycloalkyl or heterocyclic ring structure.

In some embodiments, the compound of Formula II has at least one phenyl ring, which can have the following core structure as Cy$^{10}$-L$^{10}$-Cy$^{11}$:

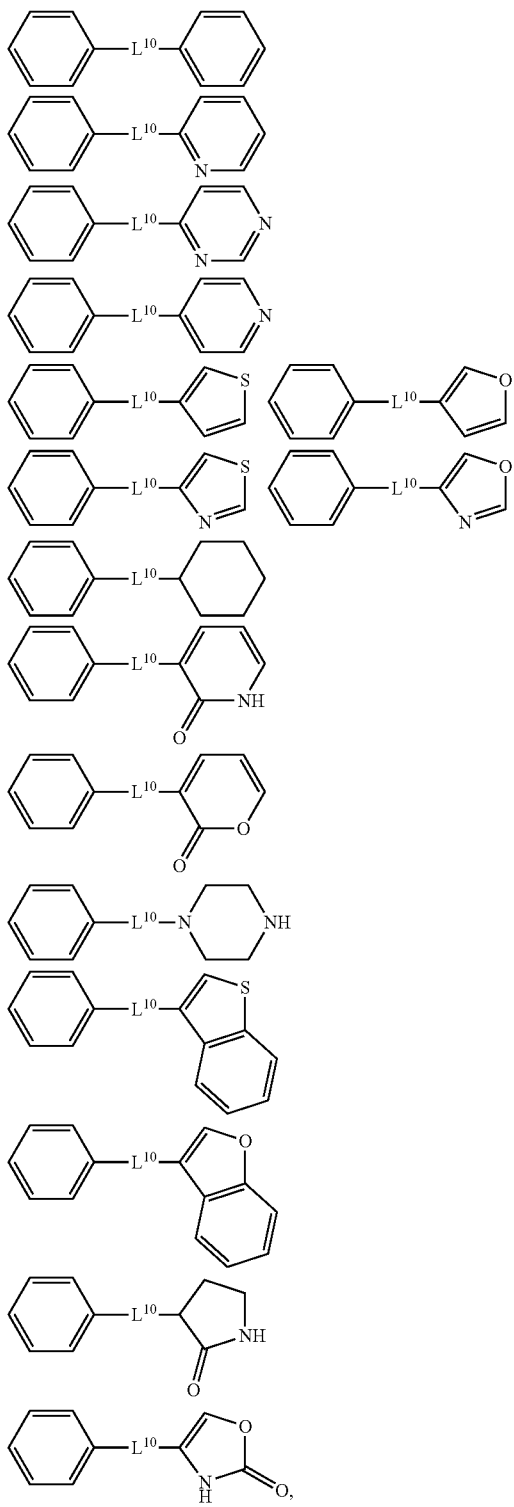

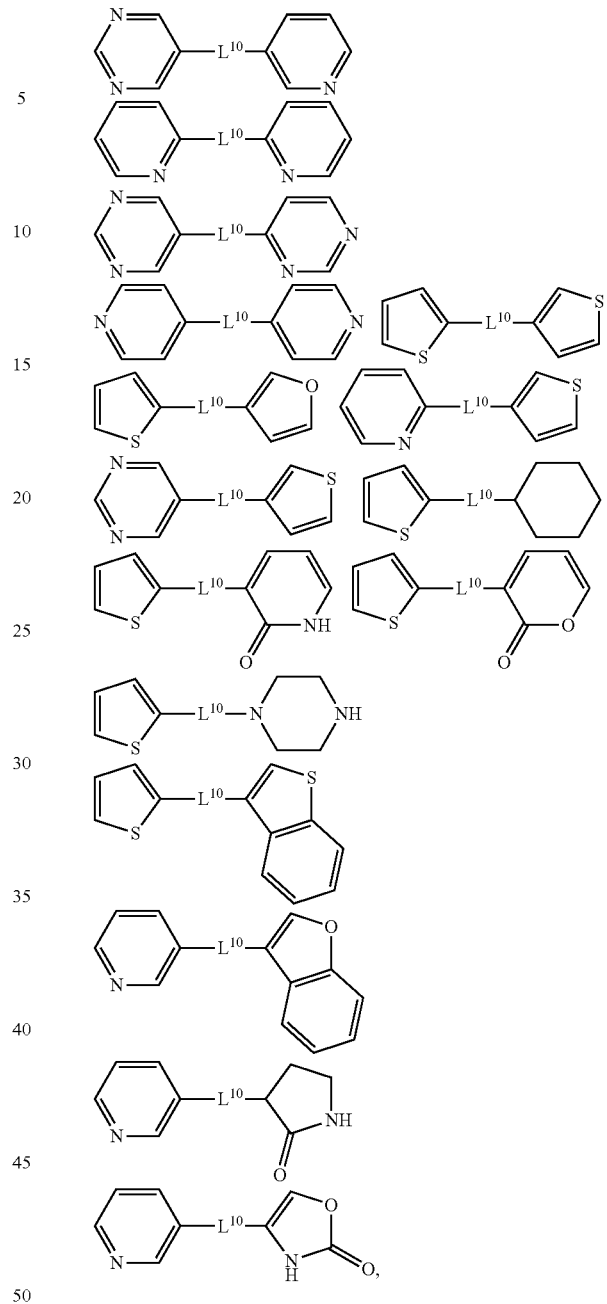

wherein Cy$^{10}$ can be the left ring or the right ring in the above drawings, i.e., the drawings are not limited to a particular direction, wherein L$^{11}$-W$^{10}$ can connect to either the left or the right ring, both of which can be optionally substituted.

In some embodiments, the compound of Formula II can have the following core structure as Cy$^{10}$-L$^{10}$-Cy$^{11}$:

wherein Cy$^{10}$ can be the left ring or the right ring in the above drawings, i.e., the drawings are not limited to a particular direction, wherein L$^{11}$-W$^{10}$ can connect to either the left or the right ring, both of which can be optionally substituted.

In some embodiments, both of Cy$^{10}$ and Cy$^{11}$ in Formula II are an aryl or heteroaryl ring. In some embodiments, the compound of Formula II has a Formula II-1:

  Formula II-1 wherein Ar$^{10}$ and Ar$^{11}$ are each independently an optionally substituted C$_{6-10}$ aryl ring, or an optionally substituted 5-10 membered heteroaryl ring. In some embodiments, Ar$^{10}$ and Ar$^{11}$ in Formula II-1 are each independently an optionally substituted phenyl ring or an optionally substituted 5 or 6 membered heteroaryl ring. In some embodiments, Ar$^{10}$ and Ar[11] in Formula II-1 are each independently an optionally substituted phenyl ring, an optionally substituted thienyl ring, an optionally substituted furanyl ring, an optionally substituted pyridyl ring, or an optionally substituted pyrimidinyl ring. In some embodiments, one of Ar[10] and Ar[11] in Formula II-1 is a bicyclic aryl or bicyclic heteroaryl ring, each of which is optionally substituted, for example, in some embodiments, Ar[11] can be optionally substituted bicyclic aryl or bicyclic heteroaryl ring.

In some embodiments, $Cy^{11}$ in Formula II is a phenyl ring. In some embodiments, the compound of Formula II has a Formula II-2:

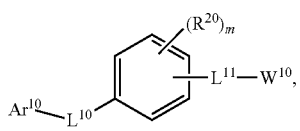

Formula II-2 wherein $Ar^{10}$, $L^{10}$, $L^{11}$, and $W^{10}$ are defined herein, see e.g., Formula II-1, m is 0, 1, 2, or 3, $R^{20}$ at each occurrence is independently halogen, $-L^{11'}\text{-}W^{10'}$, an optionally substituted $C_{1-6}$ alkyl, an optionally substituted $C_{2-6}$ alkenyl, an optionally substituted $C_{2-6}$ alkynyl, an optionally substituted $C_{1-6}$alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent $R^{20}$, or one $R^{20}$ and $L^{10}$ or $L^{11}$, together with the atoms they are bound to form an optionally substituted cycloalkyl, heterocyclyl, aryl, or heteroaryl ring;

wherein $-L^{11'}\text{-}W^{10'}$ at each occurrence is independently selected;

wherein $L^{11'}$ at each occurrence is independently null, an optionally substituted $C_{1-6}$ alkylene, an optionally substituted $C_{1-6}$ heteroalkylene, an optionally substituted $C_{2-6}$ alkenylene, an optionally substituted $C_{2-6}$ alkynylene, an optionally substituted $C_{3-6}$ cycloalkylene, an optionally substituted arylene, an optionally substituted heteroarylene, or an optionally substituted 4-7 membered heterocyclylene; and $W^{10}$ at each occurrence is independently —$OR^1$; —$COR^2$; —$COOR^{1a}$; —$OCOOR^{1a}$; —$NR^3R^4$; —$CONR^{3a}R^{4a}$; —$OCONR^{3b}R^{4b}$; —$SO_2NR^{3c}R^{4c}$; —$OSO_2NR^{3d}R^{4d}$; —$SR^5$; —$SO_2R^{5a}$; —$OCOR^{2a}$; —$OSO_2R^{5a}$ or

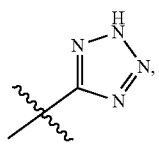

wherein $R^1$, $R^{1a}$, $R^2$, $R^{2a}$, $R^{2b}$, $R^3$, $R^4$, $R^{3a}$, $R^{3b}$, $R^{3c}$, $R^{3d}$, $R^{3e}$, $R^{4a}$, $R^{4b}$, $R^{4c}$, $R^{4d}$, $R^{4e}$, $R^5$, $R^{5a}$, and $R^{5b}$ are defined herein, see e.g., Formula II. It should be noted that each instance of the structural unit $-L^{11'}\text{-}W^{10'}$ and $-L^{11}\text{-}W^{10}$ are independently selected and can be the same or different.

In some embodiments, $Cy^{11}$ in Formula II is a benzofused ring. In some embodiments, the compound of Formula II has a Formula II-3:

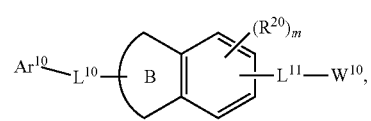

Formula II-3 wherein $Ar^{10}$, $L^{10}$, $L^{11}$, and $W^{10}$ are defined herein, see e.g., Formula II-1, m is 0, 1, 2, or 3, $R^{20}$ at each occurrence is independently halogen, $-L^{11'}\text{-}W^{10'}$, an optionally substituted $C_{1-6}$ alkyl, an optionally substituted $C_{2-6}$ alkenyl, an optionally substituted $C_{2-6}$ alkynyl, an optionally substituted $C_{1-6}$alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent $R^{20}$, or one $R^{20}$ and $L^{10}$ or $L^{11}$, together with the atoms they are bound to form an optionally substituted cycloalkyl, heterocyclyl, aryl, or heteroaryl ring;

wherein $L^{11'}$ and $W^{10'}$ are defined herein, see e.g., Formula II-2, and $-L^{11'}\text{-}W^{10'}$ at each occurrence is independently selected; and ring B is a 4-7 membered cycloalkyl ring, 4-7 membered heterocyclic ring, phenyl ring, 5 or 6 membered heteroaryl ring, each of which is optionally substituted.

In some embodiments, $Cy^{11}$ in Formula II is a benzofused bicyclic aryl or heteroaryl ring. For example, in some embodiments, $Cy^{11}$ in Formula II can have the following core structure:

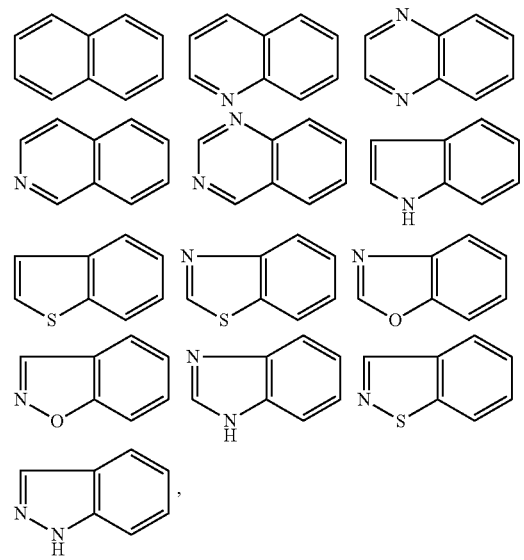

wherein the $L^{10}\text{-}Cy^{10}$ and $L^{11}\text{-}W^{10}$ can be independently connected to $Cy^{11}$ through any of the two rings, wherein the phenyl ring can be optionally substituted with 1-3 $R^{20}$ groups defined herein. For example, in the case of benzothiophene ring, in some embodiments, $L^{10}\text{-}Cy^{10}$ can be attached to the thiophene ring whereas $L^{11}\text{-}W^{10}$ can be attached to the phenyl ring, or vice versa, and in some cases, both $L^{10}\text{-}Cy^{10}$ and $L^{11}\text{-}W^{10}$ can be attached to the same ring, such as the phenyl ring.

In some embodiments, the compound of Formula II can have a structure of any of the

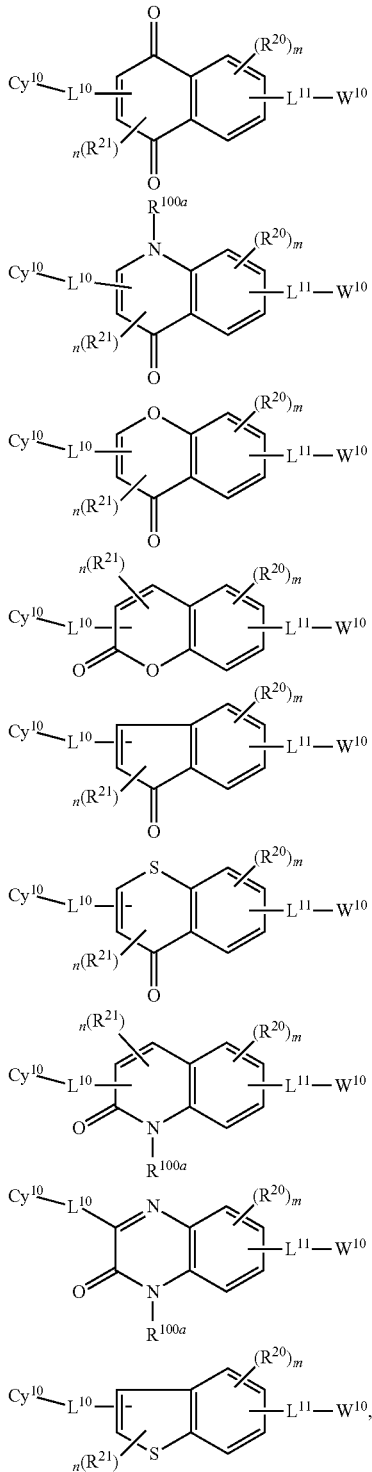

wherein: $Cy^{10}$, $L^{10}$, $R^{20}$, m, $R^{21}$, n, $R^{100a}$, $L^{11}$, and $W^{10}$ are defined herein, see e.g., Formula II and sub-formulae herein, such as Formula II-3. In some embodiments, $Cy^{10}$ is $Ar^{10}$ as defined for Formula II-3.

In some embodiments, the compound of Formula II-3 can have a Formula II-4:

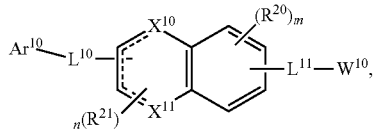

Formula II-4 wherein: $Ar^{10}$, $L^{10}$, $R^{20}$, m, $L^{11}$, and $W^{10}$ are defined herein, see e.g., Formula II-3, n is 0 or 1, $R^{21}$ at each occurrence is independently halogen, oxo, $-L^{11'}-W^{10'}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; wherein $L^{11}$ and $W^{10}$ are defined herein, see e.g., Formula II-2, and $-L^{11'}-W^{10'}$ at each occurrence is independently selected; $X^{10}$ and $X^{11}$ are each independently null, —O—, —C(O)—, —S—, $-NR^{100a}-$, —S(O)—, $-SO_2-$, or $-CR^{101a}R^{102a}-$, as valence permits;

wherein $R^{100a}$ is lone pair (as applicable), hydrogen, $COR^{2c}$, $-SO_2R^{5c}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl; or $R^{100a}$ forms an optionally substituted heterocyclic or heteroaryl ring with a $R^{20}$ or $R^{21}$ group;

$R^{101a}$ and $R^{102a}$, when present, are each independently hydrogen, —OH, halogen; optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$ alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl; or $R^{101a}$ and $R^{102a}$, together with the atoms they are bound to form an optionally substituted 3-7 membered cycloalkyl or heterocyclyl ring; or one of $R^{101a}$ and $R^{102a}$ forms an optionally substituted cycloalkyl or heterocyclyl ring together with a $R^{20}$ or $R^{21}$ group; and $R^{2c}$ and $R^{5c}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl;

or $R^{20}$ or $R^{21}$ and $L^{10}$, $X^{10}$ or $X^{11}$, together with the atoms they are bound to form an optionally substituted cycloalkyl, heterocyclyl, aryl, or heteroaryl ring.

When $X^{10}$ or $X^{11}$ forms a double bond with one of the ring carbons, it cannot be $CR^{101a}R^{102a}$ with both $R^{101a}$ and $R^{102a}$ present, as the valence of the carbon will exceed 4. In such cases, it should be understood that one of $R^{101a}$ and $R^{102a}$ is absent and $X^{10}$ or $X^{11}$ is $CR^{101a}$ or $CR^{102a}$ as defined herein.

When $X^{10}$ or $X^{11}$ forms a double bond with one of the ring carbons, it can be $NR^{100a}$ with $R^{100a}$ typically being a lone pair.

In some embodiments, the compound of Formula II has a Formula II-5:

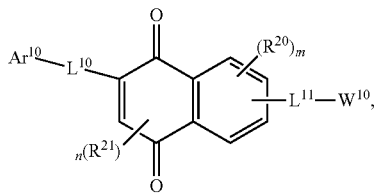

Formula II-5 wherein: $Ar^{10}$, $L^{10}$, $R^{20}$, m, $R^{21}$, n, $L^{11}$, and $W^{10}$ are defined herein, see e.g., Formula II-4.

The $Cy^{10}$ and $Cy^{11}$ in Formula II (e.g., sub-formulae described herein, such as Formula II-1 to II-4) can be connected directly or via various groups. For example, in some embodiments, $L^{10}$ in Formula II (e.g., Formula II-1 to II-5) is null, —C(O)—, optionally substituted $C_{1-4}$alkylene, optionally substituted $C_{2-4}$ alkenylene, optionally substituted $C_{3-6}$ cycloalkylene, optionally substituted 4-7 membered heterocyclylene, optionally substituted phenylene, optionally substituted 5 or 6 membered heteroarylene, —O—, —S—, —$NR^{100}$—, —S(O)—, —$SO_2$—, —$X^1$-$G^1$-, —$X^2$-$G^2$-$X^{2a}$—, —$X^{12}$-$G^{10}$-, —$X^{13}$-$G^{11}$-$X^{13a}$—, or —$CR^{101}R^{102}$—, wherein:
$X^1$, $X^2$, and $X^{2a}$ are independently optionally substituted $C_{1-4}$ alkylene, optionally substituted $C_{2-4}$ alkenylene, optionally substituted $C_{3-6}$ cycloalkylene, optionally substituted 4-7 membered heterocyclylene, optionally substituted phenylene, optionally substituted 5 or 6 membered heteroarylene, —O—, —C(O)—, —S—, —$NR^{100a}$—, —S(O)—, —$SO_2$—, or —$CR^{101a}R^{102a}$—;

$G^1$ and $G^2$ are independently optionally substituted $C_{1-4}$ alkylene, optionally substituted $C_{2-4}$ alkenylene, optionally substituted $C_{3-6}$ cycloalkylene, optionally substituted 4-7 membered heterocyclylene, optionally substituted phenylene, optionally substituted 5 or 6 membered heteroarylene, —C(O)—, —$NR^{100a}$—, —S(O)—, —$SO_2$—, or —$CR^{101a}R^{102a}$—;

preferably, in some embodiments, —$X^1$-$G^1$- or —$X^2$-$G^2$-$X^{2a}$— does not contain an O—N, S—S, S—N (except $SO_2$—N bond), or —C(O)—S bond;

$X^{12}$, $X^{13}$, and $X^{13a}$ are independently optionally substituted $C_{1-4}$ alkylene, optionally substituted $C_{2-4}$ alkenylene, optionally substituted $C_{3-6}$ cycloalkylene, optionally substituted 4-7 membered heterocyclylene, optionally substituted phenylene, optionally substituted 5 or 6 membered heteroarylene, —O—, —C(O)—, —S—, —$NR^{100a}$—, —S(O)—, —$SO_2$—, or —$CR^{101a}R^{102a}$—;

and $G^{10}$ and $G^{11}$ are independently —$X^1$-$G^1$- or —$X^2$-$G^2$-$X^{2a}$—;

in some embodiments, preferably, —$X^{12}$-$G^{10}$- or —$X^{13}$-$G^{11}$-$X^{13a}$— does not contain an O—O, O—N, S—S, S—N (except $SO_2$—N bond), or —C(O)—S bond or three (or more) consecutive heteroatoms, with the exception of O—$SO_2$—O, O—$SO_2$—N, and N—$SO_2$—N;

$R^{100}$ and $R^{100a}$ are each independently lone pair (as applicable), hydrogen, $COR^{2c}$, —$SO_2R^{5c}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl;

$R^{101}$, $R^{101a}$, $R^{102}$, and $R^{102a}$ are each independently hydrogen, —OH, halogen; optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$ alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl; or $R^{101}$ and $R^{102}$, or $R^{101a}$ and $R^{102a}$, together with the atoms they are bound to form an optionally substituted 3-7 membered cycloalkyl or heterocyclyl ring.

In some embodiments, $L^{10}$ in Formula II can be null, and $Cy^{10}$ is directly linked with $Cy^{11}$. In some embodiments, $L^{10}$ in Formula II can be null, —O—, —C(O)—, —S—, —$NR^{100}$—, —S(O)—, —$SO_2$—, or —$CR^{101}R^{102}$—. In some embodiments, $L^{10}$ in Formula II can be —$X^1$-$G^1$- or —$X^2$-$G^2$-$X^{2a}$—, wherein: $X^1$, $X^2$, and $X^{2a}$ are independently —O—, —C(O)—, —S—, —$NR^{100a}$—, —S(O)—, —$SO_2$—, or —$CR^{101a}R^{102a}$—, and $G^1$ and $G^2$ are independently —C(O)—, —$NR^{100a}$—, —S(O)—, —$SO_2$—, or —$CR^{101a}R^{102a}$—.

In some embodiments, $L^{10}$ in Formula II can be —$X^{12}$-$G^{10}$-. In some embodiments, $X^{12}$ is optionally substituted $C_{2-4}$alkenylene, preferably,

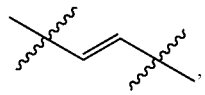 [SMILES: */C=C/*]

and $G^{10}$ is —$X^1$-$G^1$- or —$X^2$-$G^2$-$X^{2a}$—; wherein: $X^1$, $X^2$, and $X^{2a}$ are independently —O—, —C(O)—, —S—, —$NR^{100a}$—, —S(O)—, —$SO_2$—, or —$CR^{101a}R^{102a}$—; and $G^1$ and $G^2$ are independently —C(O)—, —$NR^{100a}$—, —S(O)—, —$SO_2$—, or —$CR^{101a}R^{102a}$—;

In some preferred embodiments, $L^{10}$ in Formula II can be

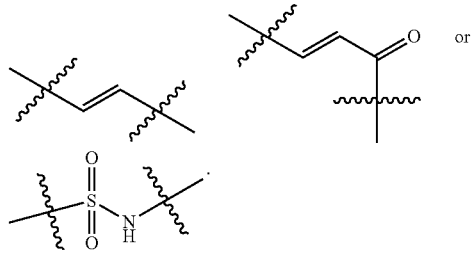

In some embodiments, the compound of Formula II can have the following core structure:

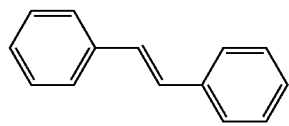

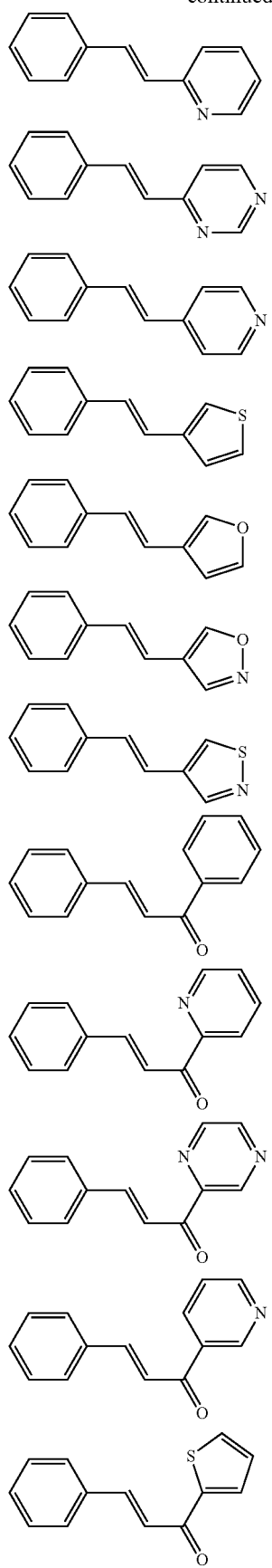
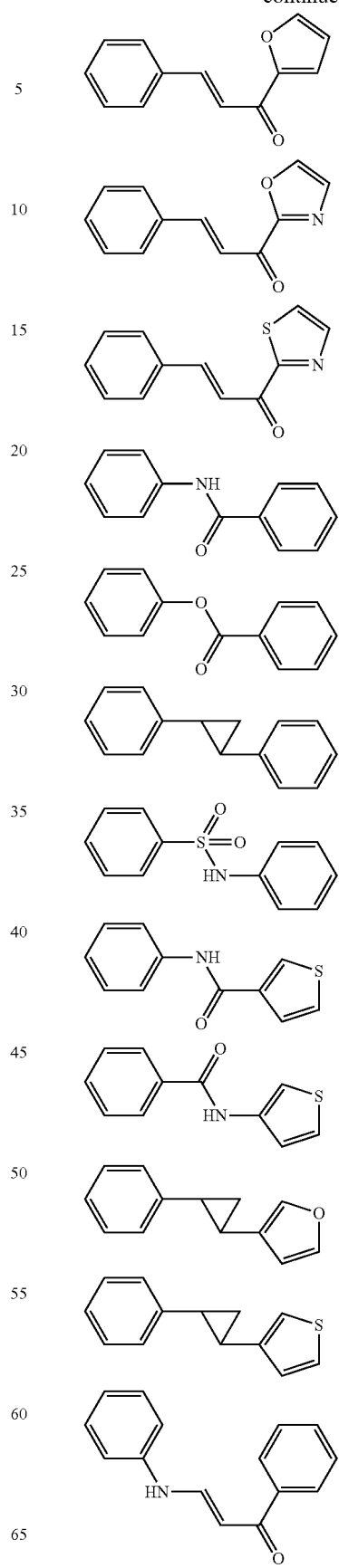

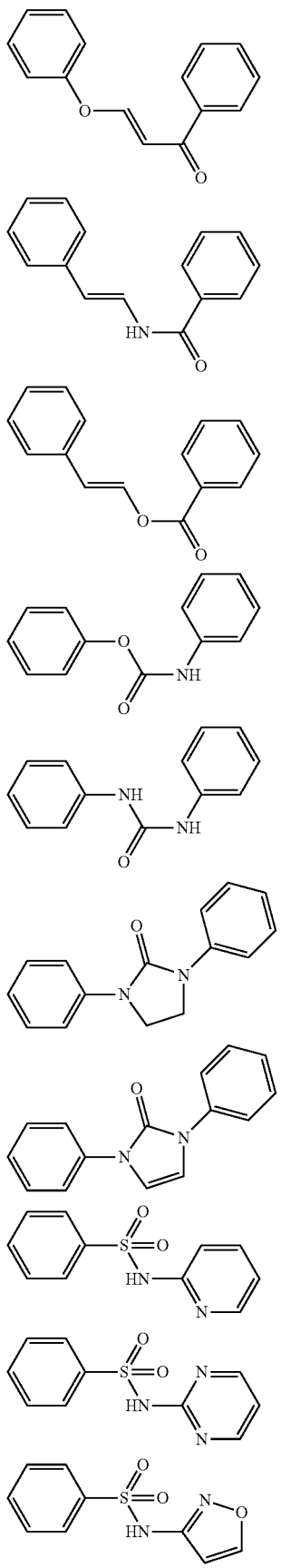

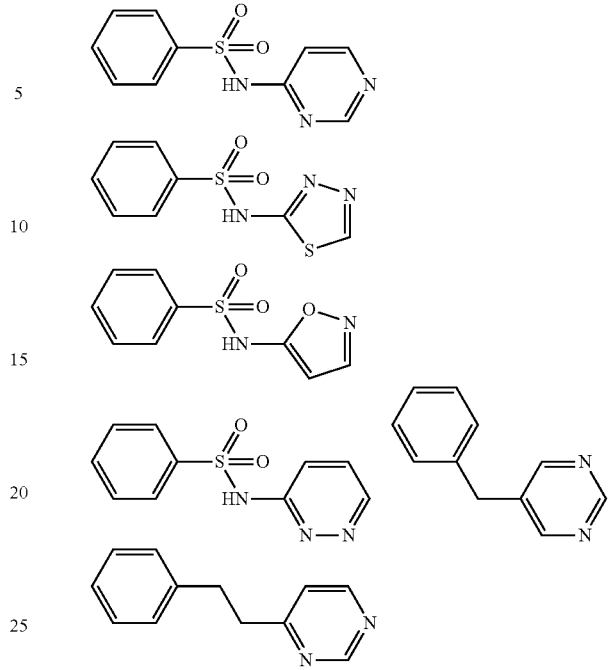

wherein $L^{11}$-$W^{10}$ can be attached to either of the rings, preferably to one of the two pheny rings or the sole phenyl ring, wherein each of the rings can be optionally substituted with one or more suitable substituents described herein, for example, each substituent can be independently selected from F; Cl; —OH; —NH$_2$; —SO$_2$NH$_2$; —SO$_2$NH(C$_{1-4}$alkyl); SO$_2$NH(C$_{1-4}$ alkanoyl); —COOH;

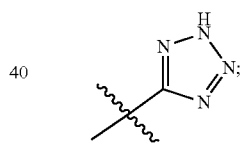

—C(O)(O—C$_{1-10}$ alkyl), —C(O)(O—C$_{2-10}$ alkenyl), —OC(O)NH$_2$; —OC(O)NH(C$_{1-4}$ alkyl)-; —O—(CO)—(C$_{1-4}$ alkyl); C$_{1-4}$ alkyl optionally substituted with 1-3 substituents independently selected from C$_{1-4}$ alkyl, C$_{1-4}$alkoxy, —OH, —NH$_2$, and fluorine; C$_{2-6}$ alkenyl optionally substituted with 1-3 substituents independently selected from C$_{1-4}$ alkyl, C$_{1-4}$alkoxy, —OH, —NH$_2$, and fluorine; C$_{2-6}$alkynyl optionally substituted with 1-3 substituents independently selected from C$_{1-4}$ alkyl, C$_{1-4}$alkoxy, —OH, —NH$_2$, and fluorine; C$_{3-6}$ cycloalkyl optionally substituted with 1-3 substituents independently selected from C$_{1-4}$ alkyl and fluorine; C$_{3-6}$ cycloalkoxy optionally substituted with 1-3 substituents independently selected from C$_{1-4}$ alkyl and fluorine; or C$_{1-4}$alkoxy optionally substituted with 1-3 substituents independently selected from C$_{1-4}$ alkyl, C$_{1-4}$alkoxy, —OH, —NH$_2$, and fluorine; optionally substituted C$_{3-6}$ cycloalkyl; optionally substituted 4-10 membered heterocyclyl; optionally substituted 5-10 membered heteroaryl; or optionally substituted C$_{6-10}$ aryl. For example, in some embodiments, the $L^{11}$-$W^{10}$ is NH$_2$ or NH(C$_{1-4}$ alkanoyl), which is connected to one of the two phenyl rings or the sole phenyl ring, whereas the other ring is optionally substituted with 1 or 2 substituents selected from methyl and methoxy.

In some particular embodiments, the compound of Formula II has a formula according to Formula II-6 or II-7:

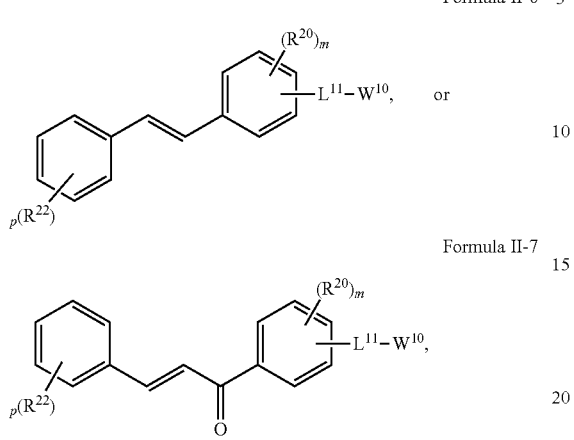

Formula II-6

Formula II-7 wherein: $L^{11}$, $W^{10}$, $R^{20}$, and m are defined herein, see e.g., Formula II-3, p is 0, 1, 2, 3, or 4, $R^{22}$ at each occurrence is independently halogen, -$L^{11'}$-$W^{10'}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent $R^{22}$ together with the atoms they are bound to form an optionally substituted cycloalkyl, heterocyclyl, aryl, or heteroaryl ring;

wherein $L^{11'}$ and $W^{10'}$ are defined herein, see e.g., Formula II-2, and -$L^{11'}$-$W^{10'}$ at each occurrence is independently selected.

$L^{11}$ in Formula II (e.g., any of the sub-formulae, such as Formula II-1 to II-7) is typically null, i.e., the $W^{10}$ group is directly attached to $Cy^{11}$, as applicable. In some embodiments, $L^{11}$ in Formula II can also be a $C_{1-4}$ alkylene, $C_{2-4}$ alkenylene, $C_{2-4}$ alkynylene or $C_{1-4}$ heteroalkylene. For example, the $W^{10}$ group can be attached to $Cy^{11}$ through a methylene or vinyl group.

Various $W^{10}$ groups are suitable for compounds of Formula II (e.g., Formula II-1 to II-7). In preferred embodiments, $W^{10}$ group at each occurrence is independently —OH, —NH$_2$, —SO$_2$NH$_2$, —SO$_2$NH(C$_{1-4}$ alkyl); —SO$_2$NH(C$_{1-4}$ alkanoyl), —COOH,

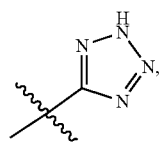

—C(O)(O—C$_{1-10}$ alkyl), —C(O)(O—C$_{2-10}$ alkenyl), —OC(O)NH$_2$, —OC(O)NH(C$_{1-4}$ alkyl)-, —O—(CO)—(C$_{1-4}$ alkyl), —O—(C$_{1-4}$ alkyl), wherein each of the C$_{1-4}$ alkyl is independently optionally substituted with 1-3 substituents independently selected from C$_{1-4}$ alkyl, C$_{1-4}$alkoxy, —OH, —NH$_2$, and fluorine. In some embodiments, $W^{10}$ group in Formula II is —OH, —OMe, —NH$_2$, —SO$_2$NH$_2$, —SO$_2$NH(Acetyl), —COOH,

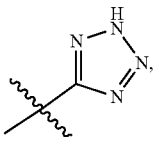 [SMILES: *c1nn[nH]n1]

or —O—C(O)—CH$_3$.

As described herein, $L^{11'}$-$W^{10'}$ can in some embodiments be selected as a substituent for $Cy^{10}$ or $Cy^{11}$, such as for $Ar^{10}$ or $Ar^{11}$. When applicable, $L^{11'}$ in Formula II, including any of the sub-formulae described herein, such as Formula II-1 to I-7, at each occurrence can be independently null, i.e., the $W^{10'}$ group is directly attached to $Cy^{10}$ or $Cy^{11}$, such as for $Ar^{10}$ or $Ar^{11}$, as applicable, or a $C_{1-4}$ alkylene, $C_{2-4}$ alkenylene, $C_{2-4}$ alkynylene or $C_{1-4}$ heteroalkylene. For example, the $W^{10'}$ group can be attached to $Cy^{10}$ or $Cy^{11}$, such as for $Ar^{10}$ or $Ar^{11}$, as applicable, through a methylene or vinyl group. When applicable, $W^{10'}$ in Formula II, including any of the sub-formulae described herein, such as Formula II-1 to II-7, at each occurrence can be independently —OH, —NH$_2$, —SO$_2$NH$_2$, —SO$_2$NH(C$_{1-4}$ alkyl), —SO$_2$NH(C$_{1-4}$ alkanoyl), —COOH,

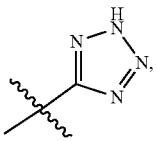 [SMILES: *c1nn[nH]n1]

—C(O)(O—C$_{1-10}$ alkyl), —C(O)(O—C$_{2-10}$ alkenyl), —OC(O)NH$_2$, —OC(O)NH(C$_{1-4}$ alkyl)-, —O—(CO)—(C$_{1-4}$ alkyl), —O—(C$_{1-4}$ alkyl), wherein each of the C$_{1-4}$ alkyl is independently optionally substituted with 1-3 substituents independently selected from C$_{1-4}$ alkyl, C$_{1-4}$alkoxy, —OH, —NH$_2$, and fluorine. In some embodiments, each instance of $W^{10'}$ in Formula II, when applicable, can be —OH, —OMe, —NH$_2$, —SO$_2$NH$_2$, —SO$_2$NH(Acetyl), —COOH, Various groups can be suitable for $R^{20}$, $R^{21}$, and $R^{22}$ in any of the applicable Formula II (e.g., Formula II-1 to II-7, as applicable). In some embodiments, each of $R^{20}$, $R^{21}$, and $R^{22}$ at each occurrence can be independently F; Cl; —OH; —NH$_2$; —SO$_2$NH$_2$; —SO$_2$NH(C$_{1-4}$alkyl); —SO$_2$NH(C$_{1-4}$ alkanoyl); —COOH;

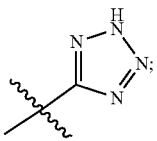 [SMILES: *c1nn[nH]n1]

—C(O)(O—C$_{1-10}$ alkyl), —C(O)(O—C$_{2-10}$ alkenyl), —OC(O)NH$_2$; —OC(O)NH(C$_{1-4}$ alkyl)-; —O—(CO)—(C$_{1-4}$ alkyl); C$_{1-4}$ alkyl optionally substituted with 1-3 substituents independently selected from C$_{1-4}$ alkyl, C$_{1-4}$alkoxy, —OH, —NH$_2$, and fluorine; C$_{2-6}$ alkenyl optionally substituted with 1-3 substituents independently selected from C$_{1-4}$ alkyl, C$_{1-4}$alkoxy, —OH, —NH$_2$, and fluorine; C$_{2-6}$alkynyl optionally substituted with 1-3 substituents independently selected from $C_{1-4}$ alkyl, $C_{1-4}$alkoxy, —OH, —NH$_2$, and fluorine; $C_{3-6}$ cycloalkyl optionally substituted with 1-3 substituents independently selected from $C_{1-4}$ alkyl and fluorine; $C_{3-6}$ cycloalkoxy optionally substituted with 1-3 substituents independently selected from $C_{1-4}$ alkyl and fluorine; or $C_{1-4}$alkoxy optionally substituted with 1-3 substituents independently selected from $C_{1-4}$ alkyl, $C_{1-4}$alkoxy, —OH, —NH$_2$, and fluorine. In some embodiments, each of $R^{20}$, $R^{21}$, and $R^{22}$ at each occurrence can be independently F; Cl; —OH; —NH$_2$, —SO$_2$NH$_2$, —SO$_2$NH(C$_{1-4}$ alkyl), —SO$_2$NH(C$_{1-4}$ alkanoyl), —COOH;

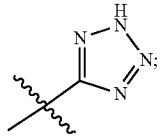 [SMILES: *c1nn[nH]n1]

—C(O)(O—C$_{1-10}$ alkyl), —C(O)(O—C$_{2-10}$ alkenyl), —OC(O)NH$_2$; —OC(O)NH(C$_{1-4}$ alkyl)-; —O—(CO)—(C$_{1-4}$ alkyl); —O—(C$_{1-6}$ alkyl); —O—(C$_{2-6}$alkenyl); C$_{1-6}$ alkyl optionally substituted with 1-3 substituents independently selected from C$_{1-4}$ alkyl, C$_{1-6}$alkoxy, —OH, —NH$_2$, and fluorine; or C$_{2-6}$ alkenyl optionally substituted with 1-3 substituents independently selected from C$_{1-4}$ alkyl, C$_{1-6}$ alkoxy, —OH, —NH$_2$, and fluorine. In some embodiments, each of $R^{20}$, $R^{21}$, and $R^{22}$ at each occurrence can be independently —OH, C$_{1-4}$ alkyl, C$_{2-6}$ alkenyl, or —O—(C$_{1-4}$ alkyl). In some embodiments, each of $R^{20}$, $R^{21}$, and $R^{22}$ at each occurrence can be independently —OH, —OMe, or

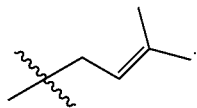 [SMILES: *CC=C(C)C]

In some embodiments, one or more instances of $R^{20}$, one or more instances of $R^{21}$, and/or one or more instances of $R^{22}$ can be independently selected $L^{11'}$-$W^{10'}$ as described herein.

Typically, m and p, as applicable, is 0, 1, 2, or 3; preferably, 1 or 2.

Typically, n, as applicable, is 0, 1, or 2; preferably 0 or 1.

In some embodiments, the compound of Formula II can have a formula according to any of Formula II-8 to II-10:

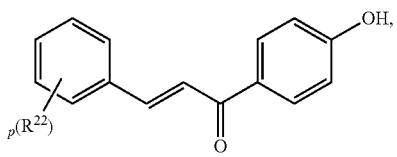

Formula II-8

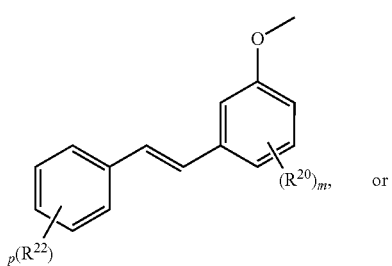

Formula II-9

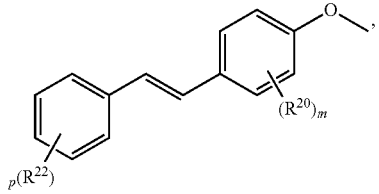

Formula II-10 wherein $R^{20}$, $R^{22}$, m, and p are defined herein. In some embodiments, m is 1 or 2, p is 1, 2, or 3. In some embodiments, each of $R^{20}$ and $R^{22}$ at each occurrence is independently F; Cl; —OH; —NH$_2$, —SO$_2$NH$_2$, —SO$_2$NH(C$_{1-4}$ alkyl), —SO$_2$NH(C$_{1-4}$ alkanoyl), —COOH;

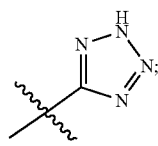

—C(O)(O—C$_{1-10}$ alkyl), —C(O)(O—C$_{2-10}$ alkenyl), —OC(O)NH$_2$; —OC(O)NH(C$_{1-4}$ alkyl)-; —O—(CO)—(C$_{1-4}$ alkyl); —O—(C$_{1-6}$ alkyl); —O—(C$_{2-6}$ alkenyl); C$_{1-6}$ alkyl optionally substituted with 1-3 substituents independently selected from C$_{1-4}$ alkyl, C$_{1-6}$alkoxy, —OH, —NH$_2$, and fluorine; or C$_{2-6}$ alkenyl optionally substituted with 1-3 substituents independently selected from C$_{1-4}$ alkyl, C$_{1-6}$alkoxy, —OH, —NH$_2$, and fluorine.

In some embodiments, the structural unit

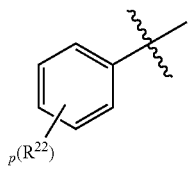

in any of the applicable Formula II can be selected from

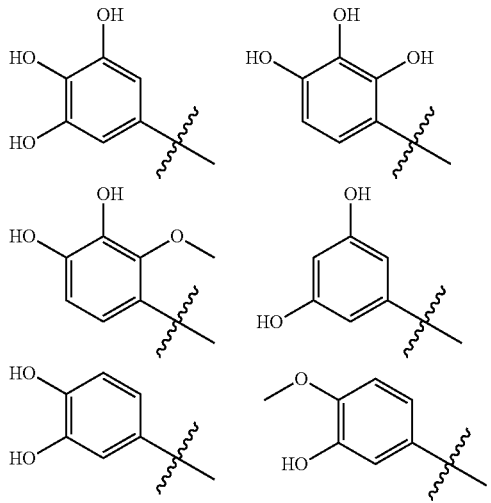

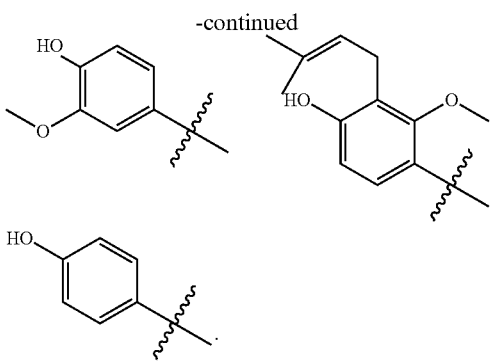

In some specific embodiments, the compound of Formula II can be:

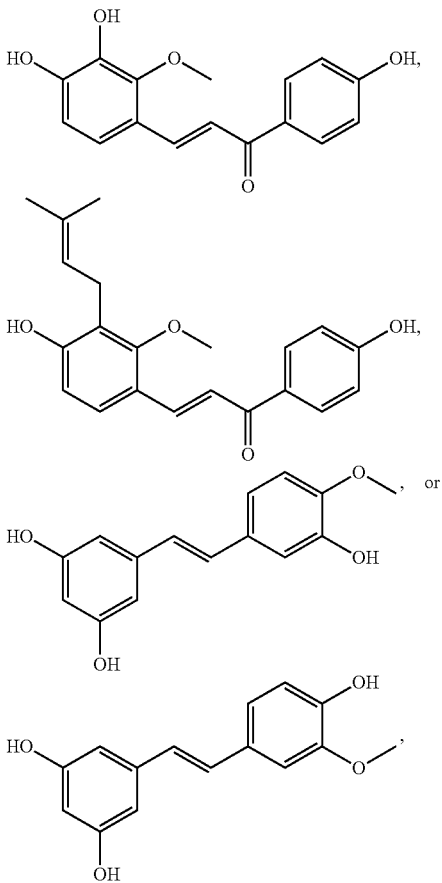

or a pharmaceutically acceptable salt or ester thereof.

In some embodiments, the compounds herein can be characterized by having a Formula III, or a pharmaceutically acceptable salt or ester thereof:

$$Ar^{20}\text{-}L^{20}\text{-}W^{20} \qquad \text{Formula III}$$

wherein $Ar^{20}$ is an optionally substituted aryl ring (e.g., $C_{6-10}$ aryl ring), or an optionally substituted heteroaryl ring (e.g., 5-10 membered heteroaryl ring);

$L^{20}$ is null, an optionally substituted $C_{1-6}$ alkylene, an optionally substituted $C_{1-6}$ heteroalkylene, an optionally substituted $C_{2-6}$ alkenylene, an optionally substituted $C_{2-6}$ alkynylene, an optionally substituted $C_{3-6}$ cycloalkylene, an optionally substituted arylene, an optionally substituted heteroaryl ene, or an optionally substituted 4-7 membered heterocyclylene, $W^{20}$ is $-OR^1$; $-COR^2$; $-COOR^{1a}$; $-OCOOR^{1a}$; $-NR^3R^4$; $-CONR^{3a}R^{4a}$; $-OCONR^{3b}R^{4b}$; $-SO_2NR^{3c}R^{4c}$; $-OSO_2NR^{3d}R^{4d}$; $-SR^5$; $-SO_2R^{5a}$; $-OCOR^{2a}$; $-OSO_2R^{5a}$; or

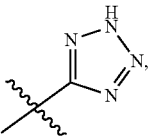

wherein:

$R^1$ and $R^{1a}$ are each independently hydrogen, optionally substituted alkyl, optionally substituted alkenyl, optionally substituted alkynyl, optionally substituted cycloalkyl, optionally substituted aryl, optionally substituted heteroaryl, or optionally substituted heterocyclyl;

$R^3$ and $R^4$ are each independently hydrogen, $-COR^{2b}$, $-SO_2R^{5b}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl, or $R^3$ and $R^4$ together with the atoms they are bound to form an optionally substituted 4-7 membered heterocyclyl;

$R^2$, $R^{2a}$, $R^{2b}$, $R^5$, $R^{5a}$, and $R^{5b}$ are each independently hydrogen, $-OH$, $-NR^{3e}R^{4e}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; and $R^{3a}$, $R^{3b}$, $R^{3c}$, $R^{3d}$, $R^{3e}$, $R^{4a}$, $R^{4b}$, $R^{4c}$, $R^{4d}$, and $R^{4e}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or $R^{3a}$ and $R^{4a}$, $R^{3b}$ and $R^{4b}$, $R^{3c}$ and $R^{4c}$, $R^{3d}$ and $R^{4d}$, or $R^{3e}$ and $R^{4e}$, together with the atoms they are bound to form an optionally substituted 4-7 membered heterocyclyl.

In some embodiments, $Ar^{20}$ in Formula III is an optionally substituted phenyl ring or an optionally substituted 5 or 6 membered heteroaryl ring. For example, in some embodiments, Ar in Formula III can be an optionally substituted phenyl ring, an optionally substituted thienyl ring, an optionally substituted furanyl ring, an optionally substituted pyridyl ring, or an optionally substituted pyrimidinyl ring. In some embodiments, Ar in Formula III can also be an optionally substituted bicyclic aryl or bicyclic heteroaryl ring, each of which is optionally substituted. In such embodiments, $L^{20}\text{-}W^{20}$ can be attached to either of the bicyclic rings.

In some embodiments, Ar in Formula III can be an optionally substituted phenyl ring, wherein two adjacent substituents together with the carbon they are attached to form an optionally substituted cycloalkyl, heterocyclyl, aryl, or heteroaryl ring.

For example, in some embodiments, Ar in Formula III can be a benzofused bicyclic aryl or heteroaryl ring. For example, in some embodiments, Ar in Formula III can have the following structure:

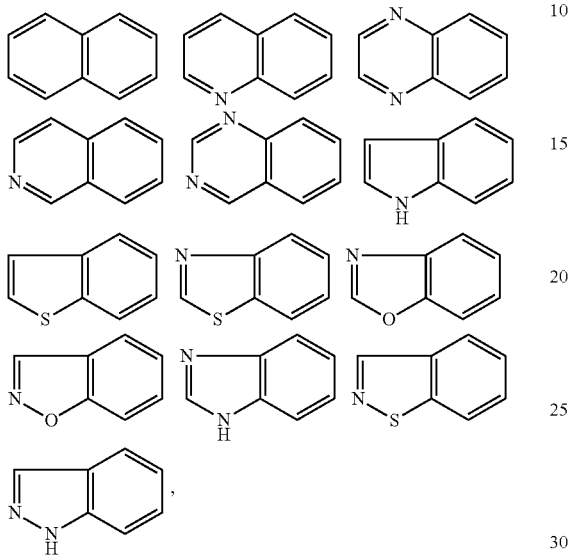

wherein -$L^{20}$-$W^{20}$ can be attached at either of the two rings, wherein either or both of the rings can be optionally substituted.

In some embodiments, the compound of Formula III can have a Formula III-1, III-2, or III-3:

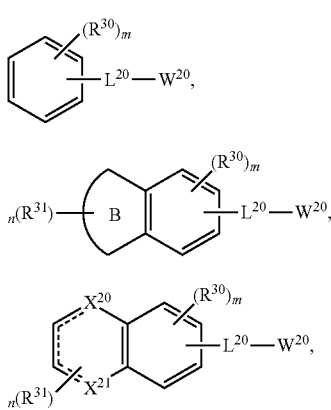

wherein $L^{20}$ and $W^{20}$ are defined herein,
m is 0, 1, 2, or 3; n is 0, 1, 2, or 3;
  each of $R^{30}$ and $R^{31}$ at each occurrence is independently halogen, -$L^{20'}$-$W^{20'}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; wherein -$L^{20'}$-$W^{20'}$ at each occurrence is independently selected; wherein $L^{20'}$ at each occurrence is independently null, an optionally substituted $C_{1-6}$ alkylene, an optionally substituted $C_{1-6}$ heteroalkylene, an optionally substituted $C_{2-6}$ alkenylene, an optionally substituted $C_{2-6}$ alkynylene, an optionally substituted $C_{3-6}$ cycloalkylene, an optionally substituted arylene, an optionally substituted heteroarylene, or an optionally substituted 4-7 membered heterocyclylene; and $W^{20'}$ at each occurrence is independently —$OR^1$; —$COR^2$; —$COOR^{1a}$; —$OCOOR^{1a}$; —$NR^3R^4$; —$CONR^{3a}R^{4a}$; —$OCONR^{3b}R^{4b}$; —$SO_2NR^{3c}R^{4c}$; —$OSO_2NR^{3d}R^{4d}$; —$SR^5$; —$SO_2R^{5a}$; —$OCOR^{2a}$; —$OSO_2R^{5a}$ or

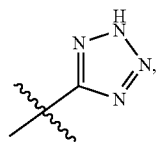

wherein $R^1$, $R^{1a}$, $R^2$, $R^{2a}$, $R^{2b}$, $R^3$, $R^4$, $R^{3a}$, $R^{3b}$, $R^{3c}$, $R^{3d}$, $R^{3e}$, $R^{4a}$, $R^{4b}$, $R^{4c}$, $R^{4d}$, $R^{4e}$, $R^5$, $R^{5a}$, and $R^{5b}$ are defined herein, see e.g., Formula III,
ring B is a 4-7 membered cycloalkyl ring, 4-7 membered heterocyclic ring, phenyl ring, 5 or 6 membered heteroaryl ring, each of which is optionally substituted 1-3 independently selected $R^{31}$;
$X^{20}$ and $X^{21}$ are each independently null, —O—, —C(O)—, —S—, —$NR^{100a}$—, —S(O)—, —$SO_2$—, or —$CR^{101a}R^{102a}$—, as valence permits;
wherein $R^{100a}$ is lone pair (as applicable), hydrogen, $COR^{2c}$, —$SO_2R^{5c}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl; or $R^{100a}$ and one of $R^{30}$ or $R^{31}$, together with the atoms they are bound to, form an optionally substituted heterocyclic or heteroaryl ring, e.g., optionally substituted 5 or 6 membered heteroaryl, or optionally substituted 4-7 membered heterocyclyl;
$R^{101a}$ and $R^{102a}$, when present, are each independently hydrogen, —OH, halogen; optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$ alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl, or $R^{101a}$ and $R^{102a}$, together with the atoms they are bound to form an optionally substituted 3-7 membered cycloalkyl or heterocyclyl ring; or one of $R^{101a}$ and $R^{102a}$ forms an optionally substituted cycloalkyl or heterocyclyl ring together with a $R^{30}$ or $R^{31}$ group; and
$R^{2c}$ and $R^{5c}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl;

or two adjacent $R^{30}$ or two adjacent $R^{31}$, or $R^{30}$ or $R^{31}$ and $X^{20}$ or $X^{21}$, together with the atoms they are bound to form an optionally substituted cycloalkyl, heterocyclyl, aryl, or heteroaryl ring.

When $X^{20}$ or $X^{21}$ forms a double bond with one of the ring carbons, it cannot be $CR^{101a}R^{102a}$ with both $R^{101a}$ and $R^{102a}$ present, as the valence of the carbon will exceed 4. In such cases, it should be understood that one of $R^{101a}$ and $R^{102a}$ is absent and $X^{20}$ or $X^{21}$ is $CR^{101a}$ or $CR^{102a}$ as defined herein. When $X^{20}$ or $X^{21}$ forms a double bond with one of the ring carbons, it can be $NR^{100a}$ with $R^{100a}$ typically being a lone pair.

It should be noted that each instance of the structural unit -$L^{20'}$-$W^{20'}$ and -$L^{20}$-$W^{20}$ are independently selected and can be the same or different.

In some embodiments, the compound of Formula III can have a structure of any of the following:

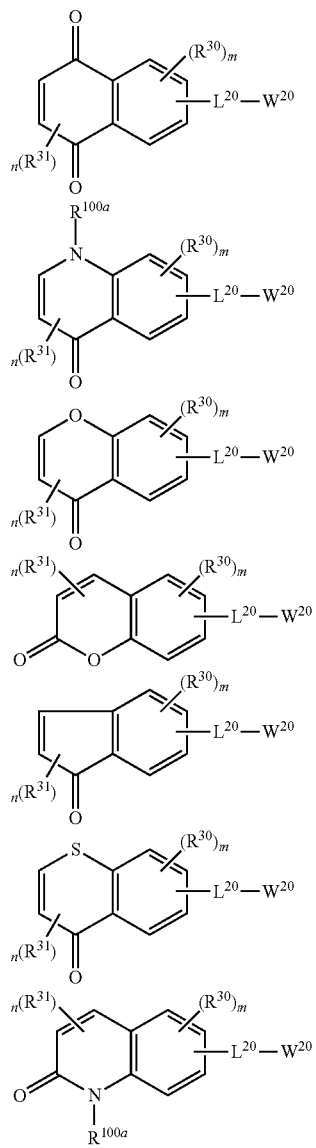
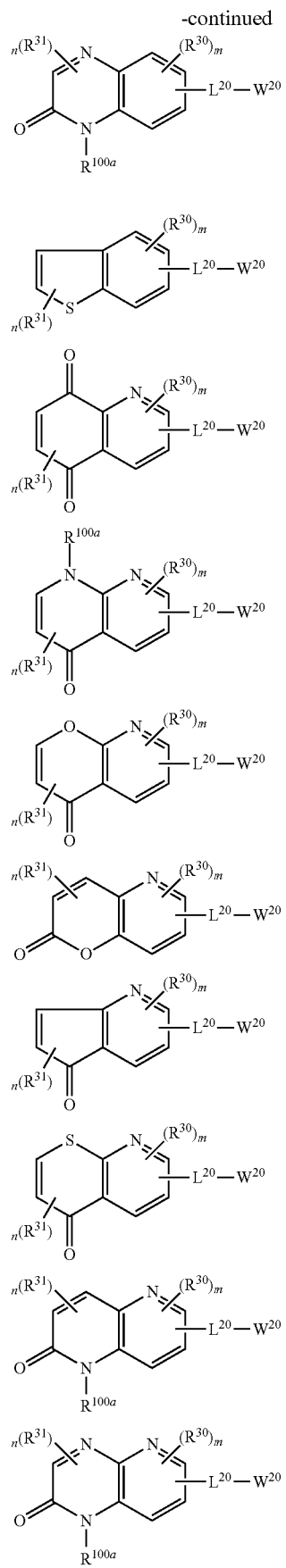

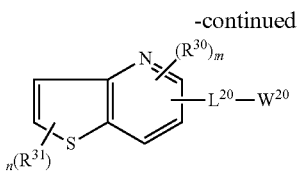

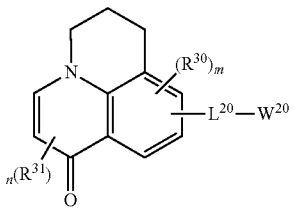

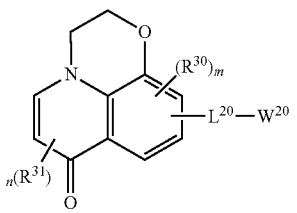

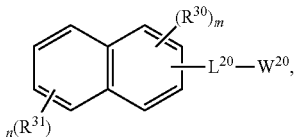

wherein: $R^{30}$, m, $R^{31}$, n, $R^{100a}$, $L^{20}$, and $W^{20}$ are defined herein, see e.g., Formula III and sub-formulae herein, such as Formula III-1 to III-3, wherein for the tricyclic structures, the piperidine ring or the morpholine ring can be optionally substituted.

$L^{20}$ in Formula III (e.g., any of the sub-formulae such as Formula III-1 to III-3) is typically null, i.e., the $W^{20}$ group is directly attached to $Ar^{20}$. In some embodiments, $L^{20}$ in Formula III can also be a $C_{1-4}$ alkylene, $C_{2-4}$ alkenylene, $C_{2-4}$ alkynylene or $C_{1-4}$ heteroalkylene. For example, the $W^{20}$ group can be attached to $Ar^{20}$, through a methylene or a vinyl group.

Various W groups are suitable for compounds of Formula III (e.g., any of the sub-formulae such as Formula III-1 to III-3). In preferred embodiments, W in Formula III can be —OH, —COOH,

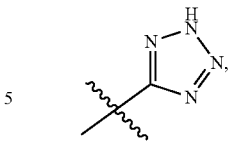

—C(O)(O—$C_{1-10}$ alkyl), —C(O)(O—$C_{2-10}$ alkenyl), —OC(O)NH$_2$, —NH$_2$, —SO$_2$NH$_2$, —SO$_2$NH($C_{1-4}$ alkyl); —SO$_2$NH($C_{1-4}$alkanoyl), —OC(O)NH($C_{1-4}$ alkyl)-, —O—(CO)—($C_{1-4}$ alkyl), —O—($C_{1-4}$ alkyl), wherein each of the $C_{1-4}$ alkyl is independently optionally substituted with 1-3 substituents independently selected from $C_{1-4}$ alkyl, $C_{1-4}$alkoxy, —OH, —NH$_2$, and fluorine. In some embodiments, $W^{20}$ group in Formula III (e.g., any of the sub-formulae such as Formula III-1 to III-3) is —OH, —NH$_2$, —SO$_2$NH$_2$, —SO$_2$NH(Acetyl), —C(O)—(O—$C_8$ alkyl), —COOH, or —O—C(O)—CH$_3$.

As described herein, $L^{20'}$-$W^{20'}$ can in some embodiments be selected as a substituent for $Ar^{20}$. When applicable, $L^{20'}$ in Formula III, including any of the sub-formulae described herein, such as Formula III-1 to III-3, at each occurrence can be independently null, i.e., the $W^{20'}$ group is directly attached to $Ar^{20}$, as applicable, or a $C_{1-4}$ alkylene, $C_{2-4}$ alkenylene, $C_{2-4}$ alkynylene or $C_{1-4}$ heteroalkylene. For example, the $W^{20'}$ group can be attached to $Ar^{20}$, as applicable, through a methylene or vinyl group. When applicable, $W^{20'}$ in Formula III, including any of the sub-formulae described herein, such as Formula III-1 to III-3, at each occurrence can be independently —OH, —COOH,

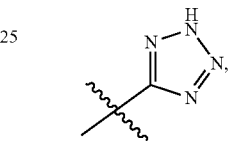

—C(O)(O—$C_{1-10}$ alkyl), —C(O)(O—$C_{2-10}$ alkenyl), —OC(O)NH$_2$, —NH$_2$, —SO$_2$NH$_2$, —SO$_2$NH($C_{1-4}$alkyl); —SO$_2$NH($C_{1-4}$alkanoyl), —OC(O)NH($C_{1-4}$ alkyl)-, —O—(CO)—($C_{1-4}$ alkyl), —O—($C_{1-4}$ alkyl), wherein each of the $C_{1-4}$ alkyl is independently optionally substituted with 1-3 substituents independently selected from $C_{1-4}$ alkyl, $C_{1-4}$alkoxy, —OH, —NH$_2$, and fluorine. In some embodiments, each instance of $W^{20'}$ in Formula III, when applicable, can be —OH, —NH$_2$, —SO$_2$NH$_2$, —SO$_2$NH(Acetyl),

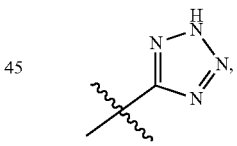

—COOH, —C(O)(O—$C_8$ alkyl) or —O—C(O)—CH$_3$.

Various groups can be suitable for $R^{30}$ and $R^{31}$ in any of the applicable Formula III (e.g., any of the sub-formulae such as Formula III-1 to III-3). In some embodiments, each of $R^{30}$ and $R^{31}$ at each occurrence can be independently F; Cl; —OH; —COOH; —OC(O)NH$_2$; —OC(O)NH($C_{1-4}$ alkyl)-; —O—(CO)—($C_{1-4}$ alkyl); $C_{1-4}$ alkyl optionally substituted with 1-3 substituents independently selected from $C_{1-4}$ alkyl, $C_{1-4}$alkoxy, —OH, —NH$_2$, and fluorine; $C_{2-6}$ alkenyl optionally substituted with 1-3 substituents independently selected from $C_{1-4}$ alkyl, $C_{1-4}$alkoxy, —OH, —NH$_2$, and fluorine; $C_{2-6}$alkynyl optionally substituted with 1-3 substituents independently selected from $C_{1-4}$ alkyl, $C_{1-4}$alkoxy, —OH, —NH$_2$, and fluorine; $C_{3-6}$ cycloalkyl optionally substituted with 1-3 substituents independently selected from $C_{1-4}$ alkyl and fluorine; $C_{3-6}$ cycloalkoxy optionally substituted with 1-3 substituents independently selected from $C_{1-4}$ alkyl and fluorine; or $C_{1-4}$alkoxy optionally substituted with 1-3 substituents independently selected from $C_{1-4}$ alkyl, $C_{1-4}$ alkoxy, —OH, —NH$_2$, and fluorine. In some embodiments, each of $R^{30}$ and $R^{31}$ at each occurrence can be independently —OH, $C_{2-6}$ alkenyl, —O—($C_{1-4}$ alkyl), —COOH, or —C(O)(O—$C_{1-10}$ alkyl). In some embodiments, each of $R^{30}$ and $R^{31}$ at each occurrence can be —OH or —OMe. In some embodiments, one or more instances of $R^{30}$ and/or one or more instances of $R^{31}$ can be independently selected $L^{20'}$-$W^{20'}$ as described herein.

Typically, m is 0, 1, 2, or 3; preferably, 2 or 3. Typically, n is 1, 2 or 3.

In some embodiments, the present disclosure also provides the following compound,

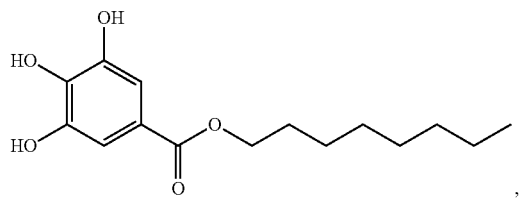 [SMILES: CCCCCCCCOC(=O)c1cc(O)c(O)c(O)c1]

a pharmaceutically acceptable salt or ester thereof.

In some embodiments, the present disclosure also provides the following compound,

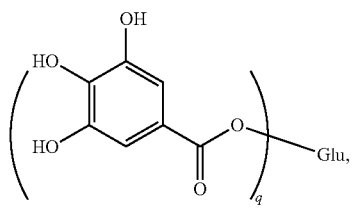

a pharmaceutically acceptable salt or ester thereof, wherein q is 1, 2, 3, 4, or 5, and Glu is a residue of glucose. In some specific embodiments, the present disclosure also provides

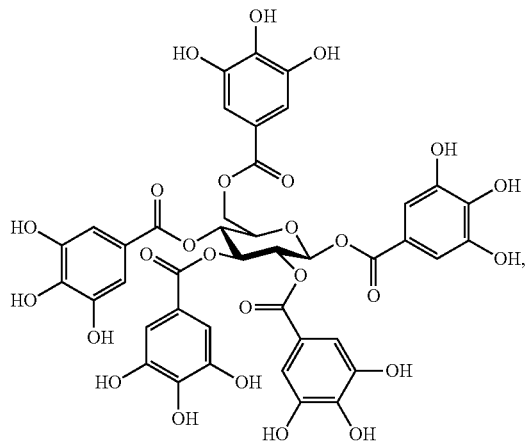

a pharmaceutically acceptable salt or ester thereof.

In some embodiments, the compounds herein can also be an alkaloid having antibacterial activity. As shown herein, certain indole alkaloids, such as *Vinca* alkaloids, tabersonine, vindoline, vinblastine, vincristine, etc., are shown to be effective in killing the microorganisms such as *B. megate-rium*. In some embodiments, the compounds herein are characterized by Formula IV-1 or IV-2, which are tabersonine or vindoline and derivatives:

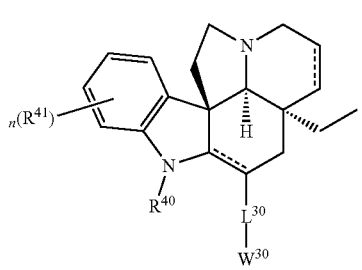

Formula IV-1

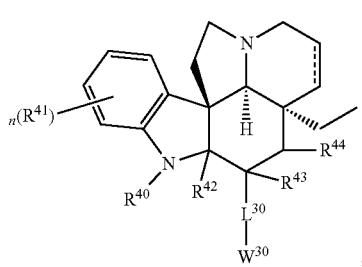

Formula IV-2 wherein:
$R^{40}$ is hydrogen; —COR$^2$; —COOR$^{1a}$; —SO$_2$R$^{5a}$; optionally substituted alkyl, optionally substituted alkenyl, optionally substituted alkynyl, optionally substituted cycloalkyl, optionally substituted aryl, optionally substituted heteroaryl, or optionally substituted heterocyclyl;

$R^{41}$ is —OR$^1$; —OCOOR$^{1a}$; —OCONR$^{3b}$R$^{4b}$; —OCOR$^{2a}$; or —OSO$_2$R$^{5a}$; n is 0 or 1;

$R^{42}$, $R^{43}$, and $R^{44}$ are each independently hydrogen, —OR$^1$, OCOR$^{2a}$; or —OSO$_2$R$^{5a}$;

$L^{30}$ is null or methylene, $W^{30}$ is —OR$^1$; —COR$^2$; —COOR$^{1a}$; —OCOOR$^{1a}$; —NR$^3$R$^4$; —CONR$^{3a}$R$^{4a}$; —OCONR$^{3b}$R$^{4b}$; —OSO$_2$NR$^{3d}$R$^{4d}$; —OCOR$^{2a}$; or —OSO$_2$R$^{5a}$ wherein:
$R^1$ and $R^{1a}$ are each independently hydrogen, optionally substituted alkyl, optionally substituted alkenyl, optionally substituted alkynyl, optionally substituted cycloalkyl, optionally substituted aryl, optionally substituted heteroaryl, or optionally substituted heterocyclyl;

$R^3$ and $R^4$ are each independently hydrogen, —COR$^{2b}$, —SO$_2$R$^{5b}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl, or $R^3$ and $R^4$ together with the atoms they are bound to form an optionally substituted 4-7 membered heterocyclyl;

$R^2$, $R^{2a}$, $R^{2b}$, $R^5$, $R^{5a}$, and $R^{5b}$ are each independently hydrogen, —OH, —NR$^{3e}$R$^{4e}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; and $R^{3a}$, $R^{3b}$, $R^{3c}$, $R^{3d}$, $R^{3e}$, $R^{4a}$, $R^{4b}$, $R^{4c}$, $R^{4d}$, and $R^{4e}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or $R^{3a}$ and $R^{4a}$, $R^{3b}$ and $R^{4b}$, $R^{3c}$ and $R^{4c}$, $R^{3d}$ and $R^{4d}$, or $R^{3e}$ and $R^{4e}$, together with the atoms they are bound to form an optionally substituted 4-7 membered heterocyclyl.

In some embodiments, the compound of Formula IV-1 or IV-2 has a formula according to one of Formula IV-3 to IV-6:

Formula IV-3

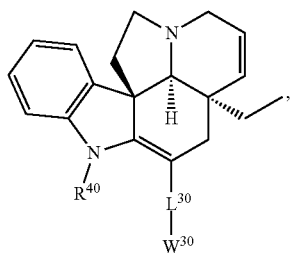

Formula IV-4

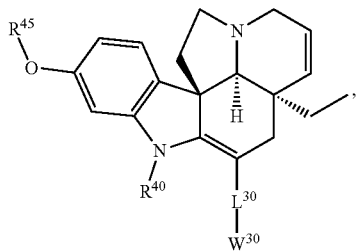

Formula IV-5

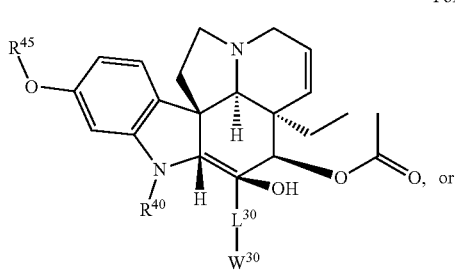

Formula IV-6

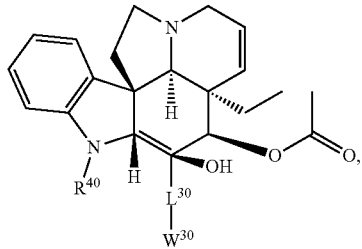

wherein $R^{45}$ is hydrogen or methyl.

In some embodiments, $R^{40}$ in any of the Formula IV-1 to IV-6 can be hydrogen, $C_{1-4}$ alkyl, or $C_{1-4}$alkanoyl.

$L^{30}$ in Formula IV-1 to IV-6 is typically null. However, in some embodiments, $L^{30}$ in Formula IV-1 to IV-6 can also be $CH_2$.

$W^{30}$ in Formula IV-1 to IV-6 is typically a carboxylic acid derivative, an amine derivative or an alcohol derivative, which are useful for the compositions and methods herein. The naturally occurring indole alkaloid tabersonine contains a $CO_2Me$ group as $W^{30}$, with $L^{30}$ being null. The $CO_2Me$ group can be transformed into the corresponding acid, amide etc. via routine transformations, or it can be reduced or transformed into an amine through a rearrangement such as Curtius rearrangement. In some embodiments, W in Formula IV-1 to IV-6 can be —OH, —$NH_2$, —$OSO_2NH_2$, —COOH, —C(O)(O—$C_{1-10}$ alkyl), —C(O)(O—$C_{2-10}$ alkenyl), —OC(O)$NH_2$, —OC(O)NH($C_{1-4}$ alkyl)-, —O—(CO)—($C_{1-4}$ alkyl), —O—($C_{1-4}$ alkyl), wherein each of the $C_{1-4}$ alkyl is independently optionally substituted with 1-3 substituents independently selected from $C_{1-4}$ alkyl, $C_{1-4}$ alkoxy, —OH, —$NH_2$, and fluorine. In some embodiments, W in Formula IV-1 to IV-6 can be —OH, —$NH_2$, —$OSO_2NH_2$, —C(O)—(O—$C_8$ alkyl), —COOH, or —OC(O)$NH_2$.

In some specific embodiments, the compound can have the following structure:

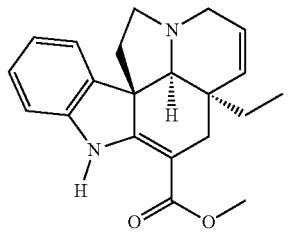

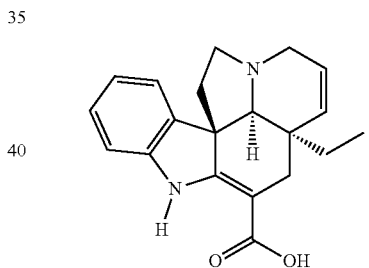

In some embodiments, the compounds herein can also be a glycoside having antibacterial activity, or a pharmaceutically acceptable salt or ester thereof. As shown herein, certain glycosides, such as ginsenosides, and gallic acid glycosides, are shown to be effective in killing the microorganisms such as *B. megaterium*. Other useful glycosides include any of those known in the art to have antibacterial activities, which can for example, include glycosides characterized by its corresponding aglyone being a phenolic compound, a flavonoid, a coumarin, a benzoic acid, or a sterol. Typically, the glycoside is a glucoside, although other glycosides can also be useful. In some embodiments, the glycosides can be characterized as amphiphilic, which can destroy biological membranes and confer antimicrobial activity to the glycosides. In some embodiments, the glycosides can also be characterized as a saponin, which for example, include various plant derived glycosides that can act as "surfactants" and can help to kill bacteria.

In some embodiments, the glycosides herein can be characterized by a Formula V:

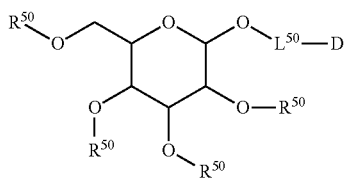

Formula V wherein each $R^{50}$ is independently hydrogen, -$L^{50}$-D, an oxygen protecting group, or a sugar residue;

$L^{50}$ is null or —C(O)—;

D is an optionally substituted aryl (e.g., $C_{6-10}$ aryl), optionally substituted heteroaryl (e.g., 5 to 14 membered heteroaryl), optionally substituted fused ring comprising two or more rings independently selected from aryl, heteroaryl, cycloalkyl and heterocyclyl (e.g., 8-14 membered, e.g., benzofused cycloalkyl/heterocyclyl, pyridofused cycloalkyl/heterocyclyl), or a steroid residue having a formula V-A:

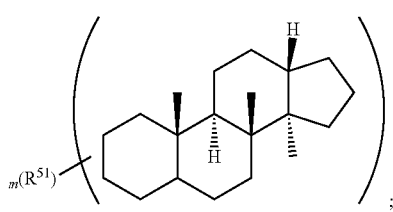

Formula V-A wherein

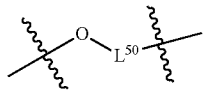

can connect to Formula V-A via the steroid backbone or any of the $R^{51}$ group(s), as valence permits, wherein $R^{51}$ at each occurrence is independently optionally substituted alkyl, optionally substituted alkenyl, optionally substituted alkynyl, —OH optionally substituted with an oxygen protecting group, oxo, halogen, optionally substituted cycloalkyl, optionally substituted alkoxy, optionally substituted cycloalkoxy, optionally substituted amino group, optionally substituted phenyl, optionally substituted heteroaryl, or optionally substituted heterocyclyl, or two $R^{51}$ groups together with the atoms they are bound to form an optionally substituted cycloalkyl, heterocyclyl, aryl, or heteroaryl ring;

m is an integer of 1-8; and wherein -$L^{50}$-D at each occurrence is independently selected.

In some embodiments, each $R^{50}$ is hydrogen.

In some embodiments, one to four $R^{50}$ can be -$L^{50}$-D which are independently selected. When two or more -$L^{50}$-D units are linked to the pyranose unit in Formula V, they are preferably the same. In some embodiments, one or more (e.g., 1 or 2) $R^{50}$ can be a sugar residue which connects to the remainder of Formula V via a glycoside bond. In some embodiments, the sugar residue is a glucose residue or a rhamnose residue.

$L^{50}$ in Formula V can be null or a carbonyl group, —C(O)—, depending on whether the linking group is a phenolic —OH or a COOH group from a benzoic acid or a heteraryl counterpart.

Various residues can be used as D, which is typically residue from a phenolic compound, a coumarin, a flavonoid, or a sterol, which in some embodiments can have antibacterial activity without the glycoside unit.

In some embodiments, D can be an optionally substituted ring selected from:

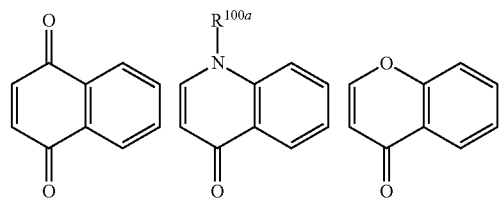

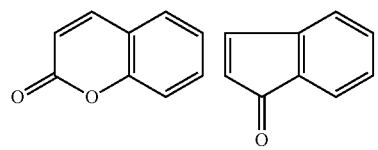

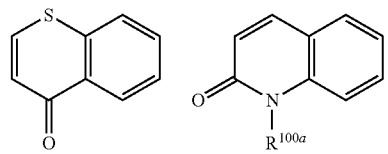

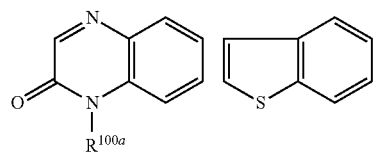

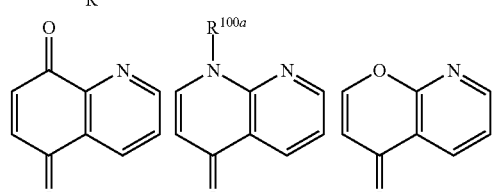

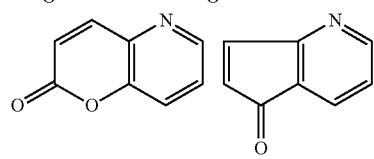

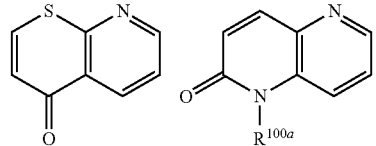

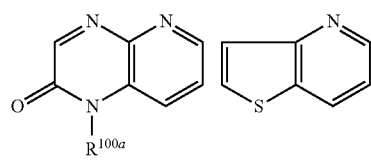

-continued

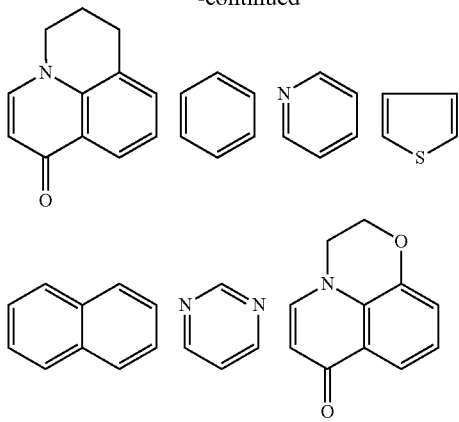

wherein
$R^{100a}$ is lone pair (as applicable), hydrogen, nitrogen protecting group, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl; or $R^{100a}$ forms an optionally substituted heterocyclic or heteroaryl ring with the pheny or pyridyl ring;
wherein

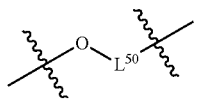

can connect to D via any of the available positions, and each of the ring systems of D is optionally substituted with 1-5 (e.g., 1, 2, or 3) substituents each independently selected from —OH; —COOH; —C(O)(O—$C_{1-10}$ alkyl); —C(O)(O—$C_{2-10}$ alkenyl); —OC(O)NH$_2$; —OC(O)NH($C_{1-4}$ alkyl)-; —O—(CO)—($C_{1-4}$ alkyl); —NH$_2$; —SO$_2$NH$_2$; —SO$_2$NH($C_{1-4}$ alkyl); —SO$_2$NH($C_{1-4}$alkanoyl); halogen; optionally substituted $C_{1-6}$ alkyl; optionally substituted $C_{2-6}$ alkenyl; optionally substituted $C_{2-6}$ alkynyl; optionally substituted $C_{3-6}$ cycloalkyl; optionally substituted $C_{1-6}$alkoxy; optionally substituted $C_{3-6}$cycloalkoxy; optionally substituted amino group; optionally substituted phenyl; optionally substituted 5 or 6 membered heteroaryl; or optionally substituted 4-7 membered heterocyclyl.

In some embodiments, each of the ring systems of D as shown above can be optionally substituted with 1-5 substituents each independently selected from F; Cl; —OH; —COOH; —C(O)(O—$C_{1-10}$ alkyl); —C(O)(O—$C_{2-10}$ alkenyl); —OC(O)NH$_2$; —OC(O)NH($C_{1-4}$ alkyl)-; —O—(CO)—($C_{1-4}$ alkyl); —NH$_2$; —SO$_2$NH$_2$; —SO$_2$NH($C_{1-4}$alkyl); —SO$_2$NH($C_{1-4}$alkanoyl); $C_{1-4}$ alkyl optionally substituted with 1-3 substituents independently selected from $C_{1-4}$ alkyl; $C_{1-4}$ alkoxy, —OH, —NH$_2$, and fluorine; $C_{2-6}$ alkenyl optionally substituted with 1-3 substituents independently selected from $C_{1-4}$ alkyl, $C_{1-4}$ alkoxy, —OH, —NH$_2$, and fluorine; $C_{2-6}$alkynyl optionally substituted with 1-3 substituents independently selected from $C_{1-4}$ alkyl, $C_{1-4}$ alkoxy, —OH, —NH$_2$, and fluorine; $C_{3-6}$ cycloalkyl optionally substituted with 1-3 substituents independently selected from $C_{1-4}$ alkyl and fluorine; $C_{3-6}$ cycloalkoxy optionally substituted with 1-3 substituents independently selected from $C_{1-4}$ alkyl and fluorine; or $C_{1-4}$ alkoxy optionally substituted with 1-3 substituents independently selected from $C_{1-4}$ alkyl, $C_{1-4}$ alkoxy, —OH, —NH$_2$, and fluorine.

In some embodiments, D can be selected from:

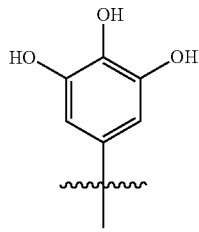

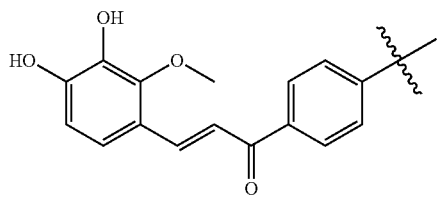

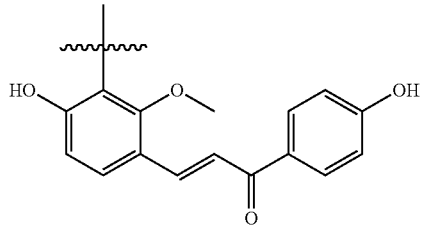

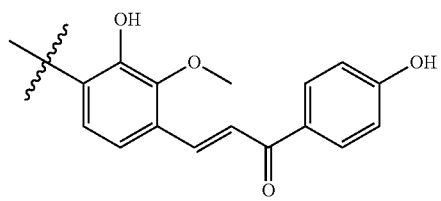

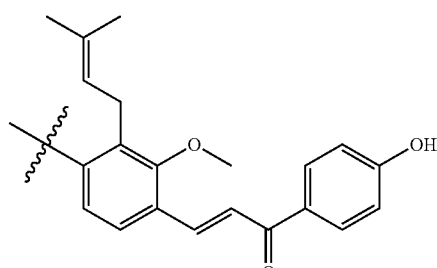

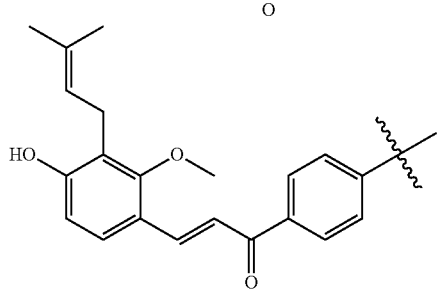

-continued

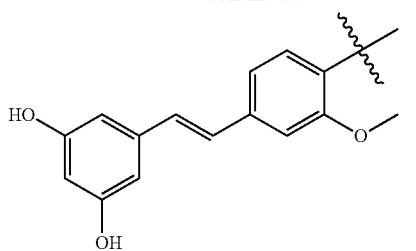

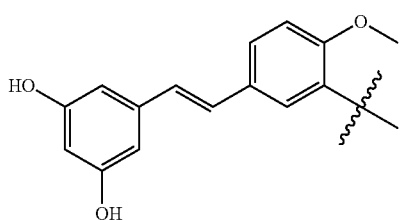

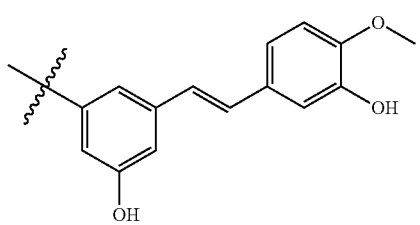

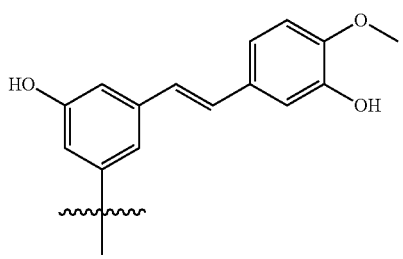

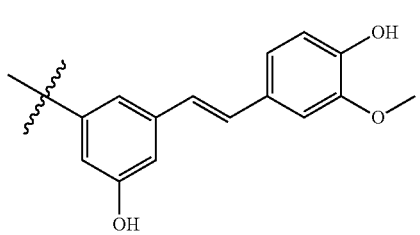

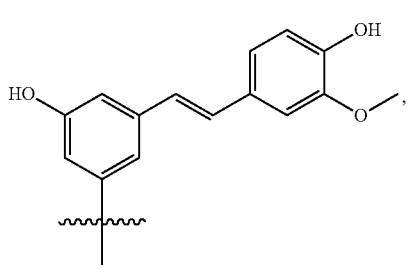

wherein each of the phenolic OH group is optionally linked to a sugar (such as glucose) via a glycoside bond.

In some embodiments, D is derived from a sterol. For example, in some embodiments, D is

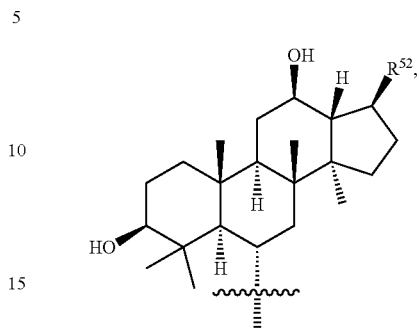

wherein $R^{52}$ is an optionally substituted alkyl or an optionally substituted alkenyl, wherein each of the remaining —OH groups in D is optionally linked to a sugar via a glycoside bond.

Preferably, $R^{52}$ can be

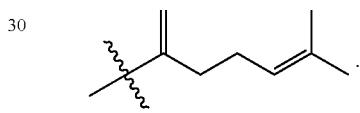

In any of the embodiments described hereinabove, the glycoside can have Formula V-1 or V-2:

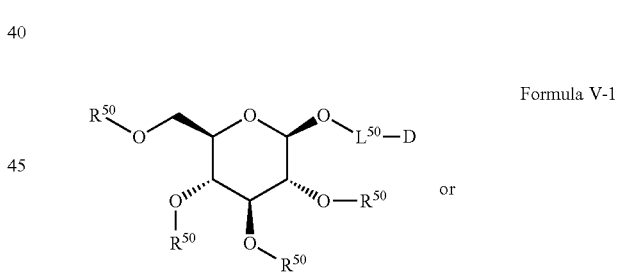

Formula V-1 or

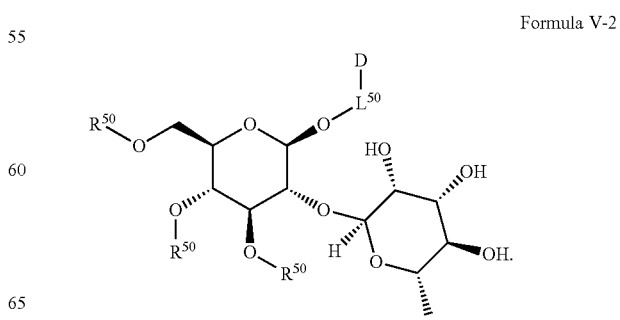

Formula V-2

In some embodiments, the glycoside can be a compound selected from:

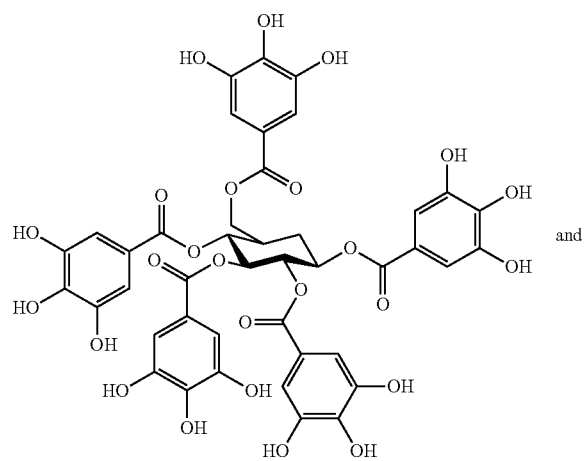

5 and

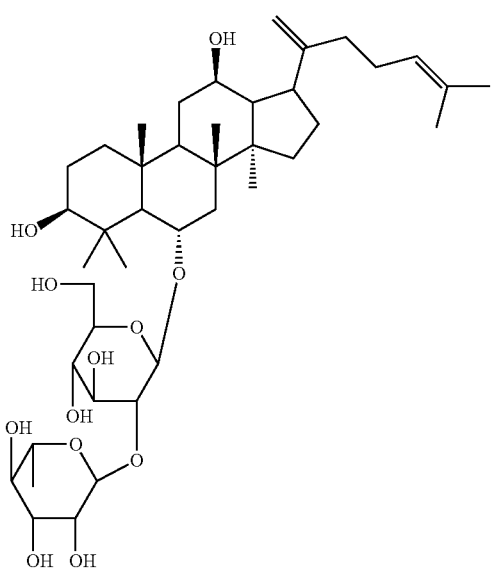

In some embodiments, the compounds herein can be any one or more of compounds selected from benzoid acid, benzyl alcohol, coumarins, catechols, polyphenols, chalconoids (including licochalcones), etc., stilbenes such as resveratrol, isoresveratrol, etc., phenolic acids, such as p-hydroxbenzoic acid, 2,4-dihydroxbenzoid acid, protocatechuic acid, gallic acid, vanillic acid, syringic acid, cinnamic acid, coumaric acids, caffeic acids, ferulic acids, chlorogenic acid, sinapic acids etc., flavonoids such as catechin, narigenin, quercetin, rutin, chrysin, etc., tannins, such as ellagic acid, and pharmaceutically acceptable salts or esters thereof and glycosides thereof.

In some embodiments, the compounds herein can be any one or more of compounds 1-8, or a pharmaceutically acceptable salt or ester thereof.

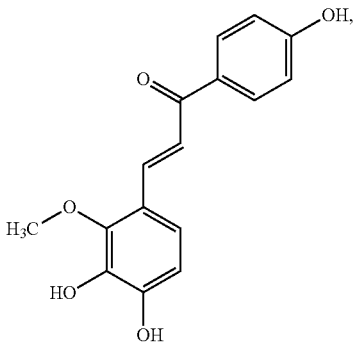

1

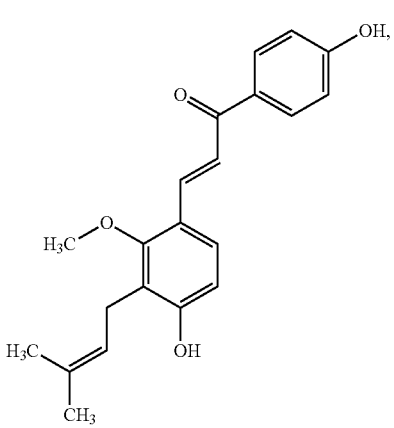

2

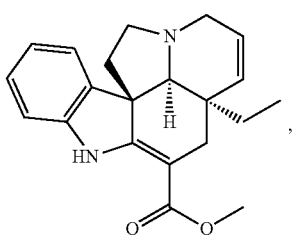

3

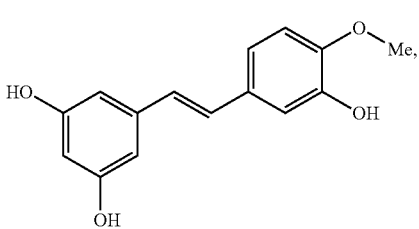

4

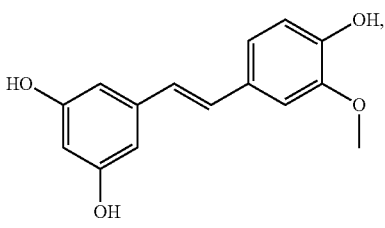

5

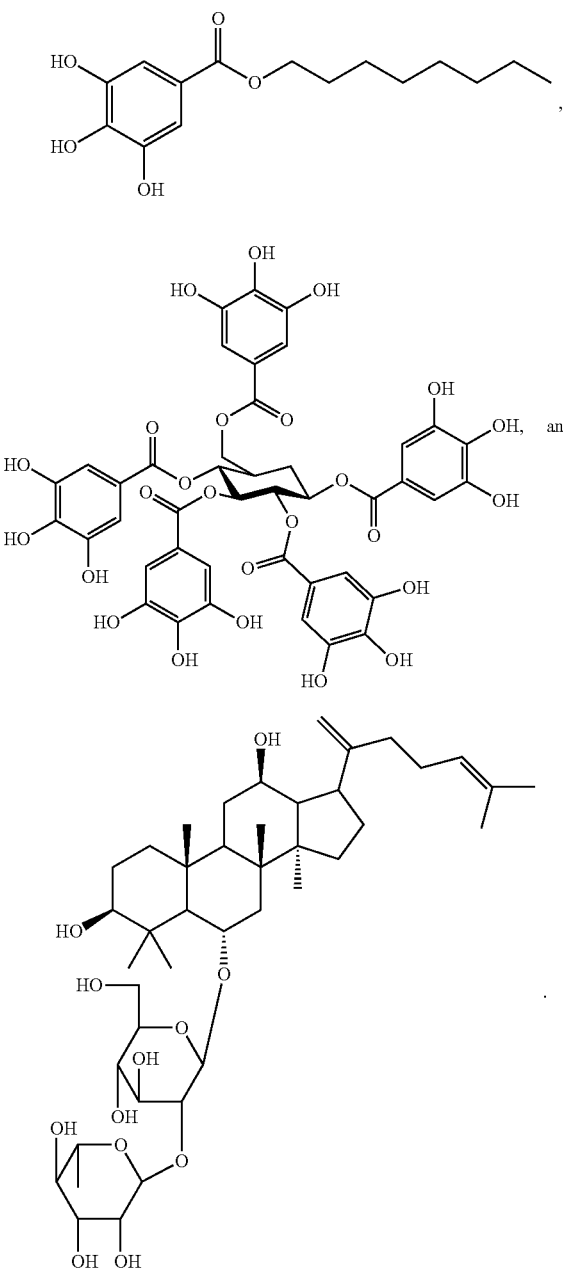

The compounds herein can be typically isolated from a natural source, or alternatively be prepared via routine chemical synthesis. For example, each of the compounds 1-8 is commercially available and has been identified as a component in a plant. Unless indicated to the contrary, in any of the embodiments described herein, the compounds can be derived from a synthetic source. Unless indicated to the contrary, in any of the embodiments described herein, the compounds can exist in an isolated form or in a substantially pure form. It should be understood that the term "isolated form" refers to a compound that has been isolated and/or enriched from its sources, such as a synthetic reaction mixture or natural sources. Typically, such isolated compounds are also substantially pure, for example, greater than 80%, 85%, 90%, 95%, or more, purity by weight. It should also be understood that a composition such as a pharmaceutical composition comprising the compound in an isolated or substantially pure form means that the compound has been isolated or purified, i.e., in an isolated or substantially pure form, prior to mixing with other ingredients of the composition.

Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Pharmaceutical Compositions

Certain embodiments are directed to a pharmaceutical composition comprising one or more of the compounds of the present disclosure, and optionally a pharmaceutically acceptable excipient. In some embodiments, the pharmaceutical composition comprises a compound of the present disclosure and a pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the compounds of the present disclosure. For example, in some embodiments, the pharmaceutical composition comprises a compound of Formula I, II, III, IV-1, IV-2, V, any sub-formulae thereof, or any one or more of compounds 1-8, or a pharmaceutically acceptable salt or ester thereof. Unless indicated to the contrary, in any of the embodiments described herein, the pharmaceutical composition can comprise a compound selected from compounds 1-8, or a pharmaceutically acceptable salt or ester thereof. Unless indicated to the contrary, in any of the embodiments described herein, the pharmaceutical composition can also be free or substantially free of a compound selected from compounds 1-8, or a pharmaceutically acceptable salt or ester thereof.

The pharmaceutical composition can include various amounts of the compounds of the present disclosure, depending on various factors such as the intended use and potency of the compounds. In some embodiments, the pharmaceutical composition comprises a therapeutically effective amount of a compound of the present disclosure and a pharmaceutically acceptable excipient. In some embodiments, a therapeutically effective amount of a compound of the present disclosure can be an amount effective to treat AMD (e.g., wet AMD, dry AMD) as described herein, which can depend on the recipient of the treatment, the stage and the severity of the AMD, the composition containing the compound, the time of administration, the route of administration, the duration of treatment, the compound potency, its rate of clearance and whether or not another drug is co-administered. In some embodiments, a therapeutically effective amount of a compound of the present disclosure can be an amount effective to kill or inhibit the growth of a microorganism, for example, *B. megaterium*, for example, in the eye (e.g., intraocular space), blood, and/or GI tract, such as intestine of the subject. In some embodiments, a therapeutically effective amount of a compound of the present disclosure can be an amount effective to kill or inhibit the growth of a microorganism, for example, one or more selected from *Staphylococcus epidermidis*, *Pseudomonas aeruginosa*, *Staphylococcus aureus*, *Staphylococcus haemolyticus*, *Pseudomonas putida*, *Stenotrophomonas maltophilia*, *Bacillus cereus*, *Bacillus megaterium*, *Lactobacillus reuteri*, *Gardnerella vaginalis*, *Enterococcus faecium*, *Cytophaga hutchinsonii*, *Bacillus licheniformis*, or *Xanthomonas oryzae*, for example, in the eye (e.g., intraocular space), blood, and/or GI tract, such as intestine of the subject. In some embodiments, a therapeutically effective amount of a compound of the present disclosure can be an amount effective to treat soft drusen symptoms such as reduce soft drusenoid lesion.

In various embodiments, the pharmaceutical compositions described herein are useful in treating AMD and/or in killing or inhibiting the growth of a microorganism herein, for example, *B. megaterium*. The microorganisms herein are not particularly limited and are generally related to microorganisms such as bacteria found in the intraocular space in the eye of a subject, more preferably, microorganisms related to AMD such as those enriched in an AMD patient. Unless otherwise specified, in any of the embodiments described herein, the microorganism can comprise *B. megaterium*. In some embodiments, the microorganism can comprise one or more selected from *Staphylococcus epidermidis*, *Pseudomonas aeruginosa*, *Staphylococcus aureus*, *Staphylococcus haemolyticus*, *Pseudomonas putida*, *Stenotrophomonas maltophilia*, *Bacillus cereus*, *Bacillus megaterium*, *Lactobacillus reuteri*, *Gardnerella vaginalis*, *Enterococcus faecium*, *Cytophaga hutchinsonii*, *Bacillus licheniformis*, or *Xanthomonas oryzae*.

Relative amounts of the active ingredient(s), the pharmaceutically acceptable excipient, and/or any additional ingredients in a pharmaceutical composition described herein will vary, depending upon the identity, size, and/or condition of the subject treated and further depending upon the route by which the composition is to be administered.

The pharmaceutical composition described herein can be formulated for delivery via any of the known routes of delivery, which include but are not limited to oral, injectable or infusable, topical, intraocular, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for injection or infusion, such as intravenous injection or infusion, subcutaneous or intramuscular injection, or intraocular such as intravitreous injection. The injectable/infusable formulations can be, for example, an aqueous solution, a suspension, a depot, an implant, or an emulsion. Excipients for the preparation of injectable/infusable formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. In some embodiments, the pharmaceutical composition is formulated for intraocular administration, such as intravitreous injection.

In some embodiments, the pharmaceutical composition is formulated for topical use. Topical formulations and excipients for topical formulations are well known in the art.

Compounds of the present disclosure can be used as a monotherapy, in combination with each other, or in a combination treatment. For example, in certain embodiments, the pharmaceutical composition described herein can further include another antibiotic and/or an anti-VEGF medication. In some embodiments, such antibiotic and/or anti-VEGF medication can be included in a separate dosage form. In some embodiments, any of the commercially available, e.g., FDA approved, antibiotics and anti-VEGF medications can be used in combination with the compounds and compositions herein. In some embodiments, the antibiotic can be a β-lactam antibiotic, an aminoglycoside antibiotic, a tetracycline antibiotic, a chloramphenicol antibiotic, a macrolide antibiotic, a glycopeptide antibiotic, a quinolone antibiotic, a nitroimidazole antibiotic, a rifamycin antibiotic, an echinocandins antibiotic, a polyene antibiotic, a pyrimidine antibiotic, an allylamines antibiotic, or an azoles antibiotic, or a combination thereof. For example, in some embodiments, the antibiotics can include one or more of the following: β-lactam antibiotics, including penicillins (e.g., penicillin V), amoxicillin, ampicillin, bacampicillin, carbenicillin, cloxacillin, dicloxacillin, flucloxacillin, mezlocillin, nafcillin, oxacillin, penicillin G, piperacillin, pivampicillin, pivmecillinam, ticarcillin, cephalosporins such as cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicid, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinome, ceftobiprole, ceftaroline, cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, cefuracetime, ceftioxide, thienamycins, monobactams, β-lactamase inhibitors, methoxypenicillins, etc.; Aminoglycoside antibiotics: including streptomycin, gentamicin, kanamycin (e.g., kanamycin A), tobramycin, amikacin, neomycin (e.g., neomycin B, neomycin C, neomycin E), ribomycin, micronomicin, azithromycin, dibekacin, sisomicin, netilmicin, paramomycin, bramycin, etc.; Tetracycline antibiotics: including tetracycline, oxytetracycline, chlortetracycline and doxycycline; chloramphenicol antibiotics: including chloramphenicol, thiamphenicol, etc.; macrolide antibiotics: including erythromycin, leucomycin, odorless erythromycin, acetylspiramycin, medimycin, josamycin, azithromycin, clarithromycin, dirithromycin, oxithromycin, telithromycin, etc.; glycopeptide antibiotics: including vancomycin, norvancomycin, teicoplanin, etc.; quinolone antibiotics: including norfloxacin, ofloxacin, ciprofloxacin, pefloxacin, gatifloxacin, enoxacin, lomefloxacin, nalidixic acid, levofloxacin, moxifloxacin, besifloxacin; nitroimidazole antibiotics: including metronidazole, tinidazole, ornidazole, etc.; rifamycinoid antibiotics: including rifampicin; echinocandin antibiotics; polyene antibiotics; pyrimidines antibiotics; allylamine antibiotics; azole antibiotics; other antibiotics: fosfomycin, capreomycin, cycloserine, lincomycin, clindamycin, mitomycin, actinomycin D, bleomycin, doxorubicin, isoniazid, pyrazinamide, cyclosporine, polymyxin B combinations such as polymyxin B/trimethoprim, polymyxin B/bacitracin, polymyxin B/neomycin/gramicidin, etc.

In some embodiments, the antibiotic can be selected from Amikacin, Amoxicillin, Ampicillin, Arsphenamine, Azithromycin, Azlocillin, Aztreonam, Bacitracin, Capreomycin, Carbenicillin, Cefaclor, Cefadroxil, Cefalexin, Cefalotin, Cefamandole, Cefazolin, Cefdinir, Cefditoren, Cefixime, Cefoperazone, Cefotaxime, Cefoxitin, Cefpodoxime, Cefprozil, Ceftazidime, Ceftibuten, Ceftizoxime, Ceftriaxone, Cefuroxime, Chloramphenicol, Cilastatin, Clarithromycin, Clavulanate, Clindamycin, Clofazimine, Cloxacillin, Colistin, Cycloserine, Dalfopristin, Dapsone, Daptomycin, Dicloxacillin, Dirithromycin, Doripenem, Doxycycline, Erythromycin, Ethambutol, Ethionamide, Flucloxacillin, Fosfomycin, Furazolidone, Fusidic acid, Gentamicin, Imipenem, Isoniazid, Kanamycin, Lincomycin, Linezolid, Loracarbef, Mafenide, Meropenem, Methicillin, Metronidazole, Mezlocillin, Minocycline, Mupirocin, Nafcillin, Neomycin, Netilmicin, Nitrofurantoin, Oxacillin, Oxytetracycline, Paromomycin, Penicillin G, Penicillin V, Piperacillin, Platensimycin, Polymyxin B, Pyrazinamide, Quinupristin, Rapamycin, Rifabutin, Rifampicin, Rifampin, Rifapentine, Rifaximin, Roxithromycin, Silver sulfadiazine, Spectinomycin, Streptomycin, Sulbactam, Sulfacetamide, Sulfadiazine, Sulfamethizole, Sulfamethoxazole, Sulfanilimide, Sulfasalazine, Sulfisoxazole, Tazobactam, Teicoplanin, Telavancin, Telithromycin, Temocillin, Tetracycline, Thiamphenicol, Ticarcillin, Tigecycline, Tinidazole, Tobramycin, Trimethoprim, Troleandomycin Vancomycin, enoxacin, lomefloxacin, nalidixic acid, ciprofloxacin, levofloxacin, gatifloxacin, moxifloxacin, ofloxacin, norfloxacin, Cefotetan, Cefonicid, Cephradine, Cephapirin, Cephalothin, Cefmetazole, Cefotaxime, Moxalactam, Cefepime, Ceftaroline fosamil, Ceftobiprole, Dalbavancin, Demeclocycline, Metacycline, Ertapenem, Fidaxomicin, geldanamycin, herbimycin, Posizolid, Radezolid, Torezolid, Oritavancin, Spiramycin, Sulfadimethoxine, Sulfonamidochrysoidine, Gemifloxacin Nadifloxacin Trovafloxacin Grepafloxacin Sparfloxacin Temafloxacin, Teixobactin, Malacidins, and combinations thereof. The antibiotics can be in any form such as in the form of or in a mixture with their respective pharmaceutically acceptable salts. The antibiotics can be formulated and administered according to its known route of administration and are not particularly limited.

Anti-VEGF medications typically include biological drugs targeting VEGF, such as Ranibizumab, Aflibercept, Bevacizumab, Conbercept, etc.

Method of Treatment

Compounds of the present disclosure are useful as therapeutic active substances for the treatment and/or prophylaxis of diseases or disorders that are associated with infections (e.g., ocular infections, such as in the intraocular space) with the microorganisms herein, such as *Bacillus megaterium*. As shown in the Examples section, representative compounds of the present disclosure show potent effect in killing or inhibiting a representative microorganism, *Bacillus megaterium* in an in vitro test. Further, examples show that by killing or inhibiting *Bacillus megaterium* in vivo, for example, in the macaque model described herein, antibiotics such as vancomycin were able to reduce drusenoid lesion induced by *Bacillus megaterium*.

Accordingly, in various embodiments, the present disclosure also provides a method of using the compounds of the present disclosure or the pharmaceutical compositions herein for treating infections a microorganism herein, such as *Bacillus megaterium*, and for treating or preventing diseases or disorders associated with such infections, such as AMD.

Unless otherwise specified, in any of the embodiments described herein, the infection can comprise ocular infections, such as in the intraocular space. Unless otherwise specified, in any of the embodiments described herein, the microorganism can comprise *B. megaterium*. In some embodiments, the microorganism can comprise one or more selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, or *Xanthomonas oryzae*.

In various embodiments, compounds of the present disclosure can be used for killing or inhibiting the growth of microorganisms herein, such as *Bacillus megaterium*. In some embodiments, compounds of the present disclosure can be used for treating or preventing AMD, such as dry or wet age-related macular degeneration with drusen symptoms, including a hard drusen, a soft drusen, a mixed drusen and/or a degraded drusen, for example, dry or wet age-related macular degeneration with soft drusen symptoms. Compounds of the present disclosure can be used either alone, in combination with each other, or in combination with another antibiotic and/or an anti-VEGF medication, e.g., as described herein.

In some embodiments, the present disclosure provides a method of killing or inhibiting the growth of a microorganism herein, such as *Bacillus megaterium*. In some embodiments, the method comprises contacting the microorganism with an effective amount of a compound of the present disclosure or a pharmaceutical composition described herein. In some embodiments, the contacting can be in vitro, ex vivo, or in vivo.

In some embodiments, the present disclosure also provides a method for killing or inhibiting the growth of a microorganism herein, such as *Bacillus megaterium*, in a subject in need thereof. In some embodiments, the method comprises administering to the subject a compound of the present disclosure (e.g., compound of Formula I, II, III, IV-1, IV-2, V, any sub-formulae thereof, or any one or more of compounds 1-8, or a pharmaceutically acceptable salt or ester thereof. Unless indicated to the contrary, in any of the embodiments described herein, the method can comprise administering to the subject a compound selected from compounds 1-8, or a pharmaceutically acceptable salt or ester thereof. Unless indicated to the contrary, in any of the embodiments described herein, the method can also comprise administering to the subject a pharmaceutical composition that is free or substantially free of a compound selected from compounds 1-8, or a pharmaceutically acceptable salt or ester thereof. In some embodiments, the compound or pharmaceutical composition is administered in an amount effective for killing or inhibiting the growth of the microorganism in the subject, for example, in the eye (e.g., intraocular space), blood, and/or GI tract, such as intestine of the subject. In some embodiments, the subject suffers from AMD. In some embodiments, the subject does not suffer from AMD. In some embodiments, the subject is at risk of developing AMD. In some embodiments, the subject has ocular infection with the microorganism herein, such as *Bacillus megaterium*. In some embodiments, the method further comprises identifying, or having identified, the subject as being infected with, e.g., in the intraocular space, the microorganism, such as *Bacillus megaterium*. In some embodiments, the subject is further administered an antibiotic and/or an anti-VEGF medication, e.g., as described herein. In such embodiments, the antibiotic and/or anti-VEGF medication can be administered to the subject either concurrently or sequentially in any order with the compounds of the present disclosure or pharmaceutical compositions herein.

In some embodiments, the present disclosure provides a method of treating or preventing AMD in a subject in need thereof. In some embodiments, the method comprises administering to the subject a therapeutically effective amount of a compound of the present disclosure (e.g., compound of Formula I, II, III, IV-1, IV-2, V), any subformulae thereof, or any one or more of compounds 1-8, or a pharmaceutically acceptable salt or ester thereof. Unless indicated to the contrary, in any of the embodiments described herein, the method can comprise administering to the subject a compound selected from compounds 1-8, or a pharmaceutically acceptable salt or ester thereof. Unless indicated to the contrary, in any of the embodiments described herein, the method can also comprise administering to the subject a pharmaceutical composition that is free or substantially free of a compound selected from compounds 1-8, or a pharmaceutically acceptable salt or ester thereof. In some embodiments, the method further comprises administering to the subject an antibiotic and/or an anti-VEGF medication, e.g., as described herein. In some embodiments, the AMD can be dry or wet age-related macular degeneration with drusen symptoms, including a hard drusen, a soft drusen, a mixed drusen and/or a degraded drusen, for example, dry or wet age-related macular degeneration with soft drusen symptoms. In some embodiments, the method further comprises identifying, or having identified, the subject as being infected with, e.g., in the intraocular space, a microorganism herein, such as *Bacillus megaterium*. In some embodiments, the subject is infected with, e.g., in the intraocular space, a microorganism herein, such as *Bacillus megaterium*. In some embodiments, the method comprises administered to the subject the compound or pharmaceutical composition in an amount effective for killing or inhibiting the growth of a microorganism herein, such as *Bacillus megaterium* in the subject, for example, in the eye (e.g., intraocular space), blood, and/or GI tract, such as intestine of the subject.

The administering herein is not limited to any particular route of administration. For example, in some embodiments, the administering can be orally, nasally, topically, intraocularly, intravitreously, transdermally, pulmonary, inhalationally, buccally, sublingually, intraperintoneally, subcutaneously, intramuscularly, intravenously, rectally, intrapleurally, intrathecally and parenterally. In some embodiments, the administering can be orally, topically, intravitreously, intramuscularly, subcutaneously, or intravenously. In some embodiments, the administering is orally. In some embodiments, the administering is intravitreously.

The dosing regimen such as amounts and frequencies will vary depending on various factors such as the recipient of the treatment, the disease or disorder being treated and the severity thereof, the composition containing the compound, the time of administration, the route of administration, the duration of treatment, the compound potency, its rate of clearance and whether or not another drug is co-administered.

Extracts

In one aspect, the present disclosure also provides an extract of certain Traditional Chinese Medicine(s) (TCMs) that have antibacterial activities. The term Traditional Chinese Medicine should be broadly construed as including both herbal and non-herbal Chinese medicinals, for example, as described in the corresponding sections of the Pharmacopoeia of the People's Republic of China (current edition). As detailed in the Examples section, various TCMs were found to have activities against a representative microorganism herein, *B. megaterium*. While some of the isolated components from these TCMs were further identified as active against *B. megaterium*, the extracts can themselves be useful for treating infections with the microorganisms herein and the associated diseases or disorders such as AMD.

Accordingly, in some embodiments, the present disclosure provides a method of treating or preventing AMD in a subject in need thereof, the method comprises administering to the subject an extract from one or more TCMs selected from Licorice (e.g., *Glycyrrhiza uralensis*), White Peony Root (e.g., *Cynanchum otophyllum*), Forsythia (e.g., *Forsythia suspense*), Fructus Aurantii (e.g., *Citrus aurantium* L.), *Rehmannia glutinosa* (e.g., *Rehmannia glutinosa* Libosch), Tangerine Peel (e.g., *Citrus reticulata* Blanco), and Notoginseng (e.g., *Panax notoginseng*). In some embodiments, the AMD can be dry or wet age-related macular degeneration with drusen symptoms, including a hard drusen, a soft drusen, a mixed drusen and/or a degraded drusen, for example, dry or wet age-related macular degeneration with soft drusen symptoms. In some embodiments, the method further comprises identifying, or having identified, the subject as being infected with, e.g., in the intraocular space, a microorganism herein, such as *Bacillus megaterium*. In some embodiments, the subject is infected with, e.g., in the intraocular space, a microorganism herein, such as *Bacillus megaterium*.

In some embodiments, the present disclosure provides a method of killing or inhibiting the growth of a microorganism herein, or a method of treating an infection with a microorganism herein, such as *Bacillus megaterium*, in a subject in need thereof, the method comprises administering to the subject an extract from one or more TCMs selected from Licorice (e.g., *Glycyrrhiza uralensis*), White Peony Root (e.g., *Cynanchum otophyllum*), Forsythia (e.g., *Forsythia suspense*), Fructus Aurantii (e.g., *Citrus aurantium*

L.), *Rehmannia glutinosa* (e.g., *Rehmannia glutinosa* Libosch), Tangerine Peel (e.g., *Citrus reticulata* Blanco), and *Notoginseng* (e.g., *Panax notoginseng*). In some embodiments, the subject suffers from AMD. In some embodiments, the subject does not suffer from AMD. In some embodiments, the subject is at risk of developing AMD. In some embodiments, the subject has ocular infection with the microorganism herein, such as *Bacillus megaterium*. In some embodiments, the method further comprises identifying, or having identified, the subject as being infected with, e.g., in the intraocular space, the microorganism, such as *Bacillus megaterium*. In some embodiments, the subject is further administered an antibiotic and/or an anti-VEGF medication, e.g., as described herein.

In some embodiments, the extract can be an extract of a single TCM. For example, in some embodiments, the method comprises administering to the subject an extract of Licorice (e.g., *Glycyrrhiza uralensis*). In some embodiments, the method comprises administering to the subject an extract of White Peony Root (e.g., *Cynanchum otophyllum*). In some embodiments, the method comprises administering to the subject an extract of *Forsythia* (e.g., *Forsythia suspense*). In some embodiments, the method comprises administering to the subject an extract of *Fructus Aurantii* (e.g., *Citrus aurantium* L.). In some embodiments, the method comprises administering to the subject an extract of *Rehmannia glutinosa* (e.g., *Rehmannia glutinosa* Libosch), Tangerine Peel (e.g., *Citrus reticulata* Blanco). In some embodiments, the method comprises administering to the subject an extract of *Notoginseng* (e.g., *Panax notoginseng*).

In some embodiments, the extract can be an extract of a combination of two or more TCMs. For example, in some embodiments, the method comprises administering to the subject an extract from two or more TCMs selected from Licorice (e.g., *Glycyrrhiza uralensis*), White Peony Root (e.g., *Cynanchum otophyllum*), *Forsythia* (e.g., *Forsythia suspense*), *Fructus aurantii* (e.g., *Citrus aurantium* L.), *Rehmannia glutinosa* (e.g., *Rehmannia glutinosa* Libosch), Tangerine Peel (e.g., *Citrus reticulata* Blanco), and *Notoginseng* (e.g., *Panax notoginseng*). In some embodiments, the method comprises administering to the subject an extract from (a) one TCM selected from Licorice (e.g., *Glycyrrhiza uralensis*), White Peony Root (e.g., *Cynanchum otophyllum*), *Forsythia* (e.g., *Forsythia suspense*), *Fructus aurantii* (e.g., *Citrus aurantium* L.), *Rehmannia glutinosa* (e.g., *Rehmannia glutinosa* Libosch), Tangerine Peel (e.g., *Citrus reticulata* Blanco), and *Notoginseng* (e.g., *Panax notoginseng*); and (b) one or more other TCMs. In some embodiments, the method comprises administering to the subject an extract from (a) 1-7, but not all, TCMs, in any combination, each independently selected from *Glycyrrhiza uralensis, Cynanchum otophyllum, Forsythia suspense, Citrus aurantium* L., *Rehmannia glutinosa* Libosch, *Citrus reticulata* Blanco, and *Panax notoginseng*; and optionally (b) one or more other TCMs.

The extract herein is typically prepared according to common practice of TCMs. See e.g., the Examples section. When two or more TCMs are used, the extract can be prepared by extracting each TCMs individually (or extracting any subgroup of the TCMs) and then combine the extracts; or extracting the two or more TCMs together. Typically, the extract is an aqueous extract. In some embodiments, non-aqueous extract can also be useful. It should also be noted that for some TCMs, various plant parts can be useful, such as leaf, stem, root, fruit, seed, etc. In embodiments herein, the extract is not limited to any specific part of the TCM plant, as applicable.

The extracts herein can exist or be administered in liquid, semisolid, or solid form or any other form. For example, the extracts can be administered as an aqueous solution, suspension, or emulsion. Alternatively, the extracts can also be made into a capsule, a tablet, a powder, etc. and be administered accordingly, typically orally. Administering the extract(s) can follow typical practice regarding TCMs and is not limited to a particular route of administration. Dosing regimen such as amounts and frequencies can be adjusted based on various factors such as the recipient of the treatment, the disease or disorder being treated and the severity thereof, the composition containing the extract, the time of administration, the route of administration, the duration of treatment, potency of the extract, its rate of clearance and whether or not another drug is co-administered. In some embodiments, the extract is administered in an amount effective for killing or inhibiting the growth of a microorganism herein, such as *Bacillus megaterium* in the subject, for example, in the eye (e.g., intraocular space), blood, and/or GI tract, such as intestine of the subject.

Antibiotics

As discussed herein, the present invention is in part based on the unexpected discovery that the intraocular environment is not sterile and certain intraocular microbiota can be pathogenic causes of AMD. Thus, any antibiotics, such as those known in the art, can be useful for treating infections with the microorganisms herein and can be used for treating or preventing AMD. Accordingly, in some embodiments, the present disclosure also provides of a method of killing or inhibiting growth of a microorganism herein, such as *Bacillus megaterium*, a method of treating an infection (e.g., ocular infection, such as in the intraocular space) with a microorganism herein, and/or a method of treating or preventing a disease or disorder associated with the microorganism or infection, such as AMD, in a subject in need thereof, the method comprises administering to the subject an effective amount of an antibiotic. In some embodiments, any of the commercially available antibiotics, e.g., those approved by the U.S. FDA, can be used. In some embodiments, the antibiotics can be characterized as a broad spectrum antibiotic. In some embodiments, the antibiotics can be an antibiotic against gram-positive bacteria. In some embodiments, the subject suffers from AMD. In some embodiments, the subject does not suffer from AMD. In some embodiments, the subject is at risk of developing AMD. In some embodiments, the subject has ocular infection, e.g., with one of the microorganisms herein, such as *Bacillus megaterium*. In some embodiments, the AMD can be dry or wet age-related macular degeneration with drusen symptoms, including a hard drusen, a soft drusen, a mixed drusen and/or a degraded drusen, for example, dry or wet age-related macular degeneration with soft drusen symptoms. In some embodiments, the method further comprises identifying, or having identified, the subject as being infected with, e.g., in the intraocular space, a microorganism herein, such as *Bacillus megaterium*. In some embodiments, the subject is infected with, e.g., in the intraocular space, a microorganism herein, such as *Bacillus megaterium*. In some embodiments, the subject is further administered an anti-VEGF medication, e.g., as described herein.

Compounds of the present disclosure (see e.g., the Compounds section) typically have antibacterial activity and therefore can be an antibiotic. However, the antibiotics described in this section can be independent of the compounds of the present disclosure (e.g., as defined herein). In some embodiments, the antibiotics are also compounds of the present disclosure. In some embodiments, the antibiotics are not compounds of the present disclosure. In some embodiments, the antibiotics and the compounds of the present disclosure are used together in a combination therapy, which can be administered to a subject in need concurrently (e.g., in a single dosage form) or sequentially in any order.

In some embodiments, the antibiotic can be a β-lactam antibiotic, an aminoglycoside antibiotic, a tetracycline antibiotic, a chloramphenicol antibiotic, a macrolide antibiotic, a glycopeptide antibiotic, a quinolone antibiotic, a nitroimidazole antibiotic, a rifamycin antibiotic, an echinocandins antibiotic, a polyene antibiotic, a pyrimidine antibiotic, an allylamines antibiotic, or an azoles antibiotic, or a combination thereof.

In some embodiments, the antibiotics can include one or more of the following: β-lactam antibiotics, including penicillins (e.g., penicillin V), amoxicillin, ampicillin, bacampicillin, carbenicillin, cloxacillin, dicloxacillin, flucloxacillin, mezlocillin, nafcillin, oxacillin, penicillin G, piperacillin, pivampicillin, pivmecillinam, ticarcillin, cephalosporins such as cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicid, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinome, ceftobiprole, ceftaroline, cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, cefuracetime, ceftioxide, thienamycins, monobactams, β-lactamase inhibitors, methoxypenicillins, etc.; Aminoglycoside antibiotics: including streptomycin, gentamicin, kanamycin (e.g., kanamycin A), tobramycin, amikacin, neomycin (e.g., neomycin B, neomycin C, neomycin E), ribomycin, micronomicin, azithromycin, dibekacin, sisomicin, netilmicin, paramomycin, bramycin, etc.; Tetracycline antibiotics: including tetracycline, oxytetracycline, chlortetracycline and doxycycline; chloramphenicol antibiotics: including chloramphenicol, thiamphenicol, etc.; macrolide antibiotics: including erythromycin, leucomycin, odorless erythromycin, acetylspiramycin, medimycin, josamycin, azithromycin, clarithromycin, dirithromycin, oxithromycin, telithromycin, etc.; glycopeptide antibiotics: including vancomycin, norvancomycin, teicoplanin, etc.; quinolone antibiotics: including norfloxacin, ofloxacin, ciprofloxacin, pefloxacin, gatifloxacin, enoxacin, lomefloxacin, nalidixic acid, levofloxacin, moxifloxacin, besifloxacin; nitroimidazole antibiotics: including metronidazole, tinidazole, ornidazole, etc.; rifamycinoid antibiotics: including rifampicin; echinocandin antibiotics; polyene antibiotics; pyrimidines antibiotics; allylamine antibiotics; azole antibiotics; other antibiotics: fosfomycin, capreomycin, cycloserine, lincomycin, clindamycin, mitomycin, actinomycin D, bleomycin, doxorubicin, isoniazid, pyrazinamide, cyclosporine, polymyxin B combinations such as polymyxin B/trimethoprim, polymyxin B/bacitracin, polymyxin B/neomycin/gramicidin, etc.

In some embodiments, the antibiotic can be selected from Amikacin, Amoxicillin, Ampicillin, Arsphenamine, Azithromycin, Azlocillin, Aztreonam, Bacitracin, Capreomycin, Carbenicillin, Cefaclor, Cefadroxil, Cefalexin, Cefalotin, Cefamandole, Cefazolin, Cefdinir, Cefditoren, Cefixime, Cefoperazone, Cefotaxime, Cefoxitin, Cefpodoxime, Cefprozil, Ceftazidime, Ceftibuten, Ceftizoxime, Ceftriaxone, Cefuroxime, Chloramphenicol, Cilastatin, Clarithromycin, Clavulanate, Clindamycin, Clofazimine, Cloxacillin, Colistin, Cycloserine, Dalfopristin, Dapsone, Daptomycin, Dicloxacillin, Dirithromycin, Doripenem, Doxycycline, Erythromycin, Ethambutol, Ethionamide, Flucloxacillin, Fosfomycin, Furazolidone, Fusidic acid, Gentamicin, Imipenem, Isoniazid, Kanamycin, Lincomycin, Linezolid, Loracarbef, Mafenide, Meropenem, Methicillin, Metronidazole, Mezlocillin, Minocycline, Mupirocin, Nafcillin, Neomycin, Netilmicin, Nitrofurantoin, Oxacillin, Oxytetracycline, Paromomycin, Penicillin G, Penicillin V, Piperacillin, Platensimycin, Polymyxin B, Pyrazinamide, Quinupristin, Rapamycin, Rifabutin, Rifampicin, Rifampin, Rifapentine, Rifaximin, Roxithromycin, Silver sulfadiazine, Spectinomycin, Streptomycin, Sulbactam, Sulfacetamide, Sulfadiazine, Sulfamethizole, Sulfamethoxazole, Sulfanilimide, Sulfasalazine, Sulfisoxazole, Tazobactam, Teicoplanin, Telavancin, Telithromycin, Temocillin, Tetracycline, Thiamphenicol, Ticarcillin, Tigecycline, Tinidazole, Tobramycin, Trimethoprim, Troleandomycin Vancomycin, enoxacin, lomefloxacin, nalidixic acid, ciprofloxacin, levofloxacin, gatifloxacin, moxifloxacin, ofloxacin, norfloxacin, Cefotetan, Cefonicid, Cephradine, Cephapirin, Cephalothin, Cefmetazole, Cefotaxime, Moxalactam, Cefepime, Ceftaroline fosamil, Ceftobiprole, Dalbavancin, Demeclocycline, Metacycline, Ertapenem, Fidaxomicin, geldanamycin, herbimycin, Posizolid, Radezolid, Torezolid, Oritavancin, Spiramycin, Sulfadimethoxine, Sulfonamidochrysoidine, Gemifloxacin Nadifloxacin Trovafloxacin Grepafloxacin Sparfloxacin Temafloxacin, Teixobactin, Malacidins, and combinations thereof.

In some embodiments, the antibiotic is administered in an amount effective for killing or inhibiting the growth of a microorganism herein, such as *Bacillus megaterium* in the subject, for example, in the eye (e.g., intraocular space), blood, and/or GI tract, such as intestine of the subject.

The antibiotics can be in any form such as in the form of or in a mixture with their respective pharmaceutically acceptable salts. The antibiotics can be formulated and administered according to its known route of administration and are not particularly limited. In some embodiments, the administering can be orally, topically, intravitreously, intramuscularly, subcutaneously, or intravenously. In some embodiments, the administering is orally. In some embodiments, the administering is intravitreously.

The dosing regimen such as amounts and frequencies will vary depending on various factors such as the recipient of the treatment, the disease or disorder being treated and the severity thereof, the composition containing the antibiotic, the time of administration, the route of administration, the duration of treatment, the potency of the antibiotic, its rate of clearance and whether or not another drug is co-administered.

Exemplary Alternative Embodiments

In some aspect, the present disclosure relates to a method for establishing a model and a model established by the method. In another aspect, disclosed herein is a method for screening a drug and the drug identified by the method. In some embodiments, the present disclosure relates to use of a microbial in establishing a model and in screening drug.

In one aspect, disclosed herein is a method for establishing a model, which method comprises infecting a model carrier with a microorganism. The microorganism can comprise or include bacteria, archaeal, protist, fungus, virus, or a combination thereof. Preferably, the microorganism comprises a bacteria, wherein the bacteria can be selected from one or more of the followings: *Clostridium, Acinetobacter, Streptococcus, Mannheimia, Fibrobacter, Prevotella, Campylobacter, Actinomyces, Hymenobacter, Escherichia, Tissierella, Klebsiella, Porphyromonas, Azospira, Aquimarina, Achromobacter, Acidithiobacillus, Burkholderia, Marinobacter, Treponema, Actinosporangium, Vibrio, Ruminococcus, Methanobrevibacter, Shigella, Frankia, Anaeroplasma* and *Coprococcus*.

In some preferred embodiments, the bacteria can be selected from one or more of the followings: *Clostridium tetanus, Clostridium perfringens, Clostridium botulinum, Acinetobacter acetate, Acinetobacter rufi, Acinetobacter baumannii, Acinetobacter hemolyticus, Acinetobacter junii, Acinetobacter johnsonii, Streptococcus pyogenes, Streptococcus hemolyticus, Porphyromonas asacharolytica, Porphyromonas gingivalis, Porphyromonas gingivalis, Campylobacter jejuni, Campylobacter coli, Campylobacter seabirds, Campylobacter* Uppsala, *Campylobacter* concisely, *Campylobacter fitus, Actinomyces israelii, Actinomyces naeslundii, Actinomyces odontolyticus, Escherichia coli, Escherichia blattae, Escherichia fergusonii, Escherichia hermannii, Escherichia vulneris, Tissierella apical, Klebsiella pneumoniae, Klebsiella odorata, Azospirillum brasilence, Achromobacter, Thiobacillus denitrificans, Thiobacillus ferrooxidans, Thiobacillus thiooxidans, Thiobacillus neapolitanus, Burkholderia, Mycobacterium marinum, Treponema Pallidum, Treponema hyodysenteriae, Vibrio metschnikovi, Ruminococcus albus, Ruminococcus flavefaciens, Methanobrevibacter ruminantium, Shigella dysenteriae, Shigella flexneri, Shigella bogdii, Shigella sonnei, Frankiaceae, Streptomyces albus, Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus* (D), *Escherichia coli, Micrococcus luteus, Bacillus subtilis, Corynebacterium aurimucosum, Finegoldia magna.*

In some preferred embodiments, the bacteria can be selected from one or more of the followings: *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus* (D), *Escherichia coli, Micrococcus luteus, Bacillus subtilis, Corynebacterium aurimucosum, Finegoldia magna.*

In some preferred embodiments, the bacteria are selected from one or more of the followings: *Pseudomonas putida, Bacillus megaterium, Propionibacterium acnes*. In a preferred embodiment, the bacterium is *Bacillus megaterium*.

In some preferred embodiments, the present disclosure relates to a method for establishing a model about cataract (Cat), which method comprises infecting the model carrier with a microorganism selected from one or more of the following: *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti,* or *Acidovorax ebreus.*

In some preferred embodiments, the present disclosure relates to a method for establishing a model about age-related macular degeneration (AMD), which method comprises infecting the model carrier with a microorganism selected from one or more of the following: *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis,* or *Xanthomonas oryzae.*

In some preferred embodiments, the present disclosure relates to a method for establishing a model about glaucoma (GLA), which method comprises infecting the model carrier with a microorganism selected from one or more of the following: *Acinetobacter baumannii, Acinetobacter calcoaceticus, Comamonas testosteroni, Mycobacterium kansasii, Bacillus thuringiensis, Citrobacter koseri, Dyadobacter fermentants,* or *Serratia marcescens.*

In some preferred embodiments, the present disclosure relates to a method for establishing a model about Behcet's disease (BD), which method comprises infecting the model carrier with a microorganism selected from one or more of the following: *Sphingomonas wittichii, Klebsiella pneumoniae, Pseudomonas fluorescens, Ralstonia pickettii, Lactobacillus crispatus, Burkholderia multivorans, Lactobacillus delbrueckii,* or *Meiothermus silvanus*(D).

In some preferred embodiments, the present disclosure relates to a method for establishing a model about Vogt-Koyanagi-Harada Syndrome (VKH), which method comprises infecting the model carrier with a microorganism selected from one or more of the following: *Escherichia coli, Micrococcus luteus, Bacillus subtilis, Corynebacterium aurimucosum,* or *Finegoldia magna.*

The model carrier can comprise be one or more of the following: human, non-human mammal, organs, tissues, tissue sections, tissue extracts, body fluids, body fluid cultures, cells, viruses, enzymes, culture media. Non-human mammal includes any mammals of an experimental, pet or economical nature. Exemplary non-human mammals include a mouse, a rat, a rabbit, a cat, a dog, a pig, a cow, an ox, a sheep, a goat, a horse, a monkey, or a non-human primate. Exemplary organs include heart, liver, lung, stomach, kidney, eye, ear, nose, tongue. The tissues, tissue sections and tissue extracts include tissues, tissue sections or tissue extracts from any part of the subject or subject animal. In some embodiments, the tissues comprise suspensory ligament, ciliary body, ciliary body and muscle, vitreum, retina, choroid, optic nerve, lens, or iris of a subject. In some embodiments, the tissue extracts comprise DNA, RNA, or protein. In some embodiments, the body fluids comprise lymph, cerebrospinal fluid, aqueous humor (AH), vitreous humor (VH), blood, sweat, or urine. In some embodiments, the body fluid cultures comprise AH and VH cultures.

In another aspect, disclosed herein is use of a microbial in establishing a model, specific, the model is established by infecting a model carrier with a microorganism. The defined range of microorganism and model carrier are as described herein.

In yet another aspect, disclosed herein is a model which is established by infecting a model carrier with a microorganism. The defined range of microorganism and model carrier are as described herein.

In yet another aspect, disclosed herein is a method for screening a drug, the method comprises (1) Applying the drug on the model; (2) Analyzing the results. Preferably, the method comprises: (1) infecting a model carrier with a microorganism to establish the model; (2) Applying the drug on the model; (3) Analyzing the results. The drug that kills or inhibits microorganisms in the model can be identified as having therapeutic or prophylactic effect.

The microorganism can comprise or include bacteria, archaeal, protist, fungus, virus, or a combination thereof. Preferably, the microorganism comprises bacteria, wherein the bacteria can be selected from one or more of the followings: Clostridium, Acinetobacter, Streptococcus, Mannheimia, Fibrobacter, Prevotella, Campylobacter, Actinomyces, Hymenobacter, Escherichia, Tissierella, Klebsiella, Porphyromonas, Azospira, Aquimarina, Achromobacter, Acidithiobacillus, Burkholderia, Marinobacter, Treponema, Actinosporangium, Vibrio, Ruminococcus, Methanobrevibacter, Shigella, Frankia, Anaeroplasma and Coprococcus.

In some preferred embodiments, the bacteria can be selected from one or more of the followings: Clostridium tetanus, Clostridium perfringens, Clostridium botulinum, Acinetobacter acetate, Acinetobacter rufi, Acinetobacter baumannii, Acinetobacter hemolyticus, Acinetobacter junii, Acinetobacter johnsonii, Streptococcus pyogenes, Streptococcus hemolyticus, Porphyromonas asacharolytica, Porphyromonas gingivalis, Porphyromonas gingivalis, Campylobacter jejuni, Campylobacter coli, Campylobacter seabirds, Campylobacter Uppsala, Campylobacter concisely, Campylobacter fitus, Actinomyces israelii, Actinomyces naeslundii, Actinomyces odontolyticus, Escherichia coli, Escherichia blattae, Escherichia fergusonii, Escherichia hermannii, Escherichia vulneris, Tissierella apical, Klebsiella pneumoniae, Klebsiella odorata, Azospirillum brasilence, Achromobacter, Thiobacillus denitrificans, Thiobacillus ferrooxidans, Thiobacillus thiooxidans, Thiobacillus neapolitanus, Burkholderia, Mycobacterium marinum, Treponema Pallidum, Treponema hyodysenteriae, Vibrio metschnikovi, Ruminococcus albus, Ruminococcus flavefaciens, Methanobrevibacter ruminantium, Shigella dysenteriae, Shigella flexneri, Shigella bogdii, Shigella sonnei, Frankiaceae, Streptomyces albus, Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus (D), Escherichia coli, Micrococcus luteus, Bacillus subtilis, Corynebacterium aurimucosum, Finegoldia magna.

In some preferred embodiments, the bacteria can be selected from one or more of the followings: Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus (D), Escherichia coli, Micrococcus luteus, Bacillus subtilis, Corynebacterium aurimucosum, Finegoldia magna.

In some preferred embodiments, the bacteria can be selected from one or more of the followings: Pseudomonas putida, Bacillus megaterium, Propionibacterium acnes.

In a preferred embodiment, the bacterium is Bacillus megaterium.

The model carrier can be one or more of the following: human, non-human mammal, organs, tissues, tissue sections, tissue extracts, body fluids, body fluid cultures, cells, viruses, enzymes, culture media. The non-human mammal includes any mammals of experimental nature, pet nature or economical nature. Exemplary non-human mammals include a mouse, a rat, a rabbit, a cat, a dog, a pig, a cow, an ox, a sheep, a goat, a horse, a monkey, or a non-human primate. Exemplary organs include heart, liver, lung, stomach, kidney, eye, ear, nose, tongue. The tissues, tissue sections and tissue extracts include tissues, tissue sections or tissue extracts from any part of the subject or subject animal. In some embodiments, the tissues comprise suspensory ligament, ciliary body, ciliary body and muscle, vitreum, retina, choroid, optic nerve, lens, or iris of a subject. In some embodiments, the tissue extracts comprise DNA, RNA, or protein. In some embodiments, the body fluids comprise lymph, cerebrospinal fluid, aqueous humor (AH), vitreous humor (VH), blood, sweat, or urine. In some embodiments, the body fluid cultures comprise AH and VH cultures.

The drug can comprise one or more of the following: a small molecule drug, a chemical drug, a macromolecule drug, a biologic drug or a natural drug (traditional Chinese medicine or traditional Chinese medicine extracts).

Preferably, the drug has a therapeutic effect on intraocular disease or disorder which comprise age-related macular degeneration (AMD), Behcet's disease (BD), Vogt-Koyanagi-Harada Syndrome (VKH), uveitis, retinopathy, keratoconjunctivitis sicca, sympathetic ophthalmia, trachoma, cataract (Cat), conjunctivitis, chalazion, glaucoma (GLA), muscae volitantes.

The chemical drug can comprise: a β-lactam antibiotic: penicillins, cephalosporins, β-lactamase inhibitor and methicillin; an aminoglycoside antibiotic: streptomycin, gentamicin, kanamycin, tobramycin, amikacin, neomycin, ribomycin and novomycin; a tetracycline antibiotic: tetracycline, oxytetracycline and chlortetracycline; a chloramphenicol antibiotic: chloramphenicol and thiamphenicol; a macrolide antibiotic: erythromycin, leucomycin, odorless erythromycin, acetylspiramycin, medimycin, josamycin and azithromycin; a glycopeptide antibiotic: vancomycin, norvancomycin and teicoplanin; a quinolone antibiotic: norfloxacin, ofloxacin, ciprofloxacin, pefloxacin and gatifloxacin; a nitroimidazole antibiotic: metronidazole, tinidazole and ornidazole; a rifamycin antibiotic: rifampin; an echinocandins antibiotic, a polyene antibiotic, a pyrimidine antibiotic, an allylamines antibiotic, an azoles antibiotic, and other antibiotic: fosfomycin, cycloserine, lincomycin, clindamycin, mitomycin, actinomycin D, bleomycin, doxorubicin, isoniazid, pyrazinamide, cyclosporine, or a combination thereof.

The biologic drug can be an antimicrobial peptide, which can comprise an insect antimicrobial peptide: lepidopteran antibacterial peptide, diptera antibacterial peptide, coleoptera antibacterial peptide, hymenoptera antibacterial peptide and silkworm antibacterial peptide; a mammalian antimicrobial peptide: porcine antibacterial peptide, sheep antibacterial peptide, bovine antibacterial peptide and human antibacterial peptide; an amphibian antibacterial peptide: xenopus; an antibacterial peptide derived from fish, mollusc, or crustacean: leopard antibacterial peptide, mussel antibacterial peptide and shrimp antibacterial peptide; a bacterial antibacterial peptide: bacitracin, gramicidin, polymyxin and nisin; plant antibacterial peptide, or a combination thereof.

The natural drug can comprise: *Astragalus, Polygonatum, Angelica*, Sanqi, *Rhizoma Imperatae*, Rhubarb Charcoal, *Curcuma aromatica*, Fritillary, *Coix* Seed, *Pinellia*, Calcined ancient ink, *Salvia Miltiorrhiza*, Arnebiaeuchroma, *Radix Isatidis, Houttuynia*, Honeysuckle, *Rhizoma Coptis, Scutellaria*, Dandelion, Purslane, Hawthorn, *Isatidis Folium, Fructus Forsythiae, Herba Artemisiae Capillaris, Andrographis Paniculata* Nees, *Radix Bupleuri*, Rhubarb, *Euphorbia Humifusa, Stemonae*, Garlic, *Cortex Phellodendri, Eucommia, Cortex Fraxini, Fructus Cnidii, Galla Chinensis*, viola *yedoensis* makino, *Fructus Mume, Radix Glycyrrhizae, Pericarpium Granati, Schisandra chinensis, Spina Gleditsiae, Terminalia Chebula, Sophora flavescens, Cortex Pseudolaricis, Epimedium, Artemisia apiacea* Hance, an extract thereof, or a combination thereof.

The drug in the present disclosure can be an oral, injectable or topical medicine which includes mucosal drug, preferably an ocular drug.

The drug in the present disclosure can be in the form of a solution, a tablet, a pill, a capsule, an injection, a powder, a powder for injection, a patch, a coating agent or a mucosal administration preparation preferably for eye drops, eye ointments or eye spray preparations, etc.

In some preferred embodiments, the present disclosure relates to a method of screening a drug for treating or preventing the cataract (Cat), the steps of the method are as follows:
(1) infecting a model carrier with the microorganism of one or more of the following: *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti*, or *Acidovorax ebreus* to establish the model;
(2) Applying the drug on the model;
(3) Analyzing the results. The drug which can kill or inhibit microorganisms in the model can be identified as having a therapeutic or prophylactic effect on Cat patients.

In some preferred embodiments, the present disclosure relates to a method of screening a drug for treating or preventing the age-related macular degeneration (AMD), the steps of the method are as follows:
(1) infecting a model carrier with the microorganism of one or more of the following: *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, or *Xanthomonas oryzae* to establish the model;
(2) Applying the drug on the model;
(3) Analyzing the results. The drug which can kill or inhibit microorganisms in the model can be identified as having a therapeutic or prophylactic effect on AMD patients.

In some preferred embodiments, the present disclosure relates to a method of screening a drug for treating or preventing the glaucoma (GLA), the steps of the method are as follows:
(1) infecting a model carrier with the microorganism of one or more of the following: *Acinetobacter baumannii, Acinetobacter calcoaceticus, Comamonas testosteroni, Mycobacterium kansasii, Bacillus thuringiensis, Citrobacter koseri, Dyadobacter fermentants*, or *Serratia marcescens* to establish the model;
(2) Applying the drug on the model;
(3) Analyzing the results. The drug which can kill or inhibit microorganisms in the model can be identified as having a therapeutic or prophylactic effect on GLA patients.

In some preferred embodiments, the present disclosure relates to a method of screening a drug for treating or preventing the Behcet's disease (BD), the steps of the method are as follows:
(1) infecting the microorganism of one or more of the following *Sphingomonas wittichii, Klebsiella pneumoniae, Pseudomonas fluorescens, Ralstonia pickettii, Lactobacillus crispatus, Burkholderia multivorans, Lactobacillus delbrueckii*, or *Meiothermus silvanus*(D) onto a model carrier to establish the model;
(2) Applying the drug on the model;
(3) Analyzing the results. The drug which can kill or inhibit microorganisms in the model can be identified as having a therapeutic or prophylactic effect on BD patients.

In some preferred embodiments, the present disclosure relates to a method of screening a drug for treating or preventing the Vogt-Koyanagi-Harada Syndrome (VKH), the steps of the method are as follows:
(1) infecting a model carrier with the microorganism of one or more of the following: *Escherichia coli, Micrococcus luteus, Bacillus subtilis, Corynebacterium aurimucosum*, or *Finegoldia magna* to establish the model;
(2) Applying the drug on the model;
(3) Analyzing the results. The drug which can kill or inhibit microorganisms in the model can be identified as having a therapeutic or prophylactic effect on VKH patients.

In yet another aspect, disclosed herein is a use of a microbial in screening a drug, specific, the steps of screening drug are as follows: infecting a model carrier with a microorganism to establish the model; applying the drug on the model; screening the drug for therapeutic or prophylactic effect. The defined range of microorganism, model carrier and drug are as described above.

In still another aspect, disclosed herein is a drug, which is identified by following steps: infecting a model carrier with a microorganism to establish the model; applying the drug on the model; screening the drug for positive result. The defined range of microorganism, model carrier and drug are as described above.

Positive result refers to the drug identified can kill or inhibit the microorganism in the model.

Exemplary Embodiments 1-25

Embodiment 1. A method for establishing a model of intraocular disease or disorder, which method comprises infecting a model carrier with a microorganism.

Embodiment 2. The method of embodiment 1, wherein the microorganism comprises bacteria, archaeal, protist, fungus, virus, or a combination thereof.

Embodiment 3. The method of embodiment 1, wherein the model carrier comprises one or more of human, non-human mammal, organs, tissues, tissue sections, tissue extracts, body fluids, body fluid cultures, cells, viruses, enzymes, culture media.

Embodiment 4. The method of embodiment 2, wherein the microorganism comprises bacteria selected from one or more of the followings: *Clostridium, Acinetobacter, Streptococcus, Mannheimia, Fibrobacter, Prevotella, Campylobacter, Actinomyces, Hymenobacter, Escherichia, Tissierella, Klebsiella, Porphyromonas, Azospira, Aquimarina, Achromobacter, Acidithiobacillus, Burkholderia, Marinobacter, Treponema, Actinosporangium, Vibrio*, Ruminococcus, *Methanobrevibacter, Shigella, Frankia, Anaeroplasma* and *Coprococcus*.

Embodiment 5. The method of embodiment 4, wherein the bacteria are selected from one or more of the followings: *Clostridium* tetanus, *Clostridium* perfringens, *Clostridium botulinum, Acinetobacter acetate, Acinetobacter rufi, Acinetobacter baumannii, Acinetobacter hemolyticus, Acinetobacter junii, Acinetobacter johnsonii, Streptococcus pyogenes, Streptococcus hemolyticus, Porphyromonas asacharolytica, Porphyromonas gingivalis, Porphyromonas gingivalis, Campylobacter jejuni, Campylobacter coli, Campylobacter seabirds, Campylobacter Uppsala, Campylobacter* concisely, *Campylobacter fitus, Actinomyces israelii, Actinomyces naeslundii, Actinomyces odontolyticus, Escherichia coli, Escherichia blattae, Escherichia fergusonii, Escherichia hermannii, Escherichia vulneris, Tissierella apical, Klebsiella pneumoniae, Klebsiella odorata, Azospirillum brasilence, Achromobacter, Thiobacillus denitrificans, Thiobacillus ferrooxidans, Thiobacillus thiooxidans, Thiobacillus neapolitanus, Burkholderia, Mycobacterium marinum, Treponema Pallidum, Treponema hyodysenteriae, Vibrio metschnikovi, Ruminococcus albus, Ruminococcus flavefaciens, Methanobrevibacter ruminantium, Shigella dysenteriae, Shigella flexneri, Shigella bogdii, Shigella sonnei, Frankiaceae, Streptomyces albus, Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus* (D), *Escherichia coli, Micrococcus luteus, Bacillus subtilis, Corynebacterium aurimucosum, Finegoldia magna*.

Embodiment 6. The method of embodiment 1, wherein the intraocular disease or disorder is selected from cataract, age-related macular degeneration, glaucoma, Behcet's disease, Vogt-Koyanagi-Harada Syndrome, or uveitis.

Embodiment 7. The method of embodiment 1, wherein the intraocular disease or disorder is cataract, wherein the method comprises infecting a model carrier with the microorganism selected from one or more of the following *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti*, or *Acidovorax ebreus*.

Embodiment 8. The method of embodiment 1, wherein the intraocular disease or disorder is age-related macular degeneration, wherein the method comprises a model carrier with the microorganism selected from one or more of the following *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, or *Xanthomonas oryzae*.

Embodiment 9. The method of embodiment 1, wherein the intraocular disease or disorder is glaucoma, wherein the method comprises infecting a model carrier with the microorganism selected from one or more of the following *Acinetobacter baumannii, Acinetobacter calcoaceticus, Comamonas testosteroni, Mycobacterium kansasii, Bacillus thuringiensis, Citrobacter koseri, Dyadobacter fermentans*, or *Serratia marcescens*.

Embodiment 10. The method of embodiment 1, wherein the intraocular disease or disorder is Behcet's disease, wherein the method comprises infecting a model carrier with the microorganism selected from one or more of the following *Sphingomonas wittichii, Klebsiella pneumoniae, Pseudomonas fluorescens, Ralstonia pickettii, Lactobacillus crispatus, Burkholderia multivorans, Lactobacillus delbrueckii*, or *Meiothermus silvanus*(D).

Embodiment 11. The method of embodiment 1, wherein the intraocular disease or disorder is Vogt-Koyanagi-Harada Syndrome, wherein the method comprises infecting a model carrier with the microorganism selected from one or more of the following *Escherichia coli, Micrococcus luteus, Bacillus subtilis, Corynebacterium aurimucosum*, or *Finegoldia magna*.

Embodiment 12. Use of a microbial in establishing a model of intraocular disease or disorder.

Embodiment 13. A model of an eye disease, which is produced by the method of embodiment 1.

Embodiment 14. Use of a microbial in preparing a model for screening a drug for an eye disease.

Embodiment 15. The use of embodiment 14, wherein the drug comprises one or more of a chemical drug, a biologic drug or a natural drug.

Embodiment 16. The use of embodiment 15, wherein the chemical drug comprises 3-lactam antibiotic, aminoglycoside antibiotic, tetracycline antibiotic, chloramphenicol antibiotic, macrolide antibiotic, glycopeptide antibiotic, quinolone antibiotic, nitroimidazole antibiotic, rifamycin antibiotic, echinocandins antibiotic, polyene antibiotic, pyrimidine antibiotic, allylamines antibiotic, azoles antibiotic, and other antibiotic, or a combination thereof.

Embodiment 17. The use of embodiment 15, wherein the biologic drug is antimicrobial peptide.

Embodiment 18. The use of embodiment 15, wherein the natural drug comprises *Astragalus, Polygonatum, Angelica,* Sanqi, *Rhizoma Imperatae,* Rhubarb Charcoal, *Curcuma aromatica,* Fritillary, *Coix* Seed, *Pinellia,* Calcined ancient ink, *Salvia Miltiorrhiza,* Arnebiaeuchroma, *Radix Isatidis, Houttuynia,* Honeysuckle, *Rhizoma Coptis, Scutellaria,* Dandelion, Purslane, Hawthorn, *Isatidis Folium, Fructus Forsythiae, Herba Artemisiae Capillaris, Andrographis Paniculata* Nees, *Radix Bupleuri,* Rhubarb, *Euphorbia Humifusa, Stemonae,* Garlic, *Cortex Phellodendri, Eucommia, Cortex Fraxini, Fructus Cnidii, Galla Chinensis,* viola *yedoensis makino, Fructus Mume, Radix Glycyrrhizae, Pericarpium Granati, Schisandra chinensis, Spina Gleditsiae, Terminalia Chebula, Sophora flavescens, Cortex Pseudolaricis, Epimedium, Artemisia apiacea* Hance, an extract thereof, or a combination thereof.

Embodiment 19. The use of embodiment 14, wherein the microorganism comprises bacteria, archaeal, protist, fungus, virus, or a combination thereof.

Embodiment 20. The use of embodiment 19, wherein the microorganism comprises bacteria which are selected from one or more of the followings: *Clostridium, Acinetobacter, Streptococcus, Mannheimia, Fibrobacter, Prevotella, Campylobacter, Actinomyces, Hymenobacter, Escherichia, Tissierella, Klebsiella, Porphyromonas, Azospira, Aquimarina, Achromobacter, Acidithiobacillus, Burkholderia, Marinobacter, Treponema, Actinosporangium, Vibrio, Ruminococcus, Methanobrevibacter, Shigella, Frankia, Anaeroplasma* and *Coprococcus.*

Embodiment 21. The use of embodiment 20, wherein the bacteria are selected from one or more of the followings: *Clostridium tetanus, Clostridium perfringens, Clostridium botulinum, Acinetobacter acetate, Acinetobacter rufi, Acinetobacter baumannii, Acinetobacter hemolyticus, Acinetobacter junii, Acinetobacter johnsonii, Streptococcus pyogenes, Streptococcus hemolyticus, Porphyromonas asacharolytica, Porphyromonas gingivalis, Porphyromonas gingivalis, Campylobacter jejuni, Campylobacter coli, Campylobacter seabirds, Campylobacter* Uppsala, *Campylobacter* concisely, *Campylobacter fitus, Actinomyces israelii, Actinomyces naeslundii, Actinomyces odontolyticus, Escherichia coli, Escherichia blattae, Escherichia ferguso-nii, Escherichia hermannii, Escherichia vulneris, Tissierella apical, Klebsiella pneumoniae, Klebsiella odorata, Azospirillum brasilence, Achromobacter, Thiobacillus denitrificans, Thiobacillus ferrooxidans, Thiobacillus thiooxidans, Thiobacillus neapolitanus, Burkholderia, Mycobacterium marinum, Treponema Pallidum, Treponema hyodysenteriae, Vibrio metschnikovi, Ruminococcus albus, Ruminococcus flavefaciens, Methanobrevibacter ruminantium, Shigella dysenteriae, Shigella flexneri, Shigella bogdii, Shigella sonnei, Frankiaceae, Streptomyces albus, Pseudomonas mendocina, Kytococcus sedentarius, Alicycliphilus denitrificans, Achromobacter xylosoxidans, Sphin-gobium japonicum, Mycobacterium abscessus, Arthrobacter aurescens, Prevotella dentalis, Sinorhizobium meliloti, Acidovorax ebreus, Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus* (D), *Escherichia coli, Micrococcus luteus, Bacillus subtilis, Corynebacterium aurimucosum, Finegoldia magna.*

Embodiment 22. The use of embodiment 14, wherein the eye disease is selected from cataract, age-related macular degeneration, glaucoma, Behcet's disease, Vogt-Koyanagi-Harada Syndrome, or uveitis.

Embodiment 23. A method for screening a drug, comprising: (1) Applying the drug on the model of embodiment 13; (2) Analyzing the results.

Embodiment 24. The method of embodiment 23, wherein the drug comprises one or more of a chemical drug, a biologic drug or a natural drug.

Embodiment 25. A drug, which is identified by the method of embodiment 23.

Additional Exemplary Embodiments B1-B104

The present disclosure also provides the following additional exemplary embodiments B1-B104.

Embodiment B1. A method of treating or preventing age-related macular degeneration (AMD) in a subject in need thereof, the method comprising administering to the subject a therapeutically effective amount of a compound of Formula I, or a pharmaceutically acceptable salt or ester thereof, or a pharmaceutical composition comprising the compound or pharmaceutically acceptable salt or ester thereof:

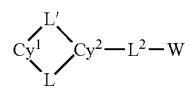

Formula I wherein:
Cy$^1$ and Cy$^2$ are each independently an optionally substituted cycloalkyl ring (e.g., C$_{3-7}$ cycloalkyl ring), an optionally substituted heterocyclic ring (e.g., 4-7 membered heterocyclic ring), an optionally substituted aryl ring (e.g., C$_{6-10}$ aryl ring), or an optionally substituted heteroaromatic ring (e.g., 5-10 membered heteroaromatic ring);
L and L' are each independently null or a linker;
L$^2$ is null, an optionally substituted C$_{1-6}$ alkylene, an optionally substituted C$_{1-6}$ heteroalkylene, an optionally substituted C$_{2-6}$ alkenylene, an optionally substituted C$_{2-6}$ alkynylene, an optionally substituted C$_{3-6}$ cycloalkylene, an optionally substituted arylene, an optionally substituted heteroaryl ene, or an optionally substituted 4-7 membered heterocyclylene, W is —OR¹; —COR²; —COOR¹ᵃ; —OCOOR¹ᵃ; —NR³R⁴; —CONR³ᵃR⁴ᵃ; —OCONR³ᵇR⁴ᵇ; —SO₂NR³ᶜR⁴ᶜ; —OSO₂NR³ᵈR⁴ᵈ; —SR⁵; —SO₂R⁵ᵃ; —OCOR²ᵃ; —OSO₂R⁵ᵃ or

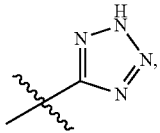

wherein:
R¹ and R¹ᵃ are each independently hydrogen, optionally substituted alkyl, optionally substituted alkenyl, optionally substituted alkynyl, optionally substituted cycloalkyl, optionally substituted aryl, optionally substituted heteroaryl, or optionally substituted heterocyclyl;

R³ and R⁴ are each independently hydrogen, —COR²ᵇ, —SO₂R⁵ᵇ, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl, or R³ and R⁴ together with the atoms they are bound to form an optionally substituted 4-7 membered heterocyclyl;

R², R²ᵃ, R²ᵇ, R⁵, R⁵ᵃ, and R⁵ᵇ are each independently hydrogen, —OH, —NR³ᵉR⁴ᵉ, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; and R³ᵃ, R³ᵇ, R³ᶜ, R³ᵈ, R³ᵉ, R⁴ᵃ, R⁴ᵇ, R⁴ᶜ, R⁴ᵈ, and R⁴ᵉ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or R³ᵃ and R⁴ᵃ, R³ᵇ and R⁴ᵇ, R³ᶜ and R⁴ᶜ, R³ᵈ and R⁴ᵈ, or R³ᵉ and R⁴ᵉ, together with the atoms they are bound to form an optionally substituted 4-7 membered heterocyclyl.

Embodiment B2. The method of embodiment B1, wherein in Formula I, at least one of Cy¹ and Cy² is an optionally substituted $C_{6-10}$ aryl ring, or an optionally substituted 5-10 membered heteroaromatic ring.

Embodiment B3. The method of embodiment B1, wherein the compound of Formula I has a Formula I-1:

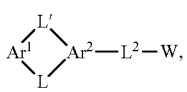

Formula I-1 wherein Ar¹ and Ar² are each independently an optionally substituted $C_{6-10}$ aryl ring, or an optionally substituted 5-10 membered heteroaromatic ring. Embodiment B4. The method of embodiment B3, wherein Ar¹ and Ar² in Formula I-1 are each independently an optionally substituted phenyl ring or an optionally substituted 5 or 6 membered heteroaromatic ring.

Embodiment B5. The method of embodiment B3, wherein Ar and Ar in Formula I-1 are each independently an optionally substituted phenyl ring, an optionally substituted thienyl ring, an optionally substituted furanyl ring, an optionally substituted pyridyl ring, or an optionally substituted pyrimidinyl ring.

Embodiment B6. The method of embodiment B1, wherein the compound of Formula I has a Formula I-2:

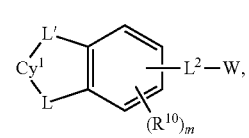

Formula I-2 wherein:
m is 0, 1, 2, or 3,
R¹⁰ at each occurrence is independently halogen, -L²'-W', an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent R¹⁰, or one R¹⁰ and L or L', together with the atoms they are bound to form an optionally substituted cycloalkyl, heterocyclyl, aryl, or heteroaryl ring;
wherein L²' and W' have the definition of L² and W in embodiment B1, respectively, and -L²'-W' at each occurrence is independently selected.

Embodiment B7. The method of embodiment B6, wherein Cy¹ in Formula I-2 is an optionally substituted phenyl ring, an optionally substituted thienyl ring, an optionally substituted furanyl ring, an optionally substituted pyridyl ring, or an optionally substituted pyrimidinyl ring.

Embodiment B8. The method of embodiment B6, wherein Cy¹ in Formula I-2 is an optionally substituted $C_{3-6}$ cycloalkyl ring or an optionally substituted 4-7 heterocyclic ring with 1 or 2 ring heteroatoms independently selected from N, O, and S.

Embodiment B9. The method of embodiment B6, wherein the compound of Formula I-2 has a Formula I-3:

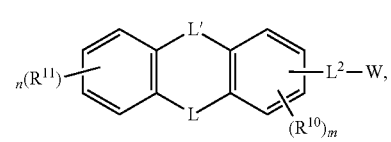

Formula I-3 wherein:
n is 0, 1, 2, or 3,
R¹¹ at each occurrence is independently halogen, -L²'-W', an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent $R^{11}$, or one $R^{11}$ and L or L'. Together with the atoms they are bound to form an optionally substituted cycloalkyl, heterocyclyl, aryl, or heteroaryl ring;

wherein $L^{2'}$ and W' have the definition of $L^2$ and W in embodiment B1, respectively, and -$L^{2'}$-W' at each occurrence is independently selected.

Embodiment B10. The method of any one of embodiments B1-9, wherein F and F in Formula I are each independently null, —C(O)—, optionally substituted $C_{1-4}$alkylene, optionally substituted $C_{2-4}$ alkenylene, —O—, —S—, —$NR^{100}$—, —S(O)—, —$SO_2$—, —$X^1$-$G^1$-, —$X^2$-$G^2$-$X^{2a}$—, or —$CR^{101}R^{102}$—, wherein:

$X^1$, $X^2$, and $X^{2a}$ are independently optionally substituted $C_{1-4}$alkylene, optionally substituted $C_{2-4}$ alkenylene, —O—, —C(O)—, —S—, —$NR^{100a}$—, —S(O)—, —$SO_2$—, or —$CR^{101a}R^{102a}$—;

$G^1$ and $G^2$ are independently optionally substituted $C_{1-4}$alkylene, optionally substituted $C_{2-4}$ alkenylene, —C(O)—, —$NR^{100a}$—, —S(O)—, —$SO_2$—, or —$CR^{101a}R^{102a}$—;

provided that —$X^1$-$G^1$- or —$X^2$-$G^2$-$X^{2a}$— does not contain an O—N, S—S, S—N(other than $SO_2$—N), or —C(O)—S bond;

$R^{100}$ and $R^{100a}$ are each independently lone pair (as applicable), hydrogen, $COR^{2c}$, —$SO_2R^{5c}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl; or $R^{100}$ or $R^{100a}$ forms an optionally substituted heterocyclic or heteroaryl ring with a $R^{10}$ or $R^{11}$ group;

$R^{101}$, $R^{101a}$, $R^{102}$, and $R^{102a}$ are each independently hydrogen, —OH, halogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$ alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl, or $R^{101}$ and $R^{102}$, or $R^{101a}$ and $R^{102a}$, together with the atoms they are bound to form an optionally substituted 3-7 membered cycloalkyl or heterocyclyl ring; or one of $R^{101}$ and $R^{102}$, or one of $R^{101a}$ and $R^{102a}$ forms an optionally substituted cycloalkyl or heterocyclyl ring together with a $R^{10}$ or $R^{11}$ group; and $R^{2c}$ and $R^{5c}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl.

Embodiment B11. The method of embodiment B10, wherein L and L' in Formula I are each independently null, —O—, —C(O)—, —S—, —$NR^{100}$—, —S(O)—, —$SO_2$—, or —$CR^{101}R^{102}$—.

Embodiment B12. The method of embodiment B10, wherein the compound of Formula I has a formula according to any one of I-4 to I-5:

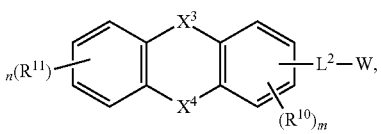

Formula I-4

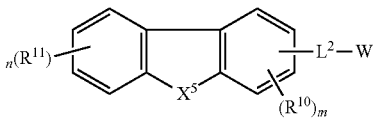

Formula I-5 wherien:

$X^3$, $X^4$, and $X^5$ are each independently null, —O—, —C(O)—, —S—, —$NR^{100a}$—, —S(O)—, —$SO_2$—, or —$CR^{101a}R^{102a}$—, and $R^{10}$, $R^{11}$, $R^{100a}$, $R^{101a}$, $R^{102a}$, W, $L^2$, m, and n are defined above.

Embodiment B13. The method of any one of embodiments B1-12, wherein $L^2$ in Formula I is null.

Embodiment B14. The method of any one of embodiments B1-12, wherein $L^2$ and each instance of $L^{2'}$ in Formula I are independently null, $C_{1-4}$ alkylene, $C_{2-4}$ alkenylene, $C_{2-4}$ alkynylene or $C_{1-4}$ heteroalkylene.

Embodiment B15. The method of any one of embodiments B1-14, wherein W and each instance of W' in Formula I are independently —OH, —$NH_2$, —$SO_2NH_2$, —$SO_2NH$($C_{1-4}$ alkyl), —$SO_2NH$($C_{1-4}$ alkanoyl), —COOH,

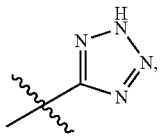 [SMILES: *c1nn[nH]n1]

—C(O)(O—$C_{1-10}$ alkyl), —C(O)(O—$C_{2-10}$ alkenyl), —OC(O)$NH_2$, —OC(O)NH($C_{1-4}$ alkyl)-, —O—(CO)—($C_{1-4}$ alkyl), —O—($C_{1-4}$ alkyl), wherein each of the $C_{1-4}$ alkyl is independently optionally substituted with 1-3 substituents independently selected from $C_{1-4}$ alkyl, $C_{1-4}$alkoxy, —OH, —$NH_2$, and fluorine.

Embodiment B16. The method of any one of embodiments B1-15, wherein W in Formula I is —OH, —$NH_2$, —$SO_2NH_2$, —$SO_2NH$(Acetyl), —COOH,

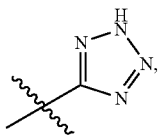

or —O—C(O)—$CH_3$.

Embodiment B17. The method of any one of embodiments B12-16, wherein the compound has a Formula I-4, or I-5, wherein:

$L^2$ and each instance of $L^{2'}$ are null,

W and each instance of W' are independently —OH, —$NH_2$, —$SO_2NH_2$, —$SO_2NH$($C_{1-4}$ alkyl), —$SO_2NH$($C_{1-4}$ alkanoyl), —COOH,

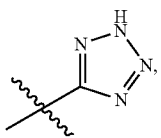 [SMILES: *c1nn[nH]n1]

—C(O)(O—C$_{1-10}$ alkyl), —C(O)(O—C$_{2-10}$ alkenyl), —OC(O)NH$_2$, —OC(O)NH(C$_{1-4}$ alkyl)-, —O—(CO)—(C$_{1-4}$ alkyl), —O—(C$_{1-4}$ alkyl), wherein each of the C$_{1-4}$ alkyl is independently optionally substituted with 1-3 substituents independently selected from C$_{1-4}$ alkyl, C$_{1-4}$ alkoxy, —OH, —NH$_2$, and fluorine;

each of R$^{10}$ and R$^{11}$ at each occurrence is independently F; Cl; —OH; —NH$_2$; —SO$_2$NH$_2$; —SO$_2$NH(C$_{1-4}$ alkyl); —SO$_2$NH(C$_{1-4}$ alkanoyl); —C(O)(O—C$_{1-10}$ alkyl), —C(O)(O—C$_{2-10}$ alkenyl); —COOH;

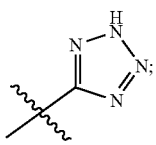 [SMILES: *c1nn[nH]n1]

—OC(O)NH$_2$; —OC(O)NH(C$_{1-4}$ alkyl)-; —O—(CO)—(C$_{1-4}$ alkyl); C$_{1-4}$ alkyl optionally substituted with 1-3 substituents independently selected from C$_{1-4}$ alkyl, C$_{1-4}$ alkoxy, —OH, —NH$_2$, and fluorine; C$_{2-6}$ alkenyl optionally substituted with 1-3 substituents independently selected from C$_{1-4}$ alkyl, C$_{1-4}$ alkoxy, —OH, —NH$_2$, and fluorine; C$_{2-6}$ alkynyl optionally substituted with 1-3 substituents independently selected from C$_{1-4}$ alkyl, C$_{1-4}$ alkoxy, —OH, —NH$_2$, and fluorine; C$_{3-6}$ cycloalkyl optionally substituted with 1-3 substituents independently selected from C$_{1-4}$ alkyl and fluorine; C$_{3-6}$ cycloalkoxy optionally substituted with 1-3 substituents independently selected from C$_{1-4}$ alkyl and fluorine; or C$_{1-4}$ alkoxy optionally substituted with 1-3 substituents independently selected from C$_{1-4}$ alkyl, C$_{1-4}$ alkoxy, —OH, —NH$_2$, and fluorine; and m is 0, 1, or 2, and n is 0, 1, 2, or 3.

Embodiment B18. The method of embodiment B17, wherein the compound has a Formula I-4, wherein X$^3$ and X$^4$ are each independently —O—, —C(O)—, —S—, —NR$^{100a}$—, or —SO$_2$—.

Embodiment B19. The method of embodiment B17, wherein the compound has a Formula I-5, wherein X$^5$ is —O—, —C(O)—, —S—, —NR$^{100a}$—, or —SO$_2$—.

Embodiment B20. The method of embodiment B18 or 19, wherein the compound has a Formula I-4 or I-5, wherein R$^{100a}$ is hydrogen or an optionally substituted C$_{1-4}$ alkyl.

Embodiment B21. The method of any one of embodiments B1-20, wherein the compound of Formula I, or a pharmaceutically acceptable salt or ester thereof, is in an isolated or substantially purified form.

Embodiment B22. A method of treating or preventing age-related macular degeneration (AMD) in a subject in need thereof, the method comprising administering to the subject a therapeutically effective amount of a compound of Formula II, or a pharmaceutically acceptable salt or ester thereof, or a pharmaceutical composition comprising the compound or pharmaceutically acceptable salt or ester thereof:

Cy$^{10}$-L$^{10}$-Cy$^{11}$-L$^{11}$-W$^{10}$    Formula II wherein:
Cy$^{10}$ and Cy$^{11}$ are each independently an optionally substituted cycloalkyl ring (e.g., C$_{3-7}$ cycloalkyl ring), an optionally substituted heterocyclic ring (e.g., 4-7 membered heterocyclic ring), an optionally substituted aryl ring (e.g., C$_{6-10}$ aryl ring), an optionally substituted heteroaromatic ring (e.g., 5-10 membered heteroaromatic ring), or an optionally substituted ring structure comprising a cycloalkyl ring or heterocyclic ring, and an aryl or heteroaryl ring, wherein the ring structure can be a fused ring;

L$^{10}$ is null or a linker;

L$^{11}$ is null, an optionally substituted C$_{1-6}$ alkylene, an optionally substituted C$_{1-6}$ heteroalkylene, an optionally substituted C$_{2-6}$ alkenylene, an optionally substituted C$_{2-6}$ alkynylene, an optionally substituted C$_{3-6}$ cycloalkylene, an optionally substituted arylene, an optionally substituted heteroarylene, or an optionally substituted 4-7 membered heterocyclylene;

W$^{10}$ is —OR$^1$; —COOR$^{1a}$; —OCOOR$^{1a}$; —COR$^2$; —NR$^3$R$^4$; —CONR$^{3a}$R$^{4a}$; —OCONR$^{3b}$R$^{4b}$; —SO$_2$NR$^{3c}$R$^{4c}$; —OSO$_2$NR$^{3d}$R$^{4d}$; —SR$^5$; —SO$_2$R$^{5a}$; —OCOR$^{2a}$; —OSO$_2$R$^{5a}$ or

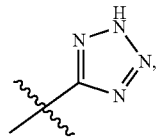

wherein:
R$^1$ and R$^{1a}$ are each independently hydrogen, optionally substituted alkyl, optionally substituted alkenyl, optionally substituted alkynyl, optionally substituted cycloalkyl, optionally substituted aryl, optionally substituted heteroaryl, or optionally substituted heterocyclyl;

R$^3$ and R$^4$ are each independently hydrogen, —COR$^{2b}$, —SO$_2$R$^{5b}$, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted phenyl, optionally substituted 5 or 6 membered heteroaryl, or optionally substituted 4-7 membered heterocyclyl, or R$^3$ and R$^4$ together with the atoms they are bound to form an optionally substituted 4-7 membered heterocyclyl;

R$^2$, R$^{2a}$, R$^{2b}$, R$^5$, R$^{5a}$, and R$^{5b}$ are each independently hydrogen, —OH, —NR$^{3e}$R$^{4e}$, an optionally substituted C$_{1-6}$ alkyl, an optionally substituted C$_{2-6}$ alkenyl, an optionally substituted C$_{2-6}$ alkynyl, an optionally substituted C$_{1-6}$ alkoxy, an optionally substituted C$_{3-6}$ cycloalkyl, an optionally substituted C$_{3-6}$ cycloalkoxy, an optionally substituted phenyl; an optionally substituted 5 or 6 membered heteroaryl; or an optionally substituted 4-7 membered heterocyclyl; and R$^{3a}$, R$^{3b}$, R$^{3c}$, R$^{3d}$, R$^{3e}$, R$^{4a}$, R$^{4b}$, R$^{4c}$, R$^{4d}$, and R$^{4e}$ are each independently hydrogen, an optionally substituted C$_{1-6}$ alkyl, an optionally substituted C$_{2-6}$ alkenyl, an optionally substituted C$_{2-6}$ alkynyl, an optionally substituted C$_{1-6}$ alkoxy, an optionally substituted C$_{3-6}$ cycloalkyl, an optionally substituted C$_{3-6}$ cycloalkoxy, an optionally substituted phenyl; an optionally substituted 5 or 6 membered heteroaryl; or an optionally substituted 4-7 membered heterocyclyl; or R$^{3a}$ and R$^{4a}$, R$^{3b}$ and R$^{4b}$, R$^{3c}$ and R$^{4c}$, R$^{3d}$ and R$^{4d}$, or R$^{3e}$ and R$^{4e}$, together with the atoms they are bound to form an optionally substituted 4-7 membered heterocyclyl.

Embodiment B23. The method of embodiment B22, wherein in Formula II, at least one of $Cy^{10}$ and $Cy^{11}$ is an optionally substituted $C_{6-10}$ aryl ring, or an optionally substituted 5-10 membered heteroaryl ring.

Embodiment B24. The method of embodiment B22, wherein the compound of Formula II has a Formula II-1:

$$Ar^{10}\text{-}L^{10}\text{-}Ar^{11}\text{-}L^{11}\text{-}W^{10} \qquad \text{Formula II-1}$$

wherein $Ar^{10}$ and $Ar^{11}$ are each independently an optionally substituted $C_{6-10}$ aryl ring, or an optionally substituted 5-10 membered heteroaryl ring.

Embodiment B25. The method of embodiment B24, wherein $Ar^{10}$ and $Ar^{11}$ in Formula II-1 are each independently an optionally substituted phenyl ring or an optionally substituted 5 or 6 membered heteroaryl ring.

Embodiment B26. The method of embodiment B24, wherein $Ar^{10}$ and $Ar^{11}$ in Formula II-1 are each independently an optionally substituted phenyl ring, an optionally substituted thienyl ring, an optionally substituted furanyl ring, an optionally substituted pyridyl ring, or an optionally substituted pyrimidinyl ring.

Embodiment B27. The method of embodiment B24, wherein one of $Ar^{10}$ and $Ar^{11}$ in Formula II-1 is a bicyclic aryl or bicyclic heteroaryl ring, each of which is optionally substituted.

Embodiment B28. The method of embodiment B24, wherein the compound of Formula II has a Formula II-2:

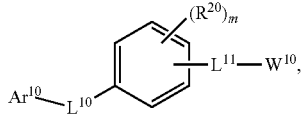

Formula II-2 wherein m is 0, 1, 2, or 3,
$R^{20}$ at each occurrence is independently halogen, $-L^{11'}\text{-}W^{10'}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl;
or two adjacent $R^{20}$, or one $R^{20}$ and $L^{10}$ or $L^{11}$, together with the atoms they are bound to form an optionally substituted cycloalkyl, heterocyclyl, aryl, or heteroaryl ring;
wherein $L^{11'}$ and $W^{10'}$ have the definition of $L^{11}$ and $W^{10}$ in embodiment B26, respectively, and $-L^{11'}\text{-}W^{10'}$ at each occurrence is independently selected.

Embodiment B29. The method of embodiment B22, wherein the compound of Formula II has a Formula II-3:

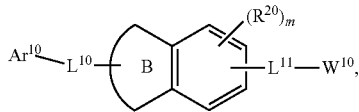

Formula II-3 wherein:
$Ar^{10}$ is an optionally substituted $C_{6-10}$ aryl ring or an optionally substituted 5-10 membered heteroaryl ring;
m is 0, 1, 2, or 3,
$R^{20}$ at each occurrence is independently halogen, $-L^{11'}\text{-}W^{10'}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent $R^{20}$, or one $R^{20}$ and $L^{10}$ or $L^{11}$, together with the atoms they are bound to form an optionally substituted cycloalkyl, heterocyclyl, aryl, or heteroaryl ring;
wherein $L^{11'}$ and $W^{10'}$ have the definition of $L^{11}$ and $W^{10}$ in embodiment B26, respectively, and $-L^{11'}\text{-}W^{10'}$ at each occurrence is independently selected; and
ring B is a 4-7 membered cycloalkyl ring, 4-7 membered heterocyclic ring, phenyl ring, 5 or 6 membered heteroaryl ring, each of which is optionally substituted.

Embodiment B30. The method of embodiment B29, wherein the compound of Formula II has a Formula II-4:

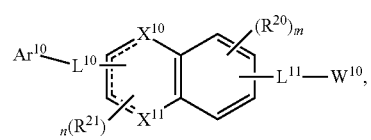

Formula II-4 wherein:
n is 0 or 1,
$R^{21}$ at each occurrence is independently halogen, $-L^{11'}\text{-}W^{10'}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl;
wherein $L^{11'}$ and $W^{10'}$ have the definition of $L^{11}$ and $W^{10}$ in embodiment B26, respectively, and $-L^{11'}\text{-}W^{10'}$ at each occurrence is independently selected;
$X^{10}$ and $X^{11}$ are each independently null, —O—, —C(O)—, —S—, —NR$^{100a}$—, —S(O)—, —SO$_2$—, or —CR$^{101a}$R$^{102a}$—, as valence permits;
wherein $R^{100a}$ is lone pair (as applicable), hydrogen, COR$^{2c}$, —SO$_2$R$^{5c}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl; or $R^{100a}$ forms an optionally substituted heterocyclic or heteroaryl ring with a $R^{20}$ or $R^{21}$ group;
$R^{101a}$ and $R^{102a}$, when present, are each independently hydrogen, —OH, halogen; optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$ alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl, or $R^{101a}$ and $R^{102a}$, together with the atoms they are bound to form an optionally substituted 3-7 membered cycloalkyl or heterocyclyl ring; or one of $R^{101a}$ and $R^{102a}$ forms an optionally substituted cycloalkyl or heterocyclyl ring together with a $R^{20}$ or $R^{21}$ group; and $R^{2c}$ and $R^{5c}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or $R^{20}$ or $R^{21}$ and $L^{10}$, $X^{10}$ or $X^{11}$, together with the atoms they are bound to form an optionally substituted cycloalkyl, heterocyclyl, aryl, or heteroaryl ring.

Embodiment B31. The method of embodiment B30, wherein the compound has a formula according to II-5:

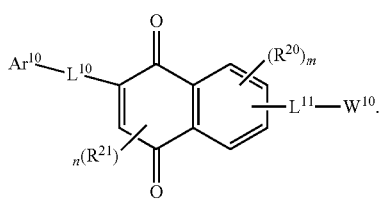

Formula II-5

Embodiment B32. The method of any one of embodiments B22-31, wherein $L^{10}$ in Formula II is null, —C(O)—, optionally substituted $C_{1-4}$alkylene, optionally substituted $C_{2-4}$ alkenylene, optionally substituted $C_{3-6}$ cycloalkylene, optionally substituted 4-7 membered heterocyclylene, optionally substituted phenylene, optionally substituted 5 or 6 membered heteroarylene, —O—, —S—, —NR$^{100}$—, —S(O)—, —SO$_2$—, —X$^1$-G$^1$-, —X$^2$-G$^2$-X$^{2a}$—, —X$^{12}$-G$^{10}$-, —X$^{13}$-G$^u$-X$^{13}$ or —CR$^{101}$R$^{102}$—, wherein:
$X^1$, $X^2$, and $X^{2a}$ are independently optionally substituted $C_{1-4}$alkylene, optionally substituted $C_{2-4}$ alkenylene, optionally substituted $C_{3-6}$ cycloalkylene, optionally substituted 4-7 membered heterocyclylene, optionally substituted phenylene, optionally substituted 5 or 6 membered heteroarylene, —O—, —C(O)—, —S—, —NR$^{100a}$—, —S(O)—, —SO$_2$—, or —CR$^{101a}$R$^{102a}$—;

$G^1$ and $G^2$ are independently optionally substituted $C_{1-4}$alkylene, optionally substituted $C_{2-4}$ alkenylene, optionally substituted $C_{3-6}$ cycloalkylene, optionally substituted 4-7 membered heterocyclylene, optionally substituted phenylene, optionally substituted 5 or 6 membered heteroaryl ene, —C(O)—, —NR$^{100a}$—, —S(O)—, —SO$_2$—, or —CR$^{101a}$R$^{102a}$—;

provided that —X$^1$-G$^1$- or —X$^2$-G$^2$-X$^{2a}$— does not contain an O—N, S—S, S—N(except SO$_2$—N bond), or —C(O)—S bond;

$X^{12}$, $X^{13}$, and $X^{13a}$ are independently optionally substituted $C_{1-4}$ alkylene, optionally substituted $C_{2-4}$ alkenylene, optionally substituted $C_{3-6}$ cycloalkylene, optionally substituted 4-7 membered heterocyclylene, optionally substituted phenylene, optionally substituted 5 or 6 membered heteroarylene, —O—, —C(O)—, —S—, —NR$^{100a}$—, —S(O)—, —SO$_2$—, or —CR$^{101a}$R$^{102a}$—;

and G$^{10}$ and G$^{11}$ are independently —X$^1$-G$^1$- or —X$^2$-G$^2$-X$^{2a}$—;

provided that —X$^{12}$-G$^{10}$- or —X$^{13}$-G$^u$-X$^{13a}$— does not contain an O—O, O—N, S—S, S—N(except SO$_2$—N bond), or —C(O)—S bond or three (or more) consecutive heteroatoms, with the exception of O—SO$_2$—O, O—SO$_2$—N, and N—SO$_2$—N;

$R^{100}$ and $R^{100a}$ are each independently lone pair (as applicable), hydrogen, COR$^{2c}$, —SO$_2$R$^{5c}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl, $R^{101}$, $R^{101a}$, $R^{102}$, and $R^{102a}$ are each independently hydrogen, —OH, halogen; optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$ alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl, or $R^{101}$ and $R^{102}$, or $R^{101a}$ and $R^{102a}$, together with the atoms they are bound to form an optionally substituted 3-7 membered cycloalkyl or heterocyclyl ring.

Embodiment B33. The method of embodiment B30, wherein the compound has Formula II-4, and $L^{10}$ in null.

Embodiment B34. The method of embodiment B32, wherein $L^{10}$ in Formula II is null, —O—, —C(O)—, —S—, —NR$^{100}$—, —S(O)—, —SO$_2$—, or —CR$^{101}$R$^{102}$—.

Embodiment B35. The method of embodiment B32, wherein $L^{10}$ in Formula II is —X$^1$-G$^1$- or —X$^2$-G$^2$-X$^{2a}$— wherein:
$X^1$, $X^2$, and $X^{2a}$ are independently —O—, —C(O)—, —S—, —NR$^{100a}$—, —S(O)—, —SO$_2$—, or —CR$^{101a}$R$^{102a}$—; and $G^1$ and $G^2$ are independently —C(O)—, —NR$^{100a}$—, —S(O)—, —SO$_2$—, or —CR$^{101a}$R$^{102a}$—.

Embodiment B36. The method of embodiment B32, wherein $L^{10}$ in Formula II is —X$^{12}$-G$^{10}$-, wherein:
$X^{12}$ is optionally substituted $C_{2-4}$ alkenylene, and G$^{10}$ is —X$^1$-G$^1$- or —X$^2$-G$^2$-X$^{2a}$—;

wherein:
$X^1$, $X^2$, and $X^{2a}$ are independently —O—, —C(O)—, —S—, —NR$^{100}$—S(O)—, —SO$_2$—, or —CR$^{101a}$R$^{102a}$—; and $G^1$ and $G^2$ are independently —C(O)—, —NR$^{100a}$—, —S(O)—, —SO$_2$—, or —CR$^{101a}$R$^{102a}$—.

Embodiment B37. The method of embodiment B36, wherein $X^{12}$ is

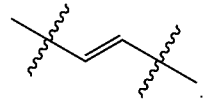 [SMILES: */C=C/*]

Embodiment B38. The method of embodiment B32, wherein $L^{10}$ in Formula II is

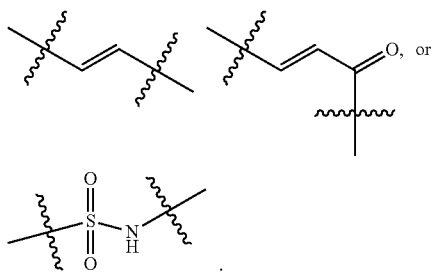

Embodiment B39. The method of embodiment B28, wherein the compound has a formula according to II-6 or II-7:

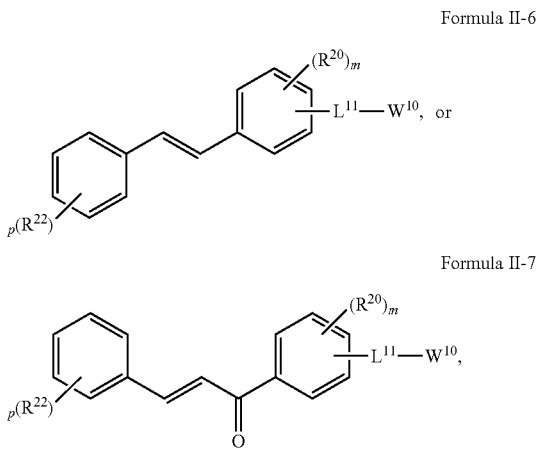

wherein:

p is 0, 1, 2, 3, or 4, $R^{22}$ at each occurrence is independently halogen, $-L^{11'}-W^{10'}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or two adjacent $R^{22}$ together with the atoms they are bound to form an optionally substituted cycloalkyl, heterocyclyl, aryl, or heteroaryl ring;

wherein $L^{11'}$ and $W^{10'}$ have the definition of $L^{11}$ and $W^{10}$ in embodiment B26, respectively, and $-L^{11'}-W^{10'}$ at each occurrence is independently selected.

Embodiment B40. The method of any one of embodiments B22-39, wherein $L^{11}$ and each instance of $L^{11'}$ in Formula II are independently null, $C_{1-4}$ alkylene, $C_{2-4}$ alkenylene, $C_{2-4}$ alkynylene, or $C_{1-4}$ heteroalkylene.

Embodiment B41. The method of any one of embodiments B22-40, wherein $W^{10}$ and each instance of $W^{10'}$ in Formula II are independently $-OH$, $-NH_2$, $-SO_2NH_2$, $-SO_2NH(C_{1-4}$ alkyl), $-SO_2NH(C_{1-4}$ alkanoyl), $-COOH$,

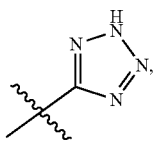 [SMILES: *c1nn[nH]n1]

$-C(O)(O-C_{1-10}$ alkyl), $-C(O)(O-C_{2-10}$ alkenyl), $-OC(O)NH_2$, $-OC(O)NH(C_{1-4}$ alkyl)-, $-O-(CO)-(C_{1-4}$ alkyl), $-O-(C_{1-4}$ alkyl), wherein each of the $C_{1-4}$ alkyl is independently optionally substituted with 1-3 substituents independently selected from $C_{1-4}$ alkyl, $C_{1-4}$ alkoxy, $-OH$, $-NH_2$, and fluorine.

Embodiment B42. The method of any one of embodiments B22-41, wherein $W^{10}$ in Formula II is $-OH$, $-NH_2$, $-SO_2NH_2$, $-SO_2NH(Acetyl)$, $-OMe$, $-COOH$,

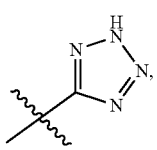

or $-O-C(O)-CH_3$.

Embodiment B43. The method of embodiment B28, wherein the compound has a formula according to any one of II-8 to II-10:

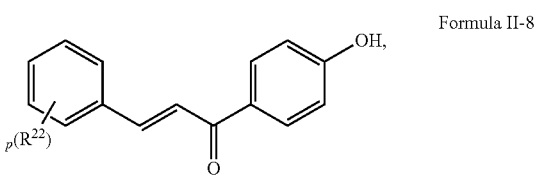

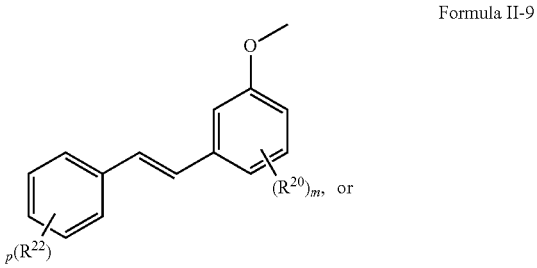

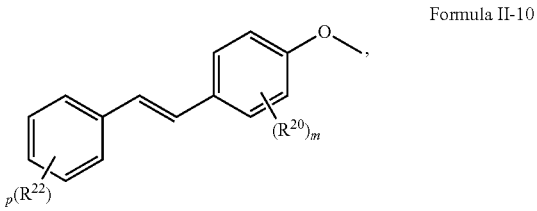

wherein m is 1 or 2, p is 1, 2, or 3, each of $R^{20}$ and $R^{22}$ at each occurrence is independently F; Cl; $-OH$; $-NH_2$, $-SO_2NH_2$, $-SO_2NH(C_{1-4}$ alkyl), $-SO_2NH(C_{1-4}$ alkanoyl), $-COOH$;

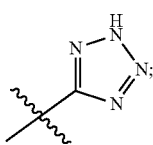 [SMILES: *c1nn[nH]n1]

—C(O)(O—C$_{1-10}$ alkyl), —C(O)(O—C$_{2-10}$ alkenyl), —OC(O)NH$_2$; —OC(O)NH(C$_{1-4}$ alkyl)-; —O—(CO)—(C$_{1-4}$ alkyl); —O—(C$_{1-6}$ alkyl); —O—(C$_{2-6}$ alkenyl); C$_{1-6}$ alkyl optionally substituted with 1-3 substituents independently selected from C$_{1-4}$ alkyl, C$_{1-6}$ alkoxy, —OH, —NH$_2$, and fluorine; or C$_{2-6}$ alkenyl optionally substituted with 1-3 substituents independently selected from C$_{1-4}$ alkyl, C$_{1-6}$ alkoxy, —OH, —NH$_2$, and fluorine.

Embodiment B44. The method of embodiment B39-43, wherein the structural unit

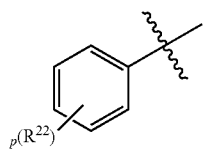

is selected from

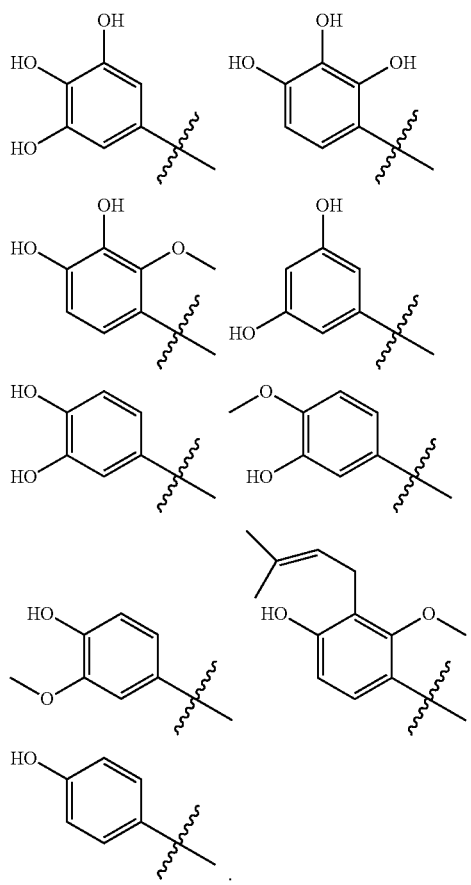

Embodiment B45. The method of embodiment B22, wherein the compound is

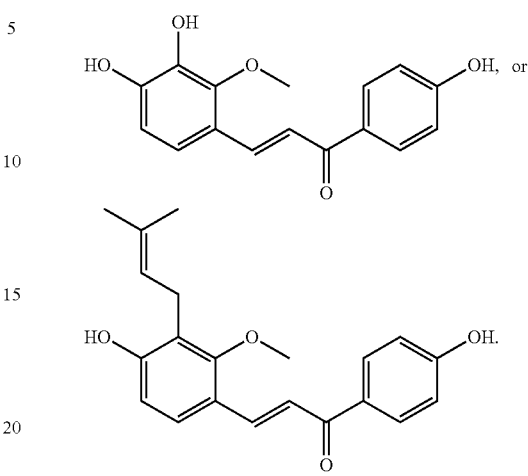

Embodiment B46. The method of embodiment B22, wherein the compound is

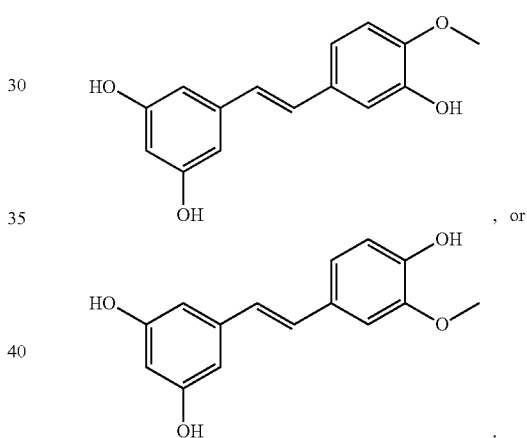

Embodiment B47. The method of any one of embodiments B22-46, wherein the compound of Formula II, or a pharmaceutically acceptable salt or ester thereof, is in an isolated or substantially purified form.

Embodiment B48. A method of treating or preventing age-related macular degeneration (AMD) in a subject in need thereof, the method comprising administering to the subject a therapeutically effective amount of a compound of Formula III, or a pharmaceutically acceptable salt or ester thereof, or a pharmaceutical composition comprising the compound or pharmaceutically acceptable salt or ester thereof:

$$Ar^{20}\text{-}L^{20}\text{-}W^{20} \qquad \text{Formula III}$$

wherein Ar$^{20}$ is an optionally substituted aryl ring (e.g., C$_{6-10}$ aryl ring), or an optionally substituted heteroaryl ring (e.g., 5-10 membered heteroaryl ring);

L$^{20}$ is null, an optionally substituted C$_{1-6}$ alkylene, an optionally substituted C$_{1-6}$ heteroalkylene, an optionally substituted C$_{2-6}$ alkenylene, an optionally substituted C$_{2-6}$ alkynylene, an optionally substituted C$_{3-6}$ cycloalkylene, an optionally substituted arylene, an optionally substituted heteroarylene, or an optionally substituted 4-7 membered heterocyclylene, $W^{20}$ is —$OR^1$; —$COR^2$; —$COOR^{1a}$; —$OCOOR^{1a}$; —$NR^3R^4$; —$CONR^{3a}R^{4a}$; —$OCONR^{3b}R^{4b}$; —$SO_2NR^{3c}R^{4c}$; —$OSO_2NR^{3d}R^{4d}$; —$SR^5$; —$SO_2R^{5a}$; —$OCOR^{2a}$; —$OSO_2R^{5a}$; or

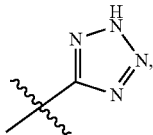 [SMILES: *c1nn[nH]n1]

wherein:
- $R^1$ and $R^{1a}$ are each independently hydrogen, optionally substituted alkyl, optionally substituted alkenyl, optionally substituted alkynyl, optionally substituted cycloalkyl, optionally substituted aryl, optionally substituted heteroaryl, or optionally substituted heterocyclyl;
- $R^3$ and $R^4$ are each independently hydrogen, —$COR^{2b}$, —$SO_2R^{5b}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl, or $R^3$ and $R^4$ together with the atoms they are bound to form an optionally substituted 4-7 membered heterocyclyl;
- $R^2$, $R^{2a}$, $R^{2b}$, $R^5$, $R^{5a}$, and $R^{5b}$ are each independently hydrogen, —OH, —$NR^{3e}R^{4e}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; and
- $R^{3a}$, $R^{3b}$, $R^{3c}$, $R^{3d}$, $R^{3e}$, $R^{4a}$, $R^{4b}$, $R^{4c}$, $R^{4d}$, and $R^{4e}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl; or $R^{3a}$ and $R^{4a}$, $R^{3b}$ and $R^{4b}$, $R^{3c}$ and $R^{4c}$, $R^{3d}$ and $R^{4d}$, or $R^{3e}$ and $R^{4e}$, together with the atoms they are bound to form an optionally substituted 4-7 membered heterocyclyl.

Embodiment B49. The method of embodiment B48, wherein Ar in Formula III is an optionally substituted phenyl ring or an optionally substituted 5 or 6 membered heteroaryl ring.

Embodiment B50. The method of embodiment B48, wherein Ar in Formula III is an optionally substituted phenyl ring, an optionally substituted thienyl ring, an optionally substituted furanyl ring, an optionally substituted pyridyl ring, or an optionally substituted pyrimidinyl ring.

Embodiment B51. The method of embodiment B48, wherein Ar in Formula III is a bicyclic aryl or bicyclic heteroaryl ring, each of which is optionally substituted.

Embodiment B52. The method of embodiment B48, wherein the compound of Formula III has a Formula III-1, III-2, or III-3:

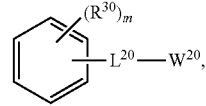

Formula III-1

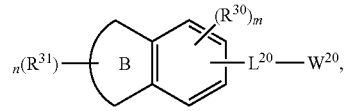

Formula III-2

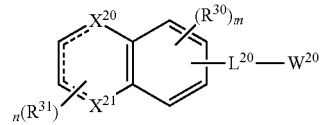

Formula III-3 wherein m is 0, 1, 2, or 3; n is 0, 1, 2, or 3;
- each of $R^{30}$ and $R^{31}$ at each occurrence is independently halogen, -$L^{20'}$-$W^{20'}$, an optionally substituted $C_{1-6}$ alkyl, an optionally substituted $C_{2-6}$ alkenyl, an optionally substituted $C_{2-6}$ alkynyl, an optionally substituted $C_{1-6}$ alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl;
- wherein $L^{20'}$ and $W^{20'}$ have the definition of F and W in embodiment B53, respectively, and -$L^{20'}$-$W^{20'}$ at each occurrence is independently selected;
- ring B is a 4-7 membered cycloalkyl ring, 4-7 membered heterocyclic ring, phenyl ring, 5 or 6 membered heteroaryl ring, each of which is optionally substituted 1-3 independently selected $R^{31}$;
- $X^{20}$ and $X^{21}$ are each independently null, —O—, —C(O)—, —S—, —$NR^{100a}$—, —S(O)—, —$SO_2$—, or —$CR^{101a}R^{102a}$—, as valence permits;
- wherein $R^{100a}$ is lone pair (as applicable), hydrogen, $COR^{2c}$, —$SO_2R^{5c}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl,
- $R^{101a}$ and $R^{102a}$ are each independently hydrogen, —OH, halogen; optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl, or $R^{101a}$ and $R^{102a}$, together with the atoms they are bound to form an optionally substituted 3-7 membered cycloalkyl or heterocyclyl ring; and
- $R^{2c}$ and $R^{5c}$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$alkoxy, an optionally substituted $C_{3-6}$ cycloalkyl, an optionally substituted $C_{3-6}$ cycloalkoxy, an optionally substituted phenyl; an optionally substituted 5 or 6 membered heteroaryl; or an optionally substituted 4-7 membered heterocyclyl;

or two adjacent R[30] or two adjacent R[31], or R[30] or R[31] and X[20] or X[21], together with the atoms they are bound to form an optionally substituted cycloalkyl, heterocyclyl, aryl, or heteroaryl ring.

Embodiment B53. The method of any one of embodiments B48-52, wherein $L^{20}$ in Formula III is null.

Embodiment B54. The method of any one of embodiments B48-52, wherein $L^{20}$ and each instance of $L^{20'}$ in Formula III are independently null, $C_{1-4}$ alkylene, $C_{2-4}$ alkenylene, $C_{2-4}$ alkynylene, or $C_{1-4}$ heteroalkylene.

Embodiment B55. The method of any one of embodiments B48-54, wherein $W^{20}$ each instance of $W^{20'}$ in Formula III are independently —OH, —NH$_2$, —SO$_2$NH$_2$, —SO$_2$NH(C$_{1-4}$ alkyl), —SO$_2$NH(C$_{1-4}$alkanoyl), —COOH,

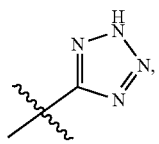 [SMILES: *c1nn[nH]n1]

—C(O)(O—C$_{1-10}$ alkyl), —C(O)(O—C$_{2-10}$ alkenyl), —OC(O)NH$_2$, —OC(O)NH(C$_{1-4}$ alkyl)-, —O—(CO)—(C$_{1-4}$ alkyl), —O—(C$_{1-4}$ alkyl), wherein each of the C$_{1-4}$ alkyl is independently optionally substituted with 1-3 substituents independently selected from C$_{1-4}$ alkyl, C$_{1-4}$alkoxy, —OH, —NH$_2$, and fluorine.

Embodiment B56. The method of any one of embodiments B48-55, wherein $W^{20}$ in Formula III is —OH, —NH$_2$, —SO$_2$NH$_2$, —SO$_2$NH(Acetyl), —COOH,

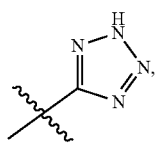 [SMILES: *c1nn[nH]n1]

—C(O)—(O—C$_8$ alkyl), or —O—C(O)—CH$_3$.

Embodiment B57. The method of any one of embodiments B52-56, wherein each of R[30] and R[31] at each occurrence is independently —OH, C$_{2-6}$ alkenyl, —O—(C$_{1-4}$ alkyl), —COOH, or —C(O)(O—C$_{1-10}$ alkyl).

Embodiment B58. The method of any one of embodiments B52-56, wherein each of R[30] and R[31] at each occurrence is —OH or —OMe.

Embodiment B59. The method of any one of embodiments B52-58, wherein when applicable, m is 2 or 3.

Embodiment B60. The method of any one of embodiments B52-58, wherein when applicable, n is 1, 2 or 3.

Embodiment B61. The method of embodiment B48, wherein the compound is

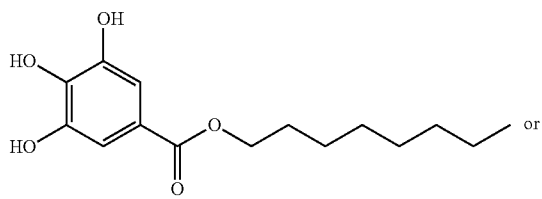

or

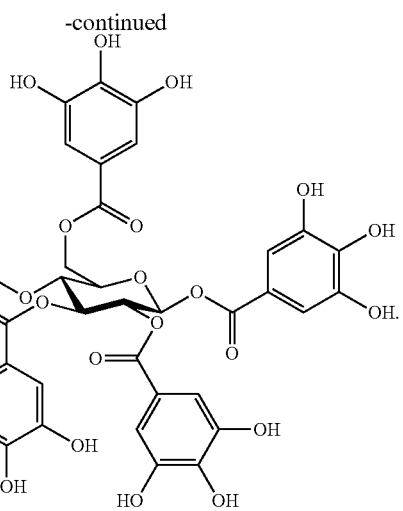

Embodiment B62. The method of any one of embodiments B48-61, wherein the compound of Formula III, or a pharmaceutically acceptable salt or ester thereof, is in an isolated or substantially purified form.

Embodiment B63. A method of treating or preventing age-related macular degeneration (AMD) in a subject in need thereof, the method comprising administering to the subject a therapeutically effective amount of a compound of Formula IV-1 or IV-2, or a pharmaceutically acceptable salt or ester thereof, or a pharmaceutical composition comprising the compound or pharmaceutically acceptable salt or ester thereof:

Formula IV-1

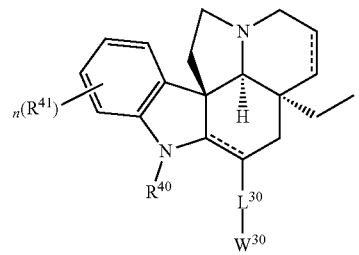

Formula IV-2

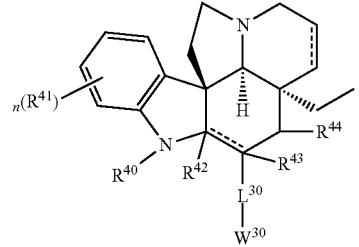

wherein:

R[40] is hydrogen; —COR[2]; —COOR[1a]; —SO$_2$R[5a]; optionally substituted alkyl, optionally substituted alkenyl, optionally substituted alkynyl, optionally substituted cycloalkyl, optionally substituted aryl, optionally substituted heteroaryl, or optionally substituted heterocyclyl;

R[41] is —OR[1]; —OCOOR[1a]; —OCONR[3b]R[4b]; —OCOR[2a]; or —OSO$_2$R[5a]; n is 0 or 1;

R[42], R[43], and R[44] are each independently hydrogen, —OR[1], OCOR[2a]; or —OSO$_2$R[5a];

L$^{30}$ is null or methylene,

W$^{30}$ is —OR$^1$; —COR$^2$; —COOR$^{1a}$; —OCOOR$^{1a}$; —NR$^3$R$^4$; —CONR$^{3a}$R$^{4a}$; —OCONR$^{3b}$R$^{4b}$; —OSO$_2$NR$^{3d}$R$^{4d}$; —OCOR$^{2a}$; or —OSO$_2$R$^{5a}$ wherein:

R$^1$ and R$^{1a}$ are each independently hydrogen, optionally substituted alkyl, optionally substituted alkenyl, optionally substituted alkynyl, optionally substituted cycloalkyl, optionally substituted aryl, optionally substituted heteroaryl, or optionally substituted heterocyclyl;

R$^3$ and R$^4$ are each independently hydrogen, —COR$^{2b}$, —SO$_2$R$^{5b}$, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted phenyl, optionally substituted 5 or 6 membered heteroaryl, or optionally substituted 4-7 membered heterocyclyl, or R$^3$ and R$^4$ together with the atoms they are bound to form an optionally substituted 4-7 membered heterocyclyl;

R$^2$, R$^{2a}$, R$^{2b}$, R$^5$, R$^{5a}$, and R$^{5b}$ are each independently hydrogen, —OH, —NR$^{3e}$R$^{4e}$, an optionally substituted C$_{1-6}$ alkyl, an optionally substituted C$_{2-6}$ alkenyl, an optionally substituted C$_{2-6}$ alkynyl, an optionally substituted C$_{1-6}$ alkoxy, an optionally substituted C$_{3-6}$ cycloalkyl, an optionally substituted C$_{3-6}$ cycloalkoxy, an optionally substituted phenyl; an optionally substituted 5 or 6 membered heteroaryl; or an optionally substituted 4-7 membered heterocyclyl; and R$^{3a}$, R$^{3b}$, R$^{3c}$, R$^{3d}$, R$^{3e}$, R$^{4a}$, R$^{4b}$, R$^{4c}$, R$^{4d}$, and R$^{4e}$ are each independently hydrogen, an optionally substituted C$_{1-6}$ alkyl, an optionally substituted C$_{2-6}$ alkenyl, an optionally substituted C$_{2-6}$ alkynyl, an optionally substituted C$_{1-6}$ alkoxy, an optionally substituted C$_{3-6}$ cycloalkyl, an optionally substituted C$_{3-6}$ cycloalkoxy, an optionally substituted phenyl; an optionally substituted 5 or 6 membered heteroaryl; or an optionally substituted 4-7 membered heterocyclyl; or R$^{3a}$ and R$^{4a}$, R$^{3b}$ and R$^{4b}$, R$^{3c}$ and R$^{4c}$, R$^{3d}$ and R$^{4d}$, or R$^{3e}$ and R$^{4e}$, together with the atoms they are bound to form an optionally substituted 4-7 membered heterocyclyl.

Embodiment B64. The method of embodiment B63, wherein the compound of Formula IV-1 or IV-2 has a formula according to one of Formula IV-3 to IV-6:

Formula IV-3

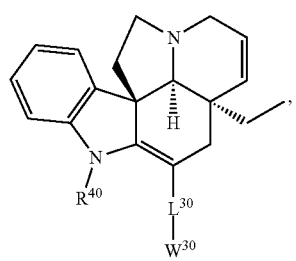

Formula IV-4

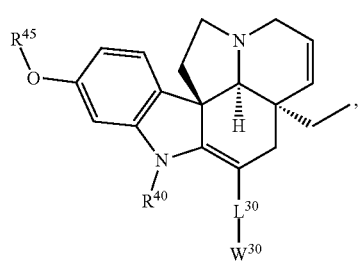

Formula IV-5

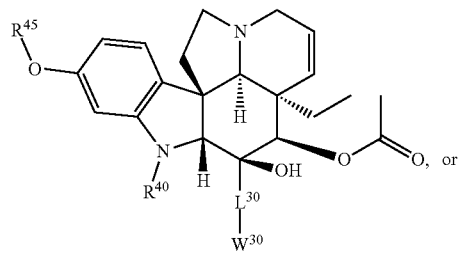

Formula IV-6

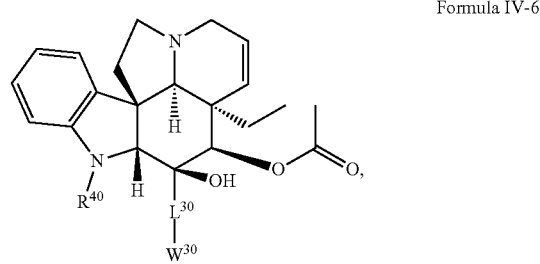

wherein R$^{45}$ is hydrogen or methyl.

Embodiment B65. The method of embodiment B63 or 64, wherein R$^{40}$ is hydrogen, C$_{1-4}$ alkyl, or C$_{1-4}$ alkanoyl.

Embodiment B66. The method of any one of embodiments B63-65, wherein L$^{30}$ is null or CH$_2$.

Embodiment B67. The method of any one of embodiments B63-66, wherein W$^{30}$ is —OH, —NH$_2$, —OSO$_2$NH$_2$, —COOH, —C(O)(O—C$_{1-10}$ alkyl), —C(O)(O—C$_{2-10}$ alkenyl), —OC(O)NH$_2$, —OC(O)NH(C$_{1-4}$ alkyl)-, —O—(CO)—(C$_{1-4}$ alkyl), —O—(C$_{1-4}$ alkyl), wherein each of the C$_{1-4}$ alkyl is independently optionally substituted with 1-3 substituents independently selected from C$_{1-4}$ alkyl, C$_{1-4}$alkoxy, —OH, —NH$_2$, and fluorine.

Embodiment B68. The method of any one of embodiments B63-67, wherein W$^{30}$ is —OH, —NH$_2$, —OSO$_2$NH$_2$, —C(O)—(O—C$_8$ alkyl), —COOH, or —OC(O)NH$_2$.

Embodiment B69. The method of embodiment B63, wherein the compound has the following formula:

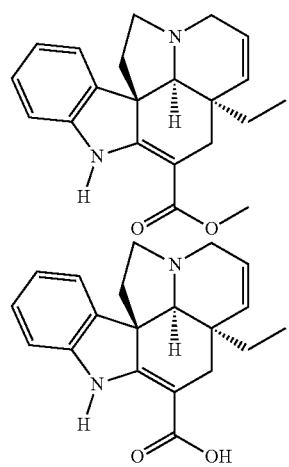

Embodiment B70. A method of treating or preventing age-related macular degeneration (AMD) in a subject in need thereof, the method comprising administering to the subject a therapeutically effective amount of a glycoside, or a pharmaceutically acceptable salt or ester thereof, or a pharmaceutical composition comprising the glycoside or pharmaceutically acceptable salt or ester thereof, wherein the aglycone of the glycoside is a phenolic compound, a flavonoid, a coumarin, a benzoic acid, or a sterol.

Embodiment B71. The method of embodiment B70, wherein the glycoside is a glucoside.

Embodiment B72. The method of embodiment B70, wherein the glycoside is an amphiphilic glycoside.

Embodiment B73. The method of embodiment B70, wherein the glycoside is a saponin.

Embodiment B74. The method of embodiment B70, wherein the glycoside has a Formula V:

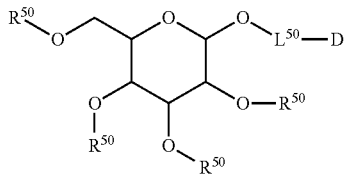

Formula V wherein each $R^{50}$ is independently hydrogen, $-L^{50}$-D, an oxygen protecting group, or a sugar residue;

$L^{50}$ is null or —C(O)—;

D is an optionally substituted aryl (e.g., $C_{6-10}$ aryl), optionally substituted heteroaryl (e.g., 5 to 14 membered heteroaryl), optionally substituted fused ring comprising two or more rings independently selected from aryl, heteroaryl, cycloalkyl and heterocyclyl (e.g., 8-14 membered, e.g., benzofused cycloalkyl/heterocyclyl, pyridofused cycloalkyl/heterocyclyl), or a steroid residue having a formula V-A:

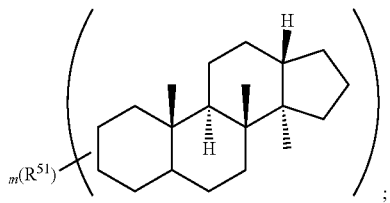

Formula V-A wherein

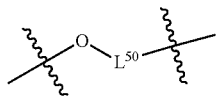

can connect to Formula V-A via the steroid backbone or any of the $R^{51}$ group(s), as valence permits, wherein $R^{51}$ at each occurrence is independently optionally substituted alkyl, optionally substituted alkenyl, optionally substituted alkynyl, —OH optionally substituted with an oxygen protecting group, oxo, halogen, optionally substituted cycloalkyl, optionally substituted alkoxy, optionally substituted cycloalkoxy, optionally substituted amino group, optionally substituted phenyl, optionally substituted heteroaryl, or optionally substituted heterocyclyl, or two $R^{51}$ groups together with the atoms they are bound to form an optionally substituted cycloalkyl, heterocyclyl, aryl, or heteroaryl ring;

m is an integer of 1-8; and wherein $-L^{50}$-D at each occurrence is independently selected.

Embodiment B75. The method of embodiment B74, wherein each $R^{50}$ is hydrogen.

Embodiment B76. The method of embodiment B74, wherein one to four $R^{50}$ are independently selected $-L^{50}$-D.

Embodiment B77. The method of any one of embodiments B74-76, wherein $L^{50}$ at each occurrence is null.

Embodiment B78. The method of any one of embodiments B74-76, wherein $L^{50}$ at each occurrence is —C(O)—.

Embodiment B79. The method of any one of embodiments B74-78, wherein D is an optionally substituted ring selected from

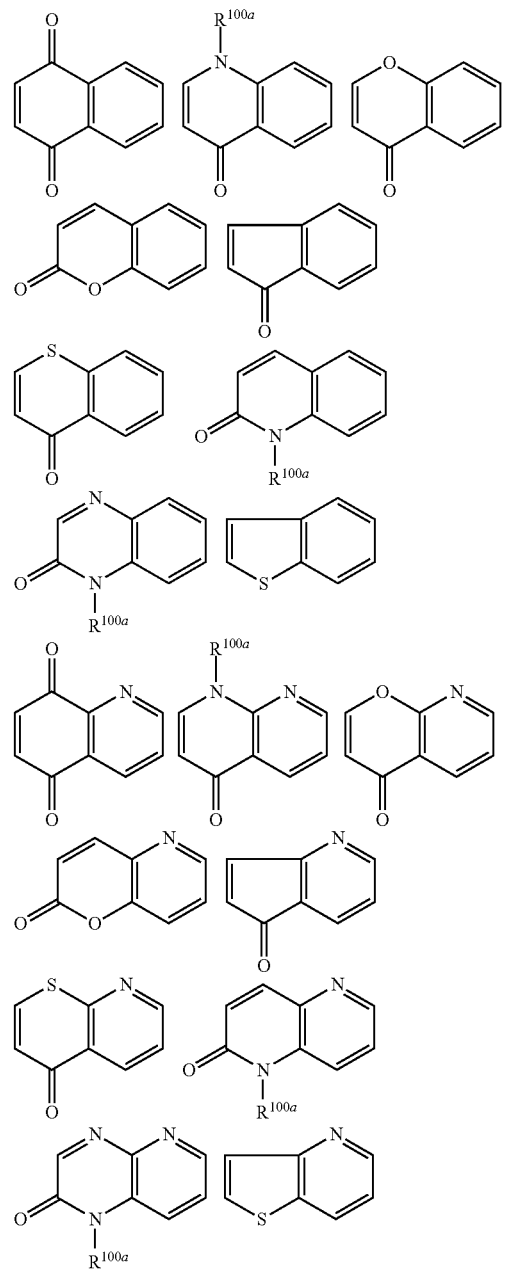

127

-continued

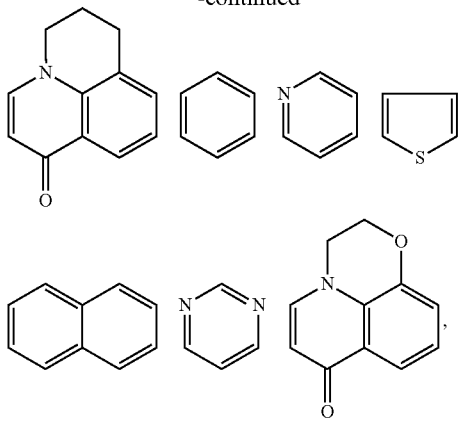

wherein
R^100a is lone pair (as applicable), hydrogen, nitrogen protecting group, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted phenyl, optionally substituted 5 or 6 membered heteroaryl, or optionally substituted 4-7 membered heterocyclyl; or R^100a forms an optionally substituted heterocyclic or heteroaryl ring with the pheny ring;

wherein

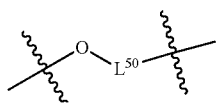

can connect to D via any of the available positions, and each of the ring systems of D is optionally substituted with 1-5 substituents each independently selected from —OH, —COOH, —C(O)(O—$C_{1-10}$ alkyl), —C(O)(O—$C_{2-10}$ alkenyl), —OC(O)NH$_2$, —OC(O)NH($C_{1-4}$ alkyl)-, —O—(CO)—($C_{1-4}$ alkyl), —NH$_2$, —SO$_2$NH$_2$, —SO$_2$NH($C_{1-4}$ alkyl), —SO$_2$NH($C_{1-4}$alkanoyl), halogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{1-6}$alkoxy, optionally substituted $C_{3-6}$ cycloalkoxy, optionally substituted amino group, optionally substituted phenyl, optionally substituted 5 or 6 membered heteroaryl, or optionally substituted 4-7 membered heterocyclyl.

Embodiment B80. The method of embodiment B79, wherein each of the ring systems of D is optionally substituted with 1-5 substituents each independently selected from F; C; —OH; —COOH; —C(O)(O—$C_{1-10}$ alkyl); —C(O)(O—$C_{2-10}$ alkenyl); —OC(O)NH$_2$; —OC(O)NH($C_{1-4}$ alkyl)-; —O—(CO)—($C_{1-4}$ alkyl); —NH$_2$; —SO$_2$NH$_2$; —SO$_2$NH($C_{1-4}$alkyl); —SO$_2$NH($C_{1-4}$alkanoyl); $C_{1-4}$ alkyl optionally substituted with 1-3 substituents independently selected from $C_{1-4}$ alkyl, $C_{1-4}$alkoxy, —OH, —NH$_2$, and fluorine; $C_{2-6}$ alkenyl optionally substituted with 1-3 substituents independently selected from $C_{1-4}$ alkyl, $C_{1-4}$alkoxy, —OH, —NH$_2$, and fluorine; $C_{2-6}$ alkynyl optionally substituted with 1-3 substituents independently selected from $C_{1-4}$ alkyl, $C_{1-4}$ alkoxy, —OH, —NH$_2$, and fluorine; $C_{3-6}$ cycloalkyl optionally substituted with 1-3 substituents independently selected from $C_{1-4}$ alkyl and fluorine; $C_{3-6}$ cycloalkoxy optionally substituted with 1-3 substituents independently selected from $C_{1-4}$ alkyl and fluorine; or $C_{1-4}$ alkoxy optionally substituted with 1-3 substituents independently selected from $C_{1-4}$ alkyl, $C_{1-4}$ alkoxy, —OH, —NH$_2$, and fluorine.

Embodiment B81. The method of embodiment B79, wherein D is selected from:

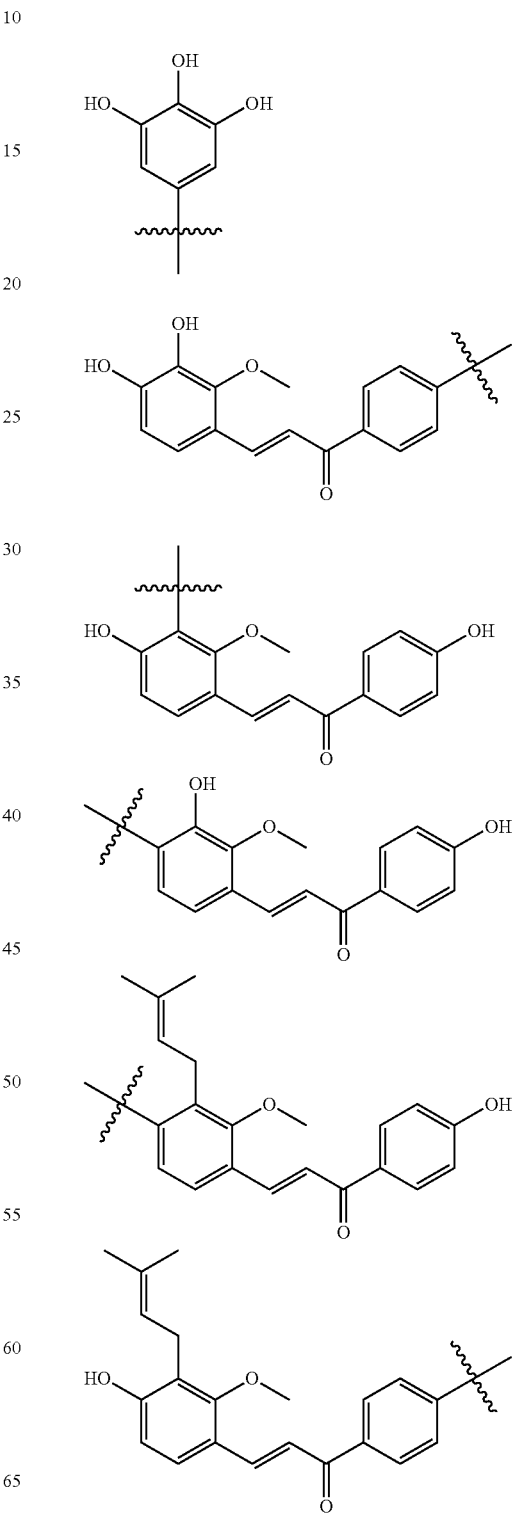

-continued

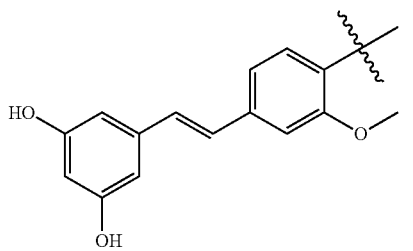

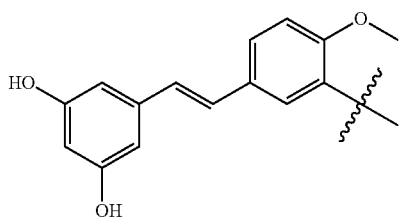

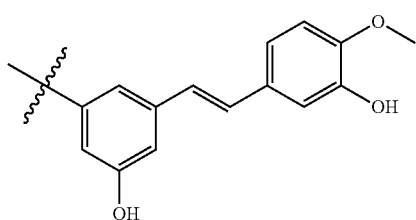

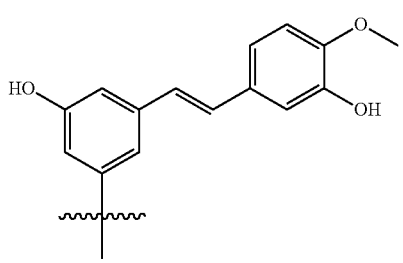

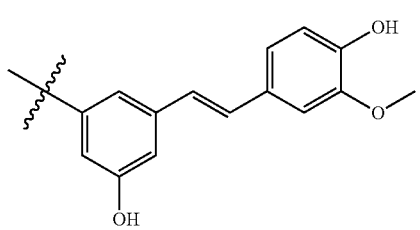

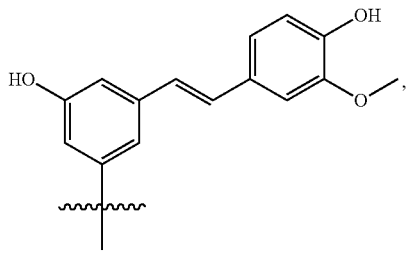

wherein each of the phenolic OH group is optionally linked to a sugar via a glycoside bond.

Embodiment B82. The method of any one of embodiments B74-78, wherein D is

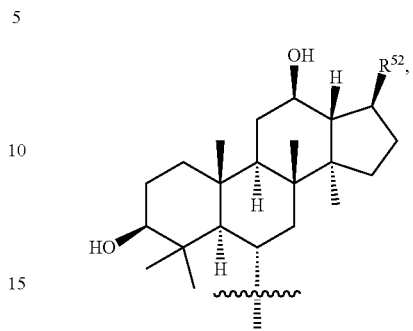

wherein $R^{52}$ is an optionally substituted alkyl or an optionally substituted alkenyl, wherein each of the remaining —OH groups in D is optionally linked to a sugar via a glycoside bond.

Embodiment B83. The method of embodiment B82, wherein $R^{52}$ is

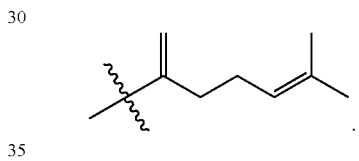

Embodiment B84. The method of any one of embodiments B74 and 76-83, wherein one or more (e.g., 1 or 2) $R^{50}$ is a sugar residue which connects to the remainder of Formula V via a glycoside bond.

Embodiment B85. The method of embodiment B84, wherein the sugar residue is a glucose residue or a rhamnose residue.

Embodiment B86. The method of embodiment B70, wherein the glycoside is a compound selected from:

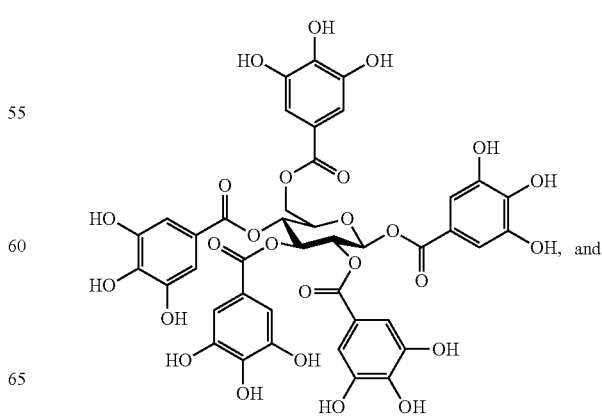

and

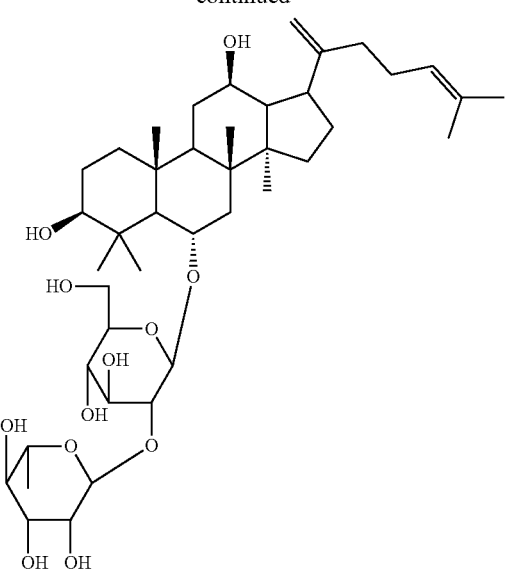

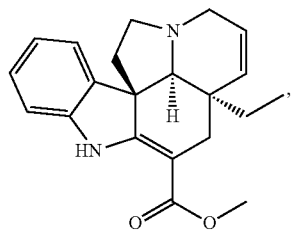

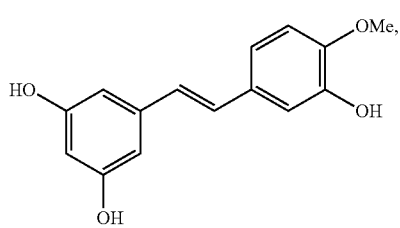

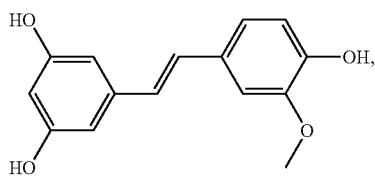

Embodiment B87. A method of treating or preventing age-related macular degeneration (AMD) in a subject in need thereof, the method comprising administering to the subject a therapeutically effective amount of a compound selected from compounds 1-8, or a pharmaceutically acceptable salt or ester thereof, or a pharmaceutical composition comprising the compound or pharmaceutically acceptable salt or ester thereof:

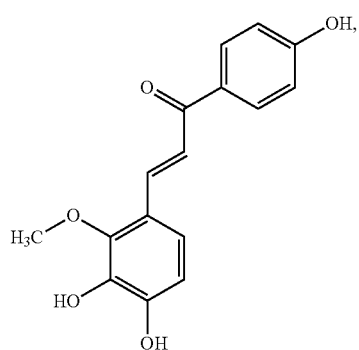

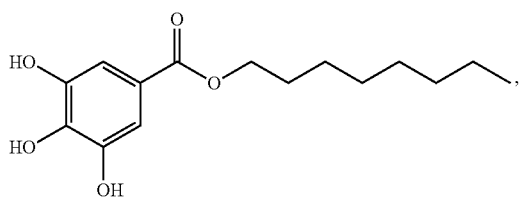

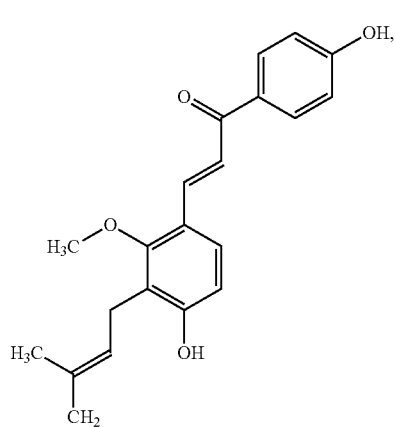

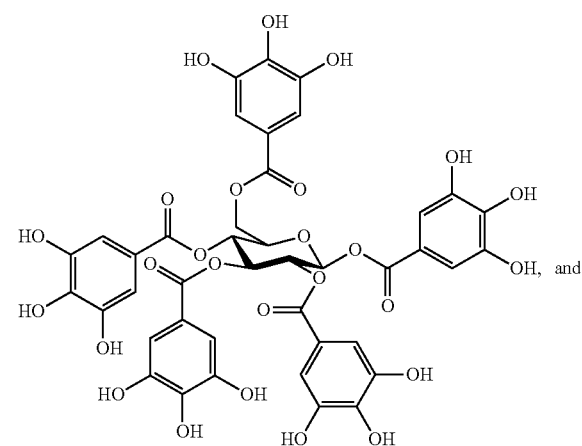

133
-continued

8

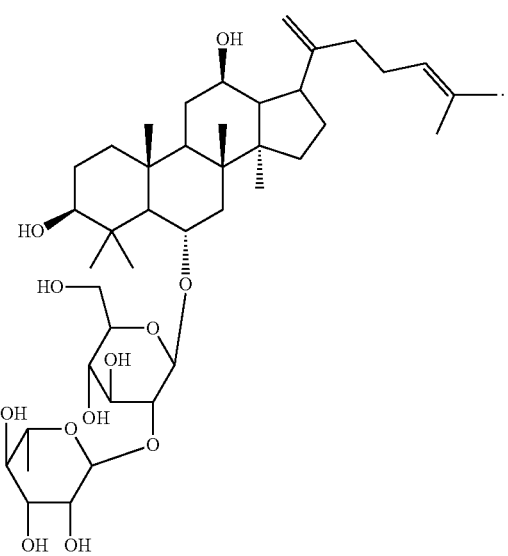

Embodiment B88. The method of embodiment B87, wherein the compound or pharmaceutical composition administered to the subject is free or substantially free of at least one of the compounds selected from compounds 1-8, or a pharmaceutically acceptable salt or ester thereof.

Embodiment B89. The method of embodiment B87, wherein the compound administered is in an isolated form or a substantially pure form.

Embodiment B90. The method of embodiment B87, wherein the compound administered is derived from a synthetic source.

Embodiment B91. The method of any one of embodiments B1-90, further comprising identifying or having identified the subject as being infected with, e.g., in the intraocular space, a microorganism.

Embodiment B92. The method of embodiment B91, wherein the microorganism comprises *Bacillus megaterium*.

Embodiment B93. The method of embodiment B91, wherein the microorganism comprises one or more selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*.

Embodiment B94. The method of any one of embodiments B91-93, wherein the compound or pharmaceutically acceptable salt or ester thereof, or the pharmaceutical composition is administered to the subject in an amount effective in killing or inhibiting the growth of the microorganism in the eye (e.g., intraocular space), blood, and/or GI tract, such as intestine of the subject.

Embodiment B95. The method of any one of embodiments B91-94, wherein the pharmaceutical composition is administered orally.

Embodiment B96. The method of any one of embodiments B91-95, wherein the pharmaceutical composition is administered topically, intravitreously, intramuscularly, subcutaneously, or intravenously.

Embodiment B97. A method of killing or inhibiting growth of a microorganism, such as *Bacillus megaterium*, treating an infection (e.g., ocular infection, such as in the intraocular space) with a microorganism, and/or treating or preventing age-related macular degeneration (AMD) in a subject in need thereof, the method comprising administering to the subject an effective amount of an antibiotic, such as an antibiotic selected from Amikacin, Amoxicillin, Ampicillin, Arsphenamine, Azithromycin, Azlocillin, Aztreonam, Bacitracin, Capreomycin, Carbenicillin, Cefaclor, Cefadroxil, Cefalexin, Cefalotin, Cefamandole, Cefazolin, Cefdinir, Cefditoren, Cefixime, Cefoperazone, Cefotaxime, Cefoxitin, Cefpodoxime, Cefprozil, Ceftazidime, Ceftibuten, Ceftizoxime, Ceftriaxone, Cefuroxime, Chloramphenicol, Cilastatin, Clarithromycin, Clavulanate, Clindamycin, Clofazimine, Cloxacillin, Colistin, Cycloserine, Dalfopristin, Dapsone, Daptomycin, Dicloxacillin, Dirithromycin, Doripenem, Doxycycline, Erythromycin, Ethambutol, Ethionamide, Flucloxacillin, Fosfomycin, Furazolidone, Fusidic acid, Gentamicin, Imipenem, Isoniazid, Kanamycin, Lincomycin, Linezolid, Loracarbef, Mafenide, Meropenem, Methicillin, Metronidazole, Mezlocillin, Minocycline, Mupirocin, Nafcillin, Neomycin, Netilmicin, Nitrofurantoin, Oxacillin, Oxytetracycline, Paromomycin, Penicillin G, Penicillin V, Piperacillin, Platensimycin, Polymyxin B, Pyrazinamide, Quinupristin, Rapamycin, Rifabutin, Rifampicin, Rifampin, Rifapentine, Rifaximin, Roxithromycin, Silver sulfadiazine, Spectinomycin, Streptomycin, Sulbactam, Sulfacetamide, Sulfadiazine, Sulfamethizole, Sulfamethoxazole, Sulfanilimide, Sulfasalazine, Sulfisoxazole, Tazobactam, Teicoplanin, Telavancin, Telithromycin, Temocillin, Tetracycline, Thiamphenicol, Ticarcillin, Tigecycline, Tinidazole, Tobramycin, Trimethoprim, Troleandomycin Vancomycin, enoxacin, lomefloxacin, nalidixic acid, ciprofloxacin, levofloxacin, gatifloxacin, moxifloxacin, ofloxacin, norfloxacin, Cefotetan, Cefonicid, Cephradine, Cephapirin, Cephalothin, Cefmetazole, Cefotaxime, Moxalactam, Cefepime, Ceftaroline fosamil, Ceftobiprole, Dalbavancin, Demeclocycline, Metacycline, Ertapenem, Fidaxomicin, geldanamycin, herbimycin, Posizolid, Radezolid, Torezolid, Oritavancin, Spiramycin, Sulfadimethoxine, Sulfonamidochrysoidine, Gemifloxacin Nadifloxacin Trovafloxacin Grepafloxacin Sparfloxacin Temafloxacin, Teixobactin, Malacidins, and combinations thereof, or a pharmaceutically acceptable salt thereof.

Embodiment B98. The method of embodiment B97, further comprising identifying, or having identified, the subject as being infected with, e.g., in the intraocular space, a microorganism selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*.

Embodiment B99. The method of embodiment B98, wherein the microorganism comprises *Bacillus megaterium*.

Embodiment B100. The method of embodiment B97 or 98, wherein the antibiotic, or pharmaceutically acceptable salt thereof, is administered to the subject in an amount effective in killing or inhibiting the growth of the microorganism in the eye (e.g., intraocular space), blood, and/or GI tract, such as intestine of the subject.

Embodiment B101. A method of killing or inhibiting growth of a microorganism, such as *Bacillus megaterium*, treating an infection (e.g., ocular infection, such as in the intraocular space) with a microorganism, and/or treating or preventing age-related macular degeneration (AMD) in a subject in need thereof, the method comprising administering to the subject a therapeutically effective amount of an extract from one or more TCMs selected from Licorice (e.g., *Glycyrrhiza uralensis*), White Peony Root (e.g., *Cynanchum otophyllum*), Forsythia (e.g., *Forsythia suspense*), Fructus Aurantii (e.g., *Citrus aurantium* L.), *Rehmannia glutinosa* (e.g., *Rehmannia glutinosa* Libosch), Tangerine Peel (e.g., *Citrus reticulata* Blanco), and Notoginseng (e.g., *Panax notoginseng*).

Embodiment B102. The method of embodiment B101, further comprising identifying, or having identified, the subject as being infected with, e.g., in the intraocular space, a microorganism selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*.

Embodiment B103. The method of embodiment B102, wherein the microorganism comprises *Bacillus megaterium*.

Embodiment B104. The method of embodiment B101 or 102, wherein the extract is administered to the subject in an amount effective in killing or inhibiting the growth of the microorganism in the eye (e.g., intraocular space), blood, and/or GI tract, such as intestine of the subject.

Additional Exemplary Embodiments C1-C133

The present disclosure also provides the following additional exemplary embodiments C1-C133.

Embodiment C1. A screening method comprising:
a) Culturing a microorganism in a suitable culture medium in the presence of a test compound;
b) Measuring the growth of the microorganism in the culture medium in the presence of the test compound; and optionally
c) Identifying a candidate therapeutics that inhibits the growth of the microorganism compared to a control,
wherein the microorganism comprises a species that is enriched in the intraocular space (e.g., aqueous humor in anterior chamber, a suspensory ligament, ciliary body, ciliary body and muscle, vitreous humor in posterior chamber, retina, choroid, optic nerve, lens, or iris) in a subject having an eye disease compared to a healthy subject, wherein the eye disease is selected from age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C2. The screening method of embodiment C1, wherein the microorganism comprises a species that is enriched in the intraocular space (e.g., aqueous humor, vitreous humor, soft drusen) in a subject having age-related macular degeneration (AMD) compared to a healthy subject.

Embodiment C3. The screening method of embodiment C1 or 2, wherein the microorganism comprises one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*.

Embodiment C4. The screening method of any one of embodiments C1-3, wherein the microorganism comprises *Bacillus megaterium* and/or *Pseudomonas putida*.

Embodiment C5. The screening method of any one of embodiments C1-3, wherein the microorganism is a substantially biologically pure population of *Bacillus megaterium*.

Embodiment C6. The screening method of any one of embodiments C1-2, wherein the microorganism comprises a mixture of microbial species substantially similar to those observed from an aqueous humor, vitreous humor, and/or soft drusen of a subject having age-related macular degeneration.

Embodiment C7. The screening method of any one of embodiments C1-2, wherein the microorganism is derived, in part or in whole, from an aqueous humor and/or vitreous humor of a subject having age-related macular degeneration.

Embodiment C8. The screening method of embodiment C1, wherein the microorganism comprises a species that is enriched in the intraocular space in a subject having Behcet's disease (BD) compared to a healthy subject.

Embodiment C9. The screening method of embodiment C1 or 8, wherein the microorganism comprises one or more species selected from *Sphingomonas wittichii, Klebsiella pneumoniae, Pseudomonas fluorescens, Ralstonia pickettii, Lactobacillus crispatus, Burkholderia multivorans, Lactobacillus delbrueckii*, and *Meiothermus silvanus*(D).

Embodiment C10. The screening method of embodiment C1 or 8, wherein the microorganism comprises a mixture of microbial species substantially similar to those observed from an aqueous humor and/or vitreous humor of a subject having Behcet's disease (BD).

Embodiment C11. The screening method of embodiment C1 or 8, wherein the microorganism is derived, in part or in whole, from an aqueous humor and/or vitreous humor of a subject having Behcet's disease (BD).

Embodiment C12. The screening method of embodiment C1, wherein the microorganism comprises a species that is enriched in the intraocular space in a subject having cataract compared to a healthy subject.

Embodiment C13. The screening method of embodiment C1 or 12, wherein the microorganism comprises one or more species selected from *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti*, and *Acidovorax ebreus*.

Embodiment C14. The screening method of embodiment C1 or 12, wherein the microorganism comprises a mixture of microbial species substantially similar to those observed from an aqueous humor and/or vitreous humor of a subject having Cat.

Embodiment C15. The screening method of embodiment C1 or 12, wherein the microorganism is derived, in part or in whole, from an aqueous humor and/or vitreous humor of a subject having Cat.

Embodiment C16. The screening method of embodiment C1, wherein the microorganism comprises a species that is enriched in the intraocular space in a subject having GLA compared to a healthy subject.

Embodiment C17. The screening method of embodiment C1 or 16, wherein the microorganism comprises one or more species selected from *Acinetobacter baumannii, Acinetobacter calcoaceticus, Comamonas testosteroni, Mycobacterium kansasii, Bacillus thuringiensis, Citrobacter koseri, Dyadobacter fermentans*, and *Serratia marcescens*.

Embodiment C18. The screening method of embodiment C1 or 16, wherein the microorganism comprises a mixture of microbial species substantially similar to those observed from an aqueous humor and/or vitreous humor of a subject having GLA.

Embodiment C19. The screening method of embodiment C1 or 16, wherein the microorganism is derived, in part or in whole, from an aqueous humor and/or vitreous humor of a subject having GLA.

Embodiment C20. The screening method of embodiment C1, wherein the microorganism comprises a species that is enriched in the intraocular space in a subject having VKH compared to a healthy subject.

Embodiment C21. The screening method of embodiment C1 or 20, wherein the microorganism comprises one or more species selected from *Escherichia coli, Micrococcus luteus, Bacillus subtilis, Corynebacterium aurimucosum*, and *Finegoldia magna*.

Embodiment C22. The screening method of embodiment C1 or 20, wherein the microorganism comprises a mixture of microbial species substantially similar to those observed from an aqueous humor and/or vitreous humor of a subject having VKH.

Embodiment C23. The screening method of embodiment C1 or 20, wherein the microorganism is derived, in part or in whole, from an aqueous humor and/or vitreous humor of a subject having VKH.

Embodiment C24. The screening method of any one of embodiments C1-23, wherein a plurality of test compounds are screened, and wherein the plurality of test compounds comprise at least one test compound that is not a known broad spectrum antibiotic or a known antibiotic having efficacy against one or more species of the microorganism.

Embodiment C25. The screening method of embodiment C24, wherein the plurality of test compounds comprise at least one test compound that is not ampicillin, vancomycin, neomycin, metronidazole, or tetracycline.

Embodiment C26. The screening method of any one of embodiments C1-23, wherein the test compound is not a known broad spectrum antibiotic or a known antibiotic having efficacy against one or more species of the microorganism.

Embodiment C27. The screening method of embodiment C26, wherein the test compound is not ampicillin, vancomycin, neomycin, metronidazole, or tetracycline.

Embodiment C28. The screening method of any one of embodiments C1-27, wherein the identifying comprises identifying a candidate therapeutics that prevents visible growth of the microorganism at or below the maximum tested concentration.

Embodiment C29. The screening method of any one of embodiments C1-27, wherein the identifying comprises identifying a candidate therapeutics that prevents visible colony formation of the microorganism at or below the maximum tested concentration.

Embodiment C30. The screening method of any one of embodiments C1-29, further comprising: d) Determining or having determined one or more microbial species as enriched in the intraocular space in a subject having an eye disease compared to a healthy subject, wherein the eye disease is selected from age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C31. A screening method comprising:
 a) Determining or having determined one or more microbial species as enriched in the intraocular space in a subject having age-related macular degeneration (AMD) compared to a healthy subject;
 b) Culturing a microorganism comprising at least one of the enriched microbial species in a suitable culture medium in the presence of a test compound;
 c) Measuring the growth of the microorganism in the culture medium in the presence of the test compound; and optionally
 d) Identifying a candidate therapeutics that inhibits the growth of the microorganism compared to a control.

Embodiment C32. The screening method of embodiment C31, wherein the microorganism comprises a mixture of microbial species substantially similar to those observed from an aqueous humor, vitreous humor and/or soft drusen of a subject having age-related macular degeneration.

Embodiment C33. The screening method of any one of embodiments C31-32, wherein the microorganism is derived, in part or in whole, from an aqueous humor and/or vitreous humor of a subject having age-related macular degeneration.

Embodiment C34. The screening method of any one of embodiments C1-33, wherein the subject is a human subject.

Embodiment C35. A method of preparing an animal model, the method comprising introducing a microorganism and/or inactivated protein therefrom to an intraocular space of an eye of an animal, wherein the microorganism comprises a species that is enriched in the intraocular space in a subject having an eye disease compared to a healthy subject, wherein the eye disease is selected from cataract (Cat), age-related macular degeneration (AMD), glaucoma (GLA), Behcet's disease (BD), Vogt-Koyanagi-Harada Syndrome (VKH), endophthalmitis (EOS), and combinations thereof, and wherein the introducing induces one or more symptoms of the eye disease.

Embodiment C36. The method of embodiment C35, wherein the microorganism comprises a species that is enriched in the intraocular space in a subject having age-related macular degeneration (AMD) compared to a healthy subject.

Embodiment C37. The method of embodiment C35 or 36, wherein the microorganism comprises one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*.

Embodiment C38. The method of any one of embodiments C35-37, wherein the microorganism comprises *Bacillus megaterium* and/or *Pseudomonas putida*.

Embodiment C39. The method of any one of embodiments C35-38, wherein the microorganism is a substantially biologically pure population of *Bacillus megaterium*.

Embodiment C40. The method of any one of embodiments C35-36, wherein the microorganism comprises a mixture of microbial species substantially similar to those observed from an aqueous humor, vitreous humor, and/or soft drusen of a subject having age-related macular degeneration.

Embodiment C41. The method of any one of embodiments C35-36, wherein the microorganism is derived, in part or in whole, from an aqueous humor and/or vitreous humor of a subject having age-related macular degeneration.

Embodiment C42. The method of any one of embodiments C35-41, wherein the animal is a non-human primate (e.g., monkey).

Embodiment C43. The method of any one of embodiments C35-41, wherein the animal is not macaque.

Embodiment C44. The method of any one of embodiments C36-43, wherein the microorganism and/or inactivated protein therefrom is injected into the subretinal space of the animal.

Embodiment C45. The method of any one of embodiments C36-44, wherein the microorganism and/or inactivated protein therefrom is injected to induce a drusenoid lesion, e.g., on retinal tissues, of the animal.

Embodiment C46. The method of any one of embodiments C36-45, wherein the microorganism and/or inactivated protein therefrom is injected to induce drusen-like nodules, e.g., under the retinal pigment epithelium layer in the eye of the animal.

Embodiment C47. The method of any one of embodiments C36-46, wherein the microorganism and/or inactivated protein therefrom is injected to induce pyroptosis, e.g., of the retinal pigment epithelium cells in the eye of the animal.

Embodiment C48. The method of any one of embodiments C36-47, wherein the microorganism and/or inactivated protein therefrom is injected to induce activation of the complement system and/or inflammation in the eye of the animal, e.g., with elevated expression of C5A, CFH, CASPASE1, and NLRP3 proteins.

Embodiment C49. The method of any one of embodiments C36-48, wherein the microorganism and/or inactivated protein therefrom is injected to induce secretion of active IL-1β and/or IL-18, e.g., by retinal pigment epithelium cells in the eye of the animal.

Embodiment C50. An animal model produced by the method of any one of embodiments C35-49.

Embodiment C51. A screening method comprising:
a) Administering a test compound to the animal model of embodiment C50;
b) Determining the severity of the one or more symptoms of the eye disease post administration; and optionally
c) Identifying a candidate therapeutics that relieves at least one of the symptoms compared to a control.

Embodiment C52. The screening method of embodiment C51, wherein the test compound is administered orally, topically, intravitreously, intramuscularly, subcutaneously, or intravenously.

Embodiment C53. The screening method of embodiment C51 or 52, wherein the identifying comprises identifying a candidate therapeutics that, when compared to a control, a) reduces a drusenoid lesion, e.g., on retinal tissues, of the animal; b) reduces drusen-like nodules, e.g., under the retinal pigment epithelium layer in the eye of the animal; c) reduces pyroptosis of the retinal pigment epithelium cells in the eye of the animal; d) reduces activation of the complement system and/or inflammation in the eye of the animal, e.g., reduces expression of C5A, CFH, CASPASE1, and NLRP3 proteins; e) reduces secretion of active IL-1β and/or IL-18 by retinal pigment epithelium cells in the eye of the animal; or f) any combination of a)-e).

Embodiment C54. The screening method of any one of embodiments C51-53, wherein the identifying comprises identifying a candidate therapeutics that, when compared to a control, kills or inhibits growth of the microorganism in the eye (e.g., intraocular space or cavity), blood, and/or GI tract, such as intestine of the animal model.

Embodiment C55. The screening method of any one of embodiments C51-54, wherein the test compound is pre-screened as being effective in inhibiting the growth of the microorganism.

Embodiment C56. The candidate therapeutics identified by any one of the screening methods of embodiments C1-34 and embodiments C51-55.

Embodiment C57. A method of treating or preventing AMD, comprising: 1) identifying or having identified a subject as being infected with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*, e.g., in the intraocular space, and 2) administering to the subject an effective amount of an antibiotic.

Embodiment C58. A method of treating or preventing AMD, comprising: 1) selecting a subject infected with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*, e.g., in the intraocular space, and 2) administering to the subject an effective amount of an antibiotic.

Embodiment C59. A method of treating a drusen symptom (e.g., soft drusen) in a subject in need thereof, the method comprising administering to the subject an effective amount of an antibiotic.

Embodiment C60. A method of reducing a drusenoid lesion, drusen-like nodules, pyroptosis of the retinal pigment epithelium cells in the eye; activation of the complement system and/or inflammation in the eye, and/or secretion of active IL-1β and/or IL-18 by retinal pigment epithelium cells in the eye, in a subject in need thereof, the method comprising administering to the subject an effective amount of an antibiotic.

Embodiment C61. The method of embodiment C59 or 60, wherein the subject suffers from AMD (e.g., dry AMD or wet AMD).

Embodiment C62. The method of embodiment C59 or 60, wherein the subject has soft drusen deposited between retinal pigment epithelium (RPE) and the Bruch's membrane; and/or retinal pigmentary changes in the macular.

Embodiment C63. The method of embodiment C59 or 60, wherein the subject is infected in the intraocular space with one or more species enriched in the intraocular space of an AMD patient compared to a healthy subject.

Embodiment C64. The method of embodiment C59 or 60, wherein the subject is infected in the intraocular space with one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis*, and *Xanthomonas oryzae*.

Embodiment C65. A method for screening a compound or combination of compounds for efficacy in treating or preventing an ocular disease, comprising:
obtaining a sample taken from aqueous humor or vitreous humor of a subject selected from a subject having the ocular disease, a family member or close genetic relation of a subject having the ocular disease, or a deceased subject known to have had the ocular disease;

culturing one or more organisms in the sample under conditions that mimic human intraocular space or in cooked meat medium to produce one or more cultures;

adding the compound or combination of compounds to the one or more cultures; and determining whether the compound or combination of compounds reduces growth or reduces population of the one or more cultures.

Embodiment C66. The method of embodiment C65, wherein the ocular disease is selected from the group consisting of age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C67. The method of embodiment C65, wherein the ocular disease is AMD.

Embodiment C68. The method of any one of embodiments C65-67, wherein the culturing comprises culturing the one or more organisms in liquid cooked meat medium.

Embodiment C69. The method of any one of embodiments C65-68, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentants, Serratia marcescens, Escherichia coli, Micrococcus luteus, Bacillus subtilis, Corynebacterium aurimucosum, Finegoldia magna*, and combinations thereof.

Embodiment C70. The method of any one of embodiments C65-68, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae*, and combinations thereof.

Embodiment C71. The method of any one of embodiments C65-70, further comprising identifying, based on the determining, a compound or combination of compounds that reduces growth or reduces population of the one or more cultures in vitro.

Embodiment C72. The method of any one of embodiment C65-71, wherein the compound or combination of compounds is one or more antibiotics.

Embodiment C73. The method of any one of embodiment C65-71, wherein the compound or combination of compounds is an extract or fraction of one or more of Calcined ancient ink, *Salvia Miltiorrhiza*, Arnebiaeuchroma, *Radix Isatidis, Houttuynia*, Honeysuckle, *Rhizoma Coptis, Scutellaria*, Dandelion, Purslane, Hawthorn, *Isatidis Folium, Fructus Forsythiae, Herba Artemisiae Capillaris, Andrographis Paniculata* Nees, *Radix Bupleuri*, Rhubarb, *Euphorbia Humifusa, Stemonae*, Garlic, *Cortex Phellodendri, Eucommia, Cortex Fraxini, Fructus Cnidii, Galla Chinensis*, viola *yedoensis makino, Fructus Mume, Radix Glycyrrhizae, Pericarpium Granati, Schisandra chinensis, Spina Gleditsiae, Terminalia Chebula, Sophora flavescens, Cortex Pseudolaricis, Epimedium*, and *Artemisia apiacea* Hance.

Embodiment C74. The method of embodiment C72, wherein the compound or combination of compounds is a combination of compounds and further comprises an extract or fraction of one or more of Calcined ancient ink, *Salvia Miltiorrhiza*, Arnebiaeuchroma, *Radix Isatidis, Houttuynia*, Honeysuckle, *Rhizoma Coptis, Scutellaria*, Dandelion, Purslane, Hawthorn, *Isatidis Folium, Fructus Forsythiae, Herba Artemisiae Capillaris, Andrographis Paniculata* Nees, *Radix Bupleuri*, Rhubarb, *Euphorbia Humifusa, Stemonae*, Garlic, *Cortex Phellodendri, Eucommia, Cortex Fraxini, Fructus Cnidii, Galla Chinensis*, viola *yedoensis makino, Fructus Mume, Radix Glycyrrhizae, Pericarpium Granati, Schisandra chinensis, Spina Gleditsiae, Terminalia Chebula, Sophora flavescens, Cortex Pseudolaricis, Epimedium*, and *Artemisia* apiacea Hance.

Embodiment C75. A method for screening a compound or combination of compounds for efficacy in treating or preventing an ocular disease, comprising:

culturing one or more organisms under conditions that mimic human intraocular space or in cooked meat medium to produce one or more cultures, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentants, Serratia marcescens, Escherichia coli, Micrococcus luteus, Bacillus subtilis, Corynebacterium aurimucosum, Finegoldia magna*, and combinations thereof;

adding the compound or combination of compounds to the one or more cultures; and determining whether the compound or combination of compounds reduces growth or reduces population of the one or more cultures.

Embodiment C76. The method of embodiment C75, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae*, and combinations thereof.

Embodiment C77. The method of any one of embodiments C75-76, wherein the ocular disease is selected from the group consisting of age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C78. The method of embodiment C77, wherein the ocular disease is AMD.

Embodiment C79. The method of any one of embodiments C75-78, wherein the culturing comprises culturing the one or more organisms in liquid cooked meat medium.

Embodiment C80. The method of any one of embodiments C75-79, further comprising identifying, based on the determining, a compound or combination of compounds that reduces growth or reduces population of the one or more cultures in vitro.

Embodiment C81. The method of any one of embodiment C75-80, wherein the compound or combination of compounds is one or more antibiotics.

Embodiment C82. The method of any one of embodiment C75-80, wherein the compound or combination of compounds is an extract or fraction of one or more of Calcined ancient ink, *Salvia Miltiorrhiza*, Arnebiaeuchroma, *Radix Isatidis*, *Houttuynia*, Honeysuckle, *Rhizoma Coptis*, *Scutellaria*, Dandelion, Purslane, Hawthorn, *Isatidis Folium*, *Fructus Forsythiae*, *Herba Artemisiae Capillaris*, *Andrographis Paniculata* Nees, *Radix Bupleuri*, Rhubarb, *Euphorbia Humifusa*, Stemonae, Garlic, *Cortex Phellodendri*, Eucommia, *Cortex Fraxini*, *Fructus Cnidii*, *Galla Chinensis*, viola *yedoensis makino*, *Fructus Mume*, *Radix Glycyrrhizae*, *Pericarpium Granati*, *Schisandra chinensis*, *Spina Gleditsiae*, *Terminalia Chebula*, *Sophora flavescens*, *Cortex Pseudolaricis*, *Epimedium*, and *Artemisia apiacea* Hance.

Embodiment C83. The method of embodiment C81, wherein the compound or combination of compounds is a combination of compounds and further comprises an extract or fraction of one or more of Calcined ancient ink, *Salvia Miltiorrhiza*, Arnebiaeuchroma, *Radix Isatidis*, *Houttuynia*, Honeysuckle, *Rhizoma Coptis*, *Scutellaria*, Dandelion, Purslane, Hawthorn, *Isatidis Folium*, *Fructus Forsythiae*, *Herba Artemisiae Capillaris*, *Andrographis Paniculata* Nees, *Radix Bupleuri*, Rhubarb, *Euphorbia Humifusa*, Stemonae, Garlic, *Cortex Phellodendri*, Eucommia, *Cortex Fraxini*, *Fructus Cnidii*, *Galla Chinensis*, viola *yedoensis makino*, *Fructus Mume*, *Radix Glycyrrhizae*, *Pericarpium Granati*, *Schisandra chinensis*, *Spina Gleditsiae*, *Terminalia Chebula*, *Sophora flavescens*, *Cortex Pseudolaricis*, *Epimedium*, and *Artemisia apiacea* Hance.

Embodiment C84. A method for screening a compound or combination of compounds for efficacy in treating or preventing an ocular disease, comprising:
obtaining a sample taken from aqueous humor or vitreous humor of a subject selected from a subject having the ocular disease, a family member or close genetic relation of a subject having the ocular disease, or a deceased subject known to have had the ocular disease; culturing one or more organisms in the sample under conditions that mimic human intraocular space or in cooked meat medium to produce one or more cultures; obtaining a solution of one or more inactivated proteins derived from the one or more cultures; mixing the compound or combination of compounds with the solution of one or more inactivated proteins; and determining whether the compound or combination of compounds bind to the one or more inactivated proteins.

Embodiment C85. The method of embodiment C84, wherein the ocular disease is selected from the group consisting of age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C86. The method of embodiment C84, wherein the ocular disease is AMD.

Embodiment C87. The method of any one of embodiments C84-86, wherein the culturing comprises culturing the one or more organisms in liquid cooked meat medium.

Embodiment C88. The method of any one of embodiments C84-87, wherein the one or more organisms are selected from the group consisting of *Staphylococcus epidermidis*, *Pseudomonas aeruginosa*, *Staphylococcus aureus*, *Staphylococcus haemolyticus*, *Pseudomonas putida*, *Stenotrophomonas maltophilia*, *Bacillus cereus*, *Bacillus megaterium*, *Lactobacillus reuteri*, *Gardnerella vaginalis*, *Enterococcus faecium*, *Cytophaga hutchinsonii*, *Bacillus licheniformis*, *Xanthomonas oryzae*, *Sphingomonas wittichii*, *Klebsiella pneumoniae*, *Pseudomonas fluorescens*, *Ralstonia pickettii*, *Lactobacillus crispatus*, *Burkholderia multivorans*, *Lactobacillus delbrueckii*, *Meiothermus silvanus*(D), *Pseudomonas mendocina*, *Kytococcus sedentarius*, *Alicycliphilus denitrificans*, *Achromobacter xylosoxidans*, *Sphingobium japonicum*, *Mycobacterium abscessus*, *Arthrobacter aurescens*, *Prevotella dentalis*, *Sinorhizobium meliloti*, *Acidovorax ebreus*, *Acinetobacter baumannii*, *Acinetobacter calcoaceticus*, *Comamonas testosteroni*, *Mycobacterium kansasii*, *Bacillus thuringiensis*, *Citrobacter koseri*, *Dyadobacter fermentans*, *Serratia marcescens*, *Escherichia coli*, *Micrococcus luteus*, *Bacillus subtilis*, *Corynebacterium aurimucosum*, *Finegoldia magna*, and combinations thereof.

Embodiment C89. The method of any one of embodiments C84-87, wherein the one or more organisms are selected from the group consisting of *Staphylococcus epidermidis*, *Pseudomonas aeruginosa*, *Staphylococcus aureus*, *Staphylococcus haemolyticus*, *Pseudomonas putida*, *Stenotrophomonas maltophilia*, *Bacillus cereus*, *Bacillus megaterium*, *Lactobacillus reuteri*, *Gardnerella vaginalis*, *Enterococcus faecium*, *Cytophaga hutchinsonii*, *Bacillus licheniformis*, *Xanthomonas oryzae*, and combinations thereof.

Embodiment C90. A method for screening a compound or combination of compounds for efficacy in treating an ocular disease, comprising:
obtaining a sample taken from aqueous humor or vitreous humor of a subject selected from a subject having the ocular disease, a family member or close genetic relation of a subject having the ocular disease, or a deceased subject known to have had the ocular disease; culturing one or more organisms in the sample under conditions that mimic human intraocular space or in cooked meat medium to produce one or more cultures; obtaining a solution of one or more inactivated proteins derived from the one or more cultures; introducing the one or more inactivated proteins into a model for mammalian inflammation; introducing the compound or combination of compounds in the model for mammalian inflammation; and determining whether the compound or combination of compounds reduces inflammatory activity in the model.

Embodiment C91. The method of embodiment C90, wherein the ocular disease is selected from the group consisting of age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C92. The method of embodiment C90, wherein the ocular disease is AMD.

Embodiment C93. The method of any one of embodiments C90-92, wherein the culturing comprises culturing the one or more organisms in liquid cooked meat medium.

Embodiment C94. The method of any one of embodiments C90-93, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Escherichia coli, Micrococcus luteus, Bacillus subtilis, Corynebacterium aurimucosum, Finegoldia magna*, and combinations thereof.

Embodiment C95. The method of any one of embodiments C90-94, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae*, and combinations thereof.

Embodiment C96. A method for screening a compound or combination of compounds for efficacy in treating or preventing an ocular disease, comprising:
culturing one or more organisms under conditions that mimic human intraocular space or in cooked meat medium to produce one or more cultures, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Escherichia coli, Micrococcus luteus, Bacillus subtilis, Corynebacterium aurimucosum, Finegoldia magna*, and combinations thereof;
obtaining a solution of one or more inactivated proteins derived from the one or more cultures;
mixing the compound or combination of compounds with the solution of one or more inactivated proteins;
and determining whether the compound or combination of compounds bind to the one or more inactivated proteins.

Embodiment C97. The method of embodiment C96, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae*, and combinations thereof.

Embodiment C98. The method of any one of embodiments C96-97, wherein the ocular disease is selected from the group consisting of age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C99. The method of embodiment C98, wherein the ocular disease is AMD.

Embodiment C100. The method of any one of embodiments C96-99, wherein the culturing comprises culturing the one or more organisms in liquid cooked meat medium.

Embodiment C101. The method of any one of embodiments C96-100, further comprising identifying, based on the determining, a compound or combination of compounds that binds the one or more inactivated proteins in vitro.

Embodiment C102. A method for screening a compound or combination of compounds for efficacy in treating or preventing an ocular disease, comprising:
culturing one or more organisms under conditions that mimic human intraocular space or in cooked meat medium to produce one or more cultures, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens, Escherichia coli, Micrococcus luteus, Bacillus subtilis, Corynebacterium aurimucosum, Finegoldia magna*, and combinations thereof;
obtaining a solution of one or more inactivated proteins derived from the one or more cultures;
introducing the one or more inactivated proteins into a model for mammalian inflammation;
introducing the compound or combination of compounds in the model for mammalian inflammation; and
determining whether the compound or combination of compounds reduces inflammatory activity in the model.

Embodiment C103. The method of embodiment C102, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae*, and combinations thereof.

Embodiment C104. The method of any one of embodiments C102-103, wherein the ocular disease is selected from the group consisting of age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C105. The method of embodiment C104, wherein the ocular disease is AMD.

Embodiment C106. The method of any one of embodiments C102-105, wherein the culturing comprises culturing the one or more organisms in liquid cooked meat medium.

Embodiment C107. The method of any one of embodiments C102-106, further comprising identifying, based on the determining, a compound or combination of compounds that reduces growth or reduces population of the one or more cultures in vitro.

Embodiment C108. The method of any one of embodiment C102-107, wherein the compound or combination of compounds is one or more anti-inflammatory compounds.

Embodiment C109. The method of any one of embodiment C102-107, wherein the compound or combination of compounds is an extract or fraction of one or more of Calcined ancient ink, *Salvia Miltiorrhiza*, Arnebiaeuchroma, *Radix Isatidis, Houttuynia*, Honeysuckle, *Rhizoma Coptis, Scutellaria*, Dandelion, Purslane, Hawthorn, *Isatidis Folium, Fructus Forsythiae, Herba Artemisiae Capillaris, Andrographis Paniculata* Nees, *Radix Bupleuri*, Rhubarb, *Euphorbia Humifusa, Stemonae*, Garlic, *Cortex Phellodendri, Eucommia, Cortex Fraxini, Fructus Cnidii, Galla Chinensis*, viola *yedoensis makino, Fructus Mume, Radix Glycyrrhizae, Pericarpium Granati, Schisandra chinensis, Spina Gleditsiae, Terminalia Chebula, Sophora flavescens, Cortex Pseudolaricis, Epimedium*, and *Artemisia apiacea* Hance.

Embodiment C110. The method of embodiment C108, wherein the compound or combination of compounds is a combination of compounds and further comprises an extract or fraction of one or more of Calcined ancient ink, *Salvia Miltiorrhiza*, Arnebiaeuchroma, *Radix Isatidis, Houttuynia*, Honeysuckle, *Rhizoma Coptis, Scutellaria*, Dandelion, Purslane, Hawthorn, *Isatidis Folium, Fructus Forsythiae, Herba Artemisiae Capillaris, Andrographis Paniculata* Nees, *Radix Bupleuri*, Rhubarb, *Euphorbia Humifusa, Stemonae*, Garlic, *Cortex Phellodendri, Eucommia, Cortex Fraxini, Fructus Cnidii, Galla Chinensis*, viola *yedoensis makino, Fructus Mume, Radix Glycyrrhizae, Pericarpium Granati, Schisandra chinensis, Spina Gleditsiae, Terminalia Chebula, Sophora flavescens, Cortex Pseudolaricis, Epimedium*, and *Artemisia apiacea* Hance.

Embodiment C111. A method for producing a mammalian model of an ocular disease, comprising:
introducing one or more microorganisms and/or one or more inactivated proteins of the one or more microorganisms into an eye of a mammal, thereby generating the mammalian model.

Embodiment C112. The method of embodiment C111, further comprising monitoring development and progression of one or more markers of the ocular disease.

Embodiment C113. The method of embodiment C112, wherein the ocular disease is selected from the group consisting of age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C114. The method of embodiment C112, wherein the ocular disease is AMD.

Embodiment C115. The method of embodiment C114, further comprising allowing sufficient time to pass after introducing the one or more microorganisms and/or one or more inactivated proteins of the one or more microorganisms, for the mammal to develop drusenoid lesions.

Embodiment C116. The method of any one of embodiments C112-115, wherein monitoring development and progression of one or more markers of the ocular disease comprises monitoring ocular inflammatory response in the mammal.

Embodiment C117. The method of any one of embodiments C114-115, wherein monitoring development and progression of one or more markers of the ocular disease comprises monitoring the formation or progression of drusenoid lesions.

Embodiment C118. The method of any one of embodiments C112-117, wherein introducing the one or more microorganisms and/or one or more inactivated proteins of the one or more microorganisms comprises intraocularly injecting the one or more microorganisms and/or one or more inactivated proteins of the one or more microorganisms.

Embodiment C119. The method of embodiment C118, wherein the intraocularly injecting comprises injecting into the vitreous humor or the aqueous humor of the mammal.

Embodiment C120. The method of any one of embodiments C112-119, wherein the mammal is a non-human primate.

Embodiment C121. The method of embodiment C120, wherein the mammal is a macaque.

Embodiment C122. The method of embodiment C120, wherein the mammal is a non-human primate other than a macaque.

Embodiment C123. The method of any one of embodiments C112-122, wherein the one or more organisms are selected from the group consisting of *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae, Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D), *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti, Acidovorax ebreus, Acinetobacter baumannii, Acinetobacter calcoaceticus, Comamonas testosteroni, Mycobacterium kansasii, Bacillus thuringiensis, Citrobacter koseri, Dyadobacter fermentants, Serratia marcescens, Escherichia coli, Micrococcus luteus, Bacillus subtilis, Corynebacterium aurimucosum, Finegoldia magna*, and combinations thereof.

Embodiment C124. The method of any one of embodiments C112-122, wherein the one or more organisms are selected from the group consisting of *Staphylococcus epi-*

*dermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis, Xanthomonas oryzae*, and combinations thereof.

Embodiment C125. A method for screening a compound or combination of compounds for efficacy in treating or preventing an ocular disease, comprising:

administering the compound or combination of compounds to the mammalian model of any one of embodiments C112-124; and determining whether the compound or combination of compounds is effective to reduce or prevent one or more symptoms of the ocular disease.

Embodiment C126. The method of embodiment C125, wherein the ocular disease is selected from the group consisting of age-related macular degeneration (AMD), Behcet's disease (BD), cataract (Cat), endophthalmitis (EOS), glaucoma (GLA), Vogt-Koyanagi-Harada Syndrome (VKH), and combinations thereof.

Embodiment C127. The method of embodiment C125, wherein the ocular disease is AMD.

Embodiment C128. The method of embodiment C127, wherein administering the compound or combination of compounds occurs after the formation of drusenoid lesions in the mammalian model.

Embodiment C129. The method of any one of embodiments C125-128, wherein the compound or combination of compounds is one or more compounds of combination of compounds identified according to any one of embodiments C71, 80, 101, and 107.

Embodiment C130. The method of any one of embodiments C125-129, wherein the compound or combination of compounds is selected from the group consisting of one or more antibiotics; one or more anti-inflammatory compounds; an extract or fraction of one or more of Calcined ancient ink, *Salvia Miltiorrhiza*, Arnebiaeuchroma, *Radix Isatidis, Houttuynia*, Honeysuckle, *Rhizoma Coptis, Scutellaria*, Dandelion, Purslane, Hawthorn, *Isatidis Folium, Fructus Forsythiae, Herba Artemisiae Capillaris, Andrographis Paniculata* Nees, *Radix Bupleuri*, Rhubarb, *Euphorbia Humifusa, Stemonae*, Garlic, *Cortex Phellodendri, Eucommia, Cortex Fraxini, Fructus Cnidii, Galla Chinensis*, viola *yedoensis makino, Fructus Mume, Radix Glycyrrhizae, Pericarpium Granati, Schisandra chinensis, Spina Gleditsiae, Terminalia Chebula, Sophora flavescens, Cortex Pseudolaricis, Epimedium*, and *Artemisia apiacea* Hance; and combinations thereof.

Embodiment C131. The method of any one of embodiments C125-130, wherein administering comprises injecting the compound or combination of compounds into an eye of the mammalian model.

Embodiment C132. The method of embodiment C131, wherein injecting comprises intraocular injection.

Embodiment C133. The method of any one of embodiments C125-132, wherein the one or more symptoms are selected from the group consisting of formation of drusenoid lesions, microbial growth or load, inflammatory molecule or marker production, and combinations thereof.

Definitions

It is meant to be understood that proper valences are maintained for all moieties and combinations thereof.

It is also meant to be understood that a specific embodiment of a variable moiety herein may be the same or different as another specific embodiment having the same identifier.

Suitable groups for the variables in compounds of Formula I, II, III, IV-1, IV-2, V, or any sub-formulae thereof, as applicable, are independently selected. The described embodiments of the present invention can be combined. Such combination is contemplated and within the scope of the present invention. For example, definitions of one of the variables can be combined with any of the definitions of any other of the variables in Formula I, II, III, IV-1, IV-2, V, or any sub-formulae thereof.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers including racemic mixtures.

As used herein, the term "compound(s) of the present disclosure" refers to any of the compounds described herein in the "Compounds" section, such as those according to Formula I, II, III, IV-1, IV-2, V, any sub-formulae thereof, or any one or more of compounds 1-8, isotopically labeled compound(s) thereof (such as a deuterated analog wherein one of the hydrogen atoms is substituted with a deuterium atom with an abundance above its natural abundance), possible stereoisomers thereof (including diastereoisomers, enantiomers, and racemic mixtures), geometric isomers thereof, tautomers thereof, conformational isomers thereof, possible zwitterions thereof, esters thereof (such as pharmaceutically acceptable esters), and/or pharmaceutically acceptable salts thereof (e.g., acid addition salt such as HCl salt or base addition salt such as Na salt). Compound(s) of the present disclosure is not limited to any particular solid state forms, for example, it can be in an amorphous form or a polymorphic form. Hydrates and solvates of the compounds of the present disclosure are considered compositions of the present disclosure, wherein the compound(s) is in association with water or solvent, respectively.

As used herein, the phrase "administration" of a compound, "administering" a compound, or other variants thereof means providing the compound or a prodrug (e.g., an ester prodrug) of the compound to the individual in need of treatment.

As used herein, the term "alkyl" as used by itself or as part of another group refers to a straight- or branched-chain aliphatic hydrocarbon. In some embodiments, the alkyl which can include one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. Non-limiting exemplary $C_{1-4}$ alkyl groups include methyl, ethyl, propyl, isopropyl, butyl, sec-butyl, tert-butyl, and iso-butyl.

As used herein, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is a $C_{3-8}$ cycloalkyl group. In another embodiment, the cycloalkyl group is a $C_{3-6}$ cycloalkyl group. "Cycloalkyl" also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Non-limiting exemplary cycloalkyl groups include cyclopropyl, cyclobutyl, cyclopentyl, cyclohexyl, cycloheptyl, cyclooctyl, norbornyl, decalin, adamantyl, cyclopentenyl, and cyclohexenyl.

As used herein, the term "alkenyl" as used by itself or as part of another group refers to an alkyl group as defined above containing one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

As used herein, the term "alkynyl" as used by itself or as part of another group refers to an alkyl group as defined above containing one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "heteroalkyl," by itself or in combination with another term, means, unless otherwise stated, a stable straight or branched-chain alkyl group, preferably having from 2 to 14 carbons, more preferably 2 to 10 carbons in the chain, one or more of which has been replaced by a heteroatom selected from S, O, P and N, and wherein the nitrogen, phosphine, and sulfur atoms can optionally be oxidized and the nitrogen heteroatom can optionally be quaternized. The heteroatom(s) S, O. P and N may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, O—$CH_3$, and —O—$CH_2$—$CH_3$. Similarly, the term "heteroalkylene" by itself or as part of another substituent means a divalent radical derived from heteroalkyl, as exemplified, but not limited by, —$CH_2$—$CH_2$—O—$CH_2$—$CH_2$— and —O—$CH_2$—$CH_2$—NH—$CH_2$—. For heteroalkylene groups, heteroatoms can also occupy either or both of the chain termini (e.g alkyleneoxy, alkylenedioxy, alkyleneamino, alkylenediamino, and the like). Still further, for alkylene and heteroalkylene linking groups, no orientation of the linking group is implied by the direction in which the formula of the linking group is written. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

As used herein, the term "alkoxy" as used by itself or as part of another group refers to a radical of the formula $OR^{a1}$, wherein $R^{a1}$ is an alkyl.

As used herein, the term "cycloalkoxy" as used by itself or as part of another group refers to a radical of the formula $OR^{a1}$, wherein $R^{a1}$ is a cycloalkyl.

As used herein, the term "alkanoyl" as used by itself or as part of another group refers to —$C(O)R^{a1}$, wherein $R^{a1}$ is hydrogen or an alkyl. For example, Q alkanoyl refers to —C(O)H, $C_2$ alkanoyl refers to —$C(O)CH_3$.

As used herein, the term "aryl" as used by itself or as part of another group refers to a monocyclic, bicyclic or tricyclic aromatic ring system having from six to fourteen carbon atoms (i.e., $C_{6-14}$ aryl). "Aryl" also includes ring systems wherein the aryl ring, as defined above, is fused with one or more cycloalkyl or heterocyclyl groups wherein the radical or point of attachment is on the aryl ring, and in such instances, the number of carbon atoms continue to designate the number of carbon atoms in the aryl ring system. In embodiments herein, an aryl ring can be designated as connecting to two groups, or an arylene, such as in A-Aryl-B. In such cases, the two points of attachments can be independently selected from any of the available positions.

As used herein, the term "heteroaryl" or "heteroaromatic" refers to monocyclic, bicyclic or tricyclic aromatic ring systems having 5 to 14 ring atoms (i.e., a 5- to 14-membered heteroaryl) and 1, 2, 3, or 4 heteroatoms independently chosen from oxygen, nitrogen and sulfur. In one embodiment, the heteroaryl has one heteroatom, e.g., one nitrogen. In another embodiment, the heteroaryl has 6 ring atoms, e.g., pyridyl. In one embodiment, the heteroaryl is a bicyclic heteroaryl having 8 to 10 ring atoms, e.g., a bicyclic heteroaryl having 1, 2, or 3 nitrogen ring atoms, such as quinolyl. As used herein, the term "heteroaryl" is also meant to include possible N-oxides. "Heteroaryl" includes ring systems wherein the heteroaryl ring, as defined above, is fused with one or more cycloalkyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. In embodiments herein, a heteroaryl ring can be designated as connecting to two groups, or a heteroarylene, such as in A-Heteroaryl-B. In such cases, the two points of attachments can be independently selected from any of the available positions.

As used herein, the term "heterocycle" or "heterocyclyl" as used by itself or as part of another group refers to saturated and partially unsaturated (e.g., containing one or two double bonds) cyclic groups containing one, two, or three rings having from three to fourteen ring members (i.e., a 3- to 14-membered heterocycle) and at least one heteroatom. Each heteroatom is independently selected from the group consisting of oxygen, sulfur, including sulfoxide and sulfone, and/or nitrogen atoms, which can be quaternized. The term "heterocyclyl" is meant to include cyclic ureido groups such as imidazolidinyl-2-one, cyclic amide groups such as β-lactam, γ-lactam, δ-lactam and s-lactam, and cyclic carbamate groups such as oxazolidinyl-2-one. In one embodiment, the heterocyclyl group is a 4-, 5-, 6-, 7- or 8-membered cyclic group containing one ring and one or two oxygen and/or nitrogen atoms. The heterocyclyl can be optionally linked to the rest of the molecule through a carbon or nitrogen atom. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more cycloalkyl groups wherein the point of attachment is either on the cycloalkyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

An "optionally substituted" group, such as an optionally substituted alkyl, an optionally substituted alkenyl, an optionally substituted alkynyl, an optionally substituted cycloalkyl, an optionally substituted heterocyclyl, an optionally substituted aryl, and an optionally substituted heteroaryl groups, refers to the respective group that is unsubstituted or substituted. In general, the term "substituted", means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. Substituents can be a carbon atom substituent, a nitrogen atom substituent, an oxygen atom substituent or a sulfur atom substituent, as applicable. Two of the optional substituents can join to form an optionally substituted cycloalkyl, heterocylyl, aryl, or heteroaryl ring. Substitution can occur on any available carbon, oxygen, or nitrogen atom, and can form a spirocycle. When a bicyclic or polycyclic ring structure is designated as connected to two groups, each point of attachment can be independently selected from any available positions on any of the rings. Typically, substitution herein does not result in an O—O, O—N, S—S, S—N(except $SO_2$—N bond), heteroatom-halogen, heteroatom-CN bond, or —C(O)—S bond or three or more consecutive heteroatoms, with the exception of O—$SO_2$—O, O—$SO_2$—N, and N—$SO_2$—N, except that some of such bonds or connections may be allowed if in a stable aromatic system.

In any of the embodiments described herein, unless otherwise indicated, the "optionally substituted" non-aromatic group can be unsubstituted or substituted with 1, 2, or 3 substituents independently selected from F, Cl, —OH, oxo (as applicable), $C_{1-4}$ alkyl, $C_{1-4}$ alkoxy, $C_{3-6}$ cycloalkyl, $C_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl and $C_{1-4}$ alkoxy. In any of the embodiments described herein, unless otherwise indicated, the "optionally substituted" aromatic group (including aryl and heteroaryl groups) can be unsubstituted or substituted with 1, 2, or 3 substituents independently selected from F, Cl, —OH, —CN, $C_{1-4}$ alkyl, $C_{1-4}$ alkoxy, $C_{3-6}$ cycloalkyl, $C_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl and $C_{1-4}$ alkoxy.

Exemplary carbon atom substituents include, but are not limited to, halogen, —CN, —$NO_2$, —$N_3$, —$SO_2$H, —$SO_3$H, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2$H, —CHO, —C(O$R^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=N$R^{bb}$)$R^{aa}$, —C(=N$R^{bb}$)O$R^{aa}$, —OC(=N$R^{bb}$)$R^{aa}$, —OC(=N$R^{bb}$)O$R^{aa}$, —C(=N$R^{bb}$)N($R^{bb}$)$_2$, —OC(=N$R^{bb}$)N($R^{bb}$)$_2$, —$NR^{bb}$C(=N$R^{bb}$)N($R^{bb}$)$_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)$_3$, —OSi($R^{aa}$)$_3$—C(=S)N($R^{bb}$)$_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)O$R^{aa}$, —SC(=O)$R^{aa}$, —P(=O)($R^{aa}$)$_2$, —P(=O)(O$R^{cc}$)$_2$, —OP(=O)($R^{aa}$)$_2$, —OP(=O)(O$R^{cc}$)$_2$, —P(=O)(N($R^{bb}$)$_2$)$_2$, —OP(=O)(N($R^{bb}$)$_2$)$_2$, —$NR^{bb}$P(=O)($R^{aa}$)$_2$, —$NR^{bb}$P(=O)(O$R^{cc}$)$_2$, —$NR^{bb}$P(=O)(N($R^{bb}$)$_2$)$_2$, —P($R^{cc}$)$_2$, —P(O$R^{cc}$)$_2$, —P($R^{cc}$)$_3^+X^-$, —P(O$R^{cc}$)$_3^+X^-$, —P($R^{cc}$)$_4$, —P(O$R^{cc}$)$_4$, —OP($R^{cc}$)$_2$, —OP($R^{cc}$)$_3^+X^-$, —OP(O$R^{cc}$)$_2$, —OP(O$R^{cc}$)$_3^+X^-$, —OP($R^{cc}$)$_4$, —OP(O$R^{cc}$)$_4$, —B($R^{aa}$)$_2$, —B(O$R^{cc}$)$_2$, —B$R^{aa}$(O$R^{cc}$), $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, wherein each alkyl, alkenyl, alkynyl, cycloalkyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$; each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups; each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ haloalkyl, $C_{2-6}$ alkenyl, $C_{2-6}$ alkynyl, $C_{3-10}$ cycloalkyl, 3-10 membered heterocyclyl, $C_{6-10}$ aryl, 5-10 membered heteroaryl, wherein each alkyl, alkenyl, alkynyl, cycloalkyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 3-10 membered heterocyclyl, and 3-10 membered heteroaryl, wherein each alkyl, alkenyl, alkynyl, cycloalkyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ cycloalkyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON($C_{1-6}$ alkyl)$_2$, —N($C_{1-6}$ alkyl)$_2$, —N($C_{1-6}$ alkyl)$_3$X$^-$, —NH($C_{1-6}$ alkyl)$_2$$^+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH(OH), —SH, —SC$_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)OC$_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ haloalkyl, $C_{2-6}$ alkenyl, $C_{2-6}$ alkynyl, $C_{3-10}$ cycloalkyl, $C_{6-100}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group. Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl, ar-$C_{1-10}$ alkyl, heteroar-$C_{1-10}$ alkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl groups, wherein each alkyl, alkenyl, alkynyl, cycloalkyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protective Groups in Organic Synthesis*, T. W. Greene and P. G. M. Wuts, 3 edition, John Wiley & Sons, 1999, incorporated by reference herein.

Exemplary oxygen atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$ $R^{aa}$, $R^{bb}$, and $R^{cc}$ are as defined herein. In certain embodiments, the oxygen atom substituent present on an oxygen atom is an oxygen protecting group. Oxygen protecting groups are well known in the art and include those described in detail in *Protective Groups in Organic Synthesis*, T. W. Greene and P. G. M. Wuts, $3^{rd}$ edition, John Wiley & Sons, 1999, incorporated herein by reference.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. The term "pharmaceutically acceptable ester" should be understood similarly.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

The term "inhibition", "inhibiting", or "inhibit," refer to the ability of a compound to reduce, slow, halt or prevent activity of a particular biological process (e.g., growth of a bacteria relative to vehicle).

The term "subject" (alternatively referred to herein as "patient") as used herein, refers to an animal, preferably a mammal, most preferably a human, who has been the object of treatment, observation or experiment. In some embodiments, the subject can be a vertebrate such as a dog, a cat, a horse or a monkey.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

Unless expressly stated to the contrary, combinations of substituents and/or variables are allowable only if such combinations are chemically allowed and result in a stable compound. A "stable" compound is a compound that can be prepared and isolated and whose structure and properties remain or can be caused to remain essentially unchanged for a period of time sufficient to allow use of the compound for the purposes described herein (e.g., therapeutic administration to a subject).

EXAMPLES

Example 1. Preparation of Bacterial Culture

The bacterial culture medium (HuanKai Microbial, Guangzhou, China) containing peptone 5 g, beef extract 3 g, NaCl 5 g, agar 15 g, and $MnSO_4$ 5 mg in 1 L $ddH_2O$ (pH=7.2) was prepared in conical flask (Drtech, Guangzhou, China) and was sterilized in the autoclave (HIRAYAMA, HEV-50, Japan) at 121° C. for 30 min. *Bacillus megaterium* (total $1*10^7$ per culture) was cultured in the incubator (HettCube 200, Germany) at 37° C. for 24 h.

Example 2. Bacterial Culture for Drug Screening

Figure 1:
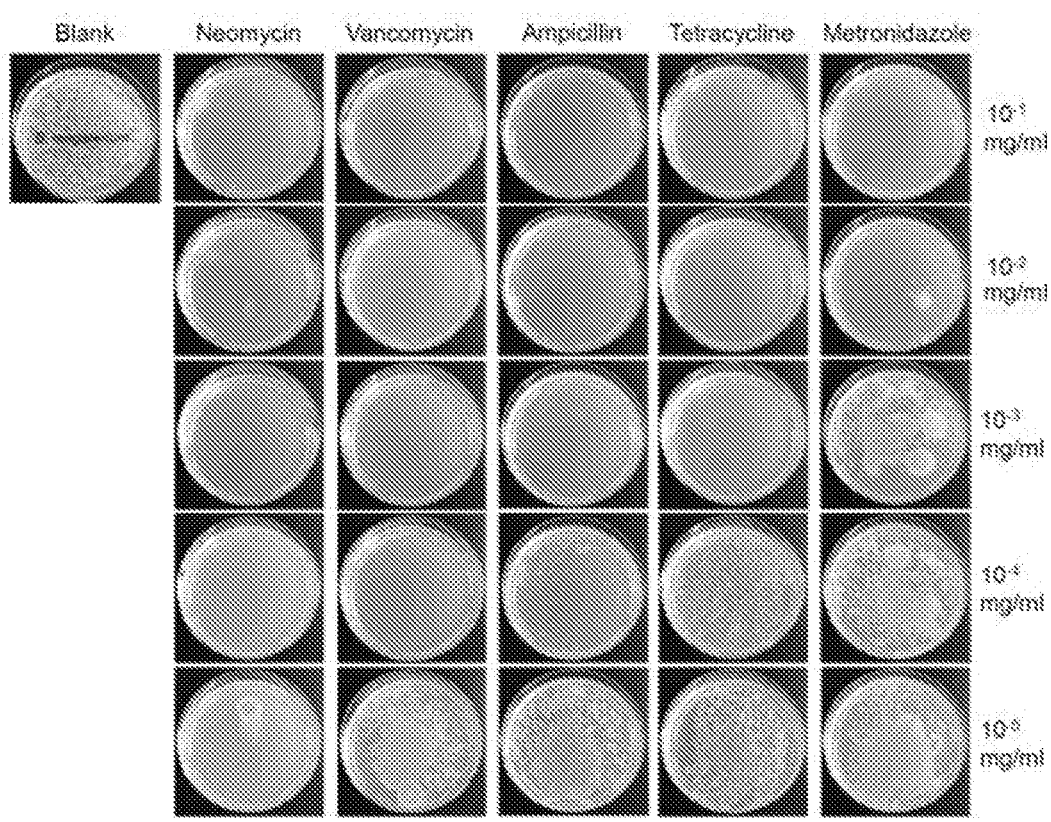
FIG. 1 illustrates the sensitivity of *Bacillus megaterium* to several antimicrobial agents.

To test whether antibiotics can control the growth of *Bacillus megaterium* in vitro and in vivo, we first carried out an antibiotic sensitivity screening test in petri dishes which were made in example 1. The sensitivity of *Bacillus megaterium* to several major antimicrobial agents including ampicillin, vancomycin, neomycin, metronidazole and tetracycline were examined using the minimum inhibitory concentration (MIC) method. Ampicillin, vancomycin, neomycin, metronidazole, and tetracycline (purchased from Sigma, USA) at various concentrations ($10^{-1}$, $10^{-2}$, $10^{-3}$, $10^{-4}$, $10^{-5}$ mg/mL) were added into cooled medium. As shown in FIG. 1 below, *Bacillus megaterium* was most sensitive to neomycin, while metronidazole was 10000-fold less effective in controlling the growth of *Bacillus megaterium*.

Example 3. Intraocular Bacterial Culture System for Drug Screening

Each culture was prepared in a 15 ml glass tube (purchased from Drtech Inc., Guangzhou China) with 6 ml cooked meat medium, sterilized dry beef granules, and 1.5 ml liquid paraffin wax (purchased from Huankai Microbial Inc., Guangzhou, China) on top. All tubes were then sterilized at 121° C. for 30 min in the HEV-to Autoclave instrument (HIRAYAMA, Japan). Aqueous or vitreous humor fluid, with or without drug to screen, was injected into above tube in sterilized cell culture hood and sealed, followed by culture with shaking (200 rpm) at 37° C. for 72 hours in the ZQTY-70F incubator (Zhichu Instrument Co., Ltd, Shanghai, China). Wax sealed tubes containing the culture medium underwent the incubation protocol but contained no aqueous or vitreous humor samples served as negative control.

Figure 2:
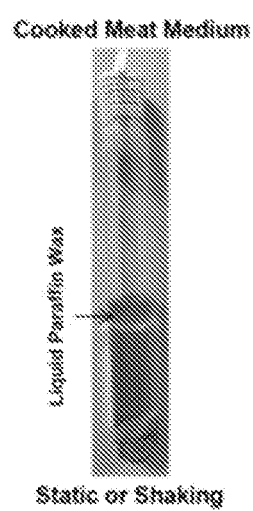
FIG. 2 illustrates cultures in liquid cooked meat medium covered by liquid paraffin wax.

Cultures using liquid cooked meat medium (FIG. 2) were found positive for bacteria. Therefore, this culture system can be used for drug sensitivity screening and the cultures can be visualized using standard light microscopes (FIG. 3).

Example 4. Intravitreal Bacterial Infection in Macaque for Drug Screening

Bacillus megaterium BNCC190686 and Propionibacterium acnes BNCC336649 were first cultured overnight at 37° C. on agar plates following the standard protocols provided by the manufacturer. The bacterial cultures were then washed in PBS and resuspended as $1 \times 10^6$ CFU/µl solutions and further diluted in PBS as injection solutions.

We chose the non-human primate macaque (Macaca fascicularis) as our model system considering the ocular anatomy and intraocular environment shared by human and macaque. The macaques were sedated by intramuscular injection of a mixture of Tiletamine Hydrochloride (2.5 mg/kg) and Xolazepam Hydrochloride (2.5 mg/kg). After topical anesthesia (0.5% Proparacaine Hydrochloride), the eyes were immediately visualized in vivo using a light microscope. The pupils were then dilated with 0.5% tropicamide and 0.5% phenylephrine to obtain the fundus photographs. Intravitreal injection of bacterial solutions (1000 CFU [colony forming units] in a volume of 50 µl) or sonication-inactivated bacterial proteins (from 1000 CFU bacteria) was performed with a 1 ml syringe and 30-gauge needle after ocular surface disinfection with 5% PVI solution. The macaques were randomly divided into four groups. Group 1: The right (OD) and left (OS) eyes of macaques were inoculated with P. acnes and B. megaterium, respectively.
Group 2: The right (OD) and left (OS) eyes of macaques were inoculated with sonication-inactivated proteins of P. acnes and B. megaterium, respectively.
Group 3: The right (OD) and left (OS) eyes of macaques were inoculated with P. acnes and Pseudomonas putida, respectively.
Group 4: The right (OD) and left (OS) eyes of macaques were inoculated with sonication-inactivated proteins of P. acnes and Pseudomonas putida, respectively.

Slit lamp and fundus examinations were conducted for all macaques within 3 days after the injection. The severity of the endophthalmitis was graded according to a previously described standard (Peyman G A, Paque J T, Meisels H I, Bennett T O. Postoperative endophthalmitis: a comparison of methods for treatment and prophlaxis with gentamicin. Ophthalmic Surg 1975; 6:45-55). The macaques were euthanized 3 days post inoculation and both eyeballs were enucleated for histopathological, intraocular cytokines, and bacteria analyses. The eyeballs were fixed in 4% paraformaldehyde for 48 h and then embedded in paraffin. Sections were cut on a microtome at 5 µm and stained with hematoxylin and eosin (H&E).

We tested whether Bacillus megaterium and Pseudomonas putida were able to induce inflammation in vivo. As shown in FIG. 4-5, intravitreal infection of live P. acnes did not induce significant intraocular inflammation. Neither did injection of sonication-inactivated proteins of P. acnes induce significant intraocular inflammation. Conversely, infection of live Bacillus megaterium (FIG. 4) and Pseudomonas putida (FIG. 5), and their proteins into the eye led to an intraocular inflammation.

To screen for a drug for treating or preventing the endophthalmitis caused by Bacillus megaterium or Pseudomonas putida, an effective amount of bacitracin, gramicidin, polymyxin or nisin was administered to the macaque eyes with intraocular inflammation, then the recovery of the ocular surface and fundus of the macaque were visualized using a light microscope.

Example 5 Analysis of Subretinal Bacterial Infection in Macaque for Drug Screening The macaques were sedated by intramuscular injection of a mixture of tiletamine hydrochloride (2.5 mg/kg) and xolazepam hydrochloride (2.5 mg/kg). After instilling topical anesthesia (0.5% proparacaine hydrochloride), the eyes were immediately visualized in vivo using a light microscope. The pupils were then dilated with 0.5% tropicamide and 0.5% phenylephrine to obtain the fundus photographs. As shown in FIG. 6, then a 35 gauge anterior chamber cannula was inserted through a sclerotomy and advanced through the vitreous. Under microscopic monitoring, 20 µl of PBS (with or without bacteria) was injected into the subretinal space between photo receptors and RPE (retinal pigment epithelium), using a NanoFil Syringe Nanofil-100 for Microinjection (World Precision Instruments, USA). All procedures were done using sterile instruments. The macaque was euthanized 47 days post inoculation and the eyeball was enucleated for histological analyses. The eyeballs were fixed in 4% paraformaldehyde for 48 h and then embedded in paraffin. Sections were cut on a microtome at 6 µm and stained with H&E.

We examined whether subretinal inoculation of AH and VH cultures, as well as the cultured single species of B. megaterium led to AMD like pathology in macaque. About 20 CFU of bacteria (in 20 µl PBS) from AH, VH, and B. megaterium cultures were injected subretinally and PBS was used as a control (illustrated in FIG. 6). The fundus examination of macaque eye was performed before (Day 0) and after bacterial inoculation on Day 1, Day 3, Day 35 (data not shown), as well as Day 47. As shown in FIG. 7, the PBS injection left only visible scar on the retina, while all bacterial inoculations led to drusenoid lesions on retinal tissues.

Next, we used the Bacillus megaterium subretinal inoculation model to test whether antibiotics might be able to change the bacteria-induced drusenoid pathology in monkey retinal tissues. Although neomycin showed the best in vitro activity controlling the expansion of Bacillus megaterium, intraocular administration of neomycin in monkey induced significant ocular complications including ophthalmatrophia (data not shown). On the other hand, intravitreous administration of vancomycin (0.5 mg, one injection on Day 2 post bacterial inoculation) resulted in a reduction in the size of drusenoid lesion in retinal tissue as shown in right of FIG. 8, as compared to the lesion shown in left of FIG. 8. These data suggest that vancomycin may be able to inhibit the growth of Bacillus megaterium in vitro and in vivo, therefore may be used to treat age-related macular degeneration.

Example 6 Disease-Specific Intraocular Microbiome could Characterize Ocular Manifestations As all human eyes we tested have intraocular microbiota, we next investigated whether a disease-specific intraocular microbiome could characterize ocular manifestations.

Test patients: 41 cataract, 20 AMD, 18 glaucoma, 9 BD, 9 VKH, and 8 EOS.

Test Methods:
(1) Taking a sample of aqueous humor and extracting DNA from the aqueous sample;
  1) Irrigating patients' conjunctival sac using 0.9% sodium chloride solution for three times;
  2) Mydriasis using atropine;
  3) Applying the ofloxacin solution on patients' eyes for 30 seconds for disinfection;
  4) Irrigating patients' conjunctival sac with tobramycin solution for three times for sterilization;
  5) Taking a sample of aqueous humor and extracting DNA from the aqueous sample,
(2) Detection of DNA extracted from aqueous humor samples using metagenomic sequencing analysis.

Results: All human eyes we tested have intraocular microbiota, FIG. 9 is a LefSe analysis graph of bacterial species that were highly enriched in the eyes of patients with different diseases, as shown in FIG. 9 patients with different diseases have different kinds of bacteria. In spite of the significant individuality presented by the intraocular microbiome, we were able to identify signature bacterial species using LDA Effect Size (LefSe)2 for each ocular disease group we tested.

Example 7. Bacillus megaterium is Enriched in Soft Drusen from AMD Patients

As detailed in PCT Application No. PCT/CN2018/112022, metagenomic sequencing analysis were carried out on aqueous humor specimens from 41 cataract (Cat), 20 AMD, 18 glaucoma (GLA), 9 Betch's disease (BD), 9 Vogt-Koyanagi-Harada Syndrome (VKH), and 8 endophthalmitis (EOS) patients. The results are briefly discussed below.

In brief, 14 bacterial species were identified as highly enriched in the AH of AMD patients using metagenomic analysis. See Table 1 below:

While *P. acnes* was found to be the most abundant microorganism in the AH of AMD patients, *Bacillus licheniformis* (*B. licheniformis*) and *Bacillus megaterium* (*B. megaterium*) were the most enriched species, among the 14 AMD-specific ones, in AMD AH specimens (Table 1). We then carried out PCR analysis to investigate whether the 14 AMD-specific bacteria could be detected in the hard or soft drusen tissues, as compared to the non-drusen retinal tissues from 6 archived ocular slides of AMD patients. Our results showed only 8 bacteria could be detected, among which *P. acnes* was the most abundant species and *B. megaterium* was the only species enriched in soft drusen. Intriguingly, the relative abundance of *P. acnes* was comparable in hard drusen, soft drusen, and dry AMD lesion tissues as compared to the non-drusen non-lesion retinal tissues. The relative abundance of *B. megaterium* was elevated by ~18 fold in soft drusen when compared to the non-drusen/non-lesion tissues. These data suggest a possible role of *B. megaterium* in drusen formation and AMD pathogenesis.

Example 8. Bacillus megaterium Induces Activation of Complement, Pyroptosis of RPE Cells In Vitro and Induces Drusenoid Lesions in Macaque Also detailed in PCT Application No. PCT/CN2018/112022, the present inventors have shown that *Bacillus megaterium* can induce activation of complement, pyroptosis of RPE cells in vitro and can induces drusenoid lesions in macaque. Briefly, the inventors found that in vitro infection of *B. megaterium*, but not *P. acnes*, led to secretion of active IL-1β and IL-18 by RPE cells, which suggests that infection of *B. megaterium* can lead to inflammation mediated by RPE.

Further, it was demonstrated that *B. megaterium* exists in both AH and retinal tissues. The inventors collected both AH and vitreous humor (VH) specimens from AMD patients and were able to detect *B. megaterium* DNA in both uncultured and cultured samples. The inventors further examined whether subretinal inoculation of AH and VH cultures which had *B. megaterium*, as well as the cultured single species of *B. megaterium* led to AMD like pathology in macaque. Briefly, about 20 CFU of bacteria (in 20 μl PBS) from AH, VH, and *B. megaterium* cultures were injected subretinally and PBS was used as a control. The fundus examination of macaque eye was performed before (Day 0) and after bacterial inoculation on Day 1, Day 3, Day 35 as well as Day

TABLE 1

| | Bacteria Name | Fold change (AMD vs Cat) | PValue (AMD vs Cat) | Q Value (AMD vs Cat) | AMD (Ave) | Cat (Ave) | Gla (Ave) | BD (Ave) | VKH (Ave) | EOS (Ave) |
|---|---|---|---|---|---|---|---|---|---|---|
| High Abandance | Bacillus licheniformis | 324.1 | 1.7E−07 | 1.7E−06 | 0.187 | 0.000 | 0.002 | 0.000 | 0.000 | 0.000 |
| | Bacillus megaterium | 11.2 | 1.2E−05 | 6.2E−05 | 0.159 | 0.014 | 0.124 | 0.004 | 0.004 | 0.000 |
| | Pseudomonas putida | 8.3 | 2.1E−05 | 3.5E−05 | 0.530 | 0.064 | 0.087 | 0.053 | 0.053 | 0.001 |
| | Stenotrophomonas maltophilia | 5.4 | 7.4E−06 | 2.5E−07 | 1.159 | 0.213 | 0.537 | 0.078 | 0.071 | 0.001 |
| | Bacillus cereus | 4.6 | 4.5E−07 | 8.9E−07 | 0.122 | 0.027 | 0.047 | 0.012 | 0.018 | 0.000 |
| | Pseudomonas aeruginosa | 1.9 | 1.3E−02 | 1.4E−02 | 0.696 | 0.375 | 0.678 | 0.059 | 0.068 | 0.000 |
| | Staphylococcus epidermidis | 1.7 | 1.4E−01 | 1.0E+00 | 3.130 | 1.501 | 1.054 | 1.000 | 1.263 | 20.668 |
| | Staphylococcus aureus | 1.6 | 1.7E−01 | 1.0E+00 | 0.610 | 0.388 | 0.302 | 0.064 | 0.067 | 0.256 |
| | Staphylococcus haemolyticus | 1.5 | 1.9E−01 | 1.0E+00 | 0.149 | 0.100 | 0.090 | 0.050 | 0.042 | 0.006 |
| Low Abandance | Xanthomonas oryzae | 73.1 | 9.2E−08 | 2.3E−07 | 0.054 | 0.001 | 0.000 | 0.000 | 0.000 | 0.000 |
| | Cytophaga hutchinsonii | 18.5 | 1.4E−04 | 1.9E−04 | 0.032 | 0.002 | 0.001 | 0.000 | 0.000 | 0.000 |
| | Enterococcus faecium | 11.4 | 1.3E−02 | 1.3E−02 | 0.039 | 0.003 | 0.022 | 0.002 | 0.000 | 0.000 |
| | Lactobacillus reuteri | 3.5 | 6.6E−02 | 1.0E+00 | 0.051 | 0.014 | 0.011 | 0.001 | 0.003 | 0.044 |
| | Gardnerella vaginalis | 2.8 | 1.3E−02 | 1.6E−02 | 0.041 | 0.015 | 0.015 | 0.019 | 0.013 | 0.000 |

47. The PBS injection left only visible scar on the retina, while all bacterial inoculations led to drusenoid lesions on retinal tissues. Drusen-like nodules were also visible under the RPE layer. Fluorescence in situ hybridization results also located *B. megaterium* in drusenoid but not in the normal tissues post inoculation. An elevation in the expression of C5A, CFH, CASPASE1, and NLRP3 proteins was also detected in the *B. megaterium* infected drusenoid lesion and para-lesion tissues as compared to the uninfected normal retina in macaque. Taken together, the data demonstrate that infection of *B. megaterium* can activate complement system and induce drusenoid pathology in vivo.

Example 9. The Test of Antibiotics to Treat AMD Through Inhibiting the Growth of Microbiota Method Antibiotic Sensitivity Testing The bacterial culture medium (HuanKai Microbial, Guangzhou, China) containing peptone 5 g, beef extract 3 g, NaCl 5 g, agar 15 g, and $MnSO_4$ 5 mg in 1 L $ddH_2O$ (pH=7.2) was prepared in conical flask (Drtech, Guangzhou, China) and was sterilized in the autoclave (HIRAYAMA, HEV-50, Japan) at 121° C. for 30 min. Antibiotics (ampicillin, vancomycin, neomycin, metronidazole, and tetracycline, purchased from Sigma, USA) at various concentrations were added into cooled medium. *Bacillus megaterium* (total $1*10^7$ per culture) was cultured in the incubator (HettCube 200, Germany) at 37° C. for 24 h.

Result

To test whether antibiotics can control the growth of *Bacillus megaterium* in vitro and in vivo, an antibiotic sensitivity screening test in petri dishes was carried out. The sensitivity of *Bacillus megaterium* to several major antimicrobial agents including Ampicillin, vancomycin, neomycin, metronidazole, and tetracycline were examined using the minimum inhibitory concentration (MIC) method. As shown in FIG. 1, *Bacillus megaterium* was most sensitive to neomycin, while metronidazole was 10000-fold less effective in controlling the growth of *Bacillus megaterium*.

Next, *Bacillus megaterium* subretinal inoculation model was used to test whether antibiotics might be able to change the bacteria-induced drusenoid pathology in monkey retinal tissues. Although neomycin showed the best in vitro activity controlling the expansion of *Bacillus megaterium*, intraocular administration of neomycin in monkey induced significant ocular complications including ophthalmatrophia (data not shown). On the other hand, intravitreous administration of vancomycin (0.5 mg, one injection on Day 2 post bacterial inoculation) resulted in a reduction in the size of drusenoid lesion in retinal tissue, as compared to the lesion shown, see FIG. 8. These data suggest that vancomycin is able to inhibit the growth of *Bacillus megaterium* in vitro and in vivo, therefore can be used to treat age-related macular degeneration.

Example 10. In Vitro Screening of Compounds that can Inhibit the Growth of Microbiota To test whether certain Traditional Chinese Medicine (TCM) can control the growth of *Bacillus megaterium* in vitro and in vivo, an antibiotic sensitivity screening test in petri dishes was carried out. The sensitivity of *Bacillus megaterium* to various components from different TCMs, including Licorice (*Glycyrrhiza uralensis*), White Peony Root (*Cynanchum otophyllum*), Forsythia (*Forsythia suspense*), Fructus Aurantii (*Citrus aurantium* LA, *Rehmannia glutinosa* (*Rehmannia glutinosa* Libosch), Tangerine Peel (*Citrus reticulata* Blanco), and Notoginseng (*Panax notoginseng*) were tested. The extract from these TCMs were tested to be positive in killing or inhibiting the growth of *Bacillus megaterium*.

The screening procedure for the TCMs is shown below.

100 g of TCMs were soaked in 300 ml of water for approximately 30 min, then boiled on fire, simmered for 20~40 min, and concentrated to about 100 ml.

Preparation of the bacterial growth buffer (Sigma-Aldrich, USA): Peptone 5.0 g, beef extract 3.0 g, NaCl 5.0 g, agar 15.0 g, and distilled water 1.0 L, at pH 7.0. Five miligram of $MnSO_4 \cdot H_2O$ was added to the culture of *Bacillus* to facilitate spore formation. The buffer was placed in a pressure cooker (HIRAYAMA, HEV-50, Japan) for 30 minutes at 120° C., then cooled down to 40-50° C.

One milliliter of TCMs solution was added to 15 ml of the growth buffer, mixed and introduced into the culture dish, and let it stand in the clean bench to solidify.

100 ul of the suspension of *Bacillus megaterium* (concentration: $1 \times 10^6$/ml) was added to the plate and evenly spreaded using a sterilized spreader, then placed in a 37° C. incubator (HettCube 200, Germany) for 24 h.

The growth of the flora on the plate were observed.

TCMs with antibacterial function were screened by pre-experimental experiments, including Licorice, White Peony Root, *Forsythia, Fructus Aurantii, Rehmannia glutinosa,* Tangerine Peel and *Notoginseng*.

Following similar screening procedures, various commercially available TCM components (each contains a single chemical compound) were also screened. Compounds 1-8 below were found to be the most active compounds in killing or inhibiting the growth of *Bacillus megaterium*. At the tested concentration, each of Compounds 1-8 effectively killed and inhibited the growth of *Bacillus megaterium* in petri dishes. Other tested compounds did not kill or inhibit the growth of *Bacillus megaterium* in petri dishes at the tested concentration.

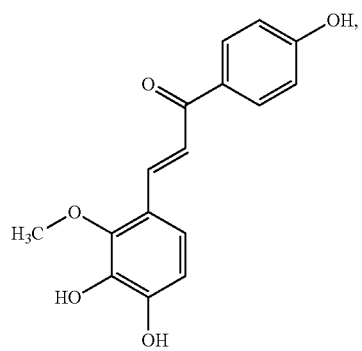

1

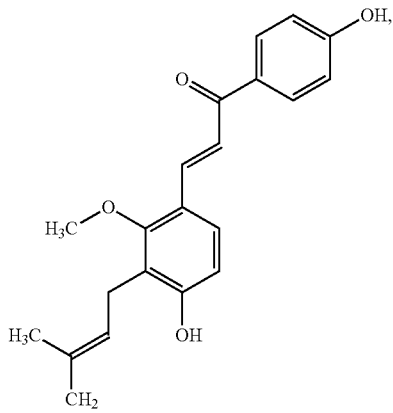

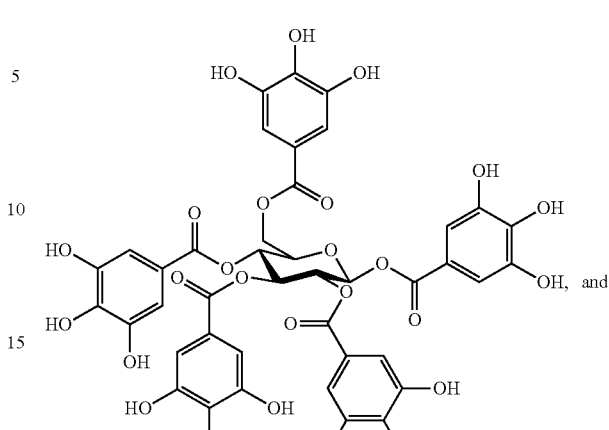

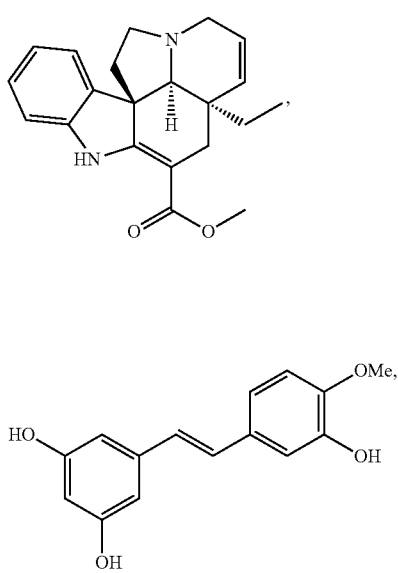

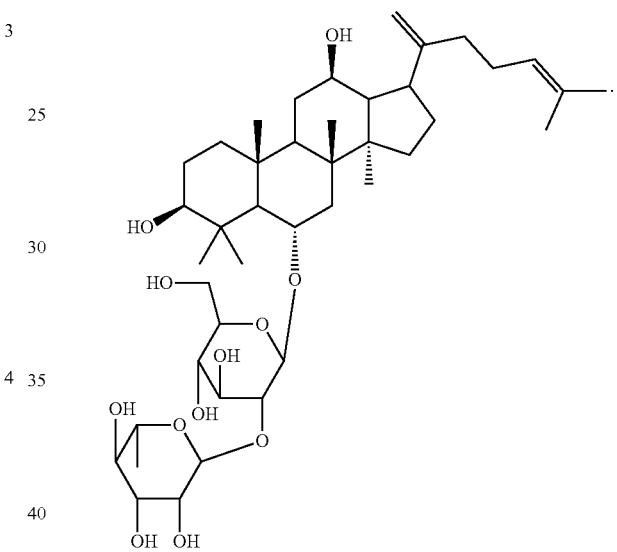

Experimental Procedure

Dissolving components: In a clean bench, TCM components (each contains a single chemical compound) were dissolved by shaking in distilled water to a concentration of 20 g/L and stood overnight at room temperature.

Preparation of the bacterial growth buffer (Sigma-Aldrich, USA)

15 ml of the buffer was plated and autoclaved for 30 minutes at 120° C.

After the culture plate was sterilized and cooled to approximately 50° C., 10 µl of each component was added, and the mixture was stood and solidified. The bacteria were plated in the center and incubated at 37° C. overnight.

The growth of the flora on the plate were observed. FIG. 10 shows pictures of the plates for compounds 1-8.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments. All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A method comprising:
   (i) identifying, or having identified, a subject as being infected with a microorganism in the intraocular space, wherein the subject has age-related macular degeneration (AMD); and
   (ii) administering to the subject a therapeutically effective amount of an active compound selected from one of compounds (1)-(8) or a pharmaceutically acceptable salt thereof, or a pharmaceutical composition comprising the active compound or pharmaceutically acceptable salt thereof, wherein compounds (1)-(8) have the following chemical structures:

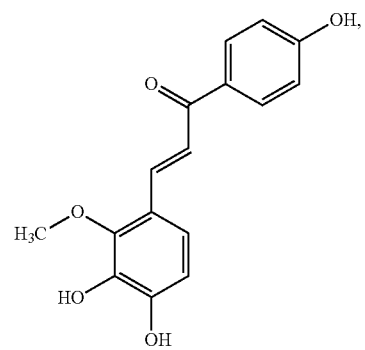
(1)

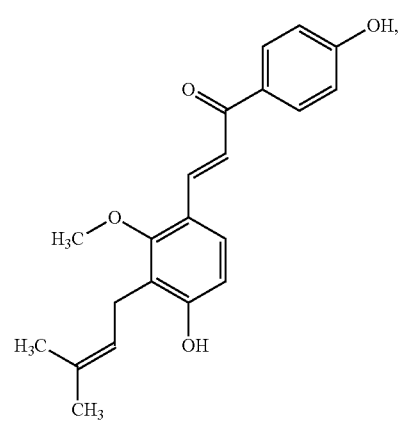
(2)

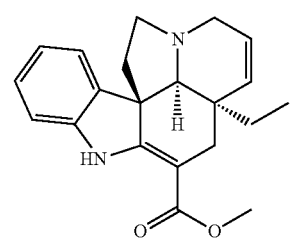
(3)

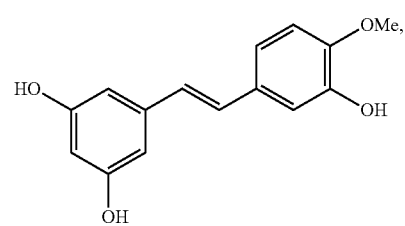
(4)

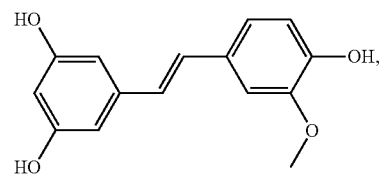
(5)

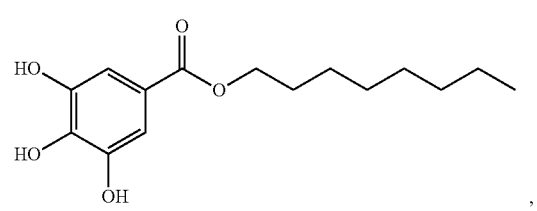
(6)

(7)

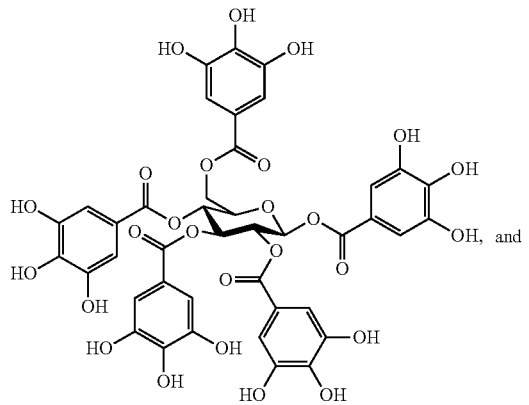

(6)

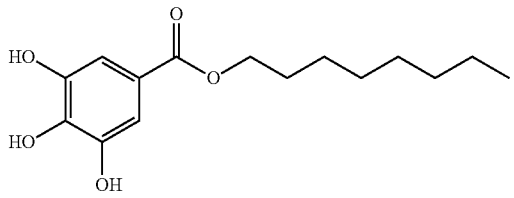

5. The method of claim 1, wherein the administering is an oral administration.

6. The method of claim 1, wherein the administering is carried out topically, intravitreously, intramuscularly, subcutaneously, or intravenously.

7. A method for ameliorating age-related macular degeneration (AMD) in a subject in need thereof, comprising:
(i) identifying, or having identified, the subject as being infected with a microorganism in the intraocular space, wherein the microorganism comprises *Bacillus megaterium*; and
(ii) administering to the subject a therapeutically effective amount of a pharmaceutical composition comprising an active compound selected from compound (6) or a pharmaceutically acceptable salt thereof, wherein compound (6) is:

(8)

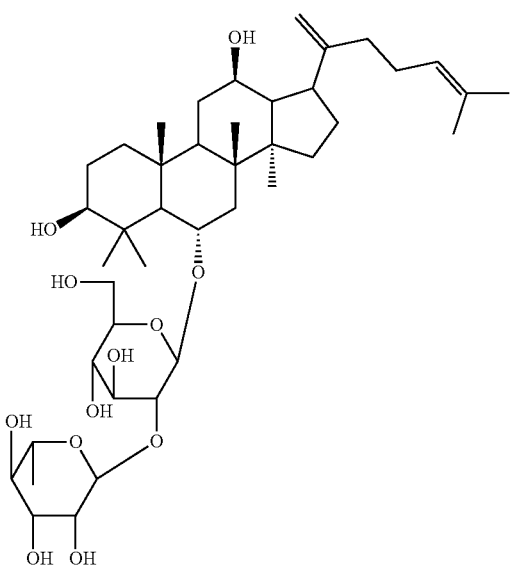

(6)

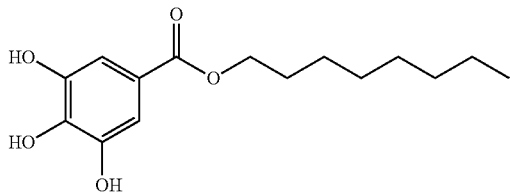

8. The method of claim 7, wherein the AMD is a dry or wet age-related macular degeneration with drusen symptoms.

9. The method of claim 8, wherein the drusen symptoms include a hard drusen, a soft drusen, a mixed drusen, and/or a degraded drusen.

10. The method of claim 8, wherein the AMD is dry or wet age-related macular degeneration with soft drusen symptoms.

wherein the therapeutically effective amount is an amount effective in killing or inhibiting the growth of the microorganism in the intraocular space.

11. The method of claim 7, wherein the pharmaceutical composition is administered in an amount effective for killing or inhibiting the growth of the microorganism in the intraocular space.

2. The method of claim 1, wherein the microorganism comprises *Bacillus megaterium*.

12. The method of claim 7, wherein the pharmaceutical composition is administered orally.

3. The method of claim 1, wherein the microorganism comprises one or more species selected from *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis,* and *Xanthomonas oryzae.*

13. The method of claim 7, wherein the pharmaceutical composition is administered topically, intravitreously, intramuscularly, subcutaneously, or intravenously.

14. A method for ameliorating age-related macular degeneration (AMD) in a subject infected with a microorganism in the intraocular space, the method comprising killing or inhibiting the growth of the microorganism in the intraocular space by administering to the subject an effective amount of a pharmaceutical composition comprising an active compound selected from compound (6), wherein the microorganism comprises *Bacillus megaterium*, and wherein compound (6) is:

4. The method of claim 1, wherein the active compound is compound (6):

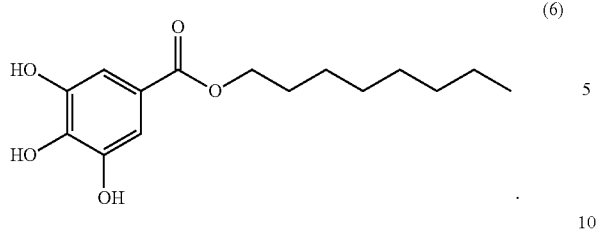

(6)

15. The method of claim 14, wherein the AMD is a dry or wet age-related macular degeneration with drusen symptoms.

16. The method of claim 15, wherein the drusen symptoms include a hard drusen, a soft drusen, a mixed drusen, and/or a degraded drusen.

17. The method of claim 15, wherein the AMD is dry or wet age-related macular degeneration with soft drusen symptoms.

18. The method of claim 14, wherein the pharmaceutical composition is administered orally.

19. The method of claim 14, wherein the pharmaceutical composition is administered topically, intravitreously, intramuscularly, subcutaneously, or intravenously.

20. The method of claim 14, wherein the pharmaceutical composition is administered intravitreously.

* * * * *